US011819539B2

(12) United States Patent
Hinderer et al.

(10) Patent No.: US 11,819,539 B2
(45) Date of Patent: Nov. 21, 2023

(54) GENE THERAPY FOR TREATING MUCOPOLYSACCHARIDOSIS TYPE II

(71) Applicant: The Trustees of the University of Pennsylvania, Philadelphia, PA (US)

(72) Inventors: Christian Hinderer, New Orleans, LA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 401 days.

(21) Appl. No.: 16/649,230

(22) PCT Filed: Sep. 21, 2018

(86) PCT No.: PCT/US2018/052129
§ 371 (c)(1),
(2) Date: Mar. 20, 2020

(87) PCT Pub. No.: WO2019/060662
PCT Pub. Date: Mar. 28, 2019

(65) Prior Publication Data
US 2020/0246439 A1 Aug. 6, 2020

Related U.S. Application Data

(60) Provisional application No. 62/573,841, filed on Oct. 18, 2017, provisional application No. 62/562,179, filed on Sep. 22, 2017, provisional application No. 62/561,769, filed on Sep. 22, 2017.

(51) Int. Cl.
| | |
|---|---|
| *C12N 9/16* | (2006.01) |
| *A61K 38/46* | (2006.01) |
| *A61P 3/00* | (2006.01) |
| *A61K 9/00* | (2006.01) |
| *A61K 35/76* | (2015.01) |
| *C12N 15/86* | (2006.01) |

(52) U.S. Cl.
CPC .......... *A61K 38/465* (2013.01); *A61K 9/0019* (2013.01); *A61K 9/0085* (2013.01); *A61K 35/76* (2013.01); *A61P 3/00* (2018.01); *C12N 15/86* (2013.01); *C12Y 301/06013* (2013.01); *C12N 2750/14143* (2013.01)

(58) Field of Classification Search
CPC .......... C12Y 301/06013; A61K 9/0019; C12N 15/86
See application file for complete search history.

(56) References Cited

U.S. PATENT DOCUMENTS

| | | | |
|---|---|---|---|
| 5,624,898 A | 4/1997 | Frey | |
| 6,033,885 A | 3/2000 | Latta et al. | |
| 6,180,603 B1 | 1/2001 | Frey | |
| 6,190,659 B1 | 2/2001 | Pancholi et al. | |
| 6,309,634 B1 | 10/2001 | Bankiewicz et al. | |
| 6,313,093 B1 | 11/2001 | Frey | |
| 6,342,478 B1 | 1/2002 | Frey | |
| 6,407,061 B1 | 6/2002 | Frey | |
| 6,569,661 B1 | 5/2003 | Qin et al. | |
| 6,596,535 B1 | 7/2003 | Carter | |
| 6,858,206 B2 | 2/2005 | Kakkis | |
| 6,953,575 B2 | 10/2005 | Bankiewicz et al. | |
| 6,991,785 B2 | 1/2006 | Frey | |
| 7,084,126 B1 | 8/2006 | Frey et al. | |
| 7,125,717 B2 | 10/2006 | Carter | |
| 7,282,199 B2 | 10/2007 | Gao et al. | |
| 7,442,372 B2 | 10/2008 | Kakkis | |
| 7,446,098 B2 | 11/2008 | Fan | |
| 7,456,683 B2 | 11/2008 | Takano et al. | |
| 7,569,544 B2 | 8/2009 | Zankel | |
| 7,588,772 B2 | 9/2009 | Kay et al. | |
| 7,592,321 B2 | 9/2009 | Whitley et al. | |
| 7,790,449 B2 | 9/2010 | Gao et al. | |
| 7,906,111 B2 | 3/2011 | Wilson et al. | |
| 7,989,502 B2 | 8/2011 | Greco et al. | |
| 8,153,604 B2 | 4/2012 | Deen et al. | |
| 8,252,745 B2 | 8/2012 | Yeomans et al. | |
| 8,283,160 B2 | 10/2012 | Frey et al. | |
| 8,318,480 B2 | 11/2012 | Gao et al. | |
| 8,501,691 B2 | 8/2013 | Yeomans et al. | |
| 8,545,837 B2 | 10/2013 | Zhu et al. | |
| 8,609,088 B2 | 12/2013 | Wolf et al. | |

(Continued)

FOREIGN PATENT DOCUMENTS

| | | |
|---|---|---|
| EP | 1310571 | 11/2002 |
| EP | 1915986 A1 | 4/2008 |

(Continued)

OTHER PUBLICATIONS

Abel et al., Genetic Demonstration of a Role for PKA in the Late Phase of LTP and in Hippocampus-Based Long-Term Memory, Cell, vol. 88(5):615-626, Mar. 1997.
Andersen et al., Herpesvirus-mediated gene delivery into the rat brain: Specificity and efficiency of the neuron-specific enolase promoter, Cell. Mol. Neurobiol., vol. 13:503-515, Oct. 1993.
Arbuthnot et al., In vitro and in vivo hepatoma cell-specific expression of a gene transferred with an adenoviral vector, Hum. Gene Ther., vol. 7:1503-14, Aug. 1996.
Belting et al., Glypican-1 Is a Vehicle for Polyamine Uptake in Mammalian Cells, Journal of Biological Chemistry, vol. 278:47181-47189, Sep. 2003.

(Continued)

*Primary Examiner* — Tekchand Saidha
(74) *Attorney, Agent, or Firm* — Howson & Howson LLP; Cathy A. Kodroff

(57) ABSTRACT

A co-therapeutic regimen comprising AAV9-mediated intrathecal/intracisternal and/or systemic delivery of an expression cassette containing a hIDS gene and two or more immunosuppressants is provided herein. Also provided are methods and kits containing these vectors and compositions useful for treating Hunter syndrome and the symptoms associated with Hunter syndrome.

30 Claims, 37 Drawing Sheets
Specification includes a Sequence Listing.

(56) References Cited

U.S. PATENT DOCUMENTS

| | | |
|---|---|---|
| 8,622,993 B2 | 1/2014 | Frey et al. |
| 8,632,764 B2 | 1/2014 | Xiao et al. |
| 8,715,661 B2 | 5/2014 | Pardridge et al. |
| 8,796,236 B2 | 8/2014 | Dodge et al. |
| 8,889,641 B2 | 11/2014 | Asokan et al. |
| 8,920,801 B2 | 12/2014 | Pardridge et al. |
| 8,999,948 B2 | 4/2015 | Tubert et al. |
| 9,089,566 B2 | 7/2015 | Kakkis |
| 9,102,949 B2 | 8/2015 | Gao et al. |
| 9,133,482 B2 | 9/2015 | Harper et al. |
| 9,186,419 B2 | 11/2015 | Xiao et al. |
| 9,186,420 B2 | 11/2015 | Koeberl |
| 9,220,677 B2 | 12/2015 | Zhu et al. |
| 9,249,424 B2 | 2/2016 | Wolf et al. |
| 9,265,843 B2 | 2/2016 | During et al. |
| 9,279,109 B2 | 3/2016 | Mihara et al. |
| 9,279,132 B2 | 3/2016 | Bosch Tubert et al. |
| 9,283,181 B2 | 3/2016 | Calias et al. |
| 9,284,357 B2 | 3/2016 | Gao et al. |
| 9,320,711 B2 | 4/2016 | Natoli et al. |
| 9,402,921 B2 | 8/2016 | Xiao et al. |
| 9,409,953 B2 | 8/2016 | Asokan et al. |
| 9,415,121 B2 | 8/2016 | Kaspar et al. |
| 9,469,851 B2 | 10/2016 | Harper et al. |
| 9,572,870 B2 | 2/2017 | Kakkis |
| 9,670,507 B2 | 6/2017 | Xiao et al. |
| 9,770,410 B2 | 9/2017 | Salamat-Miller et al. |
| 9,814,764 B2 | 11/2017 | Cancino |
| 9,821,114 B2 | 11/2017 | Cabrera et al. |
| 9,827,295 B2 | 11/2017 | McIvor et al. |
| 10,035,825 B2 | 7/2018 | Gao et al. |
| 10,370,432 B2 | 8/2019 | Esteves et al. |
| 10,912,804 B2 | 2/2021 | Byrne et al. |
| 11,253,612 B2 * | 2/2022 | Hinderer ............. C12N 15/86 |
| 2001/0043915 A1 | 11/2001 | Frey |
| 2002/0014242 A1 | 2/2002 | Scaria |
| 2002/0072498 A1 | 6/2002 | Frey |
| 2002/0082215 A1 | 6/2002 | Frey |
| 2002/0110551 A1 | 8/2002 | Chen |
| 2002/0169102 A1 | 11/2002 | Frey |
| 2003/0072793 A1 | 4/2003 | Frey et al. |
| 2003/0165434 A1 | 9/2003 | Reinhard et al. |
| 2003/0215398 A1 | 11/2003 | Frey |
| 2003/0219414 A1 | 11/2003 | Podsakoff et al. |
| 2004/0009906 A1 | 1/2004 | Kakkis et al. |
| 2004/0204379 A1 | 10/2004 | Cheng et al. |
| 2005/0026823 A1 | 2/2005 | Zankel et al. |
| 2005/0042227 A1 | 2/2005 | Zankel et al. |
| 2005/0048047 A1 | 3/2005 | Kakkis |
| 2005/0256059 A1 | 11/2005 | Benowitz |
| 2006/0057114 A1 | 3/2006 | Whitley et al. |
| 2006/0188496 A1 | 8/2006 | Bentz et al. |
| 2006/0216317 A1 | 9/2006 | Reinhard et al. |
| 2007/0036760 A1 | 2/2007 | Wilson et al. |
| 2007/0092500 A1 | 4/2007 | Frey et al. |
| 2008/0305077 A1 | 12/2008 | Frey et al. |
| 2009/0068155 A1 | 3/2009 | Frey et al. |
| 2009/0117156 A1 | 5/2009 | Passini et al. |
| 2009/0123451 A1 | 5/2009 | Dodge et al. |
| 2009/0136505 A1 | 5/2009 | Bentz et al. |
| 2009/0197338 A1 | 8/2009 | Vandenberghe et al. |
| 2009/0264506 A1 | 10/2009 | Reinhard et al. |
| 2010/0047174 A1 | 2/2010 | Kay et al. |
| 2010/0061959 A1 | 3/2010 | Frey et al. |
| 2010/0068183 A1 | 3/2010 | Whitley et al. |
| 2010/0173979 A1 | 7/2010 | Dodge et al. |
| 2010/0199366 A1 | 8/2010 | Cooper et al. |
| 2010/0221225 A1 | 9/2010 | Byrne et al. |
| 2011/0070220 A1 | 3/2011 | Koeberl |
| 2011/0070241 A1 | 3/2011 | Yang |
| 2011/0104120 A1 | 5/2011 | Xiao et al. |
| 2011/0182875 A1 | 7/2011 | Fang et al. |
| 2011/0288160 A1 | 11/2011 | During et al. |
| 2012/0009268 A1 | 1/2012 | Asokan et al. |
| 2012/0177605 A1 | 7/2012 | Kaspar et al. |
| 2012/0288489 A1 | 11/2012 | Wolf et al. |
| 2012/0315263 A1 | 12/2012 | Olmstead |
| 2012/0322861 A1 | 12/2012 | Byrne et al. |
| 2013/0039888 A1 | 2/2013 | McCarty et al. |
| 2013/0045186 A1 | 2/2013 | Gao et al. |
| 2013/0095092 A1 | 4/2013 | Quinn et al. |
| 2013/0096488 A1 | 4/2013 | Frey |
| 2013/0122591 A1 | 5/2013 | Cost et al. |
| 2013/0195801 A1 | 8/2013 | Gao et al. |
| 2013/0211380 A1 | 8/2013 | Cabrera Aquino et al. |
| 2013/0225666 A1 | 8/2013 | Kaspar et al. |
| 2013/0323207 A1 | 12/2013 | McCarty et al. |
| 2014/0045925 A1 | 2/2014 | Harper et al. |
| 2014/0056854 A1 | 2/2014 | Asokan et al. |
| 2014/0088179 A1 | 3/2014 | Davidson |
| 2014/0161788 A1 | 6/2014 | Aoyagi-Scharber et al. |
| 2014/0171491 A1 | 6/2014 | Wolf et al. |
| 2014/0219974 A1 | 8/2014 | Pan |
| 2014/0234274 A1 | 8/2014 | Xiao et al. |
| 2014/0322169 A1 | 10/2014 | Harper et al. |
| 2014/0335054 A1 | 11/2014 | Gao et al. |
| 2015/0066056 A1 | 3/2015 | Cabrera Aquino et al. |
| 2015/0079038 A1 | 3/2015 | Deverman et al. |
| 2015/0011820 A1 | 4/2015 | Xiao et al. |
| 2015/0150799 A1 | 6/2015 | Kakkis |
| 2015/0182637 A1 | 7/2015 | Barkats et al. |
| 2015/0196671 A1 | 7/2015 | Byrne et al. |
| 2015/0210771 A1 | 7/2015 | Crystal et al. |
| 2015/0252384 A1 | 9/2015 | Kaspar et al. |
| 2015/0315612 A1 | 11/2015 | Wilson et al. |
| 2016/0038613 A1 | 2/2016 | Kaspar et al. |
| 2016/0076028 A1 | 3/2016 | Flanigan et al. |
| 2016/0120960 A1 | 5/2016 | McIvor et al. |
| 2016/0166709 A1 | 6/2016 | Davidson et al. |
| 2016/0175406 A1 | 6/2016 | McCarty et al. |
| 2016/0208006 A1 | 7/2016 | Pardridge et al. |
| 2016/0243260 A1 | 8/2016 | Blits |
| 2016/0272976 A1 | 9/2016 | Kaspar et al. |
| 2016/0304904 A1 | 10/2016 | Xiao et al. |
| 2016/0310548 A1 | 10/2016 | Harper et al. |
| 2016/0369297 A1 | 12/2016 | Byrne et al. |
| 2017/0028002 A1 | 2/2017 | Byrne et al. |
| 2017/0029849 A1 | 2/2017 | Harper et al. |
| 2017/0049887 A1 | 2/2017 | Byrne et al. |
| 2017/0266483 A1 | 9/2017 | Dalebout et al. |
| 2018/0036388 A1 | 2/2018 | McIvor et al. |
| 2018/0051299 A9 | 2/2018 | Byrne et al. |
| 2018/0071373 A1 | 3/2018 | McIvor et al. |
| 2018/0099030 A1 | 4/2018 | McIvor et al. |
| 2018/0245054 A1 | 8/2018 | Kawaoka et al. |
| 2018/0264090 A1 | 9/2018 | McIvor et al. |
| 2018/0271955 A1 | 9/2018 | McIvor et al. |
| 2018/0271956 A1 | 9/2018 | McIvor et al. |
| 2018/0271957 A1 | 9/2018 | McIvor et al. |
| 2018/0289839 A1 | 10/2018 | McIvor et al. |
| 2019/0038772 A1 | 2/2019 | Hinderer |
| 2019/0269799 A1 | 9/2019 | Laoharawee et al. |
| 2019/0298812 A1 | 10/2019 | Mcivor et al. |
| 2021/0085759 A1 | 3/2021 | Mcivor et al. |
| 2021/0085760 A1 | 3/2021 | Mcivor et al. |
| 2021/0346473 A1 | 11/2021 | McIvor et al. |
| 2021/0369871 A1 | 12/2021 | McIvor et al. |
| 2022/0096659 A1 | 3/2022 | Laoharawee et al. |
| 2022/0125843 A1 | 4/2022 | Moriarity et al. |
| 2022/0125949 A1 | 4/2022 | Hinderer et al. |

FOREIGN PATENT DOCUMENTS

| | | |
|---|---|---|
| EP | 3101125 | 12/2016 |
| JP | 2016-523835 T | 8/2016 |
| JP | 2018-517414 T | 7/2018 |
| KR | 10-2016-0010526 | 1/2016 |
| WO | WO-1991/007947 A1 | 6/1991 |
| WO | WO 1993/010244 | 5/1993 |
| WO | WO-1999/006562 A1 | 2/1999 |
| WO | WO-2000/033813 A1 | 6/2000 |
| WO | WO-2000/033814 A2 | 6/2000 |
| WO | WO-2001/041782 A2 | 6/2001 |
| WO | WO 2002/002597 | 1/2002 |

(56) References Cited

FOREIGN PATENT DOCUMENTS

| | | |
|---|---|---|
| WO | WO 2002/004616 | 1/2002 |
| WO | WO-2002/032449 A2 | 4/2002 |
| WO | WO-2002/086105 A1 | 10/2002 |
| WO | WO-2003/042397 | 5/2003 |
| WO | WO-2003/072056 A2 | 9/2003 |
| WO | WO 2004/028468 A2 | 4/2004 |
| WO | WO 2004/074450 A2 | 9/2004 |
| WO | WO 2004/099423 A1 | 11/2004 |
| WO | WO-2005/033321 | 4/2005 |
| WO | WO-2006/110689 | 10/2006 |
| WO | WO 2007/095056 A2 | 8/2007 |
| WO | WO-2008/049588 A1 | 5/2008 |
| WO | WO-2008/103993 A2 | 8/2008 |
| WO | WO-2009/043936 A1 | 4/2009 |
| WO | WO 2009/097129 A1 | 8/2009 |
| WO | WO-2011/126808 | 10/2011 |
| WO | WO-2011/133890 A1 | 10/2011 |
| WO | WO 2011/154520 A1 | 12/2011 |
| WO | WO-2011/163649 A2 | 12/2011 |
| WO | WO-2012/112832 | 8/2012 |
| WO | WO-2014/022582 A1 | 2/2014 |
| WO | WO-2014/151341 | 9/2014 |
| WO | WO-2014/178863 A1 | 11/2014 |
| WO | WO-2014/186579 | 11/2014 |
| WO | WO 2014/186579 | 11/2014 |
| WO | WO-2015/013148 A2 | 1/2015 |
| WO | WO 2016/100575 A1 | 6/2016 |
| WO | WO-2016/187017 A1 | 11/2016 |
| WO | WO-2016/193431 | 12/2016 |
| WO | WO 2017/011519 | 1/2017 |
| WO | WO 2017/123757 A1 | 7/2017 |
| WO | WO 2017/136202 A1 | 8/2017 |
| WO | WO-2017/136202 A1 | 8/2017 |
| WO | WO 2017/136500 | 8/2017 |
| WO | WO 2018/093925 A1 | 5/2018 |
| WO | WO-2018/093925 A1 | 5/2018 |
| WO | WO 2018/209205 A1 | 11/2018 |
| WO | WO 2019/010335 A1 | 1/2019 |
| WO | WO 2019/060662 | 3/2019 |
| WO | WO 2018/144441 | 8/2019 |
| WO | WO 2020/018665 | 1/2020 |
| WO | WO 2021/150570 | 7/2021 |
| WO | WO 2021/70082 A1 | 8/2022 |

OTHER PUBLICATIONS

Belting et al., Proteoglycan involvement in polyamine uptake, Biochemical Journal, vol. 338:317-323, 1999.
Bucher et al., Intracisternal delivery of AAV9 results in oligodendrocyte and motor neuron transduction in the whole central nervous system of cats, Gene Therapy, vol. 21:522-528, 2014.
Cai et al., Arginase I and Polyamines Act Downstream from Cyclic AMP in Overcoming Inhibition of Exonal Growth MAG and Myelin In Vitro, Neuron, vol. 35:711-719, Aug. 2002.
Calcedo, R., et al., Worldwide Epidemiology of Neutralizing Antibodies to Adeno-Associated Viruses. Journal of Infectious Diseases, vol. 199(3):381-390, Feb. 2009.
Cardone et al., Correction of Hunter syndrome in the MPSII mouse model by AAV2/8-mediated gene delivery, Human Molecular Genetics, vol. 15(7):1225-1236, Jan. 2006.
Chen et al., Biodistribution of AAV8 Vectors Expressing Human Low-Density Lipoprotein Receptor in a Mouse Model of Homozygous Familial Hypercholesterolemia, Hum Gene Ther Clin Dev, vol. 24(4):154-160, Dec. 2013.
Chen et al., Expression of rat bone sialoprotein promoter in transgenic mice, J. Bone Miner. Res., vol. 11(5):654-664, May 1996.
Dean et al, Detection of Mucopolysaccharidosis Type II by Measurement of Iduronate-2-Sulfatase in Dried Blood Spots and Plasma Samples, Clinical Chemistry, vol. 52(4):643-649, Apr. 2006.
Deng, et al, Increased synthesis of spermidine as a result of upregulation of arginase I promotes axonal regeneration in culture and in vivo, The Journal of Neuroscience, , vol. 29(30):9545-9552, Jul. 2009.

Devereux et al., A comprehensive set of sequence analysis programs for the VAX, Nucleic Acids Res., vol. 12(1 Pt 1):387-395, Jan. 1984.
Ding et al., Modulations of glypican-1 heparan sulfate structure by inhibition of endogenous polyamine synthesis. Mapping of sperminebinding sites and heparanase, heparin lyase, and nitric oxide/nitrite cleavage sites, The Journal of Biological Chemistry, vol. 276(50):46779-46791, Dec. 2001 (ePub Sep. 2001).
Federici et al., Robust spinal motor neuron transduction following intrathecal delivery of AAV9 in pigs, Gene Therapy, vol. 19(8):852-859, Aug. 2012 (ePub Sep. 2011).
Fraldi et al., SUMF1 enhances sulfatase activities in vivo in five sulfatase deficiencies, Biochemical J, vol. 403:305-312, Apr. 2007.
Gao et al., Activated CREB is sufficient to overcome inhibitors in myelin and promote spinal axon regeneration in vivo, Neuron, vol. 44(4):609-621, Nov. 2004.
Gao et al., Adeno-associated viruses undergo substantial evolution in primates during natural infections, Proc. Natl. Acad. Sci. U.S.A., vol. 100(10):6081-6086, May 2003 (ePub Apr. 2003).
GenBank Accession No. AAS99264, capsid protein VP1 [Adeno-associated virus 9], Jun. 2004.
GenBank Accession No. AB448737.1, *Homo sapiens* SUMF1 mRNA for sulfatase modifying factor 1, complete cds, Aug. 2011.
GenBank Accession No. K03104.1, Human cytomegalovirus major immediate-early gene, enhancer, Aug. 1993.
GenBank Accession No. NC001401, Adeno-associated virus-2, complete genome, Aug. 2018.
GenBank Accession No. NP_000193.1, iduronate 2-sulfatase isoform a preproprotein [*Homo sapiens*], Dec. 2018.
GenBank Accession No. NP_877437.2, formylglycine-generating enzyme isoform 1 precursor [*Homo sapiens*], Jan. 2019.
GenBank Accession No. P22304.1, RecName: Full=Iduronate 2-sulfatase, Jan. 2019.
GenBank Accession No. X00182.1, Gallus gallus cytoplasmic beta-actin gene, Nov. 2006.
Goujon et al., A new bioinformatics analysis tools framework at EMBL-EBI, Nucleic acids research, vol. 38(S2) (2010):W695-W699, Jul. 2010 (ePub May 2010).
Gray et al., Global CNS gene delivery and evasion of anti-AAV-neutralizing antibodies by intrathecal AAV administration in non-human primates, Gene Therapy, vol. 20:450-459, Apr. 2013 (ePub Jan. 2013).
Gray et al., Optimizing promoters for recombinant adeno-associated virus-mediated gene expression in the peripheral and central nervous system using self-complementary vectors, Hu Gene Ther, vol. 22(9):1143-1153, Sep. 2011 (ePub Jun. 2011).
Grimm et al., Titration of AAV-2 particles via a novel capsid ELISA: packaging of genomes can limit production of recombinant AAV-2, Gene Therapy, vol. 6:1322-1330, Jul. 1999.
Gurda et al., Evaluation of AAV-mediated Gene Therapy for Central Nervous System Disease in Canine Mucopolysaccharidosis VII, Molecular Therapy, vol. 24(2):206-216, Feb. 2016 (ePub Oct. 2015).
Hall, BioEdit: a user-friendly biological sequence alignment editor and analysis program for Windows 95/98/NT., Nucl. Acids. Symp. Ser., vol. 41:95-98, Jan. 1999.
Hansal et al., Cutting edge: Induction of Antigen-Specific Hyporesponsiveness by Transplantation of Hemopoietic Cells Containing an MHC Class I Transgene Regulated by a Lymphocyte-Specific Promoter, J. Immunol., vol. 161:1063-1068, Jan. 1998.
Haurigot et al., Whole body correction of mucopolysaccharidosis IIIA by intracerebrospinal fluid gene therapy, Journal of Clinical Investigation, vol. 123(8):3254-3271, Aug. 2013 (ePub Jul. 2013).
Hinderer et al., Delivery of an Adeno-Associated Virus Vector into Cerebrospinal Fluid Attenuates Central Nervous System Disease in Mucopolysaccharidosis Type II Mice, Human Gene Therapy, vol. 27(11):906-915, Nov. 2016.
Hinderer et al., Intrathecal gene therapy corrects CNS pathology in a feline model of mucopolysaccharidosis, I. Molecular Therapy: The Journal of the American Society of Gene Therapy, vol. 22:2018-2027, Dec. 2014, (ePub Jul. 2014).
Hinderer et al., Neonatal Systemic AAV Induces Tolerance to CNS Gene Therapy in MPS I Dogs and Nonhuman Primates, Molecular Therapy, vol. 23(8):1298-1307, Aug. 2015.

(56) References Cited

OTHER PUBLICATIONS

Hinderer et al., Neonatal tolerance induction enables accurate evaluation of gene therapy for MPS I in a canine model, Molecular Genetics and Metabolism, vol. 119(1-2):124-130, Sep. 2016 (ePub Jun. 2016).
Hinderer et al., Widespread gene transfer in the central nervous system of cynomolgus macaques following delivery of AAV9 into the cisterna magna, Mol Ther-Methods & Clin Dev, vol. 1:14051, Dec. 2014.
Hongsheng et al., Pharmacokinetics and Bioavailability of a Therapeutic Enzyme (Idursulfase) in Cynomolgus Monkeys after Intrathecal and Intravenous Administration, PLOS One, vol. 10(4):e0122453, Apr. 2015.
Kalb, Regulation of motor neuron dendrite growth by NMDA receptor activation, Development, vol. 120(11):3063-3071, Nov. 1994.
Lock et al, Rapid, simple, and versatile manufacturing of recombinant adeno-associated viral vectors at scale, Human Gene Therapy, vol. 21(10):1259-1271, Oct. 2010.
Lock et al., Absolute determination of single-stranded and self-complementary adeno-associated viral vector genome titers by droplet digital PCR, Hu Gene Therapy Methods, vol. 25(2):115-25, Apr. 2014 (Epub Feb. 2014).
McCarty et al., Self-complementary recombinant adeno-associated virus (scAAV) vectors promote efficient transduction independently of DNA synthesis, Gene Therapy, vol. 8(16):1248-1254, Aug. 2001.
Meijering et al., Design and validation of a tool for neurite tracing and analysis in fluorescence microscopy images, Cytometry, Part A: The Journal of the International Society for Analytical Cytology, vol. 58:167-176, Apr. 2004.
Merrifield, Solid Phase Peptide Synthesis. I. The Synthesis of a Tetrapeptide, J. Am. Chem. Soc., vol. 85(14):2149-2154, Jul. 1962.
Meyer et al., Improving Single Injection CSF Delivery of AAV9-mediated Gene Therapy for SMA: A Dose-response Study in Mice and Nonhuman Primates, Molecular Therapy, vol. 23(3):477-487, Mar. 2015 (ePub Dec. 2014).
Miyatake et al., Transcriptional Targeting of Herpes Simplex Virus for Cell-Specific Replication, J. Virol., vol. 71(7):5124-32, Jul. 1997.
Motas et al., CNS-directed gene therapy for the treatment of neurologic and somatic mucopolysaccharidosis type II (Hunter syndrome), JCI Insight, vol. 1(9), Jun. 2016.
Oliveira et al., Post-training reversible inactivation of the hippocampus enhances novel object recognition memory, Learning & Memory, vol. 17(3):155-160, Feb. 2010.
Passini et al., Translational fidelity of intrathecal delivery of self-complementary AAV9-survival motor neuron 1 for spinal muscular atrophy, Hu Gene Therapy, vol. 25(7):619-630, Jul. 2014 (ePub Apr. 2014).
Patel el al., An open-source toolbox for automated phenotyping of mice in behavioral tasks, Front Behav Neurosci., vol. 8:349, Oct. 2014.
Pearson et al., Improved tools for biological sequence comparison, Proc. Natl. Acad. Sci. USA, vol. 85:2444-2448, Apr. 1988.
Piccioli et al., Neuroantibodies: ectopic expression of a recombinant anti-substance P antibody in the central nervous system of transgenic mice, Neuron, vol. 15(2):373-84, Aug. 1995.
Piccioli et al., Neuroantibodies: molecular cloning of a monoclonal antibody against substance P for expression in the central nervous system, Proc. Natl. Acad. Sci. USA, vol. 88(13):5611-5, Jul. 1991.
Polito et al., IDS Crossing of the Blood-Brain Barrier Corrects CNS Defects in MPSII Mice, American Journal of Human Genetics, vol. 85(2):296-301, Aug. 2009.
Rome et al., Direct demonstration of binding of a lysosomal enzyme, alpha-L-iduronidase, to receptors on cultured fibroblasts, Proc. Natl. Acad. Sci. USA, vol. 76(5):2331-2334, May 1979.
Sandig et al., HBV-derived promoters direct liver-specific expression of an adenovirally transduced LDL receptor gene, Gene Ther, vol. 3(11):1002-9, Nov. 1996.

Shull et al., Morphologic and biochemical studies of canine mucopolysaccharidosis I, The American Journal of Pathology, vol. 114(3):487-495, Mar. 1984.
Sievers et al., Fast, scalable generation of high-quality protein multiple sequence alignments using Clustal Omega, Molecular systems biology, vol. 7:539, Oct. 2011.
Sommer et al., Quantification of adeno-associated virus particles and empty capsids by optical density measurement, Molec. Ther. vol. 7(1):122-128, Jan. 2003.
Wang et al., Impact of pre-existing immunity on gene transfer to nonhuman primate liver with adeno-associated virus 8 vectors, Human gene therapy, vol. 22(11):1389-1401, Nov. 2011.
Watson et al., Intrathecal administration of lysomal storage in the brains of MPS I mice, Gene Therapy, vol. 13(11):917-925, Jun. 2006.
Welch et al., Single chain fragment anti-heparan sulfate antibody targets the polyamine transport system and attenuates polyamine-dependent cell proliferation, International journal of oncology, vol. 32(4):749-756, Apr. 2008.
Wheeler et al., Cerebrospinal Fluid Analysis, Aug. 2015, retrieved from http://emedicine.medscape.com/article/2093316-overview.
Wilson et al., Hunter syndrome: isolation of an iduronate-2-sulfatase cDNA clone and analysis of patient DNA, Proc. Natl. Acad. Sci. U.S.A., vol. 87(21):8531-8535, Nov. 1990.
Wobus et al., Monoclonal antibodies against the adeno-associated virus type 2 (AAV-2) capsid: epitope mapping and identification of capsid domains involved in AAV-2-cell interaction and neutralization of AAV-2 infection, J. Virol., vol. 74(19):9281-9293, Oct. 2000.
Wolf et al., Gene therapy for neurologic manifestations of mucopolysaccharidoses, Expert Opinion on Drug Delivery, vol. 12(2):283-296, Dec. 2014.
Wright et al., Manufacturing and characterizing AAV-based vectors for use in clinical studies, Gene Therapy, vol. 15(11):840-848, Apr. 2008.
Xia et al., MetaboAnalyst 2.0—a comprehensive server for metabolomic data analysis, Nucleic Acids Research, vol. 40:W127-W133, May 2012.
Xia et al., MetaboAnalyst 3.0—making metabolomics more meaningful, Nucleic Acids Research, vol. 43(W1):W251-7, Apr. 2015.
Xia et al., MetaboAnalyst: a web server for metabolomic data analysis and interpretation, Nucleic Acids Research, vol. 37:W652-W660, Jul. 2009.
Ciron et al., Gene therapy of the brain in the dog model of Hurler's syndrome, Annals of Neurology, vol. 60(2):204-213, May 2006.
De La Monte et al, GAP-43 gene expression during development: persistence in a distinctive set of neurons in the mature central nervous system, Developmental Brain Research, vol. 46:161-168, Apr. 1989.
Dirren at al., Intracerebroventricular injection of adeno-associated virus 6 and 9 vectors for cell type-specific transgene expression in the spinal cord, Hum. Gene. Therapy, vol. 25(2):109-120, Feb. 2014.
Georgiev et al., A critical importance of polyamine site in NMDA receptors for neurite outgrowth and fasciculation at early stages of P19 neuronal differentiation, Experimental Cell Research, vol. 314(14):2603-2617, Jun. 2008.
Garica et al., The characterization of a murine model of mucopolysaccharidosis II (Hunter syndrome), J Inherit Metab Dis, vol. 30(6):924-34, Nov. 2007 (ePub Sep. 2007).
Zhong et al., Expression of mRNAs encoding subunits of the NMDA receptor in developing rat brain, Journal of neurochemistry, vol. 64:531-539, Feb. 1995.
Stein et al., The osteocalcin gene: a model for multiple parameters of skeletal-specific transcriptional control, Mol. Biol. Rep., vol. 24:185-196, Aug. 1997.
Stewart and Young, Solid Phase Peptide Synthesis, pp. 27-62, Freeman, San Francisco, Jan. 1969.
Vactor et al., Heparan sulfate proteoglycans and the emergence of neuronal connectivity, Current opinion in neurobiology, vol. 16(1):40-51, Feb. 2006 (ePub Jan. 2006).
Volpi, Purification of heparin, dermatan sulfate and chondroitin sulfate from mixtures by sequential precipitation with various

(56) References Cited

OTHER PUBLICATIONS organic solvents, Journal of chromatography. B, Biomedical Applications, vol. 685(1):27-34, Oct. 1996.

Snyder et al., Comparison of adeno-associated viral vector serotypes for spinal cord and motor neuron gene delivery, Hum. Gene Ther, vol. 22(9):1129-1135, Sep. 2011.

Schreiber et al., Polyamines increase in sympathetic neurons and non-neuronal cells after axotomy and enhance neurite outgrowth in nerve growth factor-primed PC12 cells, Neuroscience, vol. 128(4):741-749, 2004.

Sanchez-Lopez et al., Underivatives polyamine analysis is plant samples by ion pair liquid chromatography coupled with electrospray tandem mass spectrometry, Plant Physiology and Biochemistry, vol. 47(7):592-598, Jul. 2009 (ePub Feb. 2009).

Reiselbach et al., Subarachnoid distribution of drugs after lumbar injection, New England Journal of Medicine, vol. 267(25):1273-1278, Dec. 1962.

Oussoren et al., Residual α-L-iduronidase activity in fibroblasts of mild to severe Mucopolysaccharidosis type I patients, Mol Genet Metab., vol. 109(4):377-381, Aug. 2013 (Epub Jun. 2013).

Muenzer et al., Enzyme replacement therapy in mucopolysaccharidosis type II (Hunter syndrome): a preliminary report, Acta Paediatr Suppl, vol. 91(s439):98-99, Jan. 2002.

Menon et al., Architecture of the canine IDUA gene and mutation underlying canine mucopolysaccharidosis I, Genomics, vol. 14(3):763-768, Nov. 1992.

Lerma, Spermine regulates N-methyl-D-aspartate receptor desensitization, Neuron, vol. 8(2):343-352, Feb. 1992.

Kakkis et al., Overexpression of the human lysosomal enzyme alpha-L-iduronidase in Chinese hamster ovary cells, Protein Expression Purif., vol. 5(3):225-232, Jun. 1994.

Hocquemiller et al., GAP43 overexpression and enhanced neurite outgrowth in mucopolysaccharidosis type IIIB cortical neuron cultures, Journal of Neuroscience Research, vol. 88(1):202-213, Aug. 2009.

Higuchi et al., Enzyme replacement therapy (ERT) procedure for mucopolysaccharidosis type II (MPS II) by intraventricular administration (IVA) in murine MPS II, Mol Genet and Metabolism, vol. 107(1-2):122-128, Sep. 2012(ePub May 2012).

Hakkinen et al., Analysis of underivatized polyamines by reversed phase liquid chromatography with electrospray tandem mass spectrometry, J Pharm Biomec Analysis, vol. 45(4):625-634, Nov. 2007 (ePub Sep. 2007).

International Search Report and Written Opinion issued on International Patent Application No. PCT/US2017/027770, dated Sep. 13, 2017.

International Patent Application No. PCT/US2016/065970, filed Dec. 9, 2016.

International Patent Application No. PCT/US2016/065974, filed Dec. 9, 2016.

International Patent Application No. PCT/US2016/065976, filed Dec. 9, 2016.

International Patent Application No. PCT/US2016/066013, filed Dec. 9, 2016.

U.S. Appl. No. 62/323,194, filed Apr. 15, 2016.
U.S. Appl. No. 62/330,938, filed May 3, 2016.
U.S. Appl. No. 62/226,357, filed Dec. 11, 2015.
U.S. Appl. No. 62/266,351, filed Dec. 11, 2015.
U.S. Appl. No. 62/266,341, filed Dec. 11, 2015.
U.S. Appl. No. 62/266,347, filed Dec. 11, 2015.
U.S. Appl. No. 62/322,055, filed Apr. 13, 2016.
U.S. Appl. No. 62/322,083, filed Apr. 13, 2016.
U.S. Appl. No. 62/322,098, filed Apr. 13, 2016.
U.S. Appl. No. 62/337,163, filed May 16, 2016.
U.S. Appl. No. 62/367,780, filed Jul. 28, 2016.
U.S. Appl. No. 62/452,494, filed Jan. 31, 2017.
U.S. Appl. No. 62/322,071, filed Apr. 13, 2016.
International Patent Application No. PCT/US2018/052129, filed Sep. 21, 2018.

Communication issued in Corresponding European Patent Application No. 17734162.5, dated Jun. 24, 2020.

Hinderer, PCT/US2018/052129, Sep. 21, 2018, WO 2019/060662, Mar. 28, 2019.

Hinderer, U.S. Appl. No. 16/075,056, filed Feb. 2, 2017, 2019/0038772, Feb. 7, 2019.

Ohlfest et al., "Phenotypic correction and long-term expression of factor VIII in hemophilic mice by immunotolerization and nonviral gene transfer using the Sleeping Beauty transposon system," Blood, vol. 105(7):2691-98, Apr. 2005.

Shin et al., "Recombinant Adeno-Associated Viral Vector Production and Purification," Myogenesis Methods in Molecular Biology (Methods and Protocols), vol. 798, Humana Press: Totowa, NJ, pp. 267-284, Jan. 2012.

Furuhama et al., "Optimum Properties of Injectable Test Solutions for Intrathecal Administration to Conscious Rats," Journal of Veterinary Medicine and Science, vol. 59(12):1103-071, Jun. 1997.

Mingozzi et al., "High AAV vector purity results in serotype and tissue-independent enhancement of transduction efficiency," Gene Therapy, vol. 17:503-510, Dec. 2009.

Doerfler et al., "Simultaneous Delivery of Dual AAV9 Vectors Induced Immune Tolerance and Correction of Pompe Disease Pathology," vol. 23: Supplement 1, S146, May 2015.

First Office Action issued on Israeli Patent Application No. 262211, dated Feb. 24, 2022.

Non-final Office Action issued on U.S. Appl. No. 16/093,413, dated Jul. 26, 2021.

Office Action issued on Japanese Patent Application No. 2018-554348, dated Jun. 2, 2021.

Office Action issued on Korean Patent Application No. 10-2018-7033163, dated Feb. 16, 2022.

Laoharawee K., et al., AAV9 Mediated Correction of Iduronate-2-Sulfatase Deficiency in the Central Nervous System of Mucopolysaccharidosis Type II Mice, Molecular Therapy, vol. 23(S1):S146 (a369), May 2015, Abstract.

Laoharawee, K., et al., Prevention of Neurocognitive Deficiency in Mucopolysaccharidosis Type II Mice by Central Nervous System-Directed, AAV9-Mediated Iduronate Sulfatase Gene Transfer, Hum Gene Ther, Aug. 2017, 28(8):626-638, Epub May 5, 2017.

Laoharawee, K., et al., Dose-Dependent Prevention of Metabolic and Neurologic Disease in Murine MPS II by ZFN-Mediated In Vivo Genome Editing, Mol Ther, Apr. 4, 2018, 26(4):1127-1136, Epub Mar. 10, 2018.

Braun, S. E., et al., Metabolic correction and cross-correction of mucopolysaccharidosis type II (Hunter syndrome) by retroviral-mediated gene transfer and expression of human iduronate-2-sulfatase, Proc Natl Acad Sci USA, Dec. 15, 1993, 90(24):11830-4.

Hordeaux, J., et al., Toxicology Study of Intra-Cisterna Magna Adeno-Associated Virus 9 Expressing Iduronate-2-Sulfatase in Rhesus Macaques, Mol Ther Methods Clin Dev, Jul. 14, 2018, 10:68-78, eCollection Sep. 21, 2018.

Urabe, et al., (2006) "Removal of Empty Capsids from Type 1 Adeno-Associated Virus Vector Stocks by Anion-Exchange Chromatography Potentiates Transgene Expression", Molecular Therapy, 13(4):823-28 (Year: 2006).

Office Action dated Apr. 25, 2022 issued in corresponding Japan Patent Application No. 2018-554348, with unofficial translation provided by local Agent.

UniProtKB Accession No. P22304, Aug. 1, 1991.

Okada et al., Scalable Purification of Adeno-associated Virus Serotype 1 (AAV1) and AAV8 Vectors, Using Dual Ion-Exchange Adsorptive Membranes, Human Gene Therapy, vol. 20(9)1013-1021, Sep. 2009.

Qu et al., Separation of adeno-associated virus type 2 empty particles from genome containing vectors by anion-exchange column chromatography, Journal of Virological Methods, vol. 140(1-2):183-192, Feb. 2007.

Swain et al., Adeno-associated virus serotypes 9 and rh10 mediate strong neuronal transduction of the dog brain, Gene Therapy, vol. 21(1):28-36, Jan. 2014.

Laoharawee, K., et al., Non-invasive intravenous administration of AAV9 transducing iduronate sulfatase leads to global metabolic

(56) References Cited

OTHER PUBLICATIONS correction and prevention of neurologic deficits in a mouse model of Hunter syndrome, Mol. Genet. Metab. Rep., 34(2023):100956, Jan. 20, 2023.
Giugliani, R., et al., RGX-121 Gene Therapy for the Treatment of Severe Mucopolysaccharidosis Type II (MPS II): Interim Analysis of Data from the First in Human Study. Gene and Cell Therapy Trials in Progress, 30(4S1): 27, abstract 52, Apr. 2022.
Nevoret, M., RGX-121 Gene Therapy for the Treatment of Severe Mucopolysaccharidosis Type II (MPS II): Interim Results of Ongoing First in Human Trial, Feb. 11, 2021, presentation at Annual WORLDSymposium™ (http://www.regenxbio.com/wp-content/uploads/2021/02/NEVORET_RGX-121-101 Presentation World 2021 vF.pdf).
Giugliani, R., RGX-121 Gene Therapy for the Treatment of Severe Mucopolysaccharidosis Type II: Interim Analysis of the First in Human Study, Feb. 9, 2022, presentation at Annual WORLDSymposium™ (http://www.regenxbio.com/wp-content/uploads/2022/02/FINAL-GiuglianiWORLD22_121_101interim.pdf).
Giugliani, R., RGX-121 Gene Therapy for the Treatment of Severe Mucopolysaccharidosis Type II: CAMPSIITE™ Phase I/II/III: A Clinical Study Update, Aug. 31, 2022, presentation at Society for the Study of Inborn Errors of Metabolism (SSIEM) Annual Symposium, Freiburg, Germany (http://www.regenxbio.com/wp-content/uploads/2022/08/SSIEM-RGX-121-101-Final_.pdf).
Regenxbio Presents Additional Positive Interim Data From the Phase I/II/III CAMPSIITE™ Trial of RGX-121 for the Treatment of MPS II (Hunter Syndrome) at the Society for the Study of Inborn Errors of Metabolism (SSIEM) Annual Symposium, Aug. 31, 2022, (https://regenxbio.gcs-web.com/news-releases/news-release-details/regenxbio-presents-additional-positive-interim-data-phase-iiiiii).
Regenxbio Presents Additional Positive Interim Data From Phase I/II Trial of RGX-121 for the Treatment of MPS II (Hunter Syndrome) at American Society of Gene and Cell Therapy's 24th Annual Meeting, May 14, 2021 (https://regenxbio.gcs-web.com/news-releases/news-release-details/regenxbio-presents-additional-positive-interim-data-phase-iii-0).
ASGCT.org, "ASGCT—American Society of Gene & Cell Therapy: 16th Annual Meeting 2013, Abstracts," Apr. 2013 pp. 1-2, retrieved from https://web.archive.org/web/20151026121322/http://www.asgct.org/meetings-educational-programs/asgct-annual-meetings/archived-annual-meetings/2013-annual-meeting/attendee/abstracts.
REGENXBIO Presents Additional Positive Interim Data from Phase I/II Trial of RGX-121 for the Treatment of MPS II (Hunter Syndrome) at 18th Annual WORLDSymposium™ 2022, Feb. 9, 2022 (https://www.prnewswire.com/news-releases/regenxbio-presents-additional-positive-interim-data-from-phase-iii-trial-of-rgx-121-for-the-treatment-of-mps-ii-hunter-syndrome-at-18th-annual-worldsymposium-2022-301478792.html).
REGENXBIO Announces Intention to File a Biologics License Application Using the Accelerated Approval Pathway for RGX-121, an AAV Therapeutic for the Treatment of MPS II, Aug. 3, 2022 (https://www.prnewswire.com/news-releases/regenxbio-announces-intention-to-file-a-biologics-license-application-using-the-accelerated-approval-pathway-for-rgx-121-an-aav-therapeutic-for-the-treatment-of-mps-ii-301598783.html).
Kanut et al., "Prevention of Neurocognitive Deficiency in Mucopolysaccharidosis Type II Mice by Central Nervous System-Directed, AAV9-Mediated Iduronate Sulfatase Gene Transfer," Human Gene Therapy, vol. 28(8): 626-638, Aug. 2017.
Sandra et al., "CNS—directed gene therapy for the treatment of neurologic and somatic mucopolysaccharidosis type Tl Hunter syndrome," JCI Insight, vol. 1(9), Jun. 2016.
Belur et al., "AAV Vector-Mediated lduronidase Gene Delivery in a Murine Model of Mucopolysaccharidosis Type I: Comparing Different Routes of Delivery to the CNS," Abstracts for the ASGCT 16th Annual Meeting, Salt Lake City, Utah, p. S140, May 2013, retrieved on Dec. 2, 2016 from http://www.nature.comjmtjjournaljv21/n1s/pdf/mt201382a.pdf.

Byrne et al., "Gene Therapy Approaches for Lysosomal Storage Disease: Next-Generation Treatment", Human Gene Therapy, vol. 23(8):808-815, Aug. 2012.
Ciron et al., "Human [alpha]-lduronidase Gene Transfer Mediated by Adena-Associated Virus Types 1. 2. and 5 in the Brain of Nonhuman Primates: Vector Diffusion and Biodistribution," Human Gene Therapv, vol. 20(4):350-360, Apr. 2009.
Wang et al . . . , "Developing a Second-Generation Clinical Candidate AAV Vector for Gene Therapy of Familial Hypercholesterolemia," Molecular Therapy: Methods & Clinical Development (Journal Pre-Proof), pp. 1-35, Apr. 2021.
Guo, "A single injection of recombinant adeno-associated virus into the lumbar cistern delivers transgene expression throughout the whole spinal cord", Mol. Neurobiol., vol. 53(5):3235-3248, Jul. 2016.
Samaranch et al., "Adena-Associated Virus Serotype 9 Transduction in the Central Nervous System of Nonhuman Primates," Human Gene Ther., vol. 23:382-389, Apr. 2012.
Samaranch et al., "Strong Cortical and Spinal Cord Transduction After AAV7 and AAV9 Delivery into the Cerebrospinal Fluid of Nonhuman Primates," Human Gene Therapy, vol. 24:526-532, May 2013.
Vulchanova et al., "Differential adeno-associated virus mediated gene transfer to sensory neurons following intrathecal delivery by direct lumbar puncture," Molecular Pain, vol. 6(31):1-9, May 2010.
Wang et al., "Widespread spinal cord transduction by intrathecal injection of rAAV delivers efficacious RNAi therapy for amyotrophic lateral sclerosis," Human Molecular Genetics, vol. 23(3):668-681, Jan. 2014 (ePub Sep. 2013).
Bielicki et al., "Recombinant human iduronate-2-sulphatase: correction of mucopolysaccharidosis-type II fibroblasts and characterization of the purified enzyme," Biochem J, vol. 289(1):241-246, Jan. 1993.
Daniele et al., "Uptake of recombinant iduronate-2-sulfatase into neuronal and glial cells in vitro," Biochim Biophys Acta., vol. 1588(3):203-209, Aug. 2002.
Genbank, "NM_010498: Mus musculus iduronate 2-sulfatase (ids), mRNA," May 2020, 5 pages, retrieved from https://www.ncbi.nlm.nih.gov/nuccore/262205477.
Ghaderi et al., "Production platforms for biotherapeutic glycoproteins. Occurrence, impact, and challenges of non-human sialvlation," Biotechnol. Genet. Eng. Rev., vol. 28:147-175, Apr. 2013.
Zuber et al., "The effect of recombinant human iduronate-2-sulfatase (idursulfase) on growth in young patients with Mucopolysaccharidosis Type II," PLoS One, vol. 9(1):1-5, Jan. 2014.
Wolf, D.A., et al., Direct Gene Transfer to the CNS Prevents Emergence of Neurologic Disease in a Murine Model of Mucopolysaccharidosis Type I, Neurobiol. Dis., 2011, 43(1): 123-133, epub Mar. 17, 2011.
Calias, P., et al., CNS Penetration of Intrathecal-Lumbar Idursulfase in the Monkey, Dog and Mouse: Implications for Neurological Outcomes of Lysosomal Storage Disorder, PLoS ONE, 2012, 7(1):e3034; Epub Jan. 18, 2012.
Cearley, C.N., and Wolfe, J.H., Transduction Characteristics of Adeno-associated Virus Vectors Expressing Cap Serotypes 7, 8, 9, and Rh10 in the Mouse Brain, Molecular Therapy, 2006, 13(3):528-537, Epub Jan. 18, 2006.
Wraith, J.E., Mucopolysaccharidosis Type II (Hunter syndrome): a clinical review and recommendations for treatment in the era of enzyme replacement, Eur. J. Pediatr., 2008, 167(3):267-277, Epub Nov. 23, 2007.
European Search Report dated Aug. 23, 2022 issued in corresponding European Patent Application No. 17734162.5.
Office Action dated Sep. 19, 2022 issued in corresponding Korean Patent Application No. 10-2018-7033163, with unofficial English translation provided by local agent.
Office Action dated Oct. 26, 2022 issued in Corresponding Japanese Patent Application No. 2020-516820, with unofficial translation provided by local Agent.
Office Action dated May 27, 2021 issued in corresponding Japanese Patent Application No. 2018-554348, with translation provided by local agent.

(56) References Cited

OTHER PUBLICATIONS

Non-Final Office action dated Aug. 23, 2022 issued in corresponding U.S. Appl. No. 16/649,230.
Hinderer, C., et al., Evaluation of Intrathecal Routes of Administration for Adeno-Associated Viral Vectors in Large Animals. Hum Gene Ther. Jan. 2018; 29(1): 15-24.
Hordeaux, J., et al., Safe and sustained expression of human iduronidase after adeno-associated virus 9 intrathecal administration in infant rhesus monkeys. Hum Gene Ther. Aug. 2019; 30(8): 957-966.
Muenzer, J., et al. A phase I/II study of intrathecal idursulfase-IT in children with severe mucopolysaccharidosis II. Gen. Med. Jan. 2016; 18(1):73-81.
Burton BK., et al., Survival in idursulfase-treated and untreated patients with MPS II: Data from the Hunter Outcome Survey (HOS). J Inherit Metab Dis (Sep. 8, 2017) 40:867-874.
Bharucha-Goebel, D., et al., Review of CSF and peripheral immune responses following intrathecal gene transfer for giant axonal neuropathy intrathecal gene transfer for giant axonal neuropathy. American Society of Gene & Cell Therapy 20th Annual Meeting; Washington, DC. May 10-13, 2017. Abstract No. 522.
Tardieu, M., et al. Intracerebral gene therapy in children with mucopolysaccharidosis type IIIB syndrome: an uncontrolled phase 1/2 clinical trial. The Lancet Neurology, Sep. 2017; 16(9); 712-20.
UniQure. Positive topline results announced from Phase I/II trial in Sanfilippo B syndrome patients using uniQure's novel AAV5-based gene therapy [press release Sep. 19, 2015]. Available from: URL: https://www.globenewswire.com/news-release/2015/09/19/769451/27963/en/Positive-Topline-Results-Announced-From-Phase-I-II-Trial-in-Sanfilippo-B-Syndrome-Patients-Using-uniQure-s-Novel-AAV5-Based-Gene-Therapy.html Accessed Jun. 26, 2023.
Gray, SJ., et al. Preclinical differences of intravascular AAV9 delivery to neurons and glia: a comparative study of adult mice and nonhuman primates. Mol Ther 2011; 19(6): 1058-69. E-pub: Apr. 12, 2011.
Belur, L., Non-Invasive Intranasal Administration of AAV9-Iduronidase Prevents Emergence of Neurologic Disease and Neurocognitive Dysfunction in a Murine Model of Mucopolysaccharidosis Type I, Genetic Disorders and Metabolic Liver Disease, May 2015, Abstract 706, 23(1):S281.
Belur, L., et al., Comparative Effectiveness of Intracerebroventricular, Intrathecal, and Intranasal Routes of AAV9 Vector Administration for Genetic Therapy of Neurologic Disease in Murine Mucopolysaccharidosis Type I, Front Mol Neurosci. May 10, 2021; 14, pp. 1-12 (618360).
"News Release—REGENXBIO Announces Interim Data from Phase I/II Trial of RGX-121 for the Treatment of Mucopolysaccharidosis Type II (MPS II)", Dec. 18, 2019, 3 pages. https://regenxbio.gcs-web.com/node/9336/pdf.
Aronovich, E.L., Lysosomal storage disease: gene therapy on both sides of the blood-brain barrier, Mol Genet Metab., Feb. 2015, 114(2):83-93.
Podetz-Pedersen, K.M., Neurologic Recovery in MPS I and MPS II Mice by AAV9-Mediated Gene Transfer to the CNS After the Development of Cognitive Dysfunction, Hum Gene Ther, Jan. 2023, 34(1-2):8-18.
Hinderer, Christian, "Intrathecal Adeno-Associated Virus Vector Delivery for Mucopolysaccharidosis Type I" (2015). Publicly Accessible Penn Dissertations. 1763 (https://repository.upenn.edu/edissertations/1763).
Gray, S.J., Gene therapy and neurodevelopmental disorders, Neuropharmacology. May 2013;68: 136-42, Epub Jun. 27, 2012.
Calias et al., Nov. 2014, "Intrathecal delivery of protein therapeutics to the brain: a critical reassessment," Pharmacology & Therapeutics, 144(2): 114-122.
Cohen-Pfeffer et al., 2017, "Intracerebroventricular Delivery as a Safe, Long-Term Route of Drug Administration," Pediatric Neurology, 67:23-25, Epub Nov. 10, 2016.
Dickson et al., 2007, "Intrathecal enzyme replacement therapy: Successful treatment of brain disease via the cerebrospinal fluid," Molecular Genetics and Metabolism, 91(1):61-68, Published online Feb. 26, 2007.
O'Reilly et al., 2013, "Gene therapy for rare diseases: summary of a National Institutes of Health workshop, Sep. 13, 2012," Human Gene Therapy, 24(4):355-362, Published online Mar. 21, 2013.
Sawamoto et al., 2018, "Gene therapy for Mucopolysaccharidoses," Molecular Genetics and Metabolism, 123(2):59-68, Published online Dec. 26, 2017.
Slavc et al., 2018, "Best practices for the use of intracerebroventricular drug delivery devices," Molecular Genetics and Metabolism, 124:184-188, Epub May 16, 2018.
Wolf, D, Nov. 2010, "Molecular Therapy for Mucopolysaccharidosis Type I," A Dissertation Submitted to the Graduate School of the University of Minnesota (173 pages).
Clarke et al., Jan. 2009, "Long-term Efficacy and Safety of Laronidase in the Treatment of Mucopolysaccharidosis I," Pediatrics, 123(1):229-240 (abstract).
Whiteman, D., et al., Development of idursulfase therapy for mucopolysaccharidosis type II (Hunter syndrome): the past, the present and the future, Drug Des Devel Ther, 2017, 11:2467-2480, Epub. Aug. 13, 2017.
Gilkes, J.A., et al., Preferred transduction with AAV8 and AAV9 via thalamic administration in the MPS IIIB model: A comparison of four rAAV serotypes, Mol Genet Metab Rep. Dec. 7, 2015;6:48-54, eCollection Mar. 2016.
Wolf, D.A., et al., Lysosomal enzyme can bypass the blood-brain barrier and reach the CNS following intranasal administration, Mol Genet Metab. May 2012;106(1): 131-4, Epub Feb. 10, 2012.
Yund, B., Cognitive, medical, and neuroimaging characteristics of attenuated mucopolysaccharidosis type II, Mol Genet Metab. Feb. 2015; 114(2): 170-177.
Zhang, Y., Several rAAV vectors efficiently cross the blood-brain barrier and transduce neurons and astrocytes in the neonatal mouse central nervous system, Mol Ther. Aug. 2011; 19(8): 1440-1448, Epub May 24, 2011.
Stanimirovic, D.B. et al., Emerging Technologies for Delivery of Biotherapeutics and Gene Therapy Across the Blood-Brain Barrier, BioDrugs. Oct. 10, 2018; 32(6): 547-559.
Tardieu, M., Intracerebral administration of adeno-associated viral vector serotype rh. 10 carrying human SGSH and SUMF1 cDNAs in children with mucopolysaccharidosis type IIIA disease: results of a phase I/II trial, Hum Gene Ther. Jun. 2014;25(6):506-16, Epub May 5, 2014.
Taylor, M., et al., Hematopoietic Stem Cell Transplantation for Mucopolysaccharidoses: Past, Present, and Future, Biol Blood Marrow Transplant. Jul. 2019; 25(7):e226-e246, Epub Feb. 14, 2019.
Schuster, D.J., et al., Biodistribution of adeno-associated virus serotype 9 (AAV9) vector after intrathecal and intravenous delivery in mouse, Front Neuroanat. Jun. 10, 2014; 8:42, eCollection 2014.
Spampanato, C., et al., Efficacy of a combined intracerebral and systemic gene delivery approach for the treatment of a severe lysosomal storage disorder, Mol Ther. May 2011; 19(5):860-9, Epub Feb. 15, 2011.
Miyake, N., et al., Intrathecal Administration of Type 9 AAV Vector Expressing Arylsulfatase A Is Effective for Reduction of Sulfatide Storage but Not for Correction of Neurological Deficits in Adult Metachromatic Leukodystrophy Model Mice with Overt Neurological Symptoms, Abstract 723, 19 (Suppl. 1), (May 2011), Page S276.
Gagliardi, C., and Bunnell, B.A., Large Animal Models of Neurological Disorders for Gene Therapy, ILAR J. 2009; 50(2): 128-143, available in PMC Jul. 17, 2009.
Lykken, E.A., et al., Recent progress and considerations for AAV gene therapies targeting the central nervous system, J Neurodev Disord. May 18, 2018;10(1): 16.
Marco, S., et al., In Vivo Gene Therapy for Mucopolysaccharidosis Type III (Sanfilippo Syndrome): A New Treatment Horizon, Human Gene Therapy, Oct. 2019, 30(10):1211-1221, Published online S4 Sep. 2019.
Hartung., S.D., et al., Correction of metabolic, craniofacial, and neurologic abnormalities in MPS I mice treated at birth with

(56) References Cited

OTHER PUBLICATIONS adeno-associated virus vector transducing the human alpha-L-iduronidase gene, Mol Ther. Jun. 2004;9(6):866-75.

Hoffman and Mayatepek, Neurological manifestations in lysosomal storage disorders—from pathology to first therapeutic possibilities, Oct. 2005;36(5):285-9.

Janson, C.G., et al., Comparison of Endovascular and Intraventricular Gene Therapy With Adeno-Associated Virus-α-L-Iduronidase for Hurler Disease, Neurosurgery. Jan. 2014; 74(1): 99-111.

Fu, et al., Neurological correction of lysosomal storage in a mucopolysaccharidosis IIIB mouse model by adeno-associated virus-mediated gene delivery, Mol Ther. Jan. 2002;5(1):42-9.

Fraldi, A., et al., Functional correction of CNS lesions in an MPS-IIIA mouse model by intracerebral AAV-mediated delivery of sulfamidase and SUMF1 genes, Hum Mol Genet. Nov. 15, 2007;16(22):2693-702, Epub Aug. 27, 2007.

Dayton, R.D., The advent of AAV9 expands applications for brain and spinal cord gene delivery, Expert Opin Biol Ther. Jun. 2012; 12(6):757-66, Epub Apr. 20, 2012.

Broomfield, et al., Ten years of enzyme replacement therapy in pediatric onset mucopolysaccharidosis II in England, Mol Genet Metab. Feb. 2020; 129(2):98-105, Epub Jul. 30, 2019.

Bailey, L., An Overview of Enzyme Replacement Therapy for Lysosomal Storage Diseases, OJIN: The Online Journal of Issues In Nursing, 2008; 13(1) Manuscript 3. https://ojin.nursingworld.org/table-of-contents/volume-13-2008/number-1-january-2008/enzyme-replacement-therapy/ Accessed Jun. 27, 2023.

Bevan, A.K., Systemic gene delivery in large species for targeting spinal cord, brain, and peripheral tissues for pediatric disorders, Mol Ther. Nov. 2011; 19(11): 1971-80, Epub Aug. 2, 2011.

Belur, L.R., Intravenous delivery for treatment of mucopolysaccharidosis type I: A comparison of AAV serotypes 9 and rh10, Mol Genet Metab Rep. Sep. 2020; 24: 100604, Published online May 20, 2020.

Office Action dated Mar. 14, 2023 issued in corresponding Taiwanese Patent Application No. 107133321, with unofficial English translation provided by local agent.

\* cited by examiner

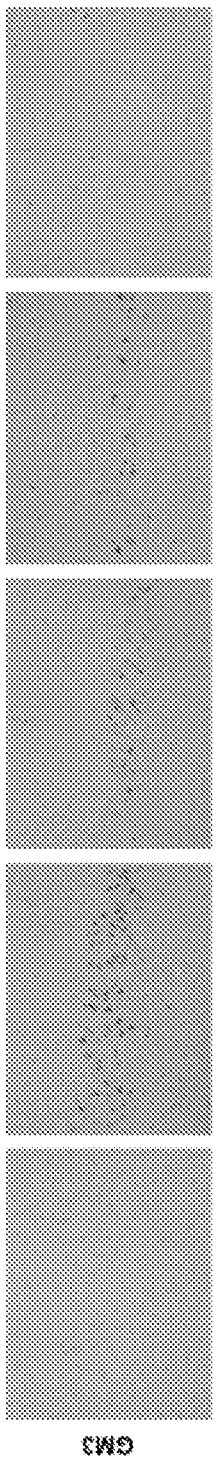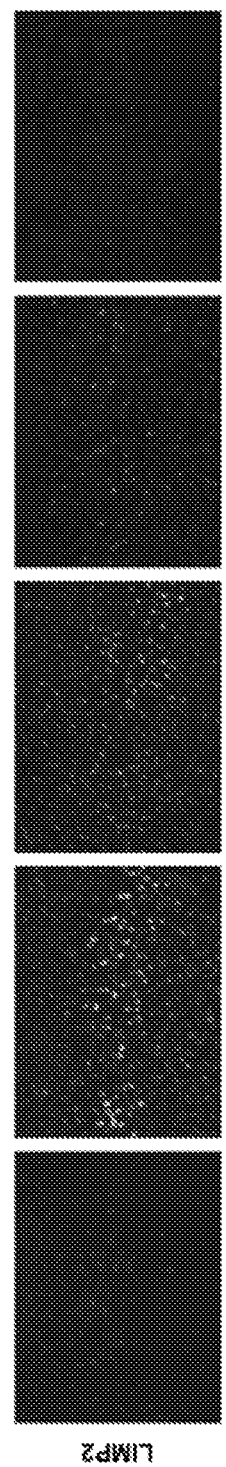

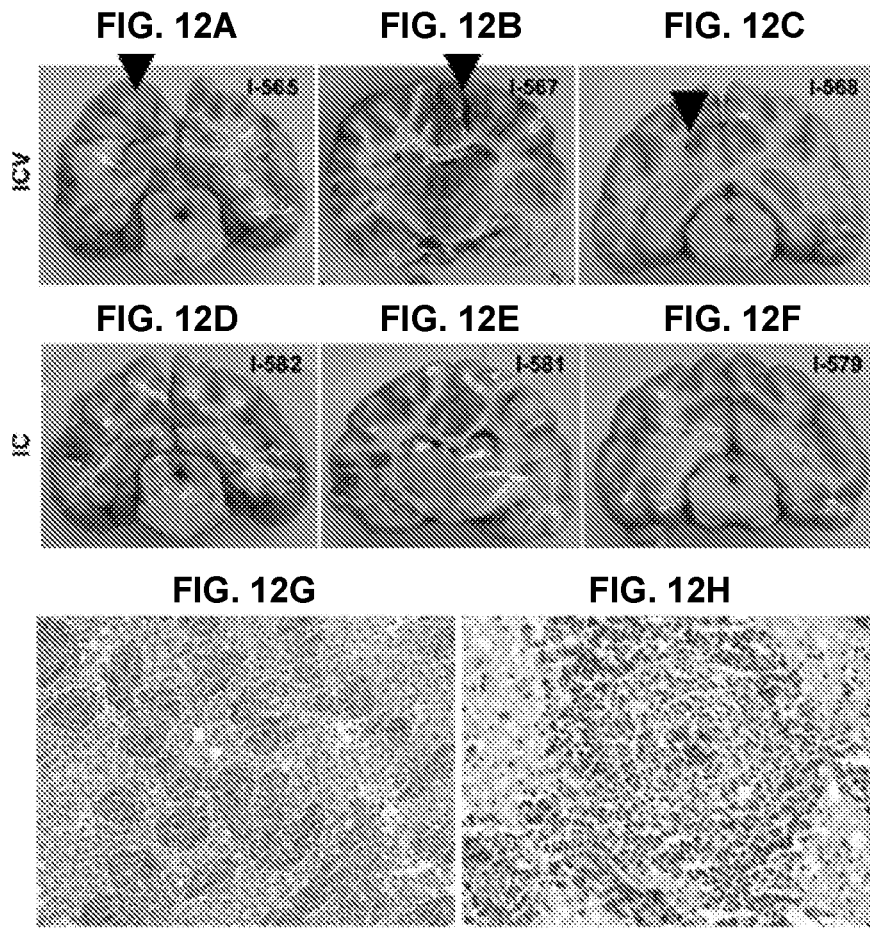
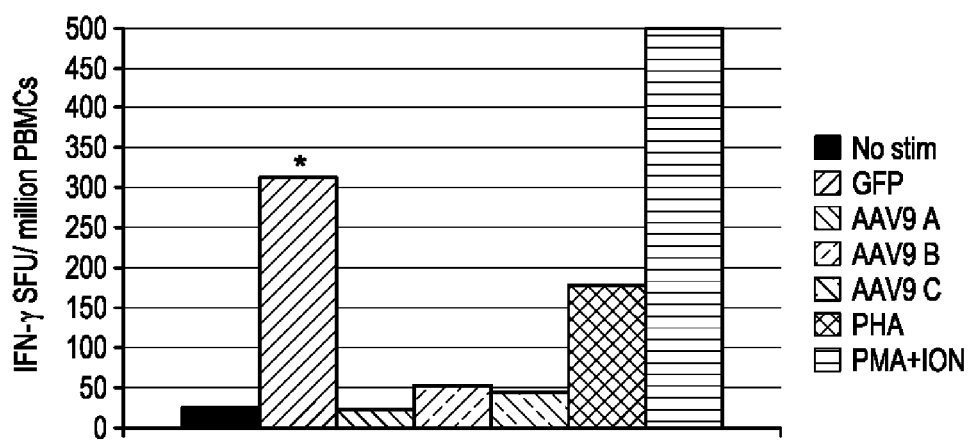
FIG. 12I

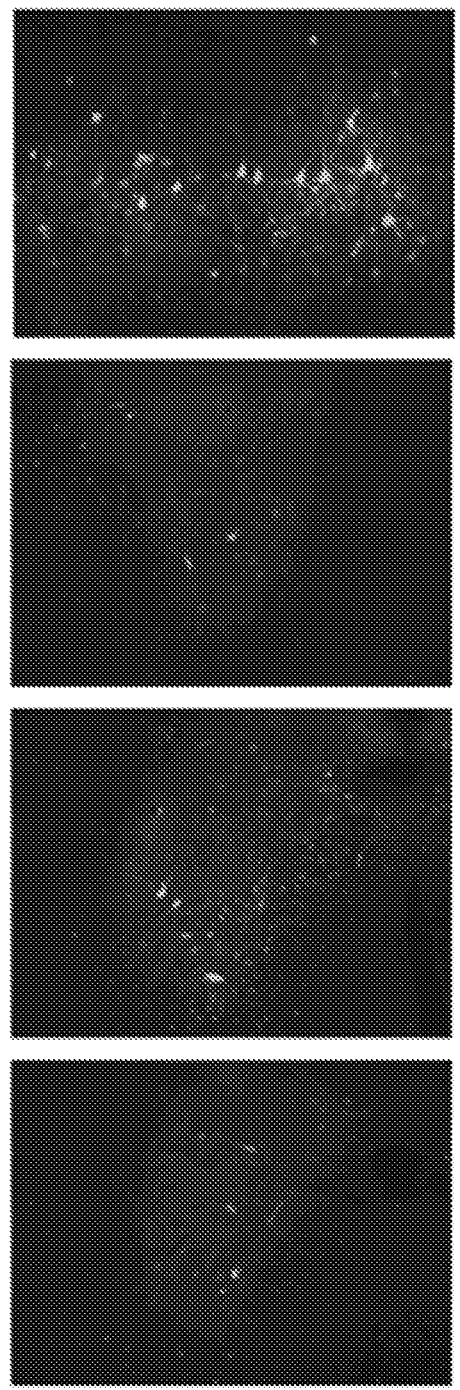
ICV      IC
FIG. 14A Lumbar, FIG. 14B Thoracic, FIG. 14C Cervical, FIG. 14D Cortex, FIG. 14E, FIG. 14F, FIG. 14G, FIG. 14H

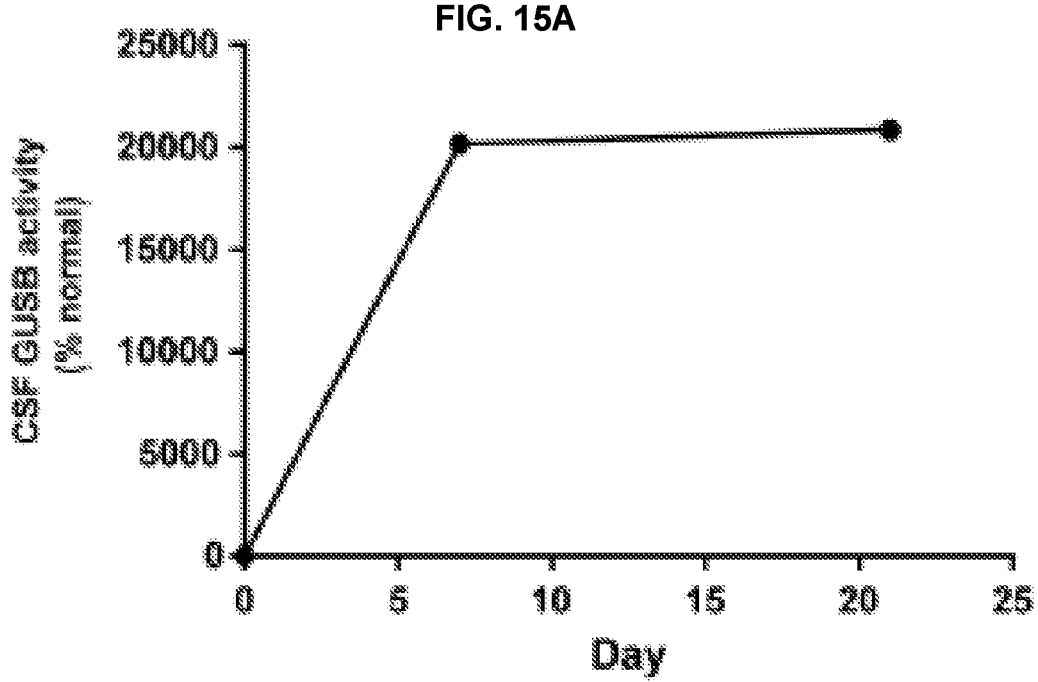
FIG. 15A
FIG. 15B
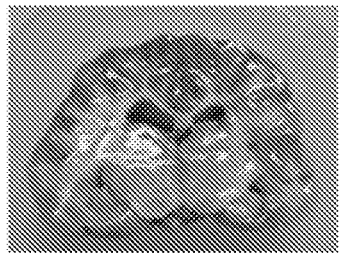
FIG. 15C
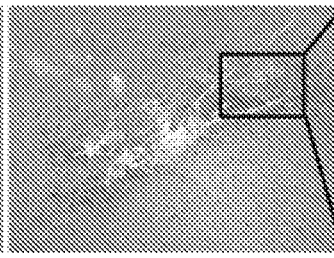
FIG. 15D
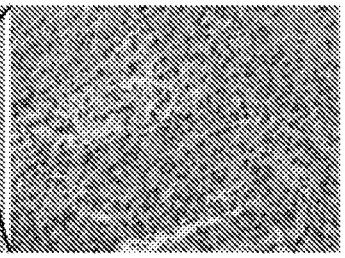

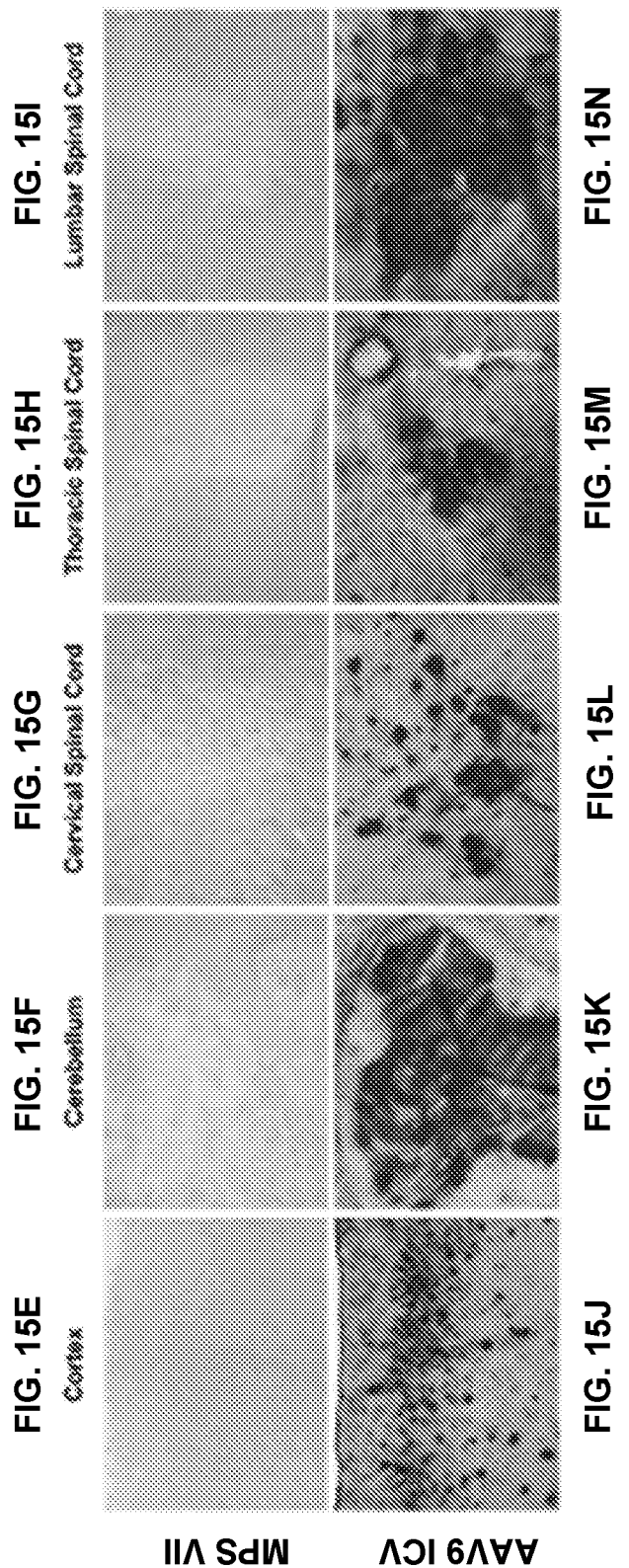

FIG. 15O
Normal
FIG. 15P
MPS VII
FIG. 15Q
AAV9 ICV
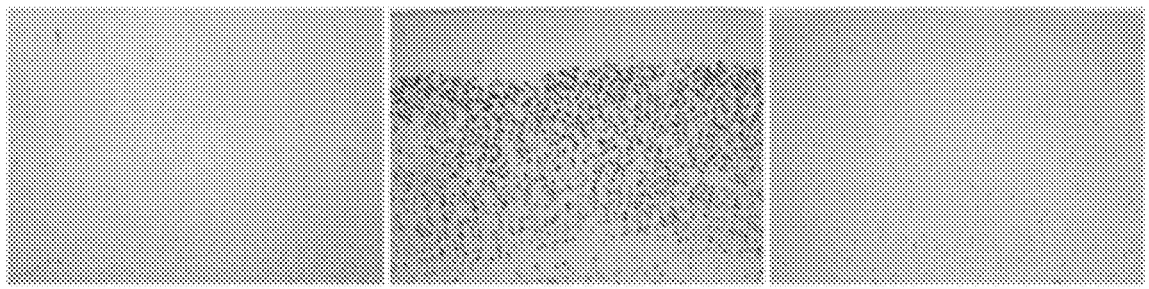
FIG. 16A
FIG. 16B
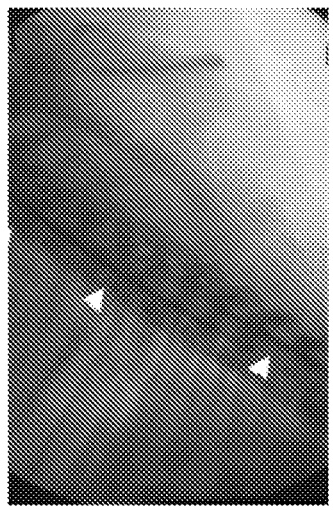
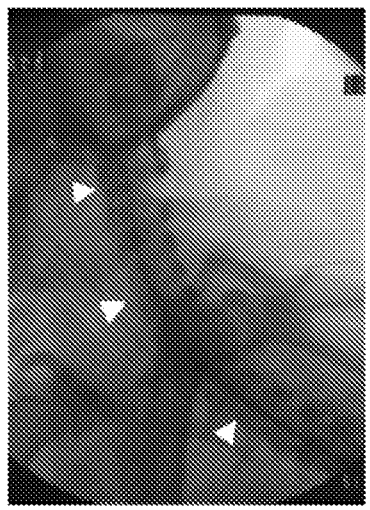

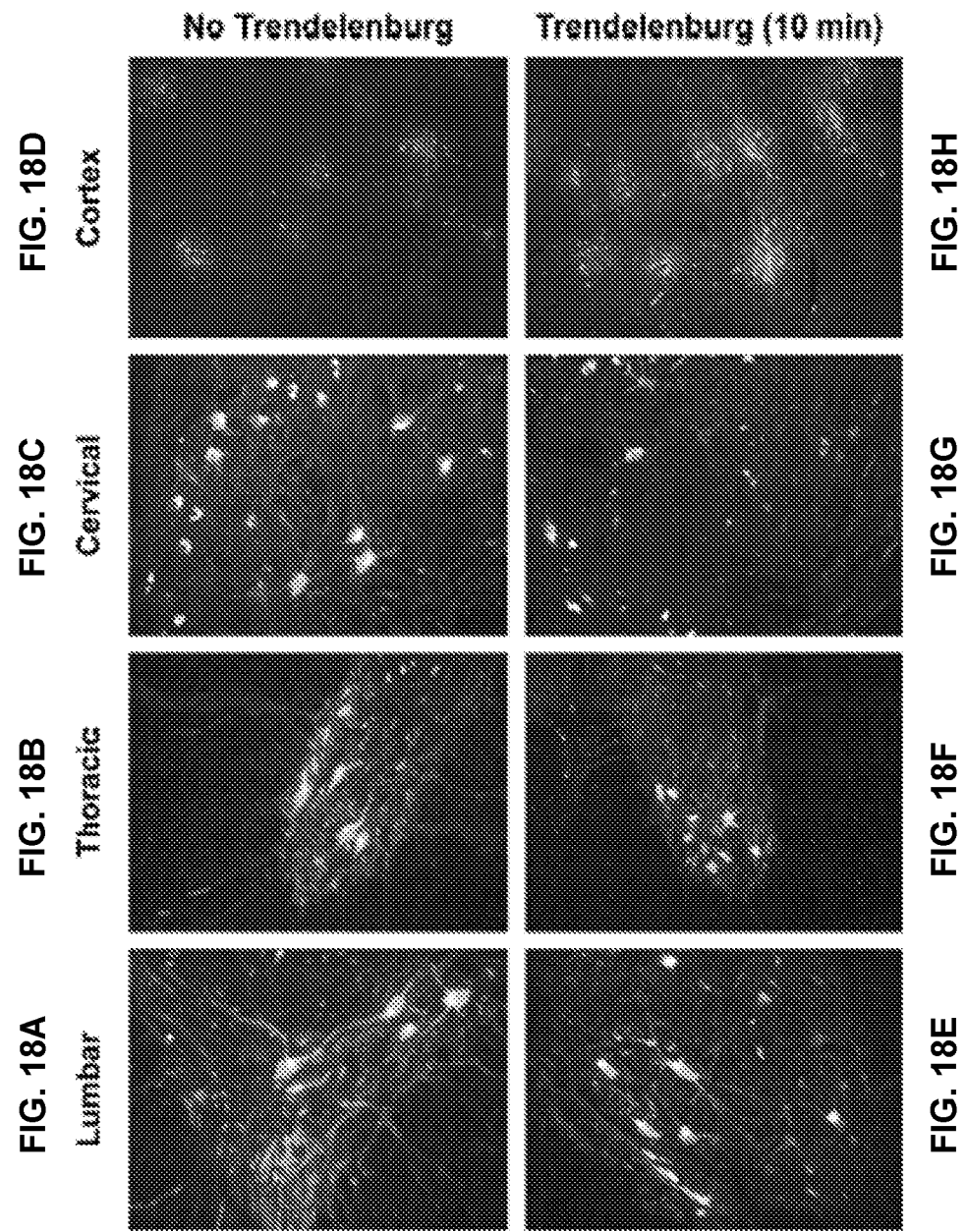

| FIG. 20A | FIG. 20B | FIG. 20C | FIG. 20D |
|---|---|---|---|
| WT | MPS | MPS + APCHA | WT + Spermine |
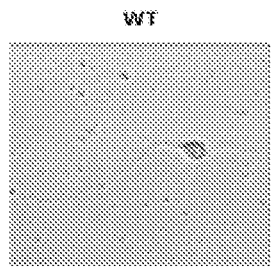 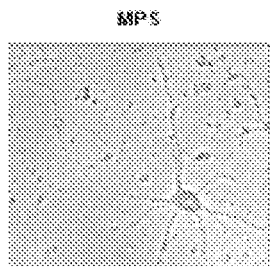 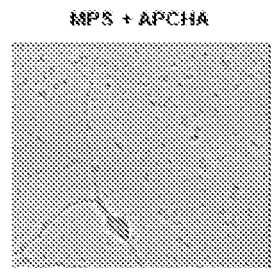 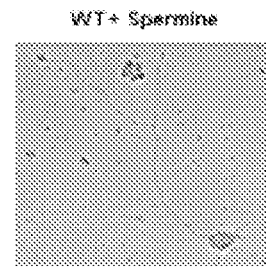
FIG. 20E
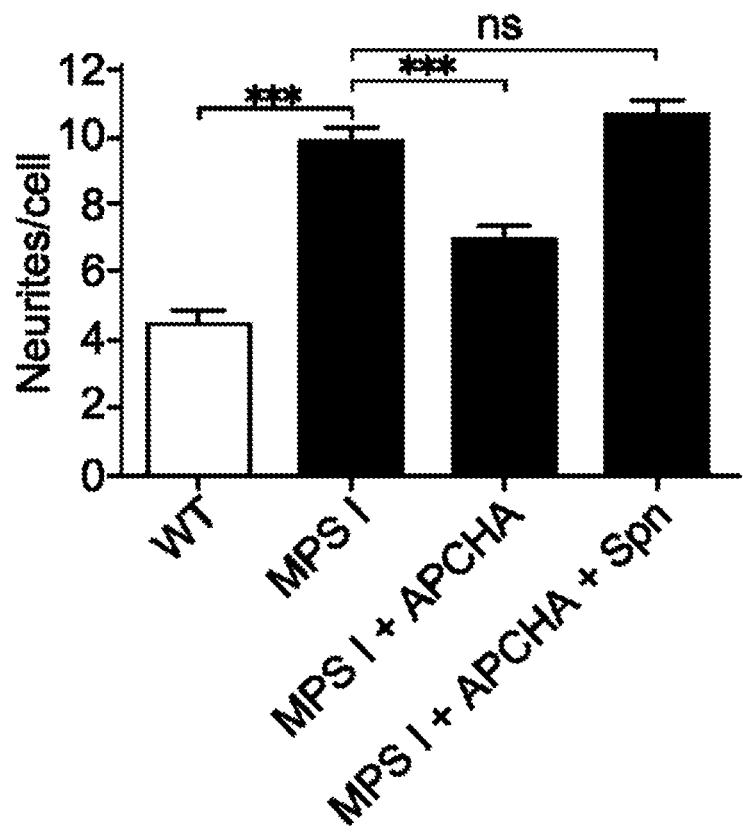

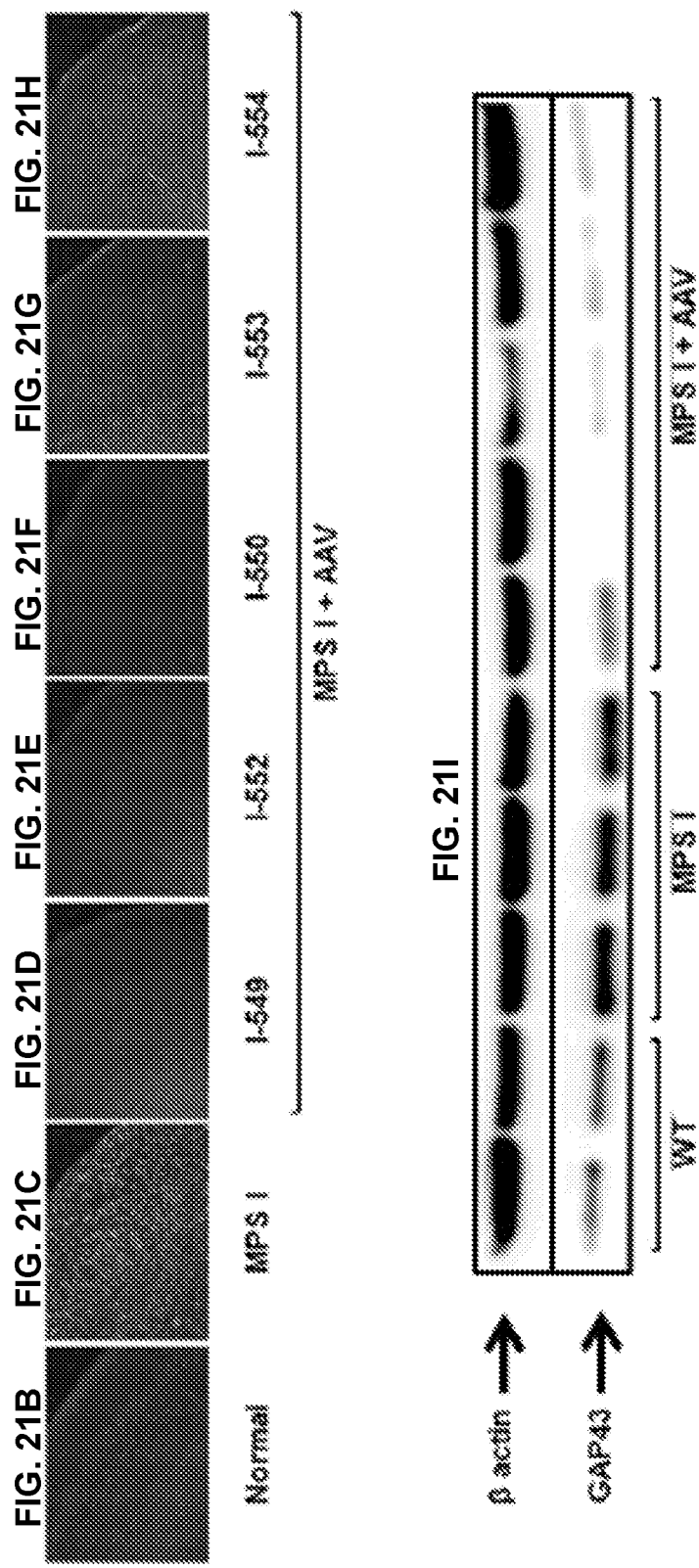

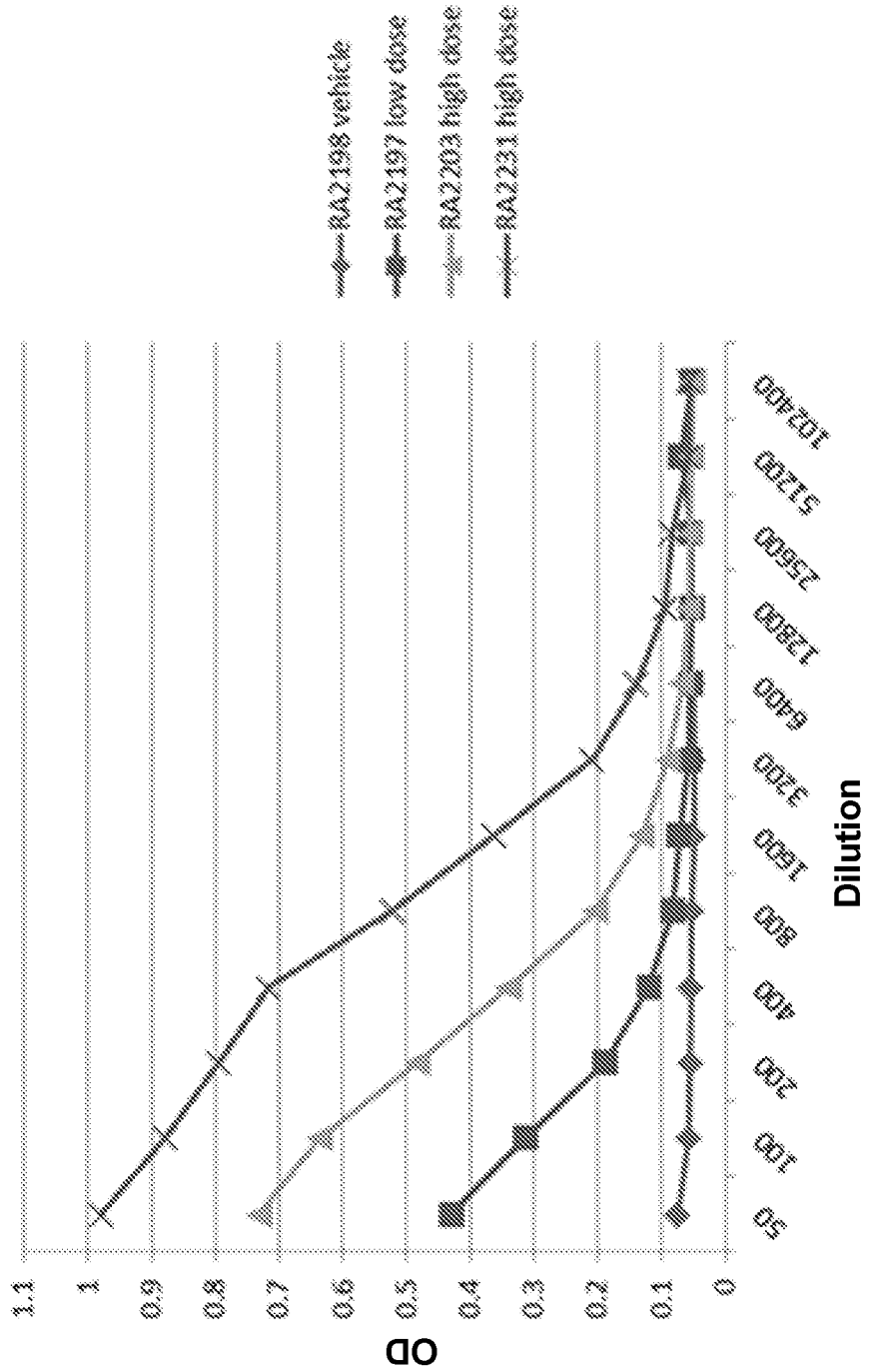

GENE THERAPY FOR TREATING MUCOPOLYSACCHARIDOSIS TYPE II

STATEMENT OF FEDERALLY FUNDED RESEARCH

This invention was made with government support under grant numbers R01DK54481, P40OD010939, and P30ES013508 from the National Institutes of Health. The US government may have certain rights in this invention.

1. INTRODUCTION

The invention relates to a gene therapy approach for treating Mucopolysaccharidosis Type II (MPS II), also known as Hunter Syndrome.

2. BACKGROUND OF THE INVENTION

MPS II, also known as Hunter syndrome, is a rare X-linked recessive genetic disease affecting 1 in 100,000 to 1 in 170,000 individuals, primarily males. This progressive and devastating disease is caused by mutations in the iduronate-2-sulfatase (IDS) gene, leading to deficiency of the lysosomal enzyme, iduronate-2-sulfatase (IDS, alternatively termed I2S)—an enzyme required for the lysosomal catabolism of heparan sulfate and dermatan sulfate. These ubiquitous polysaccharides, called GAGs (glycosaminoglycans), accumulate in tissues and organs of MPS II patients resulting in characteristic storage lesions and diverse disease sequelae. Morbidity and mortality are high in this patient population—in patients with the severe phenotype (characterized by neurocognitive deterioration) death has been reported to occur at a mean age of 11.7 years; in patients with mild or attenuated phenotype, death has been reported at 21.7 years.

Patients with MPS II appear normal at birth, but signs and symptoms of disease typically present between the ages of 18 months and 4 years in the severe form, and between 4 and 8 years in the attenuated form. Signs and symptoms common to all affected patients include short stature, coarse facial features, macrocephaly, macroglossia, hearing loss, hepato- and splenomegaly, dystosis multiplex, joint contracture, spinal stenosis and carpal tunnel syndrome. Frequent upper respiratory and ear infections occur in most patients and progressive airway obstruction is commonly found leading to sleep apnea and often death. Cardiac disease is a major cause of death in this population and is characterized by valvular dysfunction leading to right and left ventricular hypertrophy and heart failure. Death is generally attributed to obstructive airway disease or cardiac failure.

In severe forms of the disease, early developmental milestones may be met, but developmental delay is readily apparent by 18-24 months. Some patients fail hearing screening tests in the first year and other milestones are delayed, including the ability to sit unsupported, ability to walk, and speech. Developmental progression begins to plateau around 6.5 years. While half the children with MPS II become toilet trained, most children, if not all, will lose this ability as the disease progresses.

Patients with significant neurologic involvement exhibit severe behavioral disturbances, including hyperactivity, obstinacy, and aggression beginning in the second year of life and continuing to age 8-9, when neurodegeneration attenuates this behavior.

Seizures are reported in over half of severely affected patients who reach the age of 10, and by the time of death most patients with CNS involvement are severely mentally handicapped and require constant care. Although patients with attenuated disease exhibit normal intellectual functioning, MRI imaging reveals gross brain abnormalities in all patients with MPS II including white matter lesions, enlarged ventricles and brain atrophy.

Enzyme Replacement Therapy ("ERT") with recombinant idursulfase (Elaprase®, Shire Human Genetic Therapies) is the only approved treatment for Hunter syndrome and is administered as a weekly infusion. However, ERT as currently administered does not cross the blood brain barrier ("BBB") and is therefore unable to address the unmet need in patients with severe disease—i.e., MPS II with CNS/neurocognitive and behavioral involvement. Current efforts to address this issue are aimed at modifying the enzyme to enable it to cross the BBB.

3. SUMMARY OF THE INVENTION

The use of a replication deficient adeno-associated virus ("AAV") to deliver a human iduronate-2-sulfatase ("hIDS") gene to the CNS of patients (human subjects) diagnosed with MPS II, also known as Hunters syndrome, is provided herein. The goal of the treatment is to functionally replace the patient's defective iduronate-2-sulfatase via rAAV-based CNS-directed gene therapy as a viable approach to treat disease. Efficacy of the therapy can be measured by assessing (a) the prevention of neurocognitive decline in patients with MPS II (Hunter syndrome); and (b) reductions in biomarkers of disease, e.g., GAG levels and/or enzyme activity (IDS or hexosaminidase) in the CSF, serum and/or urine, and/or liver and spleen volumes. Neurocognition in infants can be measured via Bayley Scales of Infant and Toddler Development, Third Ed., BSID-III. Neurocognitive and adaptive behavioral assessments (e.g., using Bayley Scales of Infant Development and Vineland Adaptive Behavior Scales, respectively) can be performed.

In certain embodiments, a therapeutic regimen for treating human iduronate-2-sulfatase (hIDS) deficiency is provided which comprises a co-therapy. The co-therapy comprises co-administration of: (a) a suspension of replication deficient recombinant adeno-associated virus (rAAV), wherein: (i) the rAAV has an AAV9 capsid and a vector genome which comprises a nucleic acid sequence encoding hIDS under the control of regulatory sequences which direct expression of the hIDS (rAAV9.hIDS); (ii) a formulation buffer suitable for intrathecal delivery comprising a physiologically compatible aqueous buffer, and optional surfactants and excipients (b) at least a first immunosuppressive agent selected from at least one of corticosteroid, an antimetabolite, a T-cell inhibitor, a macrolide, or a cytostatic agent: and (c) at least a second immunosuppressive agent selected from at least one of a corticosteroid, an antimetabolite, a T-cell inhibitor, a macrolide, or a cytostatic agent, wherein administration of at least one immunosuppressive agent begins prior to or on the same day as delivery of the rAAV9.hIDS vector; and wherein administration of at least one of the immunosuppressive agents continues for at least 8 weeks post-vector administration. In certain embodiments, the rAAV9.hIDS has a vector genome selected from: SEQ ID NO: 3; SEQ ID NO: 11; or SEQ ID NO: 14. In certain embodiments, the patient is predosed initially with an intravenous steroid prior to vector delivery. In certain embodiments, the patient is dosed with an oral steroid following vector delivery. In certain embodiments, the regimen comprises one or more macrolides comprising tacrolimus or sirolimus, or a combination thereof. In certain embodiments, a first dose of a macrolide is delivered predosing with vector. In certain embodiments, the immune suppressive regimen is discontinued at week 48 post-dosing with the AAV9.hIDS. In certain embodiments, the suspension has a pH of 6 to 9, or a pH of 6.8 to 7.8. In certain embodiments, the rAAV9.hIDS is administrable by intrathecal injection at a dose of about $1.9 \times 10^{10}$ GC/g brain mass. In certain embodiments, the rAAV9.hIDS is administrable by intrathecal injection at a dose of about $6.5 \times 10^{10}$ GC/g brain mass.

In certain embodiments, use of a suspension comprising replication deficient recombinant adeno-associated virus (rAAV) is provided, which rAAV comprises an AAV9 capsid and a vector genome which comprises a nucleic acid sequence encoding human iduronate-2-sulfatase (hIDS) under the control of regulatory sequences which direct expression of the hIDS (rAAV9.hIDS), wherein the suspension comprises rAAV9.hIDS at a dose of about $1.3 \times 10^{10}$ genome copies (GC)/g brain mass or about $6.5 \times 10^{10}$ genome copies (GC)/g brain mass. In certain embodiments, the rAAV9.hIDS has a vector genome selected from: SEQ ID NO: 3; SEQ ID NO: 11; or SEQ ID NO: 14. In certain embodiments, the use is in a co-therapeutic regimen comprising two or more immunosuppressive agents. In certain embodiments, the two or more immunosuppressive agents comprise: at least a first immunosuppressive agent selected from at least one of corticosteroid, an antimetabolite, a T-cell inhibitor, a macrolide, or a cytostatic agent: and at least a second immunosuppressive agent selected from at least one of a corticosteroid, an antimetabolite, a T-cell inhibitor, a macrolide, or a cytostatic agent. In certain embodiments, the patient is predosed initially with an intravenous steroid prior to rAAV9.hIDS delivery. In certain embodiments, the patient is doses with an oral steroid following rAAV9.hIDS delivery. In certain embodiments, the co-therapy comprises one or more macrolides comprising tacrolimus or sirolimus, or a combination thereof. In certain embodiments, the human patient has been diagnosed with mucopolysaccharidosis II (MPS II) or severe Hunter syndrome.

In certain embodiments, an aqueous suspension comprising replication deficient recombinant adeno-associated virus (rAAV) is provided which comprises an AAV9 capsid and a vector genome which comprises a nucleic acid sequence encoding human iduronate-2-sulfatase (hIDS) under the control of regulatory sequences which direct expression of the hIDS (rAAV9.hIDS), wherein the suspension is formulated for intrathecal injection to a human in need thereof at a dose of $1.3 \times 10^{10}$ GC/g brain mass or about $6.5 \times 10^{10}$ GC/g brain mass. In certain embodiments, the suspension is for use in co-therapy with (i) at least a first immunosuppressive agent selected from at least one of a corticosteroid, an antimetabolite, a T-cell inhibitor, a macrolide, or a cytostatic agent: and (ii) at least a second immunosuppressive agent selected from at least one of a corticosteroid, an antimetabolite, a T-cell inhibitor, a macrolide, or a cytostatic agent, wherein dosing of the immunosuppressive agents begins prior to or on the same day as delivery of the AAV vector; and wherein dosing with at least one of the immunosuppressive agents continues for at least 8 weeks post-vector administration.

In certain embodiments, a method of treating a patient in need thereof with a replication deficient recombinant adeno-associated virus (rAAV) is provided which comprises a heterologous nucleic acid encoding human iduronate-2-sulfatase (hIDS) packaged in an AAV9 capsid at a dose of about $1.3 \times 10^{10}$ GC/g brain mass or about $6.5 \times 10^{10}$ GC/g brain mass by intrathecal injection. In certain embodiments, the patient has been diagnosed with mucopolysaccharidosis II (MPS II) or severe Hunter syndrome. In certain embodiments, the rAAV9.hIDS has a vector genome selected from: SEQ ID NO: 3; (b) SEQ ID NO: 11; or (c) SEQ ID NO: 14. In certain embodiments, the dose administered is at least $1.3 \times 10^{10}$ GC/g brain mass, at least $1.9 \times 10^{10}$ GC/g brain mass, at least $6.5 \times 10^{10}$ GC/g brain mass, or $9.4 \times 10^{10}$ GC/g brain mass, or about $4 \times 10^{11}$ GC/g brain mass.

These and other aspects of the invention will be apparent from the detailed description of the invention.

4. BRIEF DESCRIPTION OF THE FIGURES

FIG. 1 is a schematic representation of the AAV9.CB.hIDS vector genome. The IDS expression cassette is flanked by inverted terminal repeats (ITRs) and expression is driven by a hybrid of the cytomegalovirus (CMV) enhancer and the chicken beta actin promoter (CB7). The transgene includes the chicken beta actin intron and a rabbit beta-globin polyadenylation (polyA) signal.

FIGS. 2A-2C provides IDS expression in CNS and serum of MPS II mice after IT vector treatment. MPS II mice were treated at 2-3 months of age with an ICV injection of AAV9.CB.hIDS at one of three doses: $3 \times 10^8$ GC (low), $3 \times 10^9$ GC (mid) or $3 \times 10^{10}$ GC (high). Animals were sacrificed three weeks after injection. IDS activity was measured in CSF (FIG. 2A) whole brain homogenate (FIG. 2B) and serum (FIG. 2C). Wild type and untreated MPS II mice were used as controls.

FIG. 3 provides biodistribution of vector DNA in MPS II mice administered AAV9.CB.hIDS. MPS II mice were treated with an ICV injection of $3 \times 10^{10}$ GC of an AAV9 vector. Three weeks after injection, the animals were sacrificed and vector genomes were quantified in tissue DNA by Taqman PCR.

FIGS. 4A-4D provide correction of peripheral GAG after IT vector delivery in MPS II Mice. MPS II mice were treated at 2-3 months of age with an ICV injection of AAV9.CB.hIDS at one of three doses: $3 \times 10^8$ GC (low), $3 \times 10^9$ GC (mid), or $3 \times 10^{10}$ GC (high). Animals were sacrificed three months after injection. Hexosaminidase activity was measured in liver (FIG. 4A) and heart (FIG. 4B). Storage correction was seen at all doses in the liver and at mid- and high-doses in the heart. GAG content was measured in liver (FIG. 4C) and heart (FIG. 4D). Wild type and untreated MPS II mice were used as controls. *$p<0.05$, one way ANOVA followed by Dunnett's test.

FIGS. 5A-5L provide dose-dependent resolution of brain storage lesions in MPS II Mice. MPS II mice were treated at 2-3 months of age with an ICV injection of AAV9.CB.hIDS at one of three doses: $3 \times 10^8$ GC (low), $3 \times 10^9$ GC (mid), or $3 \times 10^{10}$ GC (high). Animals were sacrificed three months after injection, and brains were stained for the lysosomal membrane protein LIMP2 and the ganglioside GM3. Cells staining positive for GM3 (FIGS. 5A, 5C, 5 E, 5G and 5I) and LIMP2 (5B, 5D, 5F, 5H and 5J) were quantified by a blinded reviewer in four cortical brain sections from each animal Representative cortical brain sections are shown (GM3, FIG. 5K; LIMP2, FIG. 5L). Wild type and untreated MPS II mice were used as controls. *$p<0.05$, one way ANOVA followed by Dunnett's test.

FIGS. 6A-6C shows improved object discrimination in vector-treated MPS II Mice. Untreated MPS II mice and WT male littermates underwent behavioral testing at 4-5 months of age. MPS II mice were treated at 2-3 months of age with an ICV injection of AAV9.CB.hIDS at one of three doses: $3 \times 10^8$ GC (low), $3 \times 10^9$ GC (mid) or $3 \times 10^{10}$ GC (high). Two months after injection animals underwent behavioral testing.

FIG. 6A illustrates Y maze behavior and FIG. 6B illustrates contextual fear conditioning, which were evaluated 2 months after injection by a blinded reviewer. "Pre" indicated freezing time when reexposed to the enclosure 24 hours after receiving an un-signaled 1.5 mA foot shock. *$p<0.05$, two-way ANOVA followed by Sidak's multiple comparisons test. FIG. 6C shows the percentage time spent exploring a novel or familiar object in the novel object recognition task, which is used to assess long term memory. Wild type and untreated MPS II mice were used as controls. *$p<0.05$, t-test with Bonferroni correction for multiple comparisons.

FIGS. 7A-7B provide a comparison of enzyme expression and correction of brain storage lesions in MPS I mice treated with IT AAV9. MPS I mice were treated at 2-3 months of age with an ICV injection of AAV9.CB.hIDUA at one of three doses: $3\times10^8$ GC (low), $3\times10^9$ GC (mid), or $3\times10^{10}$ GC (high). One cohort of animals was sacrificed at 3 weeks post vector injection, and brains were harvested for measurement of IDUA activity. This is shown in FIG. 7A. FIG. 7B shows a second cohort of animals was sacrificed 3 months after injection, and brains were stained for the lysosomal membrane protein LIMP2. Cells staining positive for LIMP2 were quantified by a blinded reviewer in 4 cortical brain sections. Wild type and untreated MPS II mice were used as controls. *$p<0.05$, one-way ANOVA followed by Dunnett's test.

FIG. 8 illustrates the antibody response against human IDS in MPS II mice treated with ICV AAV9.CB.hIDS. MPS II mice were treated at 2-3 months of age with an ICV injection of AAV9.CB.hIDS at one of three doses: $3\times10^8$ GC (low), $3\times10^9$ GC (mid), or $3\times10^{10}$ GC (high). Serum was collected at necropsy from mice sacrificed at day 21 or day 90 post vector administration. Antibodies to human IDS were evaluated by indirect ELISA. Dashed line indicates 2 SD above the mean titer in naïve serum from untreated animals. Most animals had no detectable antibodies (in the background level of naïve sera).

FIGS. 9A-9D illustrate the normal open field activity and Y maze performance in MPS II mice. Untreated MPS II mice and WT male littermates underwent behavioral testing at 4-5 months of age. Open field activity was measured by XY axis beam breaks for horizontal activity (FIG. 9A), Z axis beam breaks for vertical activity (FIG. 9B) and percent center beam breaks for center activity (FIG. 9C). Total arm entries (FIG. 9D) were recorded during an 8 min Y maze testing session.

FIGS. 10A-10B provides a manufacturing process flow diagram.

FIG. 11 is an image of apparatus (10) for intracisternal delivery of a pharmaceutical composition, including optional introducer needle for coaxial insertion method (28), which includes a 10 cc vector syringe (12), a 10 cc prefilled flush syringe (14), a T-connector extension set (including tubing (20), a clip at the end of the tubing (22) and connector (24)), a 22 G×5" spinal needle (26), and an optional 18 G×3.5" introducer needle (28). Also illustrated is the 4-way stopcock with swive male luer lock (16).

FIGS. 12A-12I illustrate encephalitis and transgene specific T cell responses in dogs treated with ICV AAV9. One-year-old MPS I dogs were treated with a single ICV or IC injection of an AAV9 vector expressing GFP. All animals were sacrificed 14 days after injection, except for I-567 which was found dead 12 days after injection. Brains were divided into coronal sections, which revealed gross lesions near the injection site (arrowheads) in ICV treated animals (FIGS. 12A to 12F). Tissue sections from the brain regions surrounding the gross lesions were stained with hematoxylin and eosin (FIGS. 12G and 12H). Original magnification=4× (left panel), and 20× (right panel). Peripheral blood mononuclear cells were collected from one ICV treated dog (I-565) at the time of necropsy, and T cell responses against the AAV9 capsid and human IDUA protein were measured by interferon-γ ELISPOT (FIG. 12I). T cell responses to the GFP transgene product were measured using a single pool of overlapping 15 amino acid peptides covering the full GFP sequence. The peptides comprising the AAV9 capsid protein were divided into three pools (designated pool A-C). *=positive response, defined as >3-fold background (unstimulated cells) and greater than 55 spots per million cells. Phytohemagglutinin (PHA) and ionomycin with phorbol 12-myristate 13-acetate (PMA) served as positive controls for T cell activation.

FIG. 13 is a bar chart illustrating vector biodistribution in dogs treated with ICV or IC AAV9. Dogs were sacrificed 14 days after injection with a single ICV or IC injection of an AAV9 vector expressing GFP, except for animal I-567 which was necropsied 12 days after injection. Vector genomes were detected in tissue samples by quantitative PCR. Values are expressed as vector genome copies per diploid cell (GC/diploid genome). Brain samples collected from the hippocampus or cerebral cortex are indicated as either injected or uninjected hemisphere for the ICV treated dogs; for the IC treated animals these are the right and left hemispheres, respectively. Samples were not collected for PCR from the injected cerebral hemisphere of animal I-567.

FIGS. 14A to 14H show GFP expression in brain and spinal cord of dogs treated with ICV or IC AAV9. GFP expression was evaluated by direct fluorescence microscopy of brain and spinal cord samples collected from dogs treated with ICV or IC injection of an AAV9 vector expressing GFP. Representative sections are shown for samples of frontal cortex, and from the anterior horn of the spinal cord collected at the cervical, thoracic, and lumbar levels. Original magnification=10×.

FIGS. 15A-15Q show stable transgene expression and absence of encephalitis in an MPS VII dog treated with ICV AAV9 expressing the lysosomal enzyme β-glucuronidase (GUSB). A 6-week-old dog with genetic deficiency of GUSB (a model of MPS VII) was treated with a single ICV injection of an AAV9 vector expressing GUSB. GUSB enzyme activity was measured in CSF samples collected at the time of injection and on day 7 and 21 after injection (FIG. 15A). The dog was sacrificed three weeks after injection. Gross and microscopic evaluation of the brain regions surrounding the injection site was performed (FIGS. 15B to 15D). Original magnification=4× (center panel), and 10× (right panel). GUSB activity was detected in brain and spinal cord sections using a substrate which produces a red product when cleaved by active GUSB (FIGS. 15E-15N). Representative sections are shown for samples of cerebral cortex, cerebellum, and the anterior horn of the spinal cord collected at the cervical, thoracic, and lumbar levels. Original magnification=4× (cortex and cerebellum), and 10× (spinal cord). Sections of cerebral cortex collected from an untreated MPS VII dog, a normal dog, and the MPS VII dog treated with ICV AAV9 were stained for the ganglioside GM3, which pathologically accumulates in the brains of MPS VII dogs (FIGS. 15O to 15Q). Original magnification=4×.

FIGS. 16A to 16B show contrast distribution after lumbar intrathecal injection in non-human primates (NHPs). Adult cynomolgus macaques received an intrathecal injection via lumbar puncture of an AAV9 vector diluted in 5 mL of Iohexol 180. The distribution of contrast along the spinal cord was evaluated by fluoroscopy. Representative images of the thoracic and cervical regions are shown. Contrast material (arrowheads) was visible along the entire length of the spinal cord within 10 minutes of injection in all animals.

FIG. 17 is a bar chart showing vector biodistribution in NHPs treated with intrathecal AAV9. NHPs were sacrificed 14 days after intrathecal injection via lumbar puncture of an AAV9 vector diluted in 5 mL of Iohexol 180. Two of the animals were placed in the Trendelenburg position for 10 minutes after injection. Vector genomes were detected in tissue samples by quantitative PCR. Values are expressed as vector genome copies per diploid cell (GC/diploid genome).

FIGS. 18A to 18H show GFP expression in brain and spinal cord of NHPs treated with intrathecal AAV9. GFP expression was evaluated by direct fluorescence microscopy of brain and spinal cord samples collected from NHPs treated with intrathecal injection of an AAV9 vector. The vector was administered by lumbar puncture. Two of the animals were placed in the Trendelenburg position for 10 minutes after injection. Representative sections are shown for samples of frontal cortex, and from the anterior horn of the spinal cord collected at the cervical, thoracic, and lumbar levels. Due to the presence of autofluorescent material in some NHP tissues, red channel images were captured to differentiate autofluorescence from GFP signal. Autofluorescence images are overlaid in magenta. Original magnification=4× (cortex), and 10× (spinal cord).

FIGS. 19A-19B illustrate elevated CSF spermine in MPS I. A high throughput LC/MS and GC/MS metabolite screen was performed on CSF samples from MPS I dogs (n=15) and normal controls (n=15). A heatmap of the top 100 differentially detected metabolites (ANOVA) is shown (FIG. 19A). The youngest animal in the MPS I cohort (28 days of age) is indicated by an asterisk. Spermine concentration was measured by a quantitative isotope dilution LC/MS assay in CSF samples from 6 infants with MPS I and 2 normal infants (FIG. 19B).

FIGS. 20A-20J illustrate spermine dependent aberrant neurite growth in MPS I neurons. Cortical neurons harvested from E18 wild-type or MPS I mouse embryos were treated with spermine (50 ng/mL) or the spermine synthase inhibitor APCHA 24 hours after plating. Phase contrast images were acquired 96 hours after plating (FIGS. 20A to 20D). Neurite number, length and branching were quantified for 45-65 randomly selected neurons from duplicate cultures per treatment condition by a blinded reviewer (FIGS. 20E&20H, 20G&20J, and 20F&20I). *** $p<0.0001$ (ANOVA followed by Dunnett's test).

FIGS. 21A-21K illustrate normalization of CSF spermine levels and brain GAP43 expression in MPS I dogs following gene therapy. Five MPS I dogs were treated with an intrathecal injection of an AAV9 vector expressing canine IDUA at one month of age. Two of the dogs (I-549, I-552) were tolerized to IDUA by liver directed gene therapy on postnatal day 1 in order to prevent the antibody response that is elicited to IDUA in some MPS I dogs. Six months after intrathecal vector injection, IDUA activity was measured in brain tissue (FIG. 21A). Brain storage lesions were assessed by staining for the lysosomal membrane protein LIMP2 (FIGS. 21B to 21H). GAP43 was measured in cortical brain samples by western blot (FIG. 21I) and quantified relative to β-actin by densitometry (FIG. 21J). CSF spermine was measured at the time of sacrifice by isotope dilution LC/MS (FIG. 21K). Untreated MPS I dogs (n=3) and normal dogs (n=2) served as controls. * $p<0.05$ (Kruskal-Wallis test followed by Dunn's test).

FIGS. 22A-22B illustrate the use of spermine as a CSF biomarker for evaluation of CNS directed gene therapy in MPS I. Six MPS I dogs tolerized to human IDUA at birth were treated with intrathecal AAV9 expressing human IDUA ($10^{12}$ GC/kg, n=2, $10^{11}$ GC/kg, n=2, $10^{10}$ GC/kg, n=2) at one month of age. CSF spermine levels were measured six months after treatment (FIG. 22A). Three MPS I cats were treated with intrathecal AAV9 expressing feline IDUA ($10^{12}$ GC/kg). CSF spermine was quantified six months after treatment (FIG. 22B). Untreated MPS I dogs (n=3) and normal dogs (n=2) served as controls.

Figure 27:
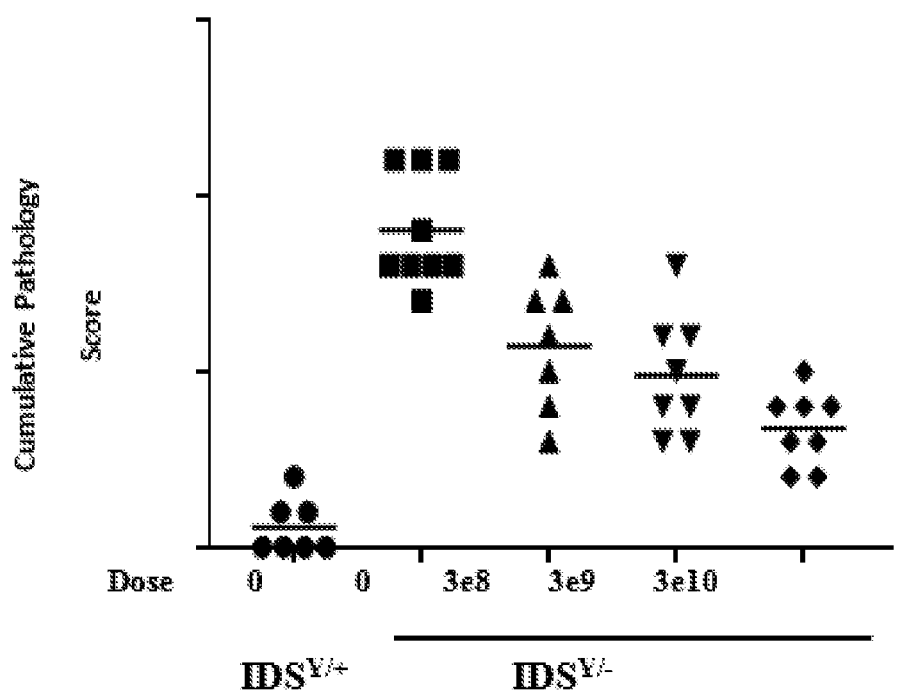

FIG. 27 illustrates dose dependent reduction of MPS II-related pathology findings in MPS II mice (IDS$^{y/-}$) treated with ICV AAV9.CB7.CI.hIDS.rBG with various doses (3e8, $3\times10^8$ GC; 3e9, $3\times10^9$ GC; 3e10, $3\times10^{10}$ GC). Cumulative Pathology Scores were evaluated and plotted on the y-axis. Heterozygous mice (IDS$^{y/-}$) served as control. Results demonstrated a dose dependent reduction of MPS II-related pathology findings in MPS II mice treated with ICV AAV9.CB7.CI.hIDS.rBG.

Figure 28:
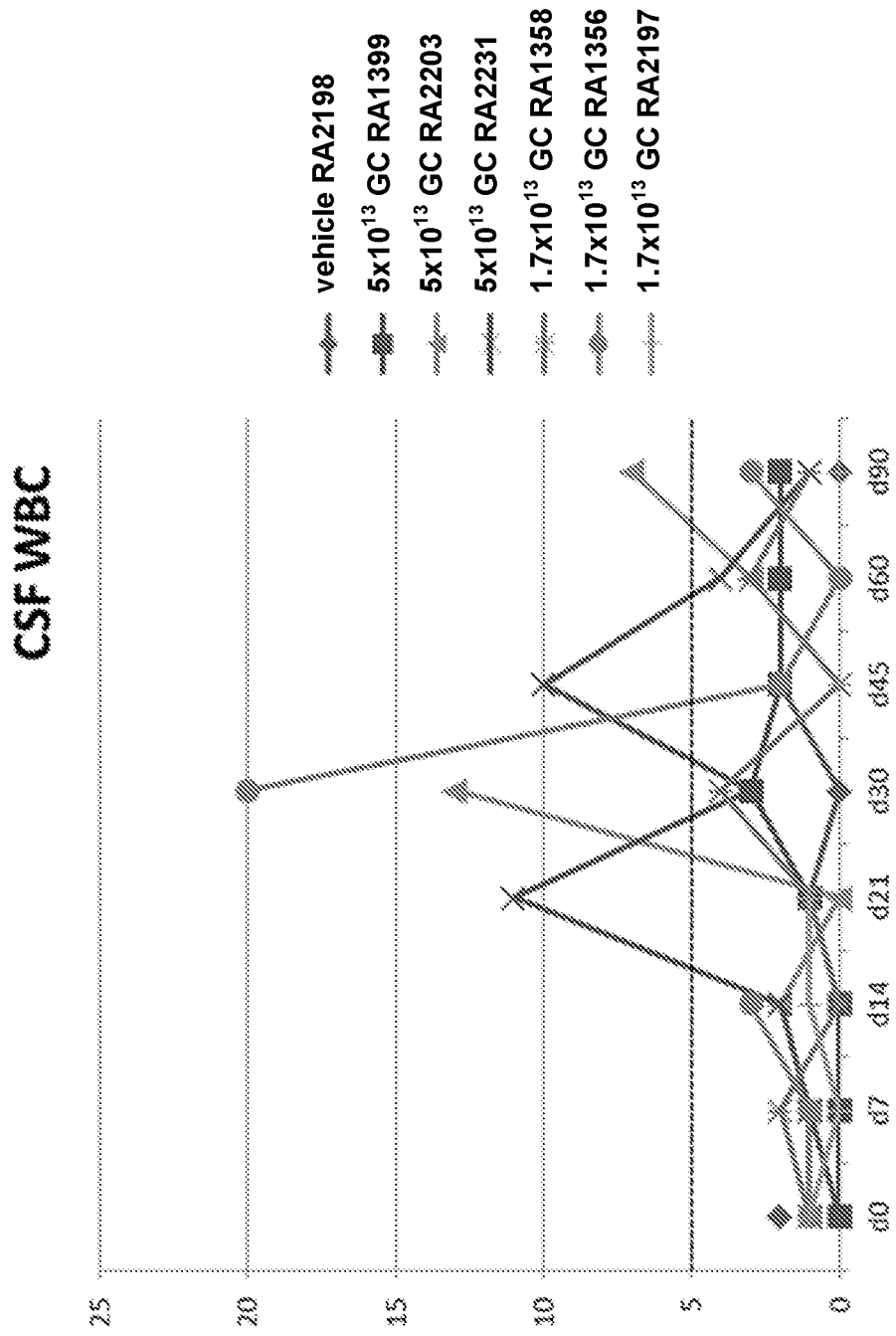

FIG. 28 illustrates CSF pleocytosis in the Rhesus Macaques described in Example 9. White blood cells (leukocytes, y axis) were counted in the CSF samples collected at various days (x axis, Day 0, Day 7, Day 14, Day 21, Day 30, Day 45, Day 60 and Day 90). Diamonds represent data from RA 2198 without treatment with AAV9.CB7.hIDS. Squares, triangles, and x represent data from RA 1399, RA 2203 and RA 2231 treated with $5\times10^{13}$ GC of AAV9.CB7.hIDS respectively. *, circles and + represent data from RA 1358, RA 1356 and RA 2197 treated with $1.7\times10^{13}$ GC of AAV9.CB7.hIDS respectively.

FIG. 29 shows ELISA results measuring anti hIDS antibody developed in the serum of NHP on Day 60 as described in Example 9. Dilution was plotted as x axis while optical density (OD) as y axis. Diamonds represent data from RA2198 without treatment with AAV9.CB7.hIDS. Squares represent data from RA2197 treated with $1.7\times10^{13}$ GC of AAV9.CB7.hIDS while triangles and x represent that of RA 2203 and RA 2231 treated with $5\times10^{13}$ GC of AAV9.CB7.hIDS respectively.

5. DETAILED DESCRIPTION OF THE INVENTION

Provided herein is a pharmaceutical composition which is administrable to a human subject in need thereof by intrathecal injection. In certain embodiments, use of a pharmaceutical composition containing the rAAV.hIDS described herein are used in preparing a medicament administrable to a human subject in need thereof by intrathecal injection. The human subject (patient) may have been previously diagnosed with mucopolysaccharidosis II (MPS II) or severe Hunter syndrome.

Potency can be measured by in vitro cell culture assays, e.g., the in vitro potency assay described in Example 5G herein, in which HEK293 or Huh7 cells are transduced with a known multiplicity of rAAV GCs per cell and the supernatant is assayed for IDS activity 72 hours post-transduction using the 4MU-iduronide enzymatic assay.

Such rAAV.hIDS vector preparations can be administered to pediatric or adult human subjects by intrathecal/intracisternal injection to achieve therapeutic levels of hIDS expression in the CNS. Patients who are candidates for treatment are pediatric and adult patients with severe or attenuated MPS II disease. Severe disease is defined as early-stage neurocognitive deficit with a developmental quotient (DQ) (BSID-III) that is at least 1 standard deviation below the mean or documented historical evidence of a decline of greater than 1 standard deviation on sequential testing.

Therapeutically effective intrathecal/intracisternal doses of the rAAV.hIDS for patients with Hunter syndrome range from about $1\times10^{11}$ to $7.0\times10^{14}$ GC (flat doses)—the equivalent of $10^9$ to $10^{11}$ GC/g brain mass of the patient. Alternatively, the following therapeutically effective flat doses can be administered to patients of the indicated age group:

In certain embodiments, the dose administered to an MPSII patient is $1.3\times10^{10}$ GC/g brain mass. In certain embodiments, the dose administered to an MPSII patient is $6.5\times10^{10}$ GC/g brain mass. In certain embodiments, the dose administered to an MPSII patient is $1.9\times10^{10}$ GC/g brain mass. In certain embodiments, the dose administered to an MPSII patient is $9.4\times10^{10}$ GC/g brain mass.

In certain embodiments, the dose administered to an MPSII patient is $1.3\times10^{9}$ GC/g brain mass. In certain embodiments, the dose administered to an MPSII patient is $1.3\times10^{11}$ GC/g brain mass. In certain embodiments, the dose administered to a MPSII patient is $1.8\times10^{11}$ GC/g brain mass. In certain embodiments, the dose administered to a MPSII patient is $2.15\times10^{11}$ GC/g brain mass. In certain embodiments, the dose administered to a MPSII patient is $5.5\times10^{11}$ GC/g brain mass.

In certain embodiments, because of the relatively rapid brain growth that occurs early in a developing child, the total dose of AAV9.hIDS administered IC depends on the assumed brain mass across different age strata. For brain mass by age for the study subjects see, e.g., (AS Dekaban, Ann Neurol, 1978 October; 4(4): 345-56.

The goal of the treatment is to functionally replace the patient's defective iduronate-2-sulfatase via rAAV-based CNS-directed gene therapy as a viable approach to treat disease. Efficacy of the therapy can be measured by assessing (a) the prevention of neurocognitive decline in patients with MPS II (Hunter syndrome); and (b) reductions in biomarkers of disease, e.g., GAG levels and/or enzyme activity (IDS or hexosaminidase) in the CSF, serum and/or urine, and/or liver and spleen volumes. Neurocognition in infants can be measured via Bayley Scales of Infant and Toddler Development, Third Ed., BSID-III. Neurocognitive and adaptive behavioral assessments (e.g., using Bayley Scales of Infant Development and Vineland Adaptive Behavior Scales, respectively) can be performed.

Prior to treatment, the MPS II patient can be assessed for neutralizing antibodies (Nab) to the capsid of the rAAV vector used to deliver the hIDS gene. Such Nabs can interfere with transduction efficiency and reduce therapeutic efficacy. MPS II patients that have a baseline serum Nab titer ≤1:5 are good candidates for treatment with the rAAV.hIDS gene therapy protocol. Treatment of MPS II patients with titers of serum Nab >1:5 may require a combination therapy, such as transient co-treatment with an immunosuppressant before and/or during treatment with rAAV.hIDS vector delivery. Optionally, immunosuppressive co-therapy may be used as a precautionary measure without prior assessment of neutralizing antibodies to the AAV vector capsid and/or other components of the formulation. In certain embodiments, prior immunosuppression therapy may be desirable to prevent potential adverse immune reaction to the hIDS transgene product, especially in patients who have virtually no levels of IDS activity, where the transgene product may be seen as "foreign." While a reaction similar to that observed in animals may not occur in human subjects, as a precaution immunosuppression therapy is recommended for all recipients of rAAV-hIDS.

Combinations of gene therapy delivery of the rAAV.hIDS to the CNS accompanied by systemic delivery of hIDS are encompassed by the methods of the invention. Systemic delivery can be accomplished using ERT infusions of idursulfase (e.g., using Elaprase), or additional gene therapy using an rAAV.hIDS with tropism for the liver (e.g., an rAAV.hIDS bearing an AAV8 capsid).

In certain embodiments, the patient is administered an AAV.hIDS via liver-directed injections in order to tolerize the patient to hIDS, and the patient is subsequently administered AAV.hIDS via intrathecal injections when the patient is an infant, child, and/or adult to express therapeutic concentrations of hIDS in the CNS.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular, suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

As used herein, a "therapeutically effective amount" refers to the amount of the AAV.hIDS composition which delivers and expresses in the target cells an amount of enzyme sufficient to ameliorate or treat one or more of the symptoms of MPS II. "Treatment" may include preventing the worsening of the symptoms of one of the MPS II syndromes and possibly reversal of one or more of the symptoms thereof. For example, a therapeutically effective amount of rAAV.hIDS is the amount which improves neurocognitive function in a patient having MPS II. Improvement of such neurocognitive function may be measured by assessing subjects' neurocognitive developmental quotient (DQ), using Bayley Scales of Infant and Toddler Development. Improvement of neurocognitive function may also be measured by assessing subjects' intelligence quotient (IQ), using methods known in the art including but not limited to, e.g., use of the Wechsler Abbreviated Scale of Intelligence (WASI) (IQ), Bayley's Infantile Development Scale, the Hopkins Verbal Learning Test (memory), and/or the Tests of Variables of Attention (TOVA). In another embodiment, a therapeutically effective amount of rAAV.hIDS is the amount which decreases pathogenic GAG, heparan sulfate, and/or hexosaminidase concentration in urine and/or cerebrospinal fluid and/or serum and/or other tissues. In still other embodiments, correction of corneal clouding may be observed, correction of lesions in the central nervous system (CNS) is observed, and/or reversal of perivascular and/or meningeal gag storage is observed.

In certain embodiments, therapeutic efficacy may be determined using one or more of the following: biomarkers in plasma (total GAG, dermatan sulfate, heparan sulfate, I2S activity), CSF (total GAG, dermatan sulfate, heparan sulfate, I2S activity) and urine (total GAG, dermatan sulfate, heparan sulfate); Neurodevelopmental parameters of cognitive and adaptive function: Bayley Scales of Infant and Toddler Development, 3rd Edition (BSID-III) or Kaufman Assessment Battery for Children, 2nd Edition (KABC-II); and/or Vineland Adaptive Behavior Scales, 3rd Edition, Comprehensive Interview Form (VABS-III). Optionally, viral shedding may be monitored by vector concentration in CSF, plasma, and urine by quantitative polymerase chain reaction (PCR) to AAV9.hIDS deoxyribonucleic acid (DNA). In certain embodiments, therapeutic efficacy may be monitored by one or more of: Immunogenicity measurements, including one or more of Neutralizing antibody titers to AAV9 and binding antibody titers to I2S in CSF and serum; enzyme-linked ImmunoSpot (ELISPOT) assay: T-cell response to AAV9 and I2S; Flow cytometry: AAV- and I2S-specific regulatory T cells; CNS structural abnormalities assessed by magnetic resonance imaging (MRI) of the brain; Liver and spleen volume assessed by MRI and ultrasound of the abdomen; Auditory capacity changes measured by auditory brainstem response (ABR) testing; Plasma and urine total GAG, heparan sulfate and dermatan sulfate in subjects who temporarily discontinue IV ERT (ELAPRASE®).

A "therapeutically effective amount" may be determined based on an animal model, rather than a human patient. Examples of a suitable murine model are described herein.

As used herein a "functional human iduronate-2-sulfatase" refers to a human iduronate-2-sulfatase enzyme which functions normally in humans without MPS II or an associated syndrome. Conversely, a human iduronate-2-sulfatase enzyme variant which causes MPS II or an associated syndrome is considered non-functional. In one embodiment, a functional human iduronate-2-sulfatase has the amino acid sequence of a wild-type human iduronate-2-sulfatase described by Wilson et al, Proc. Natl. Acad. Sci. U.S.A. 87 (21): 8531-8535 (1990), NCBI Reference Sequence NP_000193.1, reproduced in SEQ ID NO: 2 (550 amino acids); this preproprotein includes a signal peptide (amino acids 1 to 25), a pro-peptide (amino acids 26 to 33) and a mature peptide composed of amino acids 34 to 455 (a 42 kDa chain) and amino acids 456 to 550 (a 14 kDa chain) See, also, UniProtKB/Swiss-Prot (P22304.1)

As used herein, the term "NAb titer" refers to a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

As used herein, an "expression cassette" refers to a nucleic acid molecule which comprises an IDS gene, promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the IDS coding sequence described herein flanked by packaging signals of the viral genome and other expression control sequences such as those described herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, "recombinant AAV9 viral particle" refers to nuclease-resistant particle (NRP) which has an AAV9 capsid, the capsid having packaged therein a heterologous nucleic acid molecule comprising an expression cassette for a desired gene product. Such an expression cassette typically contains an AAV 5' and/or 3' inverted terminal repeat sequence flanking a gene sequence, in which the gene sequence is operably linked to expression control sequences. These and other suitable elements of the expression cassette are described in more detail below and may alternatively be referred to herein as the transgene genomic sequences. This may also be referred to as a "full" AAV capsid. Such a rAAV viral particle is termed "pharmacologically active" when it delivers the transgene to a host cell which is capable of expressing the desired gene product carried by the expression cassette.

In many instances, rAAV particles are referred to as "DNase resistant." However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a transgene to a host cell and protects these packaged genomic sequences from degradation (digestion) during nuclease incubation steps designed to remove contaminating nucleic acids which may be present from the production process.

As used herein, a "vector genome" refers to the nucleic acid sequence packaged within an AAV capsid (e.g., AAV9). Generally, for AAV, AAV ITRs are present to enable packaging of an expression cassette which comprises the nucleic acid sequence encoding the transgene product (e.g., hIDS) and its regulatory sequences. In the examples below, the expression cassette is flanked at its extreme 5' end and its extreme 3' end by AAV ITRs.

Suitably, the vector genome of a recombinant AAV (rAAV) lacks AAV sequences encoding the AAV cap gene and lacks AAV sequences encoding the AAV rep gene product, to afford a replication-incompetent rAAV.

As used herein, "AAV9 capsid" refers to the AAV9 having the amino acid sequence of GenBank accession: AAS99264, is incorporated by reference herein and the AAV vp1 capsid protein is reproduced in SEQ ID NO: 13. Some variation from this encoded sequence is encompassed by the present invention, which may include sequences having about 99% identity to the referenced amino acid sequence in GenBank accession:AAS99264, SEQ ID NO: 13 and U.S. Pat. No. 7,906,111 (also WO 2005/033321) (i.e., less than about 1% variation from the referenced sequence). Such AAV may include, e.g., natural isolates (e.g., hu31 or hu32), or variants of AAV9 having amino acid substitutions, deletions or additions, e.g., including but not limited to amino acid substitutions selected from alternate residues "recruited" from the corresponding position in any other AAV capsid aligned with the AAV9 capsid; e.g., such as described in U.S. Pat. Nos. 9,102,949, 8,927,514, US2015/349911; and WO 2016/049230A1. However, in other embodiments, other variants of AAV9, or AAV9 capsids having at least about 95% identity to the above-referenced sequences may be selected. See, e.g., US Published Patent Application No. 2015/0079038. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

The term "AAV9 intermediate" or "AAV9 vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "about" encompasses a variation within and including ±10%, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

The use of a replication deficient AAV to deliver a hIDS gene to the CNS of patients (human subjects) diagnosed with MPS II is provided. The recombinant AAV ("rAAV") vector used for delivering the hIDS gene ("rAAV.hIDS") has tropism for the CNS (e.g., an rAAV bearing an AAV9 capsid), and the hIDS transgene is controlled by specific expression control elements, e.g., a hybrid of cytomegalovirus (CMV) enhancer and the chicken beta actin promoter (CB7). In certain embodiments, pharmaceutical compositions suitable for intrathecal, intracisternal, and systemic administration, which comprise a suspension of rAAV.hIDS vectors in a formulation buffer comprising a physiologically compatible aqueous buffer, a surfactant and optional excipients are provided. The rAAV suspension is further characterized in that:

(i) the rAAV Genome Copy (GC) titer is at least $1.0 \times 10^{13}$ GC/mL;

(ii) the rAAV Empty/Full particle ratio is between 0.01 and 0.05 (95%-99% free of empty capsids) as determined by SDS-PAGE analysis (see Example 5D); in other embodiments, the rAAV9.hIDS provided herein are at least about 80%, at least about 85%, or at least about 90% free of empty capsids; and/or (iii) a dose of at least about $4 \times 10^8$ GC/g brain mass to about $4 \times 10^{11}$ GC/g brain mass of the rAAV suspension has potency.

In certain embodiments, the dose administered is at least $1.3 \times 10^{10}$ GC/g brain mass, at least $1.9 \times 10^{10}$ GC/g brain mass, at least $6.5 \times 10^{10}$ GC/g brain mass, or $9.4 \times 10^{10}$ GC/g brain mass, or about $4 \times 10^{11}$ GC/g brain mass.

In certain embodiments, the dose administered is $1.9 \times 10^{11}$ GC/brain mass to $5.6 \times 10^{11}$ GC/g brain mass, with or without immunosuppression. In certain embodiments, immunosuppression is from day −21 to day 20 and sirolimus.

Potency can be measured by in vitro cell culture assays, e.g., the in vitro potency assay described in Example 5G, in which HEK293 cells are transduced with a known multiplicity of rAAV GCs per cell and the supernatant is assayed for IDS activity 72 hours post-transduction. The function (activity) and/or the potency of hIDS may be measured in a suitable in vitro assay, e.g., using the 4MU-iduronide enzymatic assay which measures the ability of hIDS to cleave a fluorogenic substrate, 4-Methylumbelliferyl alpha-L-iduronide-2 sulfate. The specific activity is >7,500 pmol/min/µg, as measured under the described conditions. See Activity Assay Protocol on www.RnDSystems.com. Other suitable methods of measuring enzyme activity have been described [see, e.g., Kakkis, E. D., et al (1994). Protein Expression Purif. 5: 225-232; Rome, L. H., et al (1979). Proc. Natl. Acad. Sci. USA 76: 2331-2334], including those described herein. Activity may also be assessed using the method described, e.g., E. Oussoren, et al, Mol Genet Metab. 2013 August; 109(4):377-81. doi: 10.1016/j.ymgme.2013.05.016. Epub 2013 Jun. 4. Patients who are candidates for treatment are pediatric and adult patients with MPS II (Hunter syndrome) and/or the symptoms associated with MPS II.

The goal of the treatment is to functionally replace the patient's defective iduronate-2-sulfatase via rAAV-based CNS-directed gene therapy as a viable approach to treat disease. As expressed from the rAAV vector described herein, expression levels of at least about 2% as detected in the CSF, serum, neurons, or other tissue, may provide therapeutic effect. However, higher expression levels may be achieved. Such expression levels may be from 2% to about 100% of normal functional human IDS levels. In certain embodiments, higher than normal expression levels may be detected in CSF, serum, or other tissue.

Efficacy of the therapy can be measured by assessing (a) the prevention of neurocognitive decline in patients with MPS II (Hunter syndrome); and (b) reductions in biomarkers of disease, e.g., GAG levels and/or enzyme activity in the CSF, serum and/or urine, and/or liver and spleen volumes. Neurocognition in infants can be measured via Bayley Scales of Infant and Toddler Development, Third Ed., BSID-III. Neurocognitive and adaptive behavioral assessments (e.g., using Bayley Scales of Infant Development and Vineland Adaptive Behavior Scales, respectively) can be performed.

Combinations of gene therapy delivery of the rAAV.hIDS to the CNS accompanied by systemic delivery of hIDS are encompassed by certain embodiments. Systemic delivery can be accomplished using ERT (e.g., using Elaprase®), or additional gene therapy using an rAAV.hIDS with tropism for the liver (e.g., an rAAV.hIDS bearing an AAV8 capsid).

Certain embodiments also provide for the manufacture and characterization of the rAAV.hIDS pharmaceutical compositions (Example 4, infra).

5.1. AAV.hIDS Constructs and Formulations 5.1.1. Expression Cassettes

An AAV vector that comprises an expression cassette containing a hIDS gene characterized by having the nucleotide sequence of SEQ ID NO: 1 (CCDS 14685.1) is provided. This sequence is the published gene sequence encoding Genbank NP000193.1, also enclosed herein as SEQ ID NO: 2. In another embodiment, the expression cassette contains a hIDS gene characterized by having the nucleotide sequence at least about 75% identical to SEQ ID NO: 1 and encodes a functional human iduronate-2-sulfatase. In another embodiment, the expression cassette contains a hIDS gene characterized by having the nucleotide sequence at least about 80% identical to SEQ ID NO: 1 and encodes a functional human iduronate-2-sulfatase. In another embodiment, the sequence is at least about 85% identity to SEQ ID NO: 1 or at least about 90% identical to SEQ ID NO: 1 and encodes a functional human iduronate-2-sulfatase. In one embodiment, the sequence is at least about 95% identical to SEQ ID NO: 1, at least about 97% identical to SEQ ID NO: 1, or at least about 99% identical to SEQ ID NO: 1 and encodes a functional human iduronate-2-sulfatase. In one embodiment, the sequence is at least about 77% identical to SEQ ID NO: 1. In another embodiment, the expression cassette contains a hIDS coding sequence of nt 1177 to nt 2829 of SEQ ID NO: 8, also shown as nt 1937 to nt 3589 of SEQ ID NO: 11. In another embodiment, the expression cassette contains a hIDS coding sequence at least about 75%, about 80%, about 85%, about 90%, about 95%, about 97%, about 98% or about 99% identical to nt 1177 to nt 2829 of SEQ ID NO: 8 (also shown as nt 1937 to nt 3589 of SEQ ID NO: 11).

In another embodiment, a functional human iduronate-2-sulfatase may include a synthetic amino acid sequence in which all or a portion of the first 25 amino acids of the preprotein SEQ ID NO: 2, which correspond to the leader (signal) peptide, are replaced with a heterologous leader peptide. This leader peptide, e.g., such as the leader peptides from interleukin-2 (IL-2) or oncostatin, can improve transport of the enzyme out of the cell through its secretory pathway into the circulation. Suitable leader peptides are preferably, although not necessarily of human original. Suitable leader peptides may be chosen from proline.bic.nus.edu.sg/spdb/zhang270.htm, which is incorporated by reference herein, or may be determined using a variety of computational programs for determining the leader (signal) peptide in a selected protein. Although not limited, such sequences may be from about 15 to about 50 amino acids in length, or about 19 to about 28 amino acids in length, or may be larger or smaller as required. In addition, at least one in vitro assay has been described as being useful to assess the enzymatic activity of an IDS enzyme [see, e.g., Dean et al, Clinical Chemistry, 2006 April; 52(4): 643-649]. In addition to removal of all or a portion of the preproprotein (amino acids 1 to 25 of SEQ ID NO: 2), all or a portion of the proprotein (amino acids 26 to 33 of SEQ ID NO: 2) may be removed and optionally replaced with a heterologous mature peptide.

In another embodiment, the AAV vector that comprises an expression cassette further containing a SUMF1 gene characterized by having the nucleotide sequence of nt 3423 to nt 4547 of SEQ ID NO: 5 (CDS of GenBank: AB448737.1) is provided. This sequence is the published gene sequence encoding NCBI Reference Sequence: NP_877437.2, which is also enclosed herein as SEQ ID NO: 7 and SEQ ID NO: 10. Some studies have suggested that expression of sulfatases such as IDS can be limited by the availability of the sulfatase modifying factor, SUMF1, which is required for post-translational modification of IDS (Fraldi, et al, Biochemical J, 2007: 403: 305-312). In another embodiment, the expression cassette contains a SUMF1 gene characterized by having the nucleotide sequence at least about 80% identical to nt 3423 to nt 4547 of SEQ ID NO: 5 and encodes a functional human SUMF1. In another embodiment, the sequence is at least about 85% identity to nt 3423 to nt 4547 of SEQ ID NO: 5 or at least about 90% identical to nt 3423 to nt 4547 of SEQ ID NO: 5 and encodes a functional human SUMF1. In one embodiment, the sequence is at least about 95%, about 97%, or about 99% identical to nt 3423 to nt 4547 of SEQ ID NO: 5 and encodes a functional human SUMF1. In one embodiment, the sequence is at least about 76.6% identical to nt 3423 to nt 4547 of SEQ ID NO: 5. In another embodiment, the expression cassette contains a hSUMF1 coding sequence of nt 3423 to nt 4553 of SEQ ID NO: 8. In another embodiment, the expression cassette contains a hSUMF1 coding sequence at least about 75%, about 80%, about 85%, about 90%, about 95%, about 97%, about 98% or about 99% identical to nt 3423 to nt 4553 of SEQ ID NO: 8.

In one embodiment, an AAV vector that comprises an expression cassette containing a hIDS encoding sequence and a hSUMF1 encoding sequence is provided. In another embodiment, the hIDS encoding sequence and hSUMF1 encoding sequence were linked by an internal ribosome entry site (IRES). In a further embodiment, the IRES has a sequence of nt 2830 to nt 3422 of SEQ ID NO: 5 or nt 2830 to nt 3422 of SEQ ID NO: 8. In another embodiment, the expression cassette contains nt 1177 to nt 4547 of SEQ ID NO: 5 or nt 1177 to nt 4553 of SEQ ID NO: 8 comprising an hIDS encoding sequence, an IRES and an hSUMF1 encoding sequence.

Identity or similarity with respect to a sequence is defined herein as the percentage of amino acid residues in the candidate sequence that are identical (i.e., same residue) or similar (i.e., amino acid residue from the same group based on common side-chain properties, see below) with the peptide and polypeptide regions provided herein, after aligning the sequences and introducing gaps, if necessary, to achieve the maximum percent sequence identity. Percent (%) identity is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology. There are a number of algorithms, and computer programs based thereon, which are available to be used the literature and/or publicly or commercially available for performing alignments and percent identity. The selection of the algorithm or program is not a limitation of the present invention.

Examples of suitable alignment programs including, e.g., the software CLUSTALW under Unix and then be imported into the Bioedit program (Hall, T. A. 1999, BioEdit: a user-friendly biological sequence alignment editor and analysis program for Windows 95/98/NT. Nucl. Acids. Symp. Ser. 41:95-98); the Clustal Omega available from EMBL-EBI (Sievers, Fabian, et al. "Fast, scalable generation of high-quality protein multiple sequence alignments using Clustal Omega." Molecular systems biology 7.1 (2011): 539 and Goujon, Mickael, et al. "A new bioinformatics analysis tools framework at EMBL-EBI." Nucleic acids research 38.suppl 2 (2010): W695-W699); the Wisconsin Sequence Analysis Package, version 9.1 (Devereux J. et al., Nucleic Acids Res., 12:387-395, 1984, available from Genetics Computer Group, Madison, Wis., USA). The programs BESTFIT and GAP, may be used to determine the % identity between two polynucleotides and the % identity between two polypeptide sequences.

Other programs for determining identity and/or similarity between sequences include, e.g, the BLAST family of programs available from the National Center for Biotechnology Information (NCB), Bethesda, Md., USA and accessible through the home page of the NCBI at www.ncbi.nlm.nih.gov), the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used; and FASTA (Pearson W. R. and Lipman D. J., Proc. Natl. Acad. Sci. USA, 85:2444-2448, 1988, available as part of the Wisconsin Sequence Analysis Package). SeqWeb Software (a web-based interface to the GCG Wisconsin Package: Gap program).

In some embodiments, the cassette is designed to be expressed from a recombinant adeno-associated virus, and the vector genome also contains AAV inverted terminal repeats (ITRs). In one embodiment, the rAAV is pseudotyped, i.e., the AAV capsid is from a different source AAV than that the AAV which provides the ITRs. In one embodiment, the ITRs of AAV serotype 2 are used. However, ITRs from other suitable sources may be selected. Optionally, the AAV may be a self-complementary AAV.

The expression cassettes described herein utilized AAV 5' inverted terminal repeat (ITR) and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and/or 3' ITRs are used. Where a pseudotyped AAV is to be produced, the ITRs in the expression are selected from a source which differs from the AAV source of the capsid. For example, AAV2 ITRs may be selected for use with an AAV capsid having a particular efficiency for targeting CNS or tissues or cells within the CNS. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

In one embodiment, the expression cassette is designed for expression and secretion in the central nervous system (CNS), including the cerebral spinal fluid and brain. In a particularly desired embodiment, the expression cassette is useful for expression in both the CNS and in the liver, thereby allowing treatment of both the systemic and CNS-related effects of MPS II. For example, the inventors have observed that certain constitutive promoters (e.g., CMV) do not drive expression at desired levels when delivered intrathecally, thereby providing suboptimal hIDS expression levels. However, the chicken beta-actin promoter drives expression well both upon intrathecal delivery and systemic delivery. Thus, this is a particularly desirable promoter. Other promoters may be selected, but expression cassettes containing same may not have all of the advantages of those with a chicken beta-actin promoter. A variety of chicken beta-actin promoters have been described alone, or in combination with various enhancer elements (e.g., CB7 is a chicken beta-actin promoter with cytomegalovirus enhancer elements, a CAG promoter, which includes the promoter, the first exon and first intron of chicken beta actin, and the splice acceptor of the rabbit beta-globin gene), a CBh promoter [S J Gray et al, Hu Gene Ther, 2011 September; 22(9): 1143-1153.

Examples of promoters that are tissue-specific are well known for liver and other tissues (albumin, Miyatake et al., (1997) J. Vivol., 71:5124-32; hepatitis B virus core promoter, Sandig et al., (1996) Gene Ther., 3:1002-9; alpha-fetoprotein (AFP), Arbuthnot et al., (1996) Hum. Gene Ther., 7:1503-14), bone osteocalcin (Stein et al., (1997) Mol. Biol. Rep., 24:185-96); bone sialoprotein (Chen et al., (1996) J. Bone Miner. Res., 11:654-64), lymphocytes (CD2, Hansal et al., (1998) J Immunol., 161:1063-8; immunoglobulin heavy chain; T cell receptor chain), neuronal such as neuron-specific enolase (NSE) promoter (Andersen et al., (1993) Cell. Mol. Neurobiol., 13:503-15), neurofilament light-chain gene (Piccioli et al., (1991) Proc. Natl. Acad. Sci. USA, 88:5611-5), and the neuron-specific vgf gene (Piccioli et al., (1995) Neuron, 15:373-84), among others. Alternatively, a regulatable promoter may be selected. See, e.g., WO 2011/126808B2, incorporated by reference herein.

In one embodiment, the expression cassette comprises one or more expression enhancers. In one embodiment, the expression cassette contains two or more expression enhancers. These enhancers may be the same or may be different. For example, an enhancer may include an Alpha mic/bik enhancer or a CMV enhancer. This enhancer may be present in two copies which are located adjacent to one another. Alternatively, the dual copies of the enhancer may be separated by one or more sequences. In still another embodiment, the expression cassette further contains an intron, e.g, a chicken beta-actin intron, a human f3-globulin intron, and/or a commercially available Promega® intron. Other suitable introns include those known in the art, e.g., such as are described in WO 2011/126808.

Further, an expression cassette is provided with a suitable polyadenylation signal. In one embodiment, the polyA sequence is a rabbit globulin poly A. See, e.g., WO 2014/151341. Alternatively, another polyA, e.g., a human growth hormone (hGH) polyadenylation sequence, an SV40 poly A, SV50 polyA, or a synthetic polyA. Still other conventional regulatory elements may be additional or optionally included in an expression cassette.

An exemplary rAAV.hIDS vector genome is shown in nt 2 to nt 3967 of SEQ ID NO: 3, nt 11 to nt 4964 of SEQ ID NO: 5, nt 11 to nt 4964 of SEQ ID NO: 8, nt 2 to nt 3967 of SEQ ID NO: 11, or nt 2 to nt 3965 of SEQ ID NO: 14.

5.1.2. Production of rAAV.hIDS Viral Particles

Figure 1:
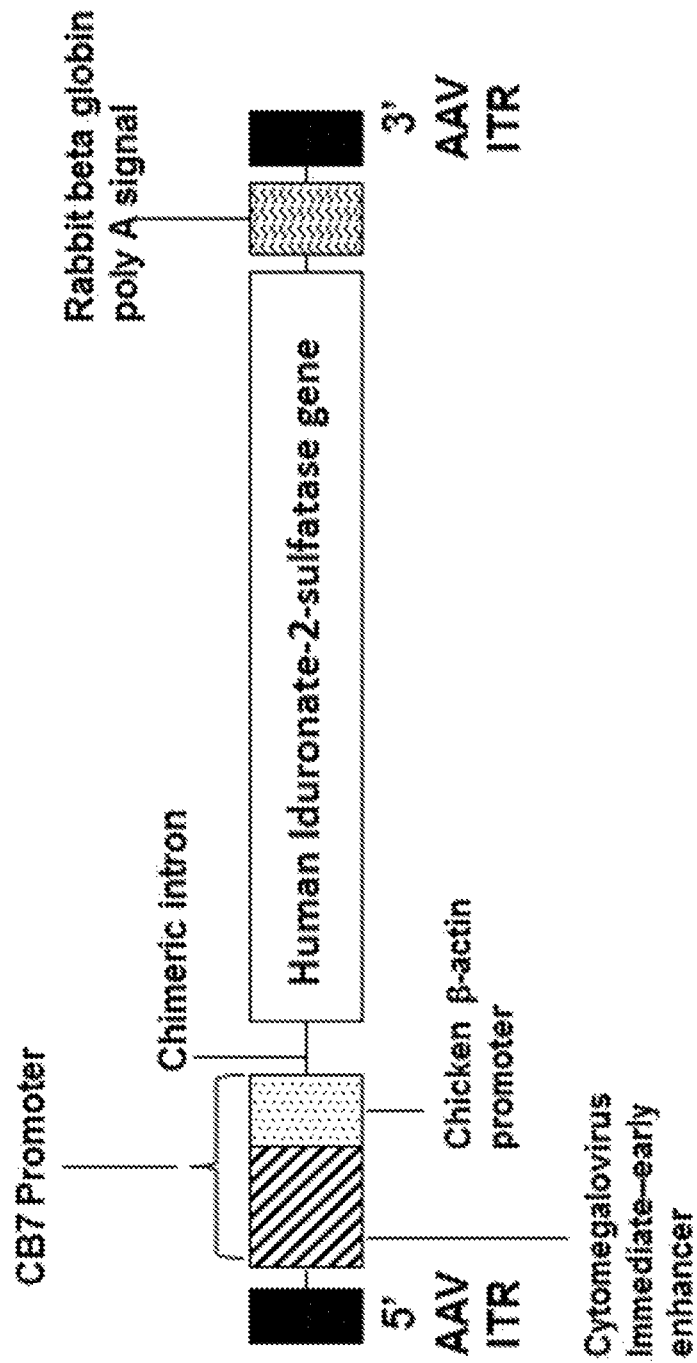

In one embodiment, a recombinant adeno-associated virus (rAAV) particle having an AAV capsid and having packaged therein a AAV inverted terminal repeats, a human iduronate-2-sulfatase (hIDS) gene under the control of regulatory sequences which control expression thereof, wherein said hIDS gene has a sequence shown in SEQ ID NO: 1 (FIG. 1) or a sequence at least about 95% identical thereto which encodes a functional human iduronate-2-sulfatase is provided. In one embodiment, the hIDS expression cassette is flanked by an AAVS' ITR and an AAV3' ITR. In another embodiment, the AAV is a single stranded AAV.

For intrathecal and/or intracisternal delivery, AAV9 is particularly desirable. Optionally, an rAAV9.hIDS vector as described herein may be co-administered with a vector designed to specifically target the liver. Any of a number of rAAV vectors with liver tropism can be used. Examples of AAV which may be selected as sources for capsids of rAAV include, e.g., rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397], AAV3B; AAVdj [US 2010/0047174]. One particularly desirable rAAV is AAV2/8.TBG.hIDS.co.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

Methods of preparing AAV-based vectors are known. See, e.g., US Published Patent Application No. 2007/0036760 (Feb. 15, 2007), which is incorporated by reference herein. The use of AAV capsids of AAV9 are particularly well suited for the compositions and methods described herein. The sequences of AAV9 and methods of generating vectors based on the AAV9 capsid are described in U.S. Pat. No. 7,906,111; US2015/0315612; WO 2012/112832; which are incorporated herein by reference. However, other AAV capsids may be selected or generated. For example, the sequences of AAV8 and methods of generating vectors based on the AAV8 capsid are described in U.S. Pat. No. 7,282,199 B2, U.S. Pat. Nos. 7,790,449, and 8,318,480, which are incorporated herein by reference. The sequences of a number of such AAV are provided in the above-cited U.S. Pat. No. 7,282,199 B2, U.S. Pat. Nos. 7,790,449, 8,318,480, and 7,906,111, and/or are available from GenBank. The sequences of any of the AAV capsids can be readily generated synthetically or using a variety of molecular biology and genetic engineering techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, oligonucleotides encoding peptides (e.g., CDRs) or the peptides themselves can generated synthetically, e.g., by the well-known solid phase peptide synthesis methods (Merrifield, (1962) J. Am. Chem. Soc., 85:2149; Stewart and Young, Solid Phase Peptide Synthesis (Freeman, San Francisco, 1969) pp. 27-62). These and other suitable production methods are within the knowledge of those of skill in the art and are not a limitation of the present invention.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid; a functional rep gene; an expression cassette composed of, at a minimum, AAV inverted terminal repeats (ITRs) and a transgene; and sufficient helper functions to permit packaging of the expression cassette into the AAV capsid protein.

To calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAV9 particles having packaged genomic sequences from genome-deficient AAV9 intermediates involves subjecting a suspension comprising recombinant AAV9 viral particles and AAV 9 capsid intermediates to fast performance liquid chromatography, wherein the AAV9 viral particles and AAV9 intermediates are bound to a strong anion exchange resin equilibrated at a pH of 10.2, and subjected to a salt gradient while monitoring eluate for ultraviolet absorbance at about 260 and about 280. Although less optimal for rAAV9, the pH may be in the range of about 10.0 to 10.4. In this method, the AAV9 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured.

Figure 11:
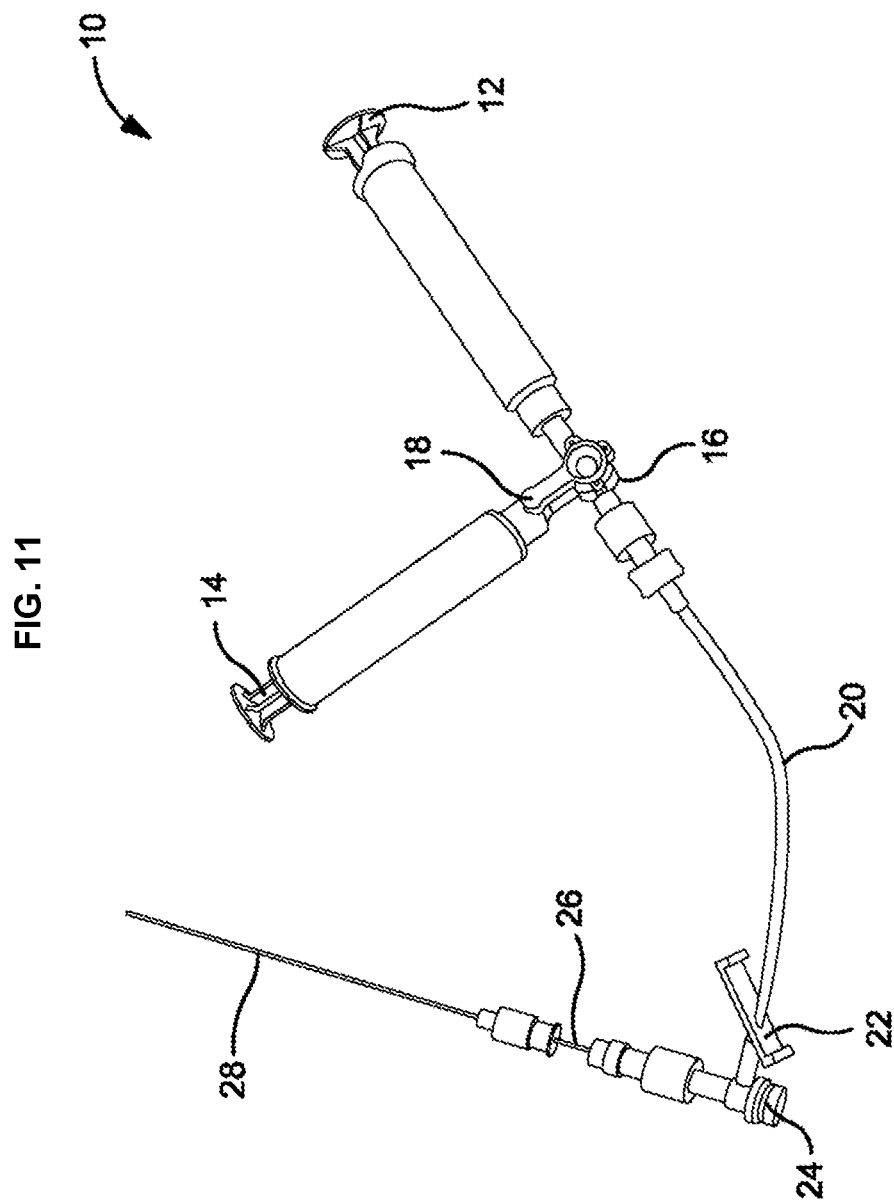

The rAAV.hIDS vector can be manufactured as shown in the flow diagram shown in FIG. 11, which is described in more detail in Section 5.4 and Example 4, infra.

5.1.3. Pharmaceutical Formulations of rAAV.hIDS

The rAAV9.hIDS formulation is a suspension containing an effective amount of AAV.hIDS vector suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one embodiment, the formulation may contain, e.g., a concentration of at least about $1 \times 10^9$ GC/mL to $3 \times 10^{13}$ GC/mL as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference.

In one embodiment, a frozen composition which contains an rAAV in a buffer solution as described herein, in frozen form, is provided. Optionally, one or more surfactants (e.g., Pluronic F68), stabilizers or preservatives is present in this composition. Suitably, for use, a composition is thawed and titrated to the desired dose with a suitable diluent, e.g., sterile saline or a buffered saline.

In one example, the formulation may contain, e.g., buffered saline solution comprising one or more of sodium chloride, sodium bicarbonate, dextrose, magnesium sulfate (e.g., magnesium sulfate·7H$_2$O), potassium chloride, calcium chloride (e.g., calcium chloride·2H$_2$O), dibasic sodium phosphate, and mixtures thereof, in water. Suitably, for intrathecal delivery, the osmolarity is within a range compatible with cerebrospinal fluid (e.g., about 275 to about 290); see, e.g., http://emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In certain embodiments, a kit is provided which includes a concentrated vector suspended in a formulation (optionally frozen), optional dilution buffer, and devices and other components required for intrathecal administration are provided. In another embodiment, the kit may additional or alternatively include components for intravenous delivery. In one embodiment, the kit provides sufficient buffer to allow for injection. Such buffer may allow for about a 1:1 to a 1:5 dilution of the concentrated vector, or more. In other embodiments, higher or lower amounts of buffer or sterile water are included to allow for dose titration and other adjustments by the treating clinician. In still other embodiments, one or more components of the device are included in the kit.

5.2. Gene Therapy Protocol 5.2.1 Target Patient Populations

Provided herein are methods for treating type II mucopolysaccharidosis comprising delivering a therapeutically effective amount of a rAAV.hIDS described herein to a patient in need thereof. In particular, provided herein are methods for preventing, treating, and/or ameliorating neurocognitive decline in a patient diagnosed with MPS II, comprising delivering a therapeutically effective amount of a rAAV.hIDS described herein to a patient in need thereof. A "therapeutically effective amount" of the rAAV.hIDS vector described herein may correct one or more of the symptoms identified in any one of the following paragraphs.

Patients who are candidates for treatment are pediatric and adult patients with MPS II (Hunter syndrome) and/or the symptoms associated with MPS II. MPS II is characterized as a mild/attenuated phenotype or a severe phenotype. Death occurs at a mean age of 11.7 years in patients with the severe phenotype (characterized by neurocognitive deterioration) and 21.7 years in patients with a mild or attenuated phenotype. The majority (two-thirds) of patients have the severe form of this disease. Patients with MPS II appear normal at birth, but signs and symptoms of disease typically present between the ages of 18 months and 4 years in the severe form and between the ages of 4 and 8 years in the attenuated form. Signs and symptoms common to all affected patients include short stature, coarse facial features, macrocephaly, macroglossia, hearing loss, hepato- and splenomegaly, dystosis multiplex, joint contractures, spinal stenosis and carpal tunnel syndrome. Frequent upper respiratory and ear infections occur in most patients and progressive airway obstruction is commonly found, leading to sleep apnea and often death. Cardiac disease is a major cause of death in this population and is characterized by valvular dysfunction leading to right and left ventricular hypertrophy and heart failure. Death is generally attributed to obstructive airway disease or cardiac failure.

In severe forms of MPS II, early developmental milestones may be met, but developmental delay is readily apparent by 18-24 months. Some patients fail hearing screening tests in the first year and other milestones are delayed, including ability to sit unsupported, ability to walk, and speech. Developmental progression begins to plateau between 3 and 5 years of age, with regression reported to begin around 6.5 years. Of the ~50% of children with MPS II who become toilet trained, most, if not all, will lose this ability as the disease progresses.

Patients with significant neurologic involvement exhibit severe behavioral disturbances including hyperactivity, obstinacy, and aggression beginning in the second year of life and continuing until age 8-9, when neurodegeneration attenuates this behavior.

Seizures are reported in over half of severely affected patients who reach the age of 10, and by the time of death most patients with CNS involvement are severely mentally handicapped and require constant care. Although patients with attenuated disease exhibit normal intellectual functioning, MRI imaging reveals gross brain abnormalities in all patients with MPS II including white matter lesions, enlarged ventricles, and brain atrophy.

A composition of the present invention avoids complications of long-term enzyme replacement therapy (ERT) related to immune response to the recombinant enzyme which can range from mild to full-blown anaphylaxis as well as complications of life-long peripheral access such as local and systemic infections. In contrast to ERT, a composition of the invention does not require life-long, repeated weekly injections. Without wishing to be bound by theory, the therapeutic method described herein is believed to be useful for correcting at least the central nervous system phenotype associated with MPS II disorders by providing efficient, long-term gene transfer afforded by vectors with high transduction efficiency which provide continuous, elevated circulating IDS levels, which provides therapeutic leverage outside the CNS compartment. In addition, provided herein are methods for providing active tolerance and preventing antibody formation against the enzyme by a variety of routes, including by direct systemic delivery of the enzyme in protein form or in the form of AAV-hIDS prior to AAV-mediated delivery into CNS.

In some embodiments, patients diagnosed with severe MPS II are treated in accordance with the methods described herein. In some embodiments, patients diagnosed with attenuated MPS II are treated in accordance with the methods described herein. In some embodiments, pediatric subjects with MPS II who have an early-stage neurocognitive deficit are treated in accordance with the methods described herein. In certain embodiments, patients age 2 years or older diagnosed with Hunter syndrome and having neurocognitive deficits or at risk of developing neurocognitive deficits are treated in accordance with the methods described herein. In certain embodiments, patients age 2 years or older with the presence of a major rearrangement or deletion mutation that is known to correlate with severe Hunter syndrome are treated in accordance with the methods described herein.

In certain embodiments, newborn babies (3 months old or younger) are treated in accordance with the methods described herein. In certain embodiments, babies that are 3 months old to 9 months old are treated in accordance with the methods described herein. In certain embodiments, children that are 9 months old to 36 months old are treated in accordance with the methods described herein. In certain embodiments, children that are 3 years old to 12 years old are treated in accordance with the methods described herein. In certain embodiments, children that are 12 years old to 18 years old are treated in accordance with the methods described herein. In certain embodiments, adults that are 18 years old or older are treated in accordance with the methods described herein.

Suitably, patients selected for treatment may include those having one or more of the following characteristics: a documented diagnosis of MPS II confirmed by the lacking or diminished IDS enzyme activity as measured in serum, plasma, fibroblasts, or leukocytes; documented evidence of early-stage neurocognitive deficit due to MPS II, defined as either of the following, if not explainable by any other neurological or psychiatric factors:—a DQ (BSID-III) that is at least 1 standard deviation below mean or documented historical evidence of a decline of greater than 1 standard deviation on sequential testing. Alternatively, increased GAGs in urine, serum, CSF, or genetic tests may be used. Prior to treatment, subjects, e.g., infants, preferably undergo genotyping to identify MPS II patients, i.e., patients that have mutations in the gene encoding hIDS. Prior to treatment, the MPS II patient can be assessed for neutralizing antibodies (Nab) to the AAV serotype used to deliver the hIDS gene. Such Nabs can interfere with transduction efficiency and reduce therapeutic efficacy. MPS II patients that have a baseline serum Nab titer ≤1:5 are good candidates for treatment with the rAAV.hIDS gene therapy protocol. Treatment of MPS II patients with titers of serum Nab >1:5 may require a combination therapy, such as transient co-treatment with an immunosuppressant before and/or during treatment with rAAV.hIDS vector delivery. Optionally, immunosuppressive co-therapy may be used as a precautionary measure without prior assessment of neutralizing antibodies to the AAV vector capsid and/or other components of the formulation. Prior immunosuppression therapy may be desirable to prevent potential adverse immune reaction to the hIDS transgene product, especially in patients who have virtually no levels of IDUA activity, where the transgene product may be seen as "foreign." Results of non-clinical studies in mice, dogs and NHPs described infra are consistent with the development of an immune response to hIDS and neuroinflammation. While a similar reaction may not occur in human subjects, as a precaution immunosuppression therapy is recommended for all recipients of rAAV-hIDS.

Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mycophenolate mofetil, methotrexate, leflunomide (Arava), cyclophosphamide, chlorambucil (Leukeran), a chloroquine (e.g., hydroxychloroquine), quinine sulfate, mefloquine, a combination of atovaquone and proguanil, sulfasalazine, mercaptopurine, fluorouracil, dactinomycin, an anthracycline, mitomycin C, bleomycin, mithramycin, IL-2 receptor- (CD25-) or CD3- directed antibodies, anti-IL-2 antibodies, abatacept (Orencia), adalimumab (Humira), anakinra (Kineret), certolizumab (Cimzia), etanercept (Enbrel), golimumab (Simponi), infliximab (Remicade), rituximab (Rituxan), tocilizumab (Actemra) and tofacitinib (Xeljanz), cyclosporine, tacrolimus, sirolimus, IFN-β, IFN-γ, an opioid, or TNF-α (tumor necrosis factor-alpha) binding agent, and combinations of these drugs. In certain embodiments, the immunosuppressive therapy may be started 0, 1, 2, 7, or more days prior to the gene therapy administration. Such therapy may involve co-administration of two or more drugs, the on the same day. In one embodiment, the two or more drugs may be. e.g., one or more corticosteroids (e.g., a prednelisone or prednisone) and optionally, MMF and/or a calcinuerin inhibitor (e.g., tacrolimus or sirolimus (i.e., rapamycin)). In one embodiment, the two or more drugs are micophenolate mofetil (MMF) and/or sirolimus. In another embodiment, the two or more drugs may be, e.g., methylprednisolone, prednisone, tacrolimus, and/or sirolimus. In certain embodiments, the drugs are MMF and tacrolimus for 0 to 15 days pre-vector delivery and maintaining for about 8 weeks with MMF and/or throughout follow-up appointments with tacrolimus. One or more of these drugs may be continued after gene therapy administration, at the same dose or an adjusted dose. In certain embodiments, patients are dosed initially with an IV steroid (e.g., methylprednisolone) to load the dose, followed by with an oral steroid (e.g., prednisolone) that is gradually tapered down so that the patient is off steroids by week 12. The corticosteroid treatment is supplemented by tacrolimus (for 24 weeks) and/or sirolimus (for 12 weeks), and can be further supplemented with MMF. When using both tacrolimus and sirolimus, the dose of each should be a low dose adjusted to maintain a blood trough level of about 4 ng/mL to about 8 ng/ml, or a total of about 8 ng/mL to about 16 ng/mL. In certain embodiments, when only one of these agents is used, the total dose for tacrolimus and/or sirolimus may be in the range of about 16 ng/mL to about 24 ng/mL. If only one of the agents is used, the label dose (higher dose) should be employed; e.g., tacrolimus at 0.15-0.20 mg/kg/day given as two divided doses every 12 hours; and sirolimus at 1 mg/m$^2$/day; the loading dose should be 3 mg/m$^2$. If MMF is added to the regimen, the dose for tacrolimus and/or sirolimus can be maintained since the mechanisms of action differ. These and other therapies may be started at about day −14 to day −1 (e.g., day −2, day 0, etc), and continue to about to up to about 1 week (7 days), or up to about 60 days, or up to about 12 weeks, or up to about 16 weeks, or up to about 24 weeks, or up to about 48 weeks, or longer, as needed. In certain embodiments, a tacrolimus-free regimen is selected.

In certain embodiments, patients will receive immune suppression as follows: corticosteroids: methylprednisolone 10 mg/kg IV once on Day 1 predose and oral prednisone starting at 0.5 mg/kg/day on Day 2 with gradual tapering and discontinuation by Week 12; Tacrolimus: 1 mg BID by mouth Day 2 to Week 24 with tapering over 8 weeks between Week 24 and 32; Sirolimus: (a loading dose on Day −2 and then sirolimus 0.5 mg/m2/day divided in BID dosing until Week 48. In certain embodiments, IS therapy is discontinued at Week 48 post dosing with the AAV9.hIDS.

Without wishing to be bound by theory, immune suppression co-therapy does one or more of the following: induces anergy or immunologic tolerance to the AAV and/or Transgene; blocks an immune response to optimize efficacy; Minimize de novo immune response against transgene; Minimize impact of pre-existing immune response to transgene; Minimize impact of pre-existing immune response to AAV; Prevent immune medicated toxicity; Minimize destruction of TG expressing cells; reduce axonopathy/DRG neurotoxicity in NHPs.

In certain embodiments, patients having one or more of the following characteristics may be excluded from treatment at the discretion of their caring physician:

Has any neurocognitive deficit not attributable to MPS II that may in the opinion of either the investigator or the medical monitor confound interpretation of study results Has any condition (e.g., history of any disease, evidence of any current disease, any finding upon physical examination, or any laboratory abnormality) that, in the opinion of the investigator, would put the subject at undue risk or would interfere with evaluation of the investigational product or interpretation of subject safety or study results Diagnosis of neuropsychiatric condition Has any contraindication to intrathecal/intracranial treatment administration, including contraindications to fluoroscopic imaging Has any contraindication to MRI Has acute hydrocephalus at time of enrollment Is currently enrolled in any other clinical study with an investigational product within 4 weeks prior to Screening or within 5 half-lives of the investigational product used in that clinical study, whichever is longer Has undergone hematopoietic stem cell transplantation (HSCT)

Has received idursulfase via intrathecal administration within 6 months prior to screening Has received intrathecal idursulfase at any time and experienced a significant adverse effect (AE) considered related to intrathecal administration that in opinion of the investigator and/or medical monitor would put the subject at undue risk.

In other embodiments, a caring physician may determine that the presence of one or more of these physical characteristics (medical history) should not preclude treatment as provided herein.

5.2.2. Dosages & Mode of Administration

Pharmaceutical compositions suitable for administration to patients comprise a suspension of rAAV.hIDS vectors in a formulation buffer comprising a physiologically compatible aqueous buffer, a surfactant and optional excipients. In certain embodiments, a pharmaceutical composition described herein is administered intrathecally. In other embodiments, a pharmaceutical composition described herein is administered intracisternally. In other embodiments, a pharmaceutical composition described herein is administered intravenously. In certain embodiments, the pharmaceutical composition is delivered via a peripheral vein by infusion over 20 minutes (±5 minutes). However, this time may be adjusted as needed or desired. However, still other routes of administration may be selected. Alternatively or additionally, routes of administration may be combined, if desired.

While a single administration of the rAAV is anticipated to be effective, administration may be repeated (e.g., quarterly, bi-annually, annually, or as otherwise needed, particularly in treatment of newborns. Optionally, an initial dose of a therapeutically effective amount may be delivered over split infusion/injection sessions, taking into consideration the age and ability of the subject to tolerate infusions/injections. However, repeated weekly injections of a full therapeutic dose are not required, providing an advantage to the patient in terms of both comfort and therapeutic outcome.

In some embodiments, the rAAV suspension has an rAAV Genome Copy (GC) titer that is at least $1.0 \times 10^{13}$ GC/mL. In certain embodiments, the rAAV Empty/Full particle ratio in the rAAV suspension is between 0.01 and 0.05 (95%-99% free of empty capsids). In some embodiments, an MPS II patient in need thereof is administered a dose of at least about $4 \times 10^8$ GC/g brain mass to about $4 \times 10^{11}$ GC/g brain mass of the rAAV suspension.

The following therapeutically effective flat doses of rAAV.hIDS can be administered to MPS II patients of the indicated age group:

Newborns: about $1 \times 10^{11}$ to about $3 \times 10^{14}$ GC;
3-9 months: about $6 \times 10^{12}$ to about $3 \times 10^{14}$ GC;
9 months-6 years: about $6 \times 10^{12}$ to about $3 \times 10^{14}$ GC;
3-6 years: about $1.2 \times 10^{13}$ to about $6 \times 10^{14}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In other embodiments, the following therapeutically effective flat doses are administered to an MPS patient of the age group:

Newborns: about $3.8 \times 10^{12}$ to about $1.9 \times 10^{14}$ GC;
3-9 months: about $6 \times 10^{12}$ to about $3 \times 10^{14}$ GC;
9-36 months: about $10^{13}$ to about $5 \times 10^{13}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In certain embodiments, one or more of these ranges are used for patients of any age. In certain embodiments, a flat dose of $2.6 \times 10^{12}$ genome copies (GC) ($2.0 \times 10^9$ GC/g brain mass) is administered to a patient that is 6 years old or older than 6 years old. In certain embodiments, a flat dose of $1.3 \times 10^{13}$ (GC) ($1.0 \times 10^{10}$ GC/g brain mass) is administered to a patient that is 6 years old or older than 6 years old. In some embodiments, the dose administered to a 12+ year old MPSII patient (including 18+ year old) is $1.4 \times 10^{13}$ genome copies (GC) ($1.1 \times 10^{10}$ GC/g brain mass). In some embodiments, the dose administered to a 12+ year old MPSII patient (including 18+ year old) is $7 \times 10^{13}$ GC ($5.6 \times 10^{10}$ GC/g brain mass). In still a further embodiment, the dose administered to an MPSII patient is at least about $4 \times 10^8$ GC/g brain mass to about $4 \times 10^{11}$ GC/g brain mass. In certain embodiments, the dose administered to MPSII newborns ranges from about $1.4 \times 10^{11}$ to about $1.4 \times 10^{14}$ GC; the dose administered to infants 3-9 months ranges from about $2.4 \times 10^{11}$ to about $2.4 \times 10^{14}$ GC; the dose administered to MPSII children 9-36 months ranges: about $4 \times 10^{11}$ to about $4 \times 10^{14}$ GC; the dose administered to MPSII children 3-12 years: ranges from about $4.8 \times 10^{11}$ to about $4.8 \times 10^{14}$ GC; the dose administered to children and adults 12+ years ranges from about $5.6 \times 10^{11}$ to about $5.6 \times 10^{14}$ GC.

In certain embodiments, a dose of at least about $4 \times 10^8$ GC/g brain mass to about $4 \times 10^{11}$ GC/g brain mass of the rAAV suspension has potency. In certain embodiments, the dose administered is at least $1.3 \times 10^{10}$ GC/g brain mass, at least $1.9 \times 10^{10}$ GC/g brain mass, at least $6.5 \times 10^{10}$ GC/g brain mass, or $9.4 \times 10^{10}$ GC/g brain mass, or about $4 \times 10^{11}$ GC/g brain mass. In certain embodiments, the dose administered to an MPSII patient is $1.3 \times 10^{10}$ GC/g brain mass. In certain embodiments, the dose administered to an MPSII patient is $6.5 \times 10^{10}$ GC/g brain mass. In certain embodiments, the dose administered to an MPSII patient is $1.9 \times 10^{10}$ GC/g brain mass. In certain embodiments, the dose administered to an MPSII patient is $9.4 \times 10^{10}$ GC/g brain mass.

In certain embodiments, because of the relatively rapid brain growth that occurs early in a developing child, the total dose of AAV9.hIDS administered IC depends on the assumed brain mass across different age strata. For brain mass by age for the study subjects see, e.g., (AS Dekaban, Ann Neurol, 1978 October; 4(4): 345-56.

TABLE

Total dose administered by age

| Subject Age | Assumed brain mass (g) | Dose 1 (total GC) | Dose 2 (total GC) |
|---|---|---|---|
| ≥4 to <9 months | 600 | $7.8 \times 10^{12}$ | $3.9 \times 10^{13}$ |
| ≥9 to <18 months | 1000 | $1.3 \times 10^{13}$ | $6.5 \times 10^{13}$ |
| ≥18 months to <3 years | 1100 | $1.4 \times 10^{13}$ | $7.2 \times 10^{13}$ |
| ≥3 years | 1300 | $1.7 \times 10^{13}$ | $8.5 \times 10^{13}$ |

Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

5.2.3. Monitoring Efficacy

Efficacy of the therapy described herein can be measured by assessing (a) the prevention of neurocognitive decline in patients with MPS II (Hunter syndrome); and (b) reductions in biomarkers of disease, e.g., GAG levels and/or enzyme activity in the CSF, serum and/or urine, and/or liver and spleen volumes. Neurocognition can be determined by measuring intelligence quotient (IQ), e.g., as measured by Bayley's Infantile Development Scale for Hurler subjects or as measured by the Wechsler Abbreviated Scale of Intelligence (WASI) for Hurler-Scheie subjects. Other appropriate measures of neurocognitive development and function may be utilized, e.g., assessing developmental quotient (DQ) using Bayley Scales of Infant Development (BSID-III), assessing memory using the Hopkins Verbal Learning Test, and/or using Tests of Variables of Attention (TOVA). Other neuropsychological function, such as vineland adaptive behavior scales, visual processing, fine motor, communication, socialization, daily living skills, and emotional and behavioral health are monitored. Magnetic Resonance Imaging (MRI) of brain to acquire volumetric, diffusion tensor imaging (DTI), and resting state data, median nerve cross-sectional area by ultrasonography, improvement in spinal cord compression, safety, liver size and spleen size are also administered.

Optionally, other measures of efficacy may include evaluation of biomarkers (e.g., polyamines as described herein) and clinical outcomes. Urine is evaluated for total GAG content, concentration of GAG relative to creatinine, as well as MPS II specific pGAGs. Serum and/or plasma is evaluated for IDS activity, anti-IDS antibodies, pGAG, and concentration of the heparin cofactor II-thrombin complex and markers of inflammation. CSF is evaluated for IDUA activity, anti-IDS antibodies, hexosaminidase (hex) activity, and pGAG (such as heparan sulfate and dermatan sulfate). The presence of neutralizing antibodies to vector (e.g., AAV9) and binding antibodies to anti-IDS antibodies may be assessed in CSF and serum. T-cell response to vector capsid (e.g., AAV9) or the hIDS transgene product may be assessed by ELISPOT assay. Pharmacokinetics of IDS expression in CSF, serum, and urine as well as vector concentration (PCR to AAV9 DNA) may also be monitored.

Combinations of gene therapy delivery of the rAAV.hIDS to the CNS accompanied by systemic delivery of hIDS are encompassed by the methods of the invention. Systemic delivery can be accomplished using ERT (e.g., using Elaprase® (idursulfase)), or additional gene therapy using an rAAV.hIDS with tropism for the liver (e.g., an rAAV.hIDS bearing an AAV8 capsid).

Additional measures of clinical efficacy associated with systemic delivery may include, e.g., Orthopedic Measures, such as bone mineral density, bone mineral content, bone geometry and strength, Bone Density measured by dual energy x-ray absorptiometry (DXA); Height (Z-scores for standing height/lying-length-for-age); Markers of Bone Metabolism: Measurements of Serum osteocalcin (OCN) and bone-specific alkaline phosphatase (BSAP), carboxy terminal telopeptide of type I collagen (ICTP) and carboxy terminal telopeptide al chain of type I collagen (CTX); Flexibility and Muscle Strength: Biodex and Physical Therapy evaluations, including 6 minute walk study (The Biodex III isokinetic strength testing system is used to assess strength at the knee and elbow for each participant); Active Joint Range of Motion (ROM); Child Health Assessment Questionnaire/Health Assessment Questionnaire (CHAQ/HAQ) Disability Index Score; Electromyographic (EMG) and/or Oxygen Utilization to Monitor an individual's cardiorespiratory fitness: peak oxygen uptake ($VO_2$ peak) during exercise testing; Apnea/Hypopnea Index (AHI); Forced Vital Capacity (FVC); Left Ventricular Mass (LVM).

In certain embodiments, a method of diagnosing and/or treating MPS II in a patient, or monitoring treatment, is provided. The method involves obtaining a cerebrospinal fluid or plasma sample from a human patient suspected of having MPS II; detecting spermine concentration levels in the sample; diagnosing the patient with a mucopolysaccharidosis selected from MPS II in the patient having spermine concentrations in excess of 1 ng/mL; and delivering an effective amount of human IDS to the diagnosed patient as provided herein.

In another aspect, the method involves monitoring and adjusting MPS II therapy. Such method involves obtaining a cerebrospinal fluid or plasma sample from a human patient undergoing therapy for MPS II; detecting spermine concentration levels in the sample by performing a mass spectral analysis; adjusting dosing levels of the MPS II therapeutic. For example, "normal" human spermine concentrations are about 1 ng/mL to 2 ng/mL or less in cerebrospinal fluid. However, patients having untreated MPS II may have spermine concentration levels of greater than 2 ng/mL and up to about 100 ng/mL. If a patient has levels approaching normal levels, dosing of any companion may be lowered. Conversely, if a patient has higher than desired MPS II levels, higher doses, or an additional therapy, e.g., ERT, may be provided to the patient.

Spermine concentration may be determined using a suitable assay. For example the assay described in J Sanchez- Lopez, et al, "Underivatives polyamine analysis is plant samples by ion pair liquid chromatography coupled with electrospray tandem mass spectrometry," Plant Physiology and Biochemistry, 47 (2009): 592-598, avail online 28 Feb. 2009; MR Hakkinen et al, "Analysis of underivatized polyamines by reversed phase liquid chromatography with electrospray tandem mass spectrometry", J Pharm Biomec Analysis, 44 (2007): 625-634, quantitative isotope dilution liquid chromatography (LC)/mass spectrometry (MS) assay. Other suitable assays may be used.

In some embodiments, efficacy of a therapeutic described herein is determined by assessing neurocognition at week 52 post-dose in pediatric subjects with MPS II who have an early-stage neurocognitive deficit. In some embodiments, efficacy of a therapeutic described herein is determined by assessing the relationship of CSF glycosaminoglycans (GAG) to neurocognition in an MPS II patient. In some embodiments, efficacy of a therapeutic described herein is determined by evaluating the effect of the therapeutic on physical changes to the CNS in an MPS II patient as measured by magnetic resonance imaging (MRI), e.g., volumetric analysis of gray and white matter and CSF ventricles. In some embodiments, efficacy of a therapeutic described herein is determined by evaluating the pharmacodynamic effect of the therapeutic on biomarkers, (e.g., GAG, HS) in cerebrospinal fluid (CSF), serum, and urine of an MPS II patient. In some embodiments, efficacy of a therapeutic described herein is determined by evaluating the impact of the therapeutic on quality of life (QOL) of an MPS II patient. In some embodiments, efficacy of a therapeutic described herein is determined by evaluating the impact of the therapeutic on motor function of an MPS II patient. In some embodiments, efficacy of a therapeutic described herein is determined by evaluating the effect of the therapeutic on growth and on developmental milestones of an MPS II patient.

As expressed from the rAAV vector described herein, expression levels of hIDS of at least about 2% as detected in the CSF, serum, or other tissue, may provide therapeutic effect. However, higher expression levels may be achieved. Such expression levels may be from 2% to about 100% of normal functional human IDS levels. In certain embodiments, higher than normal expression levels may be detected in CSF, serum, or other tissue.

In certain embodiments, the methods of treating, preventing, and/or ameliorating MPS II and/or symptoms thereof described herein result in a significant increase in neurocognitive developmental quotient (DQ) in treated patients, as assessed using Bayley Scales of Infant Development. In certain embodiments, the methods of treating, preventing, and/or ameliorating MPS II and/or symptoms thereof described herein result in a decline of DQ of no more than 15 points in treated patients relative to untreated/natural history control data in patients with Hunter Syndrome.

In certain embodiments, the methods of treating, preventing, and/or ameliorating MPS II and/or symptoms thereof described herein result in a significant increase in functional human IDS levels. In certain embodiments, the methods of treating, preventing, and/or ameliorating MPS II and/or symptoms thereof described herein result in a significant decrease in GAG levels, as measured in a sample of a patient's serum, urine and/or cerebrospinal fluid (CSF).

5.3. Combination Therapies

Combinations of gene therapy delivery of the rAAV.hIDS to the CNS accompanied by systemic delivery of hIDS are encompassed by certain embodiments of the invention. Systemic delivery can be accomplished using ERT (e.g., using Elaprase®), or additional gene therapy using an rAAV.hIDS with tropism for the liver (e.g., an rAAV.hIDS bearing an AAV8 capsid).

In certain embodiments, an intrathecal administration of rAAV9.hIDS is co-administered with a second AAV.hIDS injection, e.g., directed to the liver. In such an instance, the vectors may be same. For example, the vectors may have the same capsid and/or the same vector genomic sequences. Alternatively, the vector may be different. For example, each of the vector stocks may designed with different regulatory sequences (e.g., each with a different tissue-specific promoter), e.g., a liver-specific promoter and a CNS-specific promoter. Additionally, or alternatively, each of the vector stocks may have different capsids. For example, a vector stock to be directed to the liver may have a capsid selected from AAV8, AAVrh64R1, AAVrh64R2, rh8, rh10, AAV3B, or AAVdj, among others. In such a regimen, the doses of each vector stock may be adjusted so that the total vector delivered intrathecally is within the range of about $1\times10^8$ GC to $\times 1\times10^{14}$ GC; in other embodiments, the combined vector delivered by both routes is in the range of $1\times10^{11}$ GC to $1\times10^{16}$ GC. Alternatively, each vector may be delivered in an amount of about $10^8$ GC to about $10^{12}$ GC/vector. Such doses may be delivered substantially simultaneously, or at different times, e.g., from about 1 day to about 12 weeks apart, or about 3 days to about 30 days, or other suitable times.

In some embodiments, a method for treatment comprises: (a) dosing a patient having MPS II and/or the symptoms Hunter syndrome with a sufficient amount of hIDS enzyme or liver-directed rAAV-hIDUA to induce transgene-specific tolerance; and (b) administering an rAAV.hIDS to the patient's CNS, which rAAV.hIDS directs expression of therapeutic levels of hIDS in the patient.

In further embodiments, a method of treating a human patient having MPS II and/or the symptoms associated with Hunter syndrome is provided which involves tolerizing a patient having MPS II and/or the symptoms associated Hunter syndrome with a sufficient amount of hIDS enzyme or liver-directed rAAV-hIDS to induce transgene-specific tolerance, followed by rAAV-mediated delivery of hIDS to the patient. In certain embodiments, the patient is administered an rAAV.hIDS via liver-directed injections e.g., when the patient is less than 4 weeks old (neonatal stage) or an infant, in order to tolerize the patient to hIDS, and the patient is subsequently administered rAAV.hIDS via intrathecal injections when the patient is an infant, child, and/or adult to express therapeutic concentrations of hIDS in the CNS.

In one example, the MPS II patient is tolerized by delivering hIDS to the patient within about two weeks of birth, e.g., within about 0 to about 14 days, or about 1 day to 12 days, or about day 3 to about day 10, or about day 5 to about day 8, i.e., the patient is a newborn infant. In other embodiments, older infants may be selected. The tolerizing dose of hIDS may be delivered via rAAV. However, in another embodiment, the dose is delivered by direct delivery of the enzyme (enzyme replacement therapy). Methods of producing recombinant hIDS have been described in the literature.

Additionally, a recombinant hIDS commercially produced as Elaprase® (idursulfase) may be useful for systemic delivery. Although currently less preferred, the enzyme may be delivered via "naked" DNA, RNA, or another suitable vector. In one embodiment, the enzyme is delivered to the patient intravenously and/or intrathecally. In another embodiment, another route of administration is used (e.g., intramuscular, subcutaneous, etc). In one embodiment, the MPS II patient selected for tolerizing is incapable of expressing any detectable amounts of hIDS prior to initiation of the tolerizing dose. When recombinant human IDS enzyme is delivered, intravenous rhIDS injections may consist of about 0.5 mg/kg body weight. Alternatively, a higher or lower dose is selected. Similarly, when expressed from a vector, lower expressed protein levels may be delivered. In one embodiment, the amount of hIDS delivered for tolerizing is lower than a therapeutically effective amount. However, other doses may be selected.

Typically, following administration of the tolerizing dose, the therapeutic dose is delivered to the subject, e.g., within about three days to about 6 months post-tolerizing dose, more preferably, about 7 days to about 1 month post-tolerizing dose. However, other time points within these ranges may be selected, as may longer or shorter waiting periods.

As an alternative, immunosuppressive therapy may be given in addition to the vector—before, during and/or subsequent to vector administration Immunosuppressive therapy can include prednisolone, mycophenolate mofetil (MMF) and tacrolimus or sirolimus as described supra. A tacrolimus-free regimen described infra may be preferred."

5.4. Manufacture

One embodiment provides for the manufacture of the rAAV.hIDS pharmaceutical compositions described herein (Example 4, infra). An illustrative manufacturing process is provided in FIGS. 10A and 10B. The rAAV.hIDS vector can be manufactured as shown in the flow diagram shown in FIGS. 10A and 10B. Briefly, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed by anion exchange resin chromatography are used to purify the vector drug product and to remove empty capsids. These methods are described in more detail in International Patent Application No. PCT/US2016/065970, filed Dec. 9, 2016 and its priority documents, US Patent Application Nos. 62/322,071, filed Apr. 13, 2016 and 62/226,357, filed Dec. 11, 2015 and entitled "Scalable Purification Method for AAV9", which is incorporated by reference herein. Purification methods for AAV8, International Patent Application No. PCT/US2016/065976, filed Dec. 9, 2016 and is priority documents US Patent Application Nos. 62/322,098, filed Apr. 13, 2016 and 62/266,341, filed Dec. 11, 2015, and rh10, International Patent Application No. PCT/US16/66013, filed Dec. 9, 2016 and its priority documents, U.S. Patent Application No. 62/322,055, filed Apr. 13, 2016 and 62/266,347, entitled "Scalable Purification Method for AAVrh10", also filed Dec. 11, 2015, and for AAV1, International Patent Application No. PCT/US2016/065974, filed Dec. 9, 2016 and its priority documents US Patent Application Nos. 62/322,083, filed Apr. 13, 2016 and 62/26,351, for "Scalable Purification Method for AAV1", filed Dec. 11, 2015, are all incorporated by reference herein.

5.5. Apparatus and Method for Delivery of a Pharmaceutical Composition into Cerebrospinal Fluid In one aspect, the vectors provided herein may be administered intrathecally via the method and/or the device provided in this section and described further in the Examples and FIG. 11. Alternatively, other devices and methods may be selected. The method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient.

In another aspect, a device for intracisternal delivery of a pharmaceutical composition is provided. The device includes a first vessel containing an amount of a pharmaceutical composition, a second vessel containing an isotonic solution, and a spinal needle through which the pharmaceutical composition may be ejected from the device directly into cerebrospinal fluid within the cisterna magna of a patient. The device further includes a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle.

As used herein, the term Computed Tomography (CT) refers to radiography in which a three-dimensional image of a body structure is constructed by computer from a series of plane cross-sectional images made along an axis.

The apparatus or medical device 10 as shown in FIG. 11 includes one or more vessels, 12 and 14, interconnected via a valve 16. The vessels, 12 and 14, provide a fresh source of a pharmaceutical composition, drug, vector, or like substance and a fresh source of an isotonic solution such as saline, respectively. The vessels, 12 and 14, may be any form of medical device that enables injection of fluids into a patient.

By way of example, each vessel, 12 and 14, may be provided in the form of a syringe, cannula, or the like. For instance, in the illustrated embodiment, the vessel 12 is provided as a separate syringe containing an amount of a pharmaceutical composition and is referred to herein as a "vector syringe". Merely for purposes of example, the vessel 12 may contain about 10 cc of a pharmaceutical composition or the like.

Likewise, the vessel 14 may be provided in the form of a separate syringe, cannula, or the like that contains an amount of saline solution and may be referred to as a "flush syringe". Merely for purposes of example, the vessel 14 may contain about 10 cc of a saline solution.

As an alternative, the vessels 12 and 14 may be provided in forms other than syringes and may be integrated into a single device, such as an integrated medical injection device have a pair of separate chambers, one for the pharmaceutical composition and one for saline solution. Also, the size of the chambers or vessels may be provided as needed to contain a desired amount of fluid.

In the illustrated embodiment, the valve 16 is provided as a 4-way stopcock having a swivel male luer lock 18. The valve 16 interconnects the vessels 12 and 14 (i.e., the vector syringe and flush syringe in the illustrated embodiment), and the swivel male luer lock enables a path through the valve 16 to be closed or opened to each of the vessels 12 and 14. In this way, the path through the valve 16 may be closed to both the vector syringe and flush syringe or may be open to a selected one of the vector syringe and flush syringe. As an alternative to a 4-way stopcock, the valve may be a 3-way stopcock or fluid control device.

In the illustrated embodiment, the valve 16 is connected to one end of a length of extension tubing 20 or the like conduit for fluid. The tubing 20 may be selected based on a desired length or internal volume. Merely by way of example, the tubing may be about 6 to 7 inches in length.

In the illustrated embodiment, an opposite end 22 of the tubing 12 is connected to a T-connector extension set 24 which, in turn, is connected to a spinal needle 26. By way of example, the needle 26 may be a five inch, 22 or 25 gauge spinal needle. In addition, as an option, the spinal needle 26 may be connected to an introducer needle 28, such as a three and a half inch, 18 gauge introducer needle.

In use, the spinal needle 26 and/or optional introducer needle 28 may be advanced into a patient towards the cisterna magna. After needle advancement, Computed Tomography (CT) images may be obtained that permit visualization of the needle 26 and/or 28 and relevant soft tissues (e.g., paraspinal muscles, bone, brainstem, and spinal cord). Correct needle placement is confirmed by observation of Cerebrospinal Fluid (CSF) in the needle hub and visualization of a needle tip within the cisterna magna. Thereafter, the relatively short extension tubing 20 may be attached to the inserted spinal needle 26, and the 4-way stopcock 16 may then be attached to the opposite end of the tubing 20.

The above assembly is permitted to become "self-primed" with the patient's CSF. Thereafter, the prefilled normal saline flush syringe 14 is attached to a flush inlet port of the 4-way stopcock 16 and then the vector syringe 12 containing a pharmaceutical composition is attached to a vector inlet port of the 4-way stopcock 16. Thereafter, the output port of the stopcock 16 is opened to the vector syringe 12, and the contents of the vector syringe may be slowly injected through the valve 16 and assembled apparatus and into the patient over a period of time. Merely for purposes of example, this period of time may be approximately 1-2 minutes and/or any other time of desire.

After the contents of the vector syringe 12 are injected, the swivel lock 18 on the stopcock 16 is turned to a second position so that the stopcock 16 and needle assembly can be flushed with a desired amount of normal saline using the attached prefilled flush syringe 14. Merely by way of example, 1 to 2 cc of normal saline may be used; although greater or lesser amounts may be used as needed. The normal saline ensures that all or most of the pharmaceutical composition is forced to be injected through the assembled device and into the patient and so that little or none of the pharmaceutical composition remains in the assembled device.

After the assembled device has been flushed with the saline, the assembled device in its entirely, including the needle(s), extension tubing, stopcock, and syringes are slowly removed from the subject and placed onto a surgical tray for discarding into a biohazard waste receptacle or hard container (for the needle(s)).

A screening process may be undertaken by a principal investigator which may ultimately lead to an intracisternal (IC) procedure. The principal investigator may describe the process, procedure, the administration procedure itself, and all potential safety risks in order for the subject (or designated caregiver) to be fully informed. Medical history, concomitant medications, physical exam, vital signs, electrocardiogram (ECG), and laboratory testing results are obtained or performed and provided to a neuroradiologist, neurosurgeon, and anesthesiologist for use in screening assessment of subject eligibility for the IC procedure.

To allow adequate time to review eligibility, the following procedures may be performed at any time between the first screening visit and up to one week prior to a study visit. For example, on "Day 0", Head/Neck Magnetic Resonance Imaging (MRI) with and without gadolinium (i.e., eGFR>30 mL/min/1.73 m$^2$) may be obtained. In addition to the Head/Neck MRI, the investigator may determine the need for any further evaluation of the neck via flexion/extension studies. The MRI protocol may include T1, T2, DTI, FLAIR, and CINE protocol images.

In addition, Head/Neck MRA/MRV may be obtained as per institutional protocol (i.e., subjects with a history of intra/transdural operations may be excluded or may need further testing (e.g., radionucleotide cisternography)) that allows for adequate evaluation of CSF flow and identification of possible blockage or lack of communication between CSF spaces.

The neuroradiologist, neurosurgeon, and anesthesiologist ultimately discuss and determine the eligibility of each subject for the IC procedures based on all available information (scans, medical history, physical exam, labs, etc.). An Anesthesia pre-op evaluation may also be obtained from "Day −28" to "Day 1" that provides a detailed assessment of airway, neck (shortened/thickened) and head range-of-motion (degree of neck flexion), keeping in mind the special physiologic needs of a MPS subject.

Prior to an IC procedure, the CT Suite will confirm the following equipment and medications are present:

Adult lumbar puncture (LP) kit (supplied per institution);

BD (Becton Dickinson) 22 or 25 gauge×3-7" spinal needle (Quincke bevel);

Coaxial introducer needle, used at the discretion of the interventionalist (for introduction of spinal needle);

4 way small bore stopcock with swivel (Spin) male luer lock;

T-connector extension set (tubing) with female luer lock adapter, approximate length of 6.7 inches;

Omnipaque 180 (iohexol), for intrathecal administration;

Iodinated contrast for intravenous (IV) administration;

1% lidocaine solution for injection (if not supplied in adult LP kit);

Prefilled 10 cc normal saline (sterile) flush syringe;

Radiopaque marker(s);

Surgical prep equipment/shaving razor;

Pillows/supports to allow proper positioning of intubated subject;

Endotracheal intubation equipment, general anesthesia machine and mechanical ventilator;

Intraoperative neurophysiological monitoring (IONM) equipment (and required personnel); and 10 cc syringe containing vector; prepared and transported to CT/Operating Room (OR) suite in accordance with separate Pharmacy Manual.

Informed Consent for the procedure are confirmed and documented within the medical record and/or study file. Separate consent for the procedure from radiology and anesthesiology staff is obtained as per institutional requirements. Subject has intravenous access placed within the appropriate hospital care unit according to institutional guidelines (e.g., two IV access sites). Intravenous fluids are administered at the discretion of the anesthesiologist. At the discretion of the anesthesiologist and per institutional guidelines, subject may be induced and undergo endotracheal intubation with administration of general anesthesia in an appropriate patient care unit, holding area or the surgical/CT procedure suite.

A lumbar puncture is performed, first to remove 5 cc of cerebrospinal fluid (CSF) and subsequently to inject contrast (Omnipaque 180) intrathecally to aid visualization of the cisterna magna. Appropriate subject positioning maneuvers may be performed to facilitate diffusion of contrast into the cisterna magna.

Intraoperative neurophysiological monitoring (IONM) equipment is attached to the subject. Subject is placed onto the CT scanner table in the prone or lateral decubitus position. Adequate staff must be present to assure subject safety during transport and positioning. If deemed appropriate, subject may be positioned in a manner that provides neck flexion to the degree determined to be safe during pre-operative evaluation and with normal neurophysiologic monitor signals documented after positioning.

The following staff may be confirmed to be present and identified on-site: Interventionalist/neurosurgeon performing the procedure; Anesthesiologist and respiratory technician(s); Nurses and physician assistants; CT (or OR) technicians; Neurophysiology technician; and Site Coordinator. A "time-out" may be completed per Joint Commission/hospital protocol to verify correct subject, procedure, site, positioning, and presence of all necessary equipment in the room. The lead site investigator may then confirm with staff that he/she may proceed with prepping the subject.

The subject's skin under the skull base is shaved as appropriate. CT scout images are performed, followed by a pre-procedure planning CT with IV contrast, if deemed necessary by the interventionalist to localize the target location and to image vasculature. After the target site (cisterna magna) is identified and needle trajectory planned, the skin is prepped and draped using sterile technique as per institutional guidelines. A radiopaque marker is placed on the target skin location as indicated by the interventionalist. The skin under the marker is anesthetized via infiltration with 1% lidocaine. A 22 G or 25 G spinal needle is than advanced towards the cisterna magna, with the option to use a coaxial introducer needle.

After needle advancement, CT images are obtained using the thinnest CT slice thickness feasible using institutional equipment (ideally ≤2.5 mm). Serial CT images using the lowest radiation dose possible that allows for adequate visualization of the needle and relevant soft tissues (e.g., paraspinal muscles, bone, brainstem, and spinal cord) are obtained. Correct needle placement is confirmed by observation of CSF in the needle hub and visualization of needle tip within the cisterna magna.

The interventionalist confirms that the vector syringe is positioned close to, but outside of the sterile field. Prior to handling or administering the pharmaceutical composition in the vector syringe, gloves, mask, and eye protection are donned by staff assisting the procedure within the sterile field.

The extension tubing is attached to the inserted spinal needle, which is then attached to the 4-way stopcock. Once this apparatus is "self-primed" with the subject's CSF, the 10 cc prefilled normal saline flush syringe is attached to a flush inlet port of the 4-way stopcock. The vector syringe is then provided to the interventionalist and attached to a vector inlet port on the 4-way stop cock.

After the outlet port of the stopcock is opened to the vector syringe by placing the swivel lock of the stopcock in a first position, the contents of the vector syringe are injected slowly (over approximately 1-2 minutes), with care taken not to apply excessive force onto the plunger of the syringe during the injection. After the contents of the vector syringe are injected, the swivel lock of stopcock is turned to a second position so that the stopcock and needle assembly can be flushed with 1-2 cc of normal saline using the attached prefilled flush syringe.

When ready, the interventionist then alerts staff that he/she will remove the apparatus from the subject. In a single motion, the needle, extension tubing, stopcock, and syringes are slowly removed from the subject and placed onto a surgical tray for discarding into a biohazard waste receptacle or hard container (for the needle).

The needle insertion site is examined for signs of bleeding or CSF leakage and treated as indicated by the investigator. Site is dressed using gauze, surgical tape and/or Tegaderm dressing, as indicated. Subject is then removed from the CT scanner and placed supine onto a stretcher. Adequate staff is present to assure subject safety during transport and positioning.

Anesthesia is discontinued and subject cared for following institutional guidelines for post-anesthesia care. Neurophysiologic monitors are removed from the subject. The head of the stretcher on which the subject lies should be slightly raised (~30 degrees) during recovery. Subject is transported to a suitable post-anesthesia care unit as per institutional guidelines. After subject has adequately recovered consciousness and is in stable condition, he/she will be admitted to the appropriate floor/unit for protocol mandated assessments. Neurological assessments will be followed as per the protocol and the Primary Investigator oversees subject care in collaboration with hospital and research staff.

In one embodiment, a method for delivery of a composition provided herein comprises the steps of: advancing a spinal needle into the cisterna magna of a patient; connecting a length of flexible tubing to a proximal hub of the spinal needle and an output port of a valve to a proximal end of the flexible tubing; after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve; after connecting said first and second vessels to the valve, opening a path for fluid flow between the vector inlet port and the outlet port of the valve and injecting the pharmaceutical composition into the patient through the spinal needle; and after injecting the pharmaceutical composition, opening a path for fluid flow through the flush inlet port and the outlet port of the valve and injecting the isotonic solution into the spinal needle to flush the pharmaceutical composition into the patient. In certain embodiment, the method further comprises confirming proper placement of a distal tip of the spinal needle within the cisterna magna before connecting the tubing and valve to the hub of the spinal needle. In certain embodiments, the confirming step includes visualizing the distal tip of the spinal needle within the cisterna magna with Computed Tomography (CT) imaging. In certain embodiments, the confirming step includes observing the presence of the patient's cerebrospinal fluid in the hub of the spinal needle.

In the above-described method, the valve may be a stopcock with a swivel luer lock adapted to swivel to a first position permitting flow from the vector inlet port to the outlet port while simultaneously blocking flow through the flush inlet port and to a second position permitting flow from the flush inlet port to the outlet port while simultaneously blocking flow through the vector inlet port, and wherein the swivel luer lock is positioned into said first position when said pharmaceutical composition is injected the patient and is positioned into said second position when said pharmaceutical composition is being flushed into said patient by the isotonic solution. In certain embodiments, after injecting the isotonic solution into the spinal needle to flush the pharmaceutical composition into the patient, the spinal needle is withdrawn from the patient with the tubing, valve, and first and second vessels connected thereto as an assembly. In certain embodiments, the valve is a 4-way stopcock with a swivel male luer lock. In certain embodiments, the first and second vessels are separate syringes. In certain embodiments, a T-connector is located at the hub of the spinal needle and interconnects the tubing to the spinal needle. Optionally, the spinal needle includes an introducer needle at the distal end of the spinal needle. The spinal needle may be a five inch, 22 or 24 gauge spinal needle. In certain embodiments, the introducer needle is a 3.5 inch, 18 gauge introducer needle.

In certain aspects, the method utilizes a device which is composed of, at a minimum, a first vessel for containing an amount of a pharmaceutical composition; a second vessel for containing an isotonic solution; a spinal needle through which the pharmaceutical composition may be ejected from the device directly into cerebrospinal fluid within the cisterna magna of a patient; and a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle. In certain embodiments, the valve is a stopcock with a swivel luer lock adapted to swivel to a first position permitting flow from the first inlet port to the outlet port while simultaneously blocking flow through the second inlet port and to a second position permitting flow from the second inlet port to the outlet port while simultaneously blocking flow through the first inlet port. Optionally, the valve is a 4-way stopcock with a swivel male luer lock. In certain embodiments, the first and second vessels are separate syringes. In certain embodiments, the spinal needle is interconnected to the valve via a length of flexible tubing. A T-connector may interconnect the tubing to the spinal needle. In certain embodiments, the spinal needle is a five inch, 22 or 24 gauge spinal needle. In certain embodiments, the device further comprises an introducer needle connected to a distal end of the spinal needle. Optionally, the introducer needle is a 3.5 inch, 18 gauge introducer needle.

This method and this device may each optionally be used for intrathecal delivery of the compositions provided herein. Alternatively, other methods and devices may be used for such intrathecal delivery.

The following examples are illustrative only and are not a limitation on the invention described herein.

6. EXAMPLES

Example 1: Protocol for Treatment of Human Subjects

This Example relates to a gene therapy treatment for patients that have MPS II, i.e., Hunter syndrome. In this example, the gene therapy vector, AAV9.CB.hIDS, a replication deficient adeno-associated viral vector 9 (AAV9) expressing a modified hIDS gene encoding the wild-type hIDS enzyme, is administered to the central nervous system (CNS) of the MPS II patients. Doses of the AAV vector are injected directly into the CNS under general anesthesia. Efficacy of treatment is assessed using clinical measures of neurocognitive development and/or surrogate markers, including biomarkers, e.g., a decrease in pathogenic GAG and/or heparin sulfate (HS) concentration in the subject's CSF or serum, as described herein.

A. Gene Therapy Vector

The gene therapy vector is a non-replicating recombinant adeno-associated virus (AAV) vector of serotype 9 expressing human iduronate-2-sulfatase (IDS), and is referred to in this Example as AAV9.CB. IDS (see FIG. 1). The AAV9 serotype allows for efficient expression of the hIDS product in the CNS following IC administration.

The IDS expression cassette is flanked by inverted terminal repeats (ITRs) and expression is driven by a hybrid of the cytomegalovirus (CMV) enhancer and the chicken beta actin promoter (CB7). The transgene includes the chicken beta actin intron and a rabbit beta-globin polyadenylation (polyA) signal.

The vector is suspended in formulation buffer (Elliots B Solution, 0.001% Pluronic F68). The construct was packaged in an AAV9 capsid, purified and titered as previously described in M. Lock et al, Human Gene Ther, 21: 1259-1271 (2010). The manufacturing process is described in more detail in Example 4 below.

Vector Production:

A series of vectors were generated. One plasmid contains a codon-optimized IDS sequence (nt 1177 to nt 2829 of SEQ ID NO: 11). Two others used a short version of the CB7 promoter (CB6) and expressed a second protein called SUMF1 [SEQ ID NO: 7 and SEQ ID NO: 10]. The vector genome produced, AAV.CB7.CI.hIDSco.RBG, has a sequence of nt 2 to nt 3967 of SEQ ID NO: 11 while AAV.CB6.hIDSco.IRES.hSUMF1co, has a sequence of nt 11 to nt 4964 of SEQ ID NO: 8. The plasmids were constructed by codon-optimizing and synthesizing the hIDS sequence and the resulting construct was then cloned into the plasmid pENN.AAV.CB7.CI.RBG or pENN.AAV.CB6.CI.RBG, an AAV2 ITR-flanked expression cassette containing CB7 or CB6, CI and RBG expression elements to give the said vector genome.

Still further plasmids were created containing the native human IDS cDNA; these plasmids are termed herein pAAV.CB7.CI.hIDS.RBG and pAAV.CB6.CI.hIDS.IRES.SUMF1.RBG. The vector genomes derived from these plasmids [nt 2 to nt 3967 of SEQ ID NO: 3 and nt 11 to nt 4964 of SEQ ID NO: 5] is single-stranded DNA genome with AAV2 derived ITRs flanking the hIDS expression cassette. Expression from the transgene cassette is driven by a CB7 or CB6 promoter, a hybrid between a CMV immediate early enhancer (C4) and the chicken beta actin promoter, while transcription from this promoter is enhanced by the presence of the chicken beta actin intron (CI). The polyA signal for the expression cassette is the RBG polyA. The plasmids were constructed by synthesizing the hIDS sequence and the resulting construct was then cloned into the plasmid pENN.AAV.CB7.CI.RBG or pENN.AAV.CB6.CI.RBG, an AAV2 ITR-flanked expression cassette containing CB7, CI and RBG expression elements to give the said vector genome.

Description of the Sequence Elements:

Inverted terminal repeats (ITR): AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

CMV immediate early enhancer (382 bp, C4; GenBank #K03104.1). This element is present in the vector genome plasmid.

Chicken beta-actin promoter (282 bp; CB; GenBank #X00182.1) is used to drive high-level hIDS expression.

Chicken beta-actin intron: The 973 bp intron from the chicken beta actin gene (GenBank #X00182.1) is present in the vector expression cassette. The intron is transcribed, but removed from the mature messenger RNA (mRNA) by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression. This element is present in both vector genome and plasmids.

Iduronate-2-sulfatase coding sequence: The hIDS sequence was synthesized [SEQ ID NO: 1]. The encoded protein is 550 amino acids [SEQ ID NO: 2; Genbank NP_000193, UnitProtKB/Swiss-Prot (P22304.1)], described earlier in the specification. See, SEQ ID NOs: 1 and 2. A codon-optimized hIDS coding sequence is shown in nt 3423 to nt 4553 of SEQ ID NO: 8 as well as nt 1937 to nt 3589 of SEQ ID NO: 11.

Polyadenylation Signal: The 127 bp rabbit beta-globin polyadenylation signal (GenBank #V00882.1) provides cis sequences for efficient polyadenylation of the antibody mRNA. This element functions as a signal for transcriptional termination, a specific cleavage event at the 3' end of the nascent transcript and addition of a long polyadenyl tail. This element is present in both vector genome and plasmids.

B. Dosing & Route of Administration

Patients that are ages ≥4 months to <5 years receive a single intrathecal/intracisternal dose of rAAV9.CB7.hIDS which ranges from $2.6 \times 10^{12}$ GC ($2.0 \times 10^9$ GG/g brain mass) (low dose) to $1.3 \times 10^{14}$ GC ($1.0 \times 10^{11}$ GC/g brain mass (high dose)). A patient can be treated with a dose of $1.3 \times 10^{10}$ GC/g brain mass or a dose of $6.5 \times 10^{10}$ GC/g brain mass.

In certain embodiments, AAV9.hIDS is administered via infusion into the cisterna magna (IC) via a suboccipital route of administration. Insertion of the needle into the IC is done via CT guidance. General anesthesia and endotracheal intubation is required during the procedure. A head/neck MRI during screening is used to show suitable anatomy.

In certain embodiments, a lumbar puncture is performed, first to remove 5 cc of CSF and subsequently to inject contrast IT to aid visualization of the cisterna magna. CT (with contrast) is utilized to guide needle insertion and administration of rAAV9.CB7.hIDUA into the suboccipital space.

The following therapeutically effective flat doses are administered to patients of the indicated age group:
Newborns: about $1 \times 10^{11}$ to about $3 \times 10^{14}$ GC;
3-9 months: about $6 \times 10^{12}$ to about $3 \times 10^{14}$ GC;
9 months-6 years: about $6 \times 10^{12}$ to about $3 \times 10^{14}$ GC;
3-6 years: about $1.2 \times 10^{13}$ to about $6 \times 10^{14}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In other embodiments, the following therapeutically effective flat doses are administered to an MPS patient of the age group:
Newborns: about $3.8 \times 10^{12}$ to about $1.9 \times 10^{14}$ GC;
3-9 months: about $6 \times 10^{12}$ to about $3 \times 10^{14}$ GC;
9-36 months: about $10^{13}$ to about $5 \times 10^{13}$ GC;
6-12 years: about $1.2 \times 10^{13}$ to about $6 \times 10^{14}$ GC;
12+ years: about $1.4 \times 10^{13}$ to about $7.0 \times 10^{14}$ GC;
18+ years (adult): about $1.4 \times 10^{13}$ to about $7.0 \times 10^{14}$ GC.

In order to ensure that empty capsids are removed from the dose of rAAV9.CB7.hIDS that is administered to patients, empty capsids are separated from vector particles by cesium chloride gradient ultracentrifugation or by ion exchange chromatography during the vector purification process, as discussed herein.

Immunosuppressive therapy may be given in addition to the vector.

Immunosuppressive therapy includes corticosteroids (methylprednisolone 10 mg/kg intravenously [IV] once on Day −2 and oral prednisone starting at 0.5 mg/kg/day on Day −1 with gradual tapering and discontinuation by Week 16), tacrolimus (0.2 mg/kg/day by mouth [PO] Days −2 to Week 24), and sirolimus (once daily [QD] from Day −2 until the Week 48 visit). An illustrative sirolimus dose may include (6 mg PO Day −2 then 2 mg QD from Day −1 until the Week 48 visit). Sirolimus dose adjustments can be made to maintain whole blood trough concentrations within 16-24 ng/mL. Adjustments may also be made to the other drugs in the regimen, including delivering the drugs for a shorter or longer time period. In most subjects, dose adjustments can be based on the equation: new dose=current dose×(target concentration/current concentration). Subjects may continue on the new maintenance dose for at least 7-14 days before further dosage adjustment with concentration monitoring. Optionally, patients can be permitted to remain on a stable regimen of intravenous enzyme replacement therapy (ERT, e.g., ALDURAZYME™ [laronidase], as well as any supportive measures (e.g., physical therapy). Patients are monitored for any adverse event. Serious adverse events may include possible drug-induced liver injury with hyperbilirubinemia defined as ALT ~3×the ULN and bilirubin ~2×ULN (>35% direct) termed "Hy's Law" events.

In some embodiments, the immunosuppressive therapy regimen is as follows:

Corticosteroids

In the morning of vector administration (Day 1 predose), patients receive methylprednisolone 10 mg/kg IV (maximum of 500 mg) over at least 30 minutes. The methylprednisolone is administered before the lumbar puncture and intrathecal (IC) injection of rAAV9.CB7.hIDUA. Premedication with acetaminophen and an antihistamine is optional.

On Day 2, oral prednisone is started with the goal to discontinue prednisone by Week 12. The dose of prednisone is as follows: Day 2 to the end of Week 2: 0.5 mg/kg/day. Week 3 and 4: 0.35 mg/kg/day. Week 5-8: 0.2 mg/kg/day. Week 9-12: 0.1 mg/kg.

Prednisone is discontinued after Week 12. The exact dose of prednisone can be adjusted to the next higher clinically practical dose.

Sirolimus: 2 days prior to vector administration (Day −2): a loading dose of sirolimus 1 mg/m² every 4 hours×3 doses is administered. From Day −1: sirolimus 0.5 mg/m/day divided in twice a day dosing with target blood level of 4-8 ng/ml. Sirolimus is discontinued after the Week 48 visit.

Tacrolimus: Tacrolimus is started on Day 2 (the day following rAAV9.CB7.hIDUA administration) at a dose of 1 mg twice daily and adjusted to achieve a blood level 4-8 ng/mL for 24 Weeks. Starting at Week 24 visit, tacrolimus is tapered off over 8 weeks. At week 24 the dose is decreased by approximately 50%. At Week 28 the dose is further decreased by approximately 50%. Tacrolimus is discontinued at Week 32.

C. Patient Subpopulations

Suitable patients include, male or female subjects in age:
Newborns;
3-9 months of age;
9-36 months of age;
3-12 years of age;
12+ years of age;
18+ years of age (adult).

D. Measuring Clinical Objectives

Primary clinical objectives include preventing and/or optionally reversing the neurocognitive decline associated with MPS II defects. Clinical objectives may be determined by measuring neurocognition, e.g., as measured by Bayley Scales of Infant and Toddler Development, Third Edition, BSID-III. Other appropriate measures are adaptive behavioral assessments, e.g., as measured by Vineland Adaptive Behavior Scales, Second Edition (VABS-II), and quality of life measure, e.g., as measured by Infant Toddler Quality of Life Questionnaire™ (ITQOL).

Secondary endpoints include evaluation of biomarkers and clinical outcomes. Optionally hearing may be assessed as a secondary endpoint. Urine is evaluated for total GAG content, as well as heparan sulfate. Serum is evaluated for IDS activity, anti-IDS antibodies, GAG, and concentration of the heparin cofactor II-thrombin complex. CSF is evaluated for GAG, IDS activity, anti-IDS antibodies, and heparin sulfate. The presence of anti-IDS antibodies is assessed, as is the pharmacokinetics of IDS expression in CSF and serum. Volumetric analysis of gray and white matter and CSF ventricles is also performed by MRI.

Example 2: Studies in Murine Models of Mucopolysaccharidosis Type II—Delivery of an Adeno-Associated Virus Vector into CSF Attenuates Central Nervous System Disease in Mucopolysaccharidosis Type II Mice A. AAV9 Delivery into Cerebrospinal Fluid Corrects CNS Disease Mucopolysaccharidosis type II (MPS II) is an X-linked lysosomal storage disorder typically manifesting in early childhood with bone and joint deformities, cardiac and respiratory disease, and developmental delay. Systemic delivery of the deficient enzyme, iduronate-2-sulfatase (IDS), improves many symptoms of MPS II, but because the enzyme does not cross the blood-brain barrier, there is currently no effective method to prevent the progression of central nervous system (CNS) disease. Using a mouse model of MPS II, AAV serotype 9 vector-mediated delivery of the IDS gene was evaluated as a means of achieving continuous IDS expression in the CNS. IDS knockout mice received a single injection into the lateral ventricle of one of three vector doses (low—$3\times10^8$, mid—$3\times10^9$ or high—$3\times10^{10}$ genome copies) and were sacrificed either three weeks after vector administration for assessment of vector biodistribution and IDS expression (n=7-8 mice per group), or 3 months after vector administration to evaluate the impact of gene transfer on disease progression (n=7-8 mice per group). IDS activity was detectable in cerebrospinal fluid, reaching 15% of wild-type levels in the low-dose cohort and 268% of normal at the highest dose. Brain enzyme activity ranged from 2.7% of normal in the low-dose cohort to 32% in the high-dose cohort. Quantification of brain storage lesions by staining for the ganglioside GM3 indicated dose-dependent correction, with 35%, 46%, and 86% reductions in the low-, mid-, and high-dose cohorts, respectively. Treated mice also demonstrated improved cognitive function in a novel object recognition test. These findings indicate that intrathecal AAV-mediated gene transfer serves as a platform for sustained enzyme delivery to the CNS, addressing this critical unmet need for patients with MPS II.

B. Pharmacologic and Neurobehavioral Effects of AAV9.CB.hIDS

A knockout mouse model (IDS-knockout; $IDS^{y/-}$) of MPS II was created by replacing exons 4 and 5 of the IDS gene with the neomycin resistance gene (see Garcia et al., 2007, J Inherit Metab Dis, 30:924-34). The model exhibits no detectable enzyme activity and develops histological storage lesions similar to those found in MPS II patients. The IDS-knockout mouse exhibits many of the clinical features of MPS II, including skeletal abnormalities. The neurobehavioral phenotype of the mice has not been extensively evaluated, although some studies have indicated abnormalities (Muenzer et al., 2001, Acta Paediatr Suppl, 91(439): 99-9) and therefore is a relevant model for studying the effects of AAV9.CB.hIDS as a treatment for MPS II. In fact, this is the same knockout mouse model which has been used to assess the effect of enzyme replacement therapy in MPS II in support of clinical trials in this population. The following study carried out in this MPS II mouse model established the therapeutic activity AAV9.CB.hIDS.

C. Materials and Methods

Vectors. The human IDUA and IDS cDNAs were cloned into an expression construct containing a chicken beta actin promoter, CMV enhancer, intron, and rabbit beta globin polyadenylation sequence. The expression constructs were flanked by AAV2 inverted terminal repeats. AAV9 vectors were generated from these constructs by triple transfection of HEK 293 cells and iodixanol purification as previously described (Lock et al. (2010). Hum Gene Ther 21: 1259-71).

Animal procedures. All animal protocols were approved by the Institutional Animal Care and Use Committee of the University of Pennsylvania. IDS knockout mice were obtained from Jackson Laboratory (Stock no: 024744) and bred in house. Wild type C57BL/6 males from the colony served as controls. At 2-3 months of age, animals were anesthetized with isoflurane and injected ICV with 5 μL vector diluted in sterile phosphate buffered saline. CSF was collected at the time of necropsy by suboccipital puncture with a 32-gauge needle connected to polyethylene tubing. Terminal serum samples were collected by cardiac puncture Animals were euthanized by exsanguination under ketamine/xylazine anesthesia. Death was confirmed by cervical dislocation. The brain, heart, lungs, liver and spleen were collected on dry ice. For histology experiments, the brain was divided into an anterior half which was fixed for LIMP2 immunohistochemistry, and a posterior half fixed for GM3 immunohistochemistry. Two cohorts of mice were used for behavior experiments. An initial cohort of wild type and IDS KO mice was tested in a battery of procedures to determine if gene deletion affected learning and memory. A second cohort of mice treated with low, medium or high vector doses of AAV9.CB.hIDS ($3\times10^8$, $3\times10^9$, or $3\times10^{10}$ genome copies (GC) respectively) was used to investigate the feasibility of IT delivery as strategy to rescue of behavior deficits.

Behavior procedures: All behavior procedures were performed by operators blinded to genotype and treatment group.

Open Field Activity: Spontaneous activity in an open field was measured with a Photobeam Activity System (PAS)-Open Field (San Diego Instruments). Mice were individually placed in the arena for a single 10 minute trial. Horizontal and vertical beam breaks were collected to assess general locomotion and rearing activity.

Y maze: Short term memory was assessed with a standard Y-shaped maze (San Diego Instruments). The sequence and number of arm entries was recorded during an 8 min trial. A spontaneous alternation (SA) was defined as sequential entry into all three arms of the maze without immediately returning to a previously entered arm. Total arm entries (AE) were collected as a measure of motor activity. The percent spontaneous alternation was calculated as % SA=(SA/(AE−2) *100).

Contextual fear conditioning: Conditioning experiments were performed as described by Abel et al. *Cell.* 1997 Mar. 7; 88(5):615-26. On the training day, mice were allowed to explore the unique conditioning chamber (Med Associates) for 300 seconds. A non-signaled, 1.5 mA continuous footshock was delivered between 248-250 seconds. After an additional 30 seconds in the chamber, the mice were returned to their home cage. Twenty-four hours later, recall of spatial context was assessed for 5 consecutive minutes in the same chamber where training occurred. Memory was assessed with software used to score freezing behavior (Freezescan, CleverSystems). The percent freezing in the 2.5 minutes prestimulus epoch of the training session is compared to the percent freezing upon reexposure to the chamber. An increase in freezing indicates that learning has occurred.

Novel object recognition: The experimental apparatus consisted of a grey rectangular arena (60 cm×50 cm×26 cm) on a white floor and two unique objects: 3.8×3.8×15 cm metal bars and 3.2 cm dia.×15 cm PVC pipes. Prior to exposure to the apparatus, mice were handled 1-2 minutes/day for five days. During a five day habituation phase, mice were allowed to explore an empty arena for five minutes/day. During the training phase, mice explored two of the same objects for 15 minutes to establish familiarization. In the recall phase 24 hours later, mice were returned to the arena with one now-familiar object and a novel object. Mice will preferentially explore the novel object. A reduced preference for novelty suggests a failure to recall the familiar object and thus a learning deficit. All sessions were recorded, and time spent exploring objects was scored with an open source image analysis program (Patel el al., Front Behav Neurosci. 2014 Oct. 8; 8:349).

Enzyme and GAG assays. GAG, Hex and IDUA assays were performed as previously described (Hinderer et al. (2015). Mol Ther 23: 1298-307). IDS activity was measured by incubating 10 µL sample with 20 µL of 1.25 mM 4-methylumbelliferyl α-L-idopyranosiduronic acid 2-sulfate (Santa Cruz Biotechnology) dissolved in 0.1 M sodium acetate with 0.01 M lead acetate, pH 5.0. After incubating 2 hours at 37° C., 45 µL of McIlvain's buffer (0.4 M sodium phosphate, 0.2 M sodium citrate, pH 4.5) and 5 µL recombinant human iduronidase (Aldurazyme, 0.58 mg/mL, Genzyme) were added to the reaction mixture and incubated overnight at 37° C. The mixture was diluted in glycine buffer, pH 10.9, and released 4-MU was quantified by fluorescence (excitation 365 nm, emission 450 nm) compared with standard dilutions of free 4-MU.

Histology. The brain was divided into an anterior half which was fixed for LIMP2 immunohistochemistry, and a posterior half fixed for GM3 immunohistochemistry. LIMP2 and GM3 immunohistochemistry were performed as previously described (Hinderer et al. (2015). Mol Ther 23: 1298-307). The number of cells staining positive for LIMP2 and GM3 was quantified in 4 brain sections from each animal by a blinded reviewer.

Vector biodistribution. Tissues for vector biodistribution analysis were quickly dissected and frozen on dry ice. Samples were stored at −80° C. until the time of analysis. DNA was isolated from tissues using the QIAmp DNA Mini Kit and vector genomes quantified by TaqMan PCR as described (Wang, et al. (2011). Hum. Gene Ther. 22: 1389-1401).

ELISA for anti-hIDS antibodies. Polystyrene ELISA plates were coated overnight with recombinant human IDS (R&D Systems) 5 µg/mL in PBS titrated to pH 5.8. Plates were washed and blocked 1 hour in 2% bovine serum albumin in neutral PBS. Plates were then incubated with serum samples diluted 1:1000 in PBS. Bound antibody was detected with HRP conjugated goat anti-mouse antibody (Abcam) diluted 1:10,000 in PBS with 2% BSA. The assay was developed using tetramethylbenzidine substrate and stopped with 2 N sulfuric acid before measuring absorbance at 450 nm. Titers were determined from a standard curve generated by serial dilution of a positive serum sample arbitrarily assigned a titer of 1:10,000.

Statistics. Tissue GAG content, Hex activity, and brain storage lesions in treated and untreated mice were compared using a one-way ANOVA followed by Dunnett's multiple comparisons test. Open field and Y maze date were analyzed with Students t-test. A two-way ANOVA and Dunnett's post-hoc analysis was applied to the fear conditioning data to assess trial and genotype effects. For the novel object recognition test, time exploring the novel object vs familiar object was compared using a t-test for each group, followed by a Bonferroni correction for multiple comparisons.

Figure 2A:
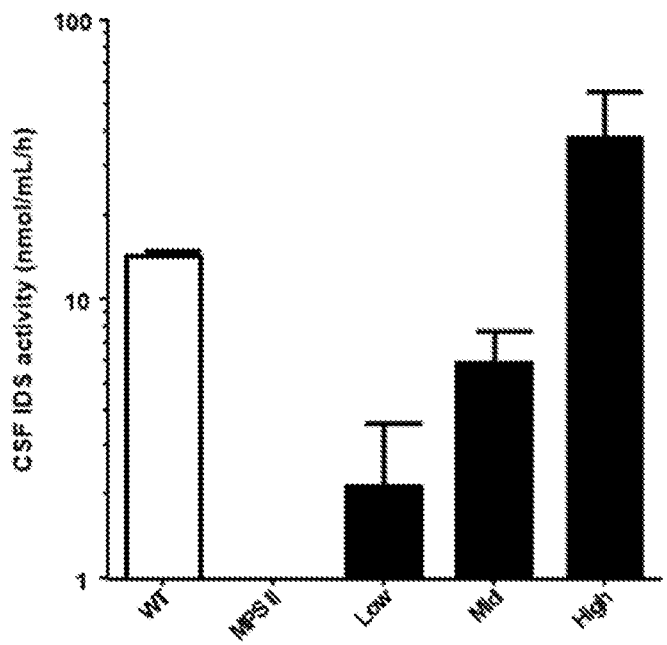
Figure 2B:
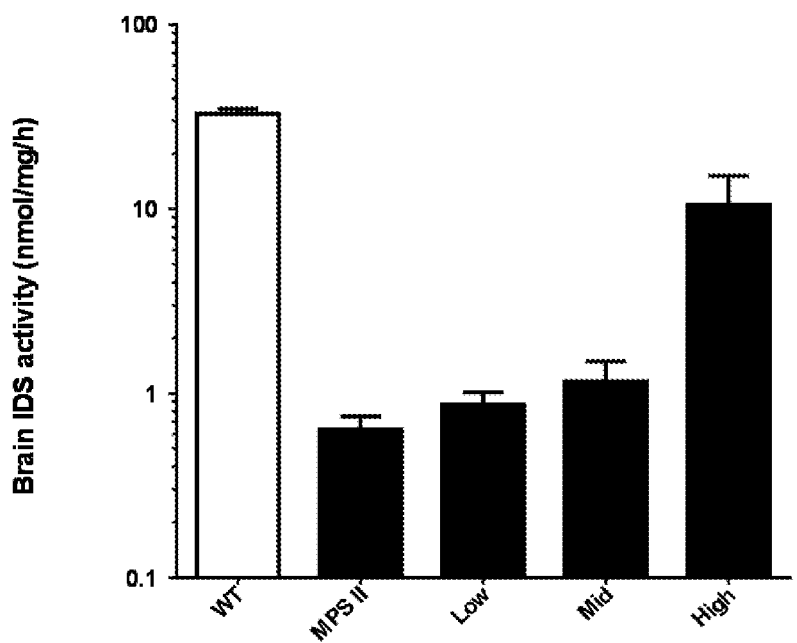
Figure 2C:
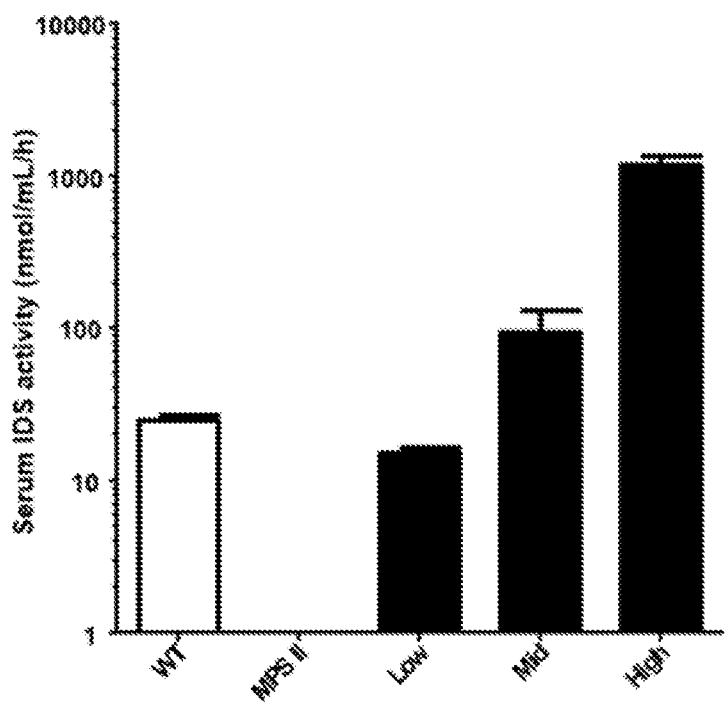
Figure 3:
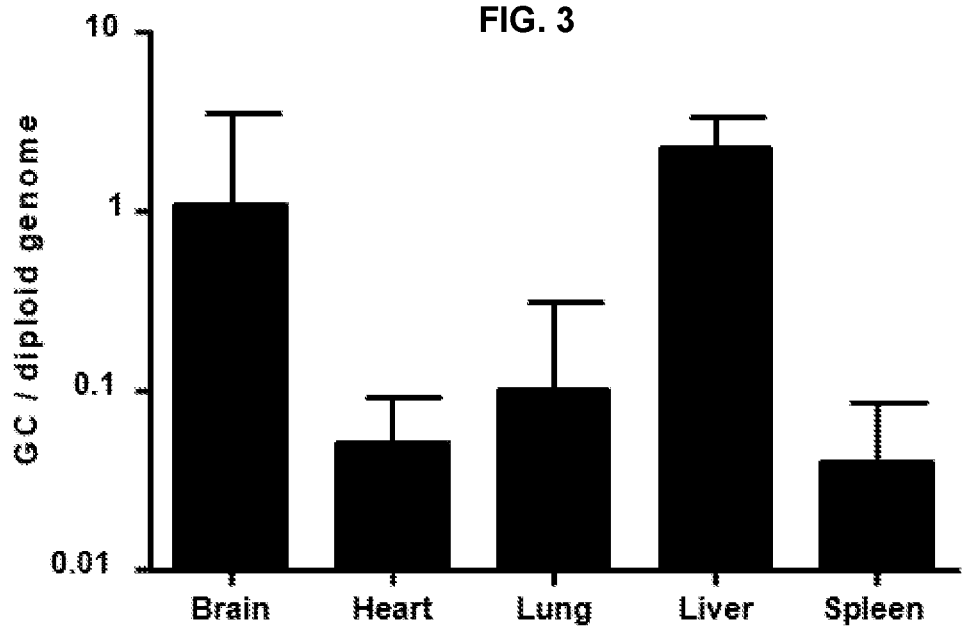
Figure 8:
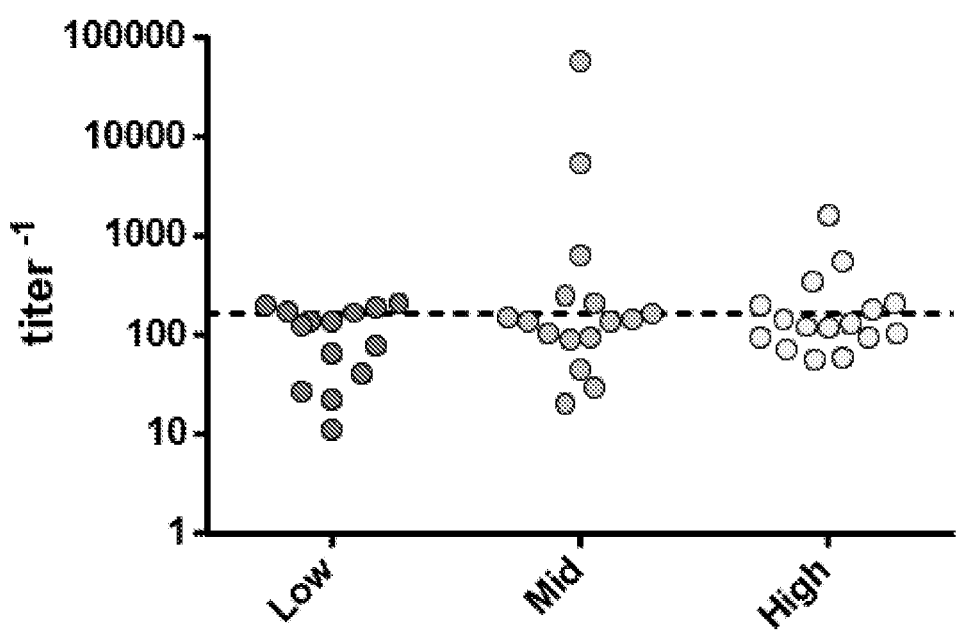

Four age-matched groups of male IDS-knockout mice and one group of wild type littermates (8 mice per group (n=8)) received the following treatments at 2-3 months of age:
Group 1: Untreated
Group 2: Intracerebroventricular AAV9.CB.hIDS Low dose $3\times10^8$ GC ($1.875\times10^9$ GC/g brain mass)
Group 3: Intracerebroventricular AAV9.CB.hIDS Mid dose $3\times10^9$ GC ($1.875\times10^{10}$ GC/g brain mass)
Group 4: Intracerebroventricular AAV9.CB.hIDS High dose $3\times10^{10}$ GC ($1.875\times10^{11}$ GC/g brain mass)
Group 5: Untreated wild type littermates
D. Results:

Male $IDS^{Y-}$ mice between 2 and 3 months of age were treated with an intracerebroventricular (ICV) injection of an AAV9 vector expressing human IDS from a chicken beta actin promoter with a cytomegalovirus enhancer (AAV9.CB.hIDS). In an initial cohort, mice were treated with one of three vector doses [$3\times10^8$, $3\times10^9$, or $3\times10^{10}$ genome copies (GC)] and sacrificed 3 weeks after vector administration for assessment of vector biodistribution and IDS expression. Untreated $IDS^{y/-}$ mice and wild type male littermates served as controls. Tissues were harvested for biodistribution analysis. Analysis of vector biodistribution in the high-dose group demonstrated efficient brain targeting, with an average of one vector genome per host diploid genome (FIG. 3). Consistent with previous studies of AAV delivery into CSF, there was also vector escape to the periphery and efficient hepatic targeting, with more than one vector genome per host diploid genome (FIG. 3). Brain tissue, CSF, and serum all exhibited dose-dependent increases in IDS activity, which approached or exceeded wild type levels in the high-dose group (FIGS. 2A-2C). Antibodies to human IDS were detected in serum of several animals in the mid- and high-dose cohorts, although this did not appear to significantly affect circulating enzyme activity (FIG. 8).

In order to evaluate the therapeutic potential of IT AAV9-mediated delivery of the IDS gene, an additional cohort of $IDS^{y/-}$ mice was treated with equivalent vector doses, then evaluated at later time points to assess the impact of gene transfer on disease progression. Two months after vector administration the mice were subjected to behavioral and neurocognitive tests. Three months after treatment the animals were sacrificed and tissues harvested for histological and biochemical assessment of disease activity.

Figure 4A:
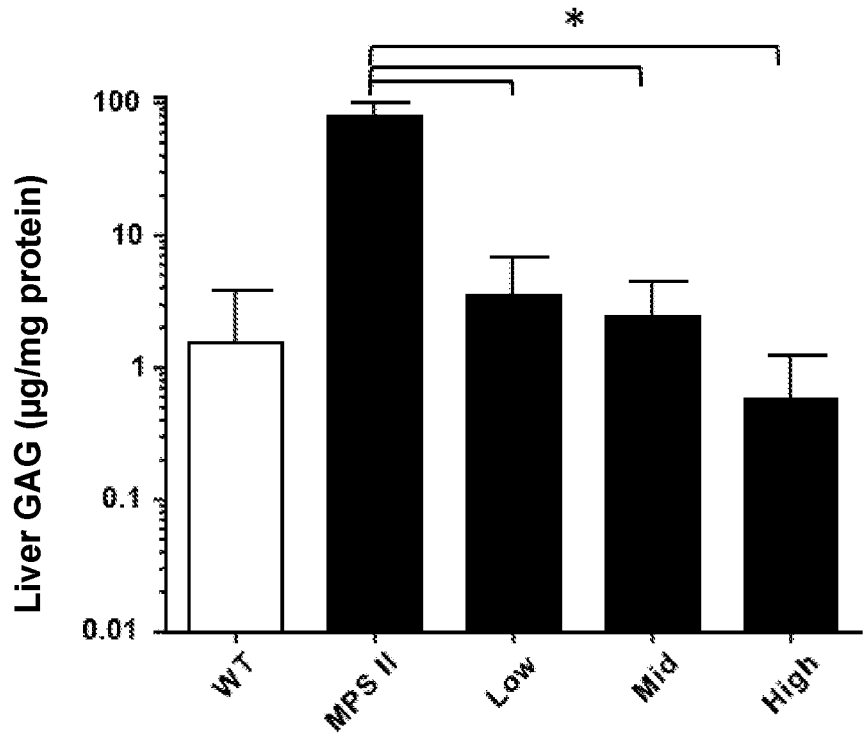
Figure 4B:
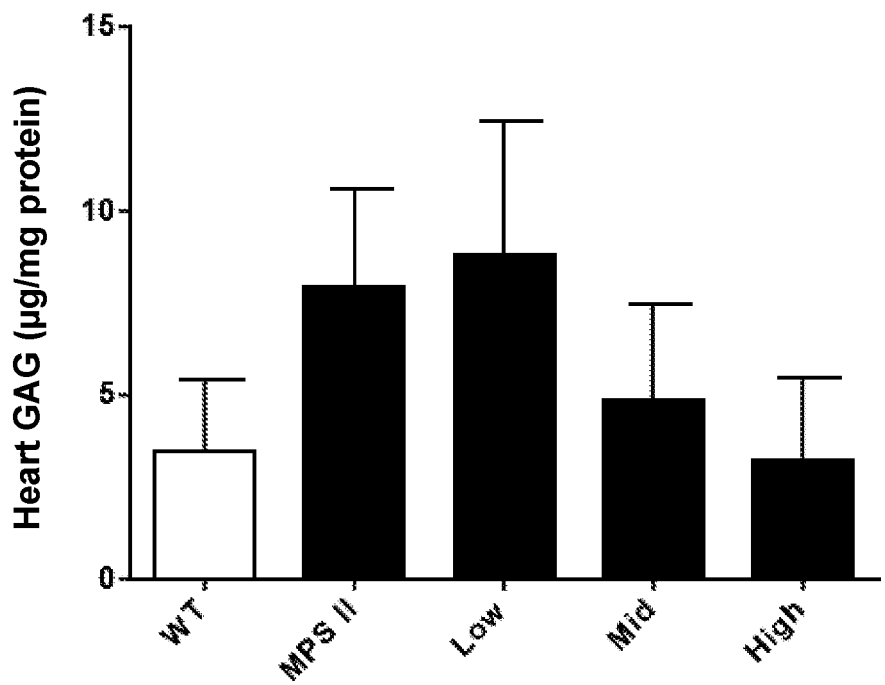
Figure 4C:
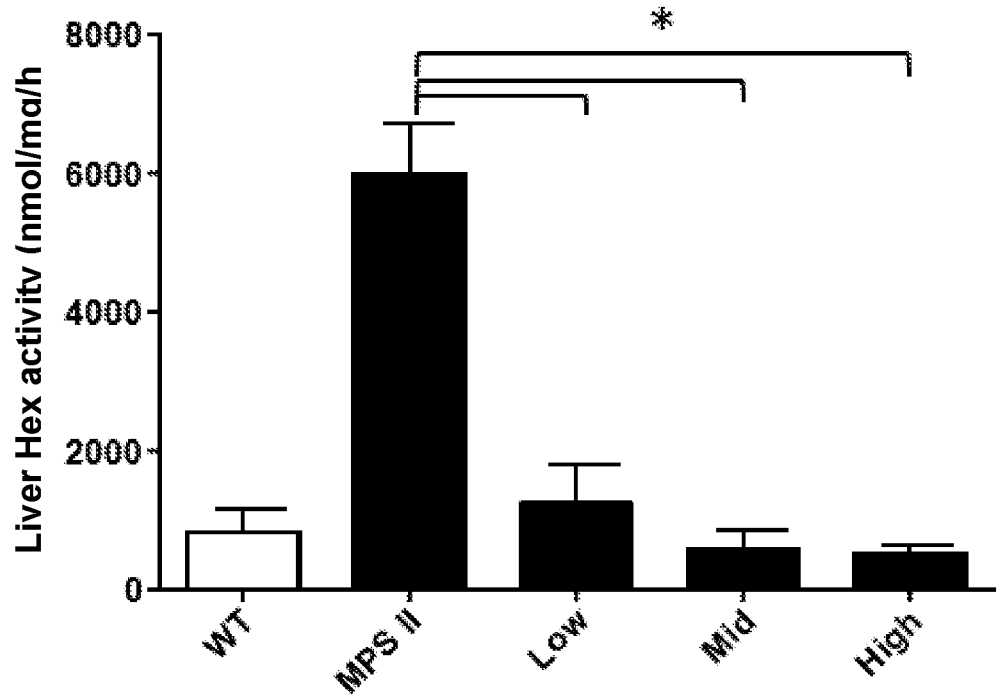
Figure 4D:
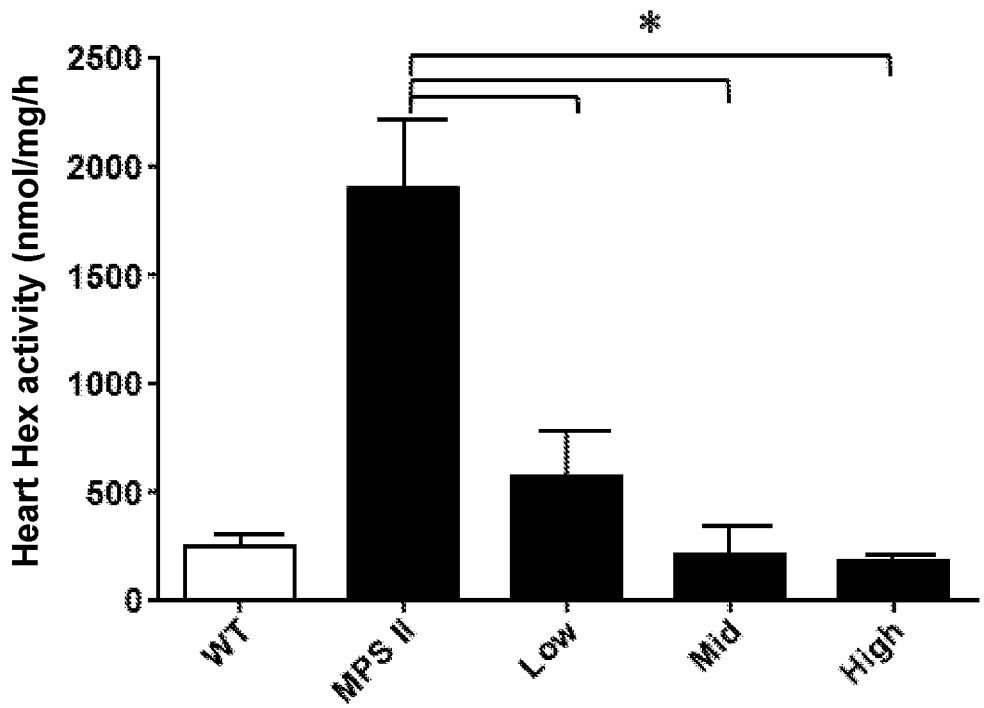

Consistent with high levels of serum enzyme activity, GAG storage was reduced in the liver, and there was a nonsignificant trend toward normalization of GAG storage in the heart (FIGS. 4A-4B). In addition, activity of the lysosomal enzyme hexosaminidase (Hex), which is upregulated in the setting of GAG storage, was normalized in both tissues (FIGS. 4C-4D). These data indicate potential for systemic therapeutic activity after intrathecal administration of AAV9.CB.hIDS.

Figure 5K:
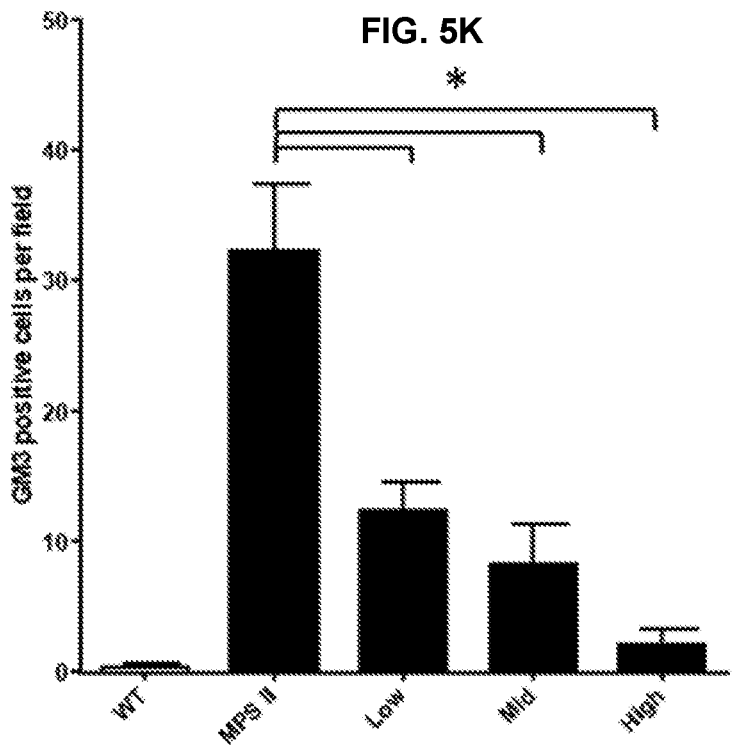
Figure 5L:
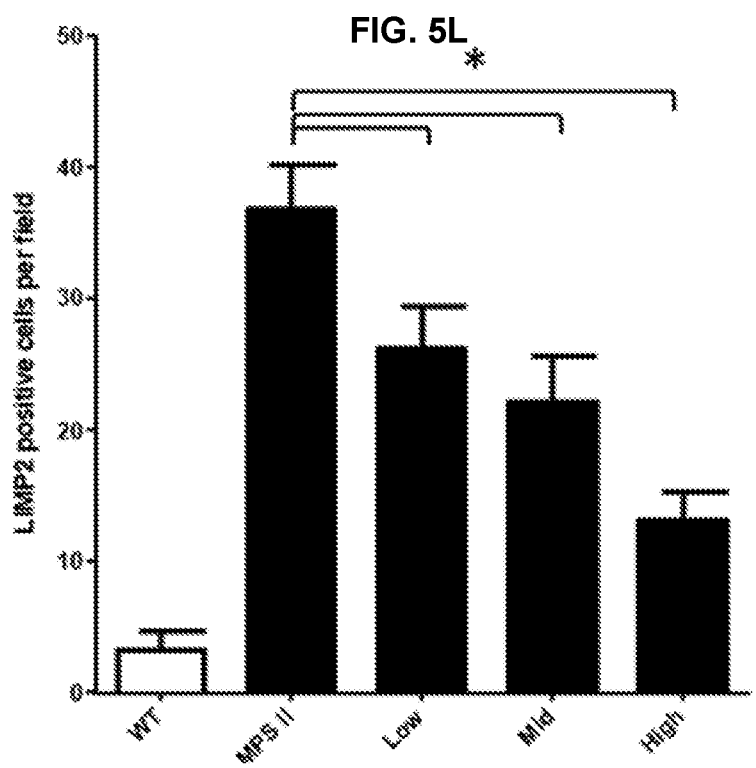

The brains of untreated MPS II mice showed clear histological evidence of lysosomal storage in neurons, including accumulation of the lysosomal membrane protein LIMP2, as well as secondary storage of gangliosides including GM3 (FIG. 5L). Treated mice demonstrated a dose-dependent decrease in neuronal storage lesions evident by both LIMP2 and GM3 staining (FIGS. 5A-5L). Based on this data the low dose of $1.875\times10^9$ GC/g was estimated to be the Minimum Effective Dose (MED) in mice, as this was the lowest dose at which mice exhibited a significant (approximately 50%) reduction in both GM3 and LIMP2 storage lesions. Other studies in MPSII mice evaluated a wide dosage of the clinical candidate and identified a minimally effective dose (MED) of $1.3\times10^9$ GC/g brain mass. The selection of MED, which represents the lowest dose evaluated, was based on dose-dependent changes in I2S activity levels as well as CNS and peripheral characteristics of MPS II including biomarkers, histopathology and neurobehavioral function.

Figure 6A:
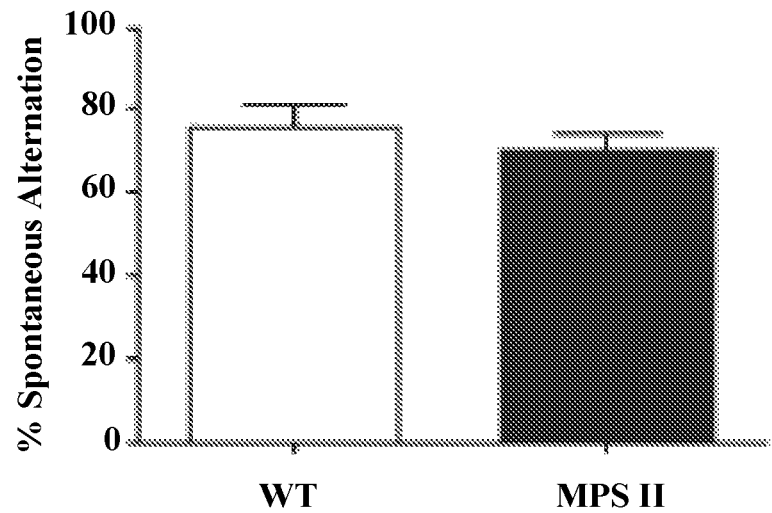
Figure 6B:
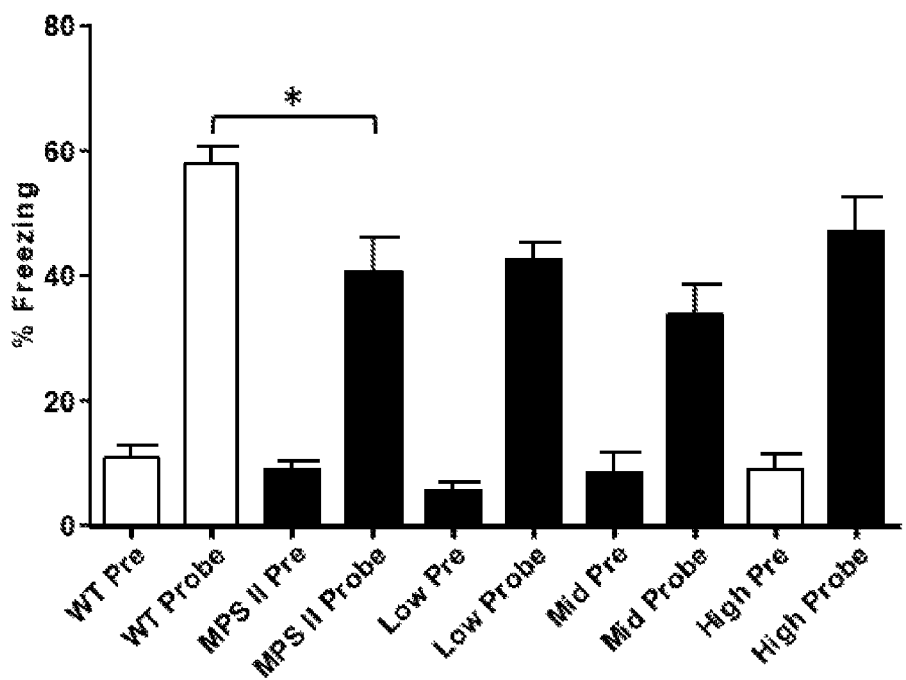
Figure 6C:
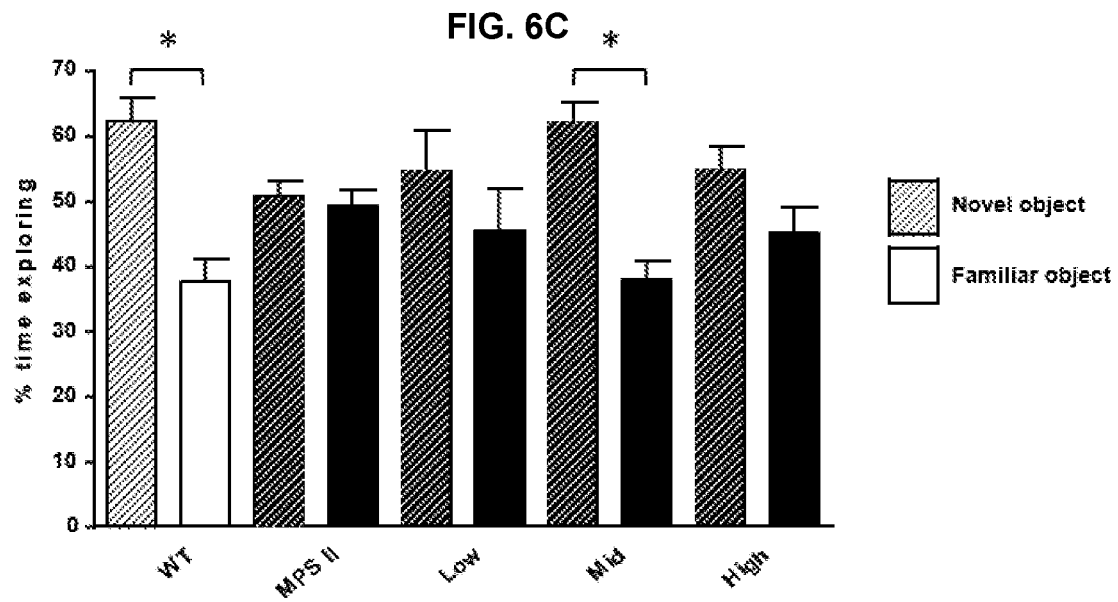
Figure 9A:
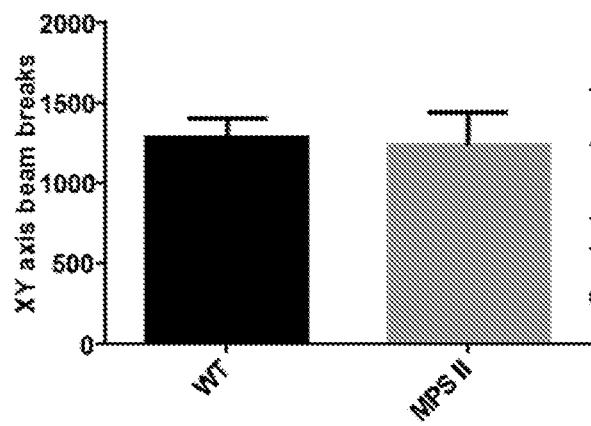
Figure 9B:
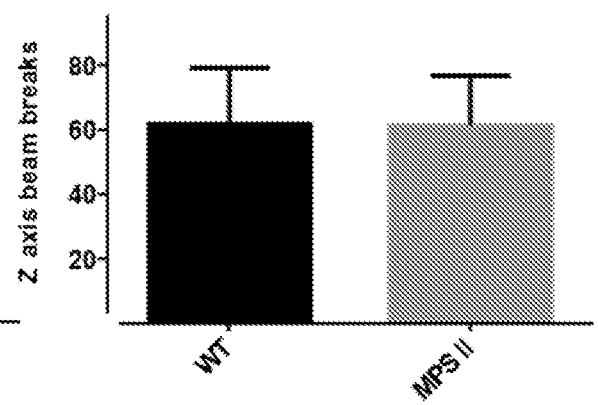
Figure 9C:
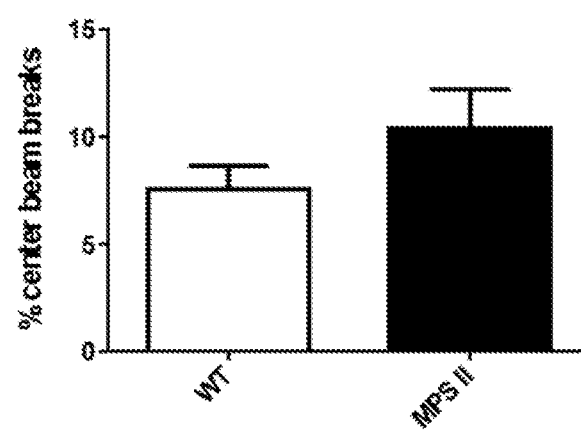

Behavioral testing was performed when the mice reached 4-5 months of age, 2 months after vector administration. A comprehensive battery of tests was performed to evaluate general behavior as well as short and long-term memory. $IDS^{y/-}$ mice showed normal exploratory activity in an open field arena (FIGS. 9A-9C). Spontaneous alternations in a Y-maze (FIG. 9D) were used to assess short term working memory. $IDS^{y/-}$ mice had similar numbers of arm entries and equivalent spontaneous alternations to wild type littermates, demonstrating intact short term memory. Long term memory was assessed using classic contextual fear conditioning (FC) and novel object recognition (NOR). In FC, the association of an aversive stimulus with a specific context evokes freezing behavior upon reexposure to that context. All mice showed an increase in the percent time freezing during the recall phase of the test demonstrating that learning occurred, however $IDS^{y/-}$ mice showed reduced freezing relative to wild type littermates (FIG. 6A). In treated animals, there was no clear improvement in contextual fear conditioning, although treatment effects were difficult to evaluate due to the small difference between normal and untreated $IDS^{y/-}$ mice (FIG. 6B). In NOR, mice are allowed to explore a pair of similar objects. Twenty four hours after training, one now-familiar object is replaced with a novel object. Mice have an innate propensity to explore the novel object; failure to do so demonstrates a lack of recognition of the familiar object and reveals a memory deficit. Wild type mice demonstrated a preference for a novel object, but $IDS^{y/-}$ mice did not show a preference. Remarkably, intrathecal AAV9 gene therapy rescued the long term NOR deficits observed in the $IDS^{y/-}$ mice (FIG. 6C). Object discrimination appeared to be improved in all treated $IDS^{y/-}$ mice, with all groups exhibiting a trend toward greater percentage time exploring a novel object compared with a familiar one. The preference for the novel object was statistically significant only in the mid-dose cohort, although the study was not sufficiently powered to compare the relative degree of rescue of behavioral deficits among dosing groups (FIGS. 6A-6C).

Figure 7A:
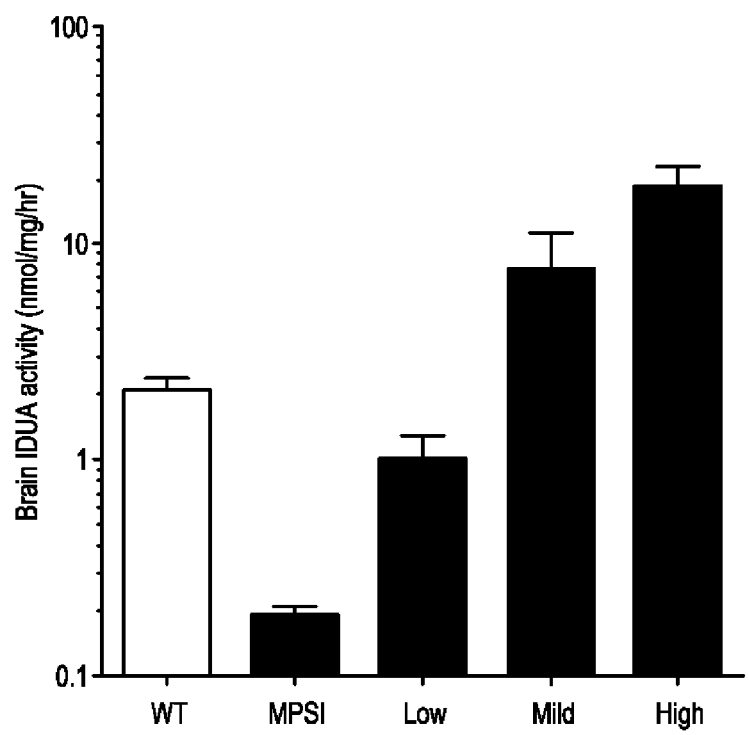
Figure 7B:
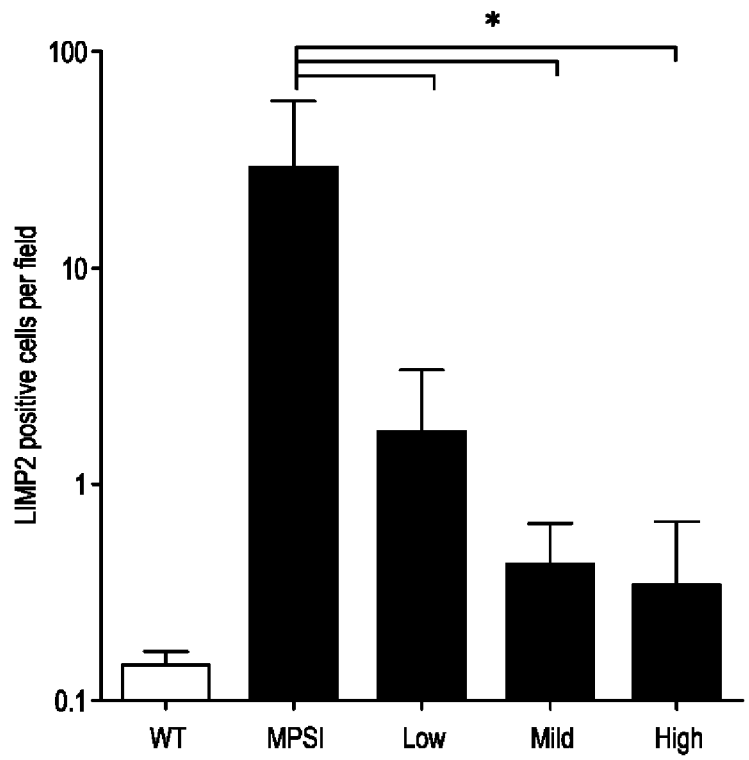

One drawback of evaluating IT AAV delivery in a murine disease model is that the extremely small mouse CNS—with a brain mass of just 0.4 g and CSF volume of 40 µL—may not accurately model the diffusion of vector and secreted enzyme in the human brain, which is 3,500-fold larger. In previous studies of the related lysosomal storage disease mucopolysaccharidosis Type I (MPSI), we utilized naturally occurring large animal disease models to address this issue. [Hinderer et al, Mol Therapy: the Journal of the Am Soc Gen Therapy, 2014: 22: 2018-2027; Hinderer et al, Mol Therapy: the Journal of the Am Soc Gen Therapy, 2015: 23: 1298-1307]. With average brain masses of 30 g and 72 g, respectively, the MPS I cat and dog provided much more realistic models to address the challenge of achieving widespread vector and enzyme delivery in the human brain. Studies carried out in these models provided critical evidence of the efficacy of IT AAV9 delivery for MPS I [Hinderer et al, Mol Therapy: the Journal of the Am Soc Gen Therapy, 2014: 22: 2018-2027; Hinderer et al, Mol Therapy: the Journal of the Am Soc Gen Therapy, 2015: 23: 1298-1307]. In order to determine whether similar efficacy would be possible using this same approach in MPS II, we performed a parallel dose-ranging study in MPS I mice to examine the relative efficiency of enzyme expression and cross-correction in MPS II. MPS I mice were treated with a vector identical to that used for $IDS^{y/-}$ mice, with the exception of the α-L-iduronidase (IDUA) transgene in place of IDS. As with the MPS II study, MPS I mice were treated with doses of $3\times10^8$, $3\times10^9$, or $3\times10^{10}$ GC (n=8 per group) at 2-3 months of age and sacrificed at day 21 post-treatment for measurement of brain enzyme activity or at 3 months post-treatment for histological analysis. There was a similar dose response in brain enzyme expression to that observed in $IDS^{y/-}$ mice, although expression of IDUA appeared somewhat more efficient compared with IDS, both in absolute enzyme activity and relative to wild type expression levels (FIG. 7A). Correction of brain storage lesions was similar between the two disease models, although treatment appeared modestly more effective in MPS I mice at the lowest vector dose (FIGS. 7A-7B). Together these results suggest that IT AAV9-mediated gene transfer for MPS II yields correction of brain storage lesions nearly as efficient as that observed in MPS I, and that this approach remains effective when scaled up from mice. However, slightly higher vector doses compared to MPS I may be necessary in MPS II in order to overcome less efficient enzyme expression in the brain.

In the present study, IT delivery of an AAV9 vector carrying the human IDS gene in MPS II mice resulted in therapeutic levels of expression in the CNS and resolution of brain storage lesions. Functional improvement was indicated by greater novel object discrimination in treated mice compared with untreated controls. Neurocognitive deficits have not been previously well characterized in IDS$^{Y/-}$ mice. These findings demonstrate that IDS$^{Y/-}$ mice have normal exploratory activity in the open field as well as similar arm entries in the Y-maze relative to wild type littermates. These locomotor assessments are critical in considering other types of behavior that require normal exploration. The IDS$^{Y/-}$ mice have been found to have intact short term working memory demonstrated by similar spontaneous alternations in the Y-maze compared to controls. In contrast, Higuchi et al. [Mol Genet and Metabolism, 2012: 107: 122-128] reported reduced spontaneous alternations and increased arm entries in 32 week old IDS$^{Y/-}$ mice. The differing Y-maze results may be due to the different age at testing and underscore the progressive nature of MPS II. We assessed the impact of IDS deficiency on two forms of long term memory. A mild deficit was identified in contextual fear conditioning in the IDS$^{Y/-}$ mouse. Although IDS$^{Y/-}$ mice were able to recall the context in which they received an aversive stimulus, they showed a significantly reduced freezing response compared to wild type littermates. IDS$^{Y/-}$ mice that received IT delivery of AAV9 showed freezing responses similar to uninjected mice. Therefore, no recovery was detected. A long term memory deficit was also found in novel object recognition. In NOR, IDS$^{Y/-}$ mice showed no preference for a novel object relative to a familiar object. Vector treated mice demonstrated recovery of the NOR deficit seen in untreated IDS$^{Y/-}$ mice. Object discrimination was statistically significant only in the mid-dose cohort, although with 8 animals per group, the study was not well powered to evaluate the dose response of behavioral endpoints. The ability of IT delivery of AAV9 to differentially affect recovery of two types of long term memory may be due to different neural substrates required for each task. Contextual fear conditioning is a hippocampal-dependent task as opposed to NOR which requires the perienteorhinal cortex [Oliveira, et al, Post-training reversible inactivation of the hippocampus enhances novel object recognition memory. Learning & memory (Cold Spring Harbor, N.Y.) 2010; 17:155-160; Abel, et al, Cell 1997; 88:615-626].

Comparison of the efficiency of IT AAV9 delivery in mouse models of MPS II and MPS I indicated that enzyme expression and tissue correction were similar between the two diseases, providing evidence that IT AAV delivery for MPS II is efficient enough to yield widespread disease correction in the context of much larger brain sizes and CSF volumes, as has previously been shown in large animal models of MPS I [Hinderer et al, Mol Therapy: the Journal of the Am Soc Gen Therapy, 2014: 22: 2018-2027; Hinderer et al, Mol Therapy: the Journal of the Am Soc Gen Therapy, 2015: 23: 1298-1307]. Interestingly, expression of the deficient enzyme was somewhat less efficient in MPS II compared with MPS I. This could simply be a product of the expression efficiency of these particular vectors, although the control elements in the expression constructs were identical. Some studies have suggested that expression of sulfatases such as IDS can be limited by the availability of the sulfatase modifying factor, SUMF1, which is required for post-translational modification of IDS [Fraldi, et al, Biochemical J, 2007: 403: 305-312. However, pilot experiments evaluating co-expression of IDS and SUMF1 have not demonstrated more active IDS expression (data not shown). Regardless, correction of storage lesions was nearly as efficient in MPS II mice as in MPS I mice, indicating that gene transfer should be similarly effective for both MPS I and MPS II patients, though in the latter case modestly higher vector doses may be necessary for optimal outcomes.

In addition to CNS gene transfer, there was significant liver transduction and peripheral enzyme expression in treated MPS II mice, indicating possible systemic benefits of IT AAV9 delivery in MPS II. This is consistent with studies of IT AAV delivery in a variety of other species [Passini et al, Hu Gene Therapy, 2014; 25: 619-630; Hinderer et al, Molecular Therapy—Methods & Clinical Development 2014; 1; Hinderer et al, Molecular therapy: the journal of the American Society of Gene Therapy 2014; 22:2018-2027; Hinderer, et al, Molecular therapy: the journal of the American Society of Gene Therapy 2015; 23:1298-1307; Gurda, et al, Molecular therapy: the journal of the American Society of Gene Therapy 2015; Higuchi et al, cited above; Haurigot, et al, J Clin Invest, 2013: 123: 3254-3271; Gray et al, Gene Therapy, 2013: 20: 450-459]. Notably, liver transduction after IT AAV vector delivery varies substantially among species, so it is not yet clear whether humans would exhibit significant peripheral expression.

This study demonstrates that IT AAV9 delivery achieves effective IDS gene transfer to the brain and resolve CNS manifestation of MPS II, supporting the advancement of this approach into the clinic.

These data provide preliminary evidence that AAV9.CB.hIDS can improve neurocognitive deficits in MPS II mice.

Example 3: Non-Human Primate Studies

A study in non-human primates (NHPs) is performed to evaluate the safety and effect of AAV9.CB.hIDS in adult male rhesus macaques. The objective of the study is to evaluate local, acute, and chronic toxicities of intrathecal (IT) AAV9.CB.hIDS and to define the biodistribution of the vector. A total of 21 male macaques are treated with an IT injection of AAV9.CB.hIDS at one of two doses of AAV9.CB.hIDS ($5.6 \times 10^{11}$ or $1.875 \times 10^{11}$ GC/g brain mass) or with vehicle control diluent. The low dose is approximately 100-fold greater than the MED in MPS II mice (MED of $1.875 \times 10^9$ GC/g) and corresponds to the lowest dose producing statistically significant histological improvements in MPS II mice and neurobehavioral changes thought to reflect cognitive function. The higher dose (approximately 300× the MED) is the maximal concentration at which the vector can be formulated and is limited by the requirement to maintain an injection volume that can be safely administered to the CSF (<10% CSF volume). During the injection procedure, animals are maintained under general anesthesia. A spinal needle is placed into the suboccipital space; placement is verified via fluoroscopy, and the dose is administered in a total volume of 1 mL. Serum and CSF is collected for clinical pathology assessments at Days 0, 3, 7, 14, 21 and 30 after injection and monthly thereafter. On Days 14, 90, and 180 after injection, 3 male macaques from each dose group (6 total per time point) are sacrificed for pathology and biodistribution. Vehicle treated animals serve as controls. Full histopathology is performed on tissues from all animals, and analysis of vector biodistribution is conducted for the high-dose cohort. DNA extraction and detection of vector genomes by quantitative PCR are performed as previously described (see Chen et al, 2013, Hum Gene Ther Clin Dev, 24(4): 154-160). This assay has a sensitivity greater than 20 vector genome copies per μg of DNA, and spike controls are included to verify reaction efficiency in individual samples. Biodistribution, biochemistry, and immunogenicity data is collected at 14 days, 3 months and 6 months.

In a study of rhesus macaque dosed with $1.8 \times 10^{11}$ or $5.5 \times 10^{11}$ rAAV9.CB8.hIDS vector in combination with immunosuppression (MMF and sirolimus/rapamycin), the following was observed. There were no AEs associated with the administration procedure, and no vector-related abnormalities on clinical general observations, body weight change, organ weights, CBC, serum chemistry, or coagulation parameters. IS procedure caused intestinal signs with increase of some inflammation parameters and anemia that were not related to vector administration. Humoral immune response to hIDS was prevented by IS and was absent or reduced to a minimal (close to background) response in other animals. There was no T cell response to hIDS in IS animals and minimal to moderate response to AAV9 in the LD group only. No rebound immune response was seen following the withdrawal of MMF on Day 60. Both high and low dose groups had minimal to mild axonopathy of the spinal cord dorsal white matter tracts and sciatic nerve Minimal to mild neuronal cell body degeneration with mononuclear cell infiltration in the dorsal root ganglia, that project in the dorsal white matter tracts, and trigeminal ganglia. No inflammation was seen within the brain or spinal cord, despite the presence of high vector copy number. High levels of AAV vector genomes were detected throughout the brain, spinal cord, and dorsal root ganglia. Significant vector biodistribution was also found in the periphery, especially in the liver.

Example 4: Manufacture of rAAV9.CB7.hIDS Vector

The AAV9.CB7.hIDS is produced by triple plasmid transfection of human HEK293 MCB cells with: (i) the hIDS vector genome plasmid, (ii) an AAV helper plasmid termed pAAV29 containing the AAV rep2 and cap 9 wild-type genes and (iii) a helper adenovirus plasmid termed pAdAF6(Kan).

Cloning of the plasmid pAAV.CB7.CI.hIDS.RGB is as described in Example 1 above. The vector genome derived from this plasmid is a single-stranded DNA genome with AAV2 derived ITRs flanking the hIDS expression cassette. Expression from the transgene cassette is driven by a CB7 promoter, a hybrid between a cytomegalovirus (CMV) immediate early enhancer (C4) and the chicken beta actin promoter, while transcription from this promoter is enhanced by the presence of the chicken beta actin intron (CI). The polyA signal for the expression cassette is the rabbit beta-globin (RBG) polyA. The plasmid was constructed by codon-optimizing and synthesizing the hIDS sequence [nt 1177 to nt 2829 of SEQ ID NO: 8, and nt 1937 to nt 3589 of SEQ ID NO: 11] and the resulting construct was then cloned into the plasmid pENN.AAV.CB7.CI.RBG (p1044), an AAV2 ITR-flanked expression cassette containing CB7, CI and RBG expression elements to give pAAV.CB7.CI.hIDS.RBG.

Cloning of the cis plasmid pAAV.CB7CIhIDS.RGB.KanR: The vector genome was excised from this plasmid using the PacI restriction enzyme and cloned into a pKSS-based plasmid backbone (p2017) containing the kanamycin resistance gene. The final vector genome plasmid is pAAV.CB7.CI.hIDS.RBG.KanR.

AAV2/9 helper plasmid pAAV29KanRGXRep2: The AAV2/9 helper plasmid pAAV29KanRGXRep2 encodes the 4 wild-type AAV2 rep proteins and the 3 wild-type AAV VP capsid proteins from AAV9. To create the chimeric packaging construct, first the AAV2 cap gene from plasmid p5E18, containing the wild type AAV2 rep and cap genes, was removed and replaced with a PCR fragment of the AAV9 cap gene amplified from liver DNA. The resulting plasmid was given the identifier pAAV2-9 (p0008). Note that the AAV p5 promoter which normally drives rep expression is moved in this construct from the 5' end of rep to the 3' end of cap. This arrangement serves to introduce a spacer between the promoter and the rep gene (i.e. the plasmid backbone), down-regulate expression of rep and increase the ability to support vector production. The plasmid backbone in p5E18 is from pBluescript KS. The AAV2/9 helper plasmid pAAV29KanRGXRep2 encodes the 4 wild-type AAV2 rep proteins, the 3 wild-type AAV VP capsid proteins from AAV9, and kanamycin resistance.

pAdDeltaF6(Kan) adenovirus helper plasmid is 15,770 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 Kb to 12 kb. Finally the ampicillin resistance gene was replaced by the kanamycin resistance gene to give pAdAF6 (Kan). The functional elements of the E2, E4 and VAI adenoviral genes necessary for AAV vector production remain in this plasmid. The adenoviral E1 essential gene functions are supplied by the HEK293 cells. DNA plasmid sequencing was performed by Qiagen Genomic Services and revealed 100% homology with the following important functional elements of the reference sequence pAdDeltaF6 (Kan) p1707FH-Q: E4 ORF6 3692-2808 bp; E2A DNA binding protein 11784-10194 bp; VA RNA region 12426-13378 bp.

Figure 10A:
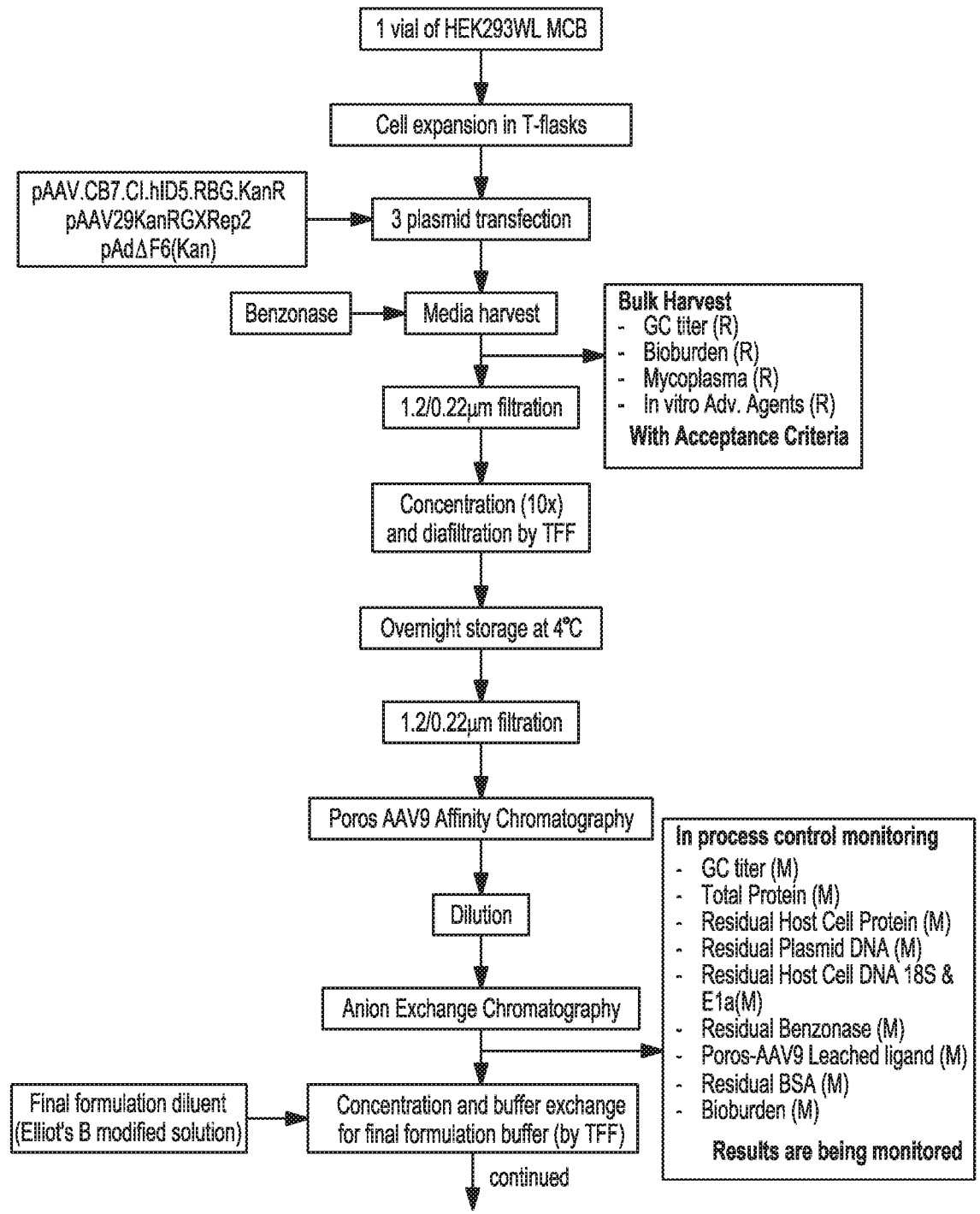
Figure 10B:
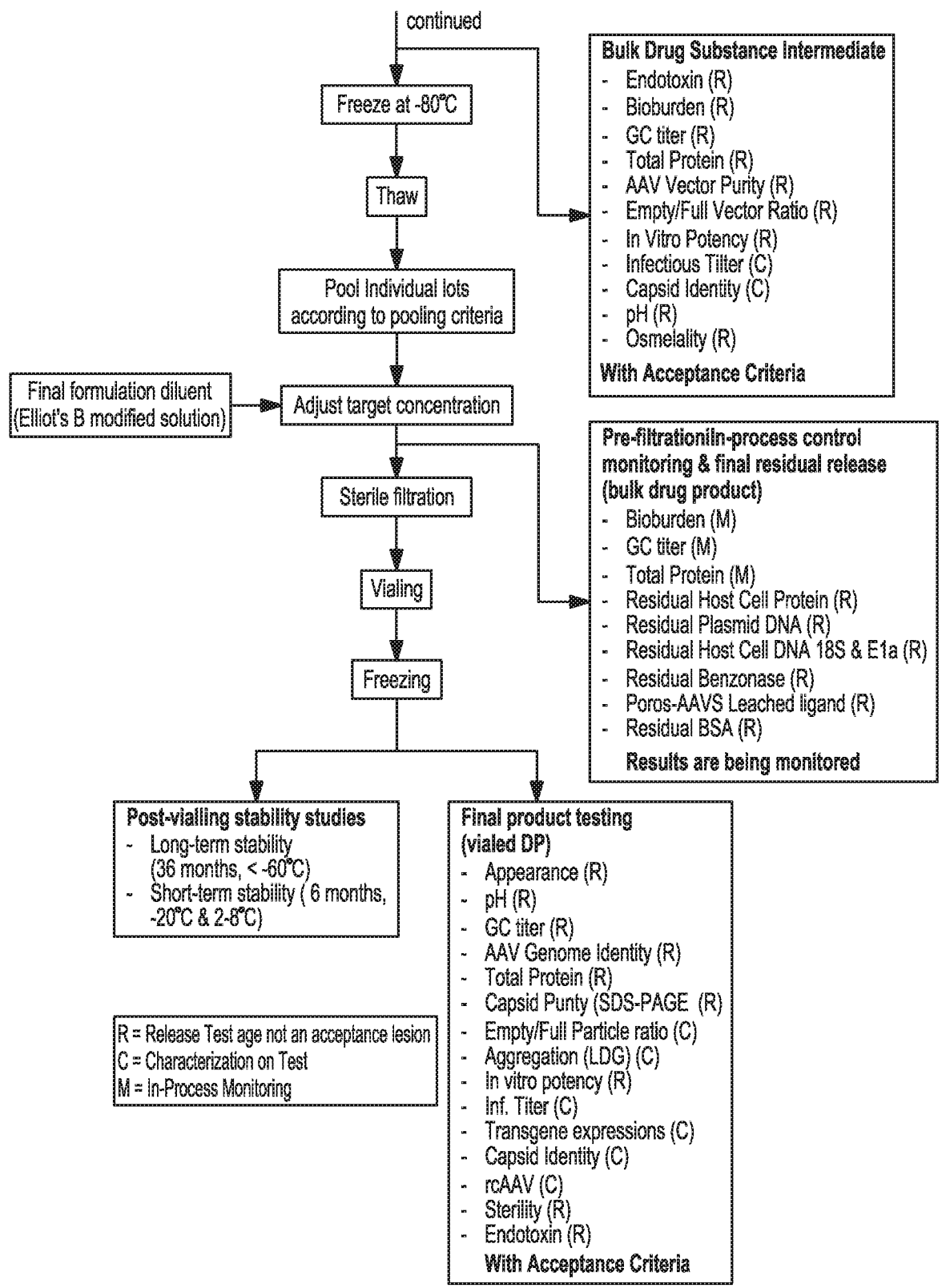

A flow diagram summarizing the manufacturing process is provided in FIGS. 10A-10B.

Cell Seeding: A qualified human embryonic kidney 293 cell line will be used for the production process. Cells will be expanded to $5 \times 10^9$-$5 \times 10^{10}$ cells using Corning T-flasks and CS-10, which will allow sufficient cell mass to be generated for seeding up to 50 HS-36 for vector production per BDS lot. Cells will be cultivated in medium composed of Dulbecco's Modified Eagle Medium (DMEM), supplemented with 10% gamma irradiated, US-sourced, Fetal Bovine Serum (FBS). The cells are anchorage dependent and cell disassociation will be accomplished using TrypLE Select, an animal product-free cell dissociation reagent. Cell seeding is accomplished using sterile, single-use disposable bioprocess bags and tubing sets. The cells are maintained at 37° C. (±2° C.), in 5% (±0.5%) $CO_2$ atmosphere. Cell culture media is replaced with fresh, serum free DMEM media and transfected with the three production plasmids using an optimized PEI-based transfection method. All plasmids used in the production process are produced in the context of a CMO quality system and infrastructure utilizing the most salient features of cGMP manufacturing; traceability, document control, and materials segregation.

Sufficient DNA plasmid transfection complex is prepared in the BSC to transfect up to 50 HS-36 (per BDS batch). Initially a DNA/PEI mixture is prepared containing 7.5 mg of pAAV.CB7.CI.hIDS.RBG.KanR vector genome plasmid, 150 mg of pAdDeltaF6(Kan), 75 mg of pAAV29KanRGXRep2 AAV helper plasmid and GMP grade PEI (PEIPro, PolyPlus Transfection SA). This plasmid ratio was determined to be optimal for AAV production in small scale optimization studies. After mixing well, the solution is allowed to sit at room temperature for 25 min and then added to serum-free media to quench the reaction and then added to the HS-36's. The transfection mixture is equalized between all 36 layers of the HS-36 and the cells are incubated at 37° C. (±2° C.) in a 5% (±0.5%) $CO_2$ atmosphere for 5 days.

Cell Media Harvesting: Transfected cells and media are harvested from each HS-36 using disposable bioprocess bags by aseptically draining the medium out of the units. Following the harvest of media, the ~80 liter volume is supplemented with $MgCl_2$ to a final concentration of 2 mM (co-factor for Benzonase) and Benzonase nuclease (Cat #: 1.016797.0001, Merck Group) are added to a final concentration of 25 units/ml. The product (in a disposable bioprocess bag) is incubated at 37° C. for 2 hr in an incubator to provide sufficient time for enzymatic digestion of residual cellular and plasmid DNA present in the harvest as a result of the transfection procedure. This step is performed to minimize the amount of residual DNA in the final vector. After the incubation period, NaCl is added to a final concentration of 500 mM to aid in the recovery of the product during filtration and downstream tangential flow filtration.

Clarification: Cells and cellular debris are removed from the product using a depth filter capsule (1.2 µm/0.22 um) connected in series as a sterile, closed tubing and bag set that is driven by a peristaltic pump. Clarification assures that downstream filters and chromatography columns are protected from fouling and bioburden reduction filtration ensures that at the end of the filter train, any bioburden potentially introduced during the upstream production process is removed before downstream purification. The harvest material is passed through a Sartorius Sartoguard PES capsule filter (1.2/0.22 µm) (Sartorius Stedim Biotech Inc.).

Large-scale Tangential Flow Filtration: Volume reduction (10-fold) of the clarified product is achieved by Tangential Flow Filtration (TFF) using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, we utilize a 100 kDa, PES membrane for concentration that is then diafiltrated with 4 volumes of a buffer composed of: 20 mM Tris pH 7.5 and 400 mM NaCl. The diafiltered product is stored overnight at 4° C. and then further clarified with a 1.2 µm/0.22 um depth filter capsule to remove any precipitated material.

Affinity Chromatography: The diafiltered product is applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured. Following application, the column is washed to remove additional feed impurities followed by a low pH step elution (400 mM NaCl, 20 mM Sodium Citrate; pH 2.5) that is immediately neutralized by collection into a $\frac{1}{10}$th volume of a neutralization buffer (Bis Tris Propane, 200 mM, pH 10.2).

Anion Exchange Chromatography: To achieve further reduction of in-process impurities including empty AAV particles, the Poros-AAV2/9 elution pool is diluted 50-fold (20 mM Bis Tris Propane, 0.001% Pluronic F68; pH 10.2) to reduce ionic strength to enable binding to a CIMultus Q monolith matrix (BIA Separations). Following a low-salt wash, vector product is eluted using a 60 CV NaCl linear salt gradient (10-180 mM NaCl). This shallow salt gradient effectively separates capsid particles without a vector genome (empty particles) from particles containing vector genome (full particles) and results in a preparation enriched for full capsids. Fractions are collected into tubes containing $\frac{1}{100}$th volume of 0.1% pluronic F68 and $\frac{1}{27}$th volume of Bis Tris pH 6.3 to minimize non-specific binding to tubes and the length of exposure to high pH respectively. The appropriate peak fraction is collected, and the peak area assessed and compared to previous data for determination of the approximate vector yield.

Final Formulation and Sterile Filtration to yield the BDS: TFF is used to achieve final formulation on the pooled AEX fractions with a 100 kDa membrane. This is achieved by diafiltration with 4 volumes of formulation buffer (Elliots B solution, 0.001% Pluronic F68) and concentrated to yield the BDS, whereby the peak area from the anion exchange chromatography is compared to previous data in order to estimate the concentration factor to achieve a titer of $\geq 5 \times 10^{13}$ GC/ml. Samples are removed for BDS testing (described in the section below). The filtered Purified Bulk is stored in sterile polypropylene tubes and frozen at $\leq -60°$ C. in a quarantine location until release for Final Fill. Preliminary stability study indicates that the DP does not lose activity following freezing and thawing in our proposed formulation buffer. Additional studies are underway to assess stability following prolonged storage at $-80°$ C.

Final Fill: The frozen BDS is thawed, pooled, diluted to the target titer using the final formulation buffer, terminally filtered through a 0.22 um filter (Millipore, Billerica, Mass.) and filled into West Pharmaceutical's "Ready-to-Use" (pre-sterilized) 2 ml glass vials and 13 mm stoppers and seals at a fill volume $\geq 0.6$ ml to $\leq 2.0$ ml per vial. Individually labeled vials are labeled according to the specifications below. Labeled vials are stored at $\leq -60°$ C.

The vector (drug product) is vialed at a single fixed concentration and the only variable is the volume per vial. To achieve lower dose concentrations the drug product is diluted with Elliots B solution, 0.001% Pluronic F68. The high dose vector is used directly without dilution while the low vector requires a 1:5 dilution in the formulation buffer which is conducted by the pharmacy at the time of dosing.

Example 5: Testing of Vector

Characterization assays including serotype identity, empty particle content and transgene product identity are performed. Descriptions of the assays appear below.

A. Vector Genome Identity: DNA Sequencing

Viral Vector genomic DNA is isolated and the sequence determined by 2-fold sequencing coverage using primer walking. Sequence alignment is performed and compared to the expected sequence. B. Vector Capsid Identity: AAV Capsid Mass spectrometry of VP3

Confirmation of the AAV2/9 serotype of the vector is achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectra (MS) method was developed that allows for subtraction of the host protein products and deriving capsid peptide sequence from mass spectra.

C. Genomic Copy (GC) Titer

The oqPCR based genomic copy titer is determined over a range of serial dilutions and compared to the cognate plasmid standard (pAAV.CB7.CI.hIDS.RBG.KanR). The oqPCR assay utilizes sequential digestion with DNase I and Proteinase K, followed by qPCR analysis to measure encapsidated vector genomic copies. DNA detection is accomplished using sequence specific primers targeting the RBG polyA region in combination with a fluorescently tagged probe hybridizing to this same region. Comparison to the plasmid DNA standard curve allows titer determination without the need of any post-PCR sample manipulation. A number of standards, validation samples and controls (for background and DNA contamination) have been introduced into the assay. The assay is qualified by establishing and defining assay parameters including sensitivity, limit of detection, range of qualification and intra and inter assay precision. An internal AAV9 reference lot is established and used to perform the qualification studies. Note that our previous experience suggests that the titer obtained by the optimized qPCR assay described here is generally 2.5 fold higher than that achieved by our standard qPCR technique which was used for the generation of the pre-clinical data.

D. Empty to Full Particle Ratio

The total particle content of the drug product is determined by SDS-PAGE analysis. A reference vector preparation purified on an iodixanol gradient is analyzed by various methods (analytical ultracentrifugation, electron microscopy and absorbance at 260/280 nm) to established that the preparation contains >95% genome-containing (full) particles. This reference material is serially diluted to known genome copy numbers (and thus by extension, particle numbers) and each dilution is run on an SDS PAGE gel along with a similar dilution series of the drug product. Peak area volumes of both the reference material and drug product VP3 protein bands are determined by densitometry and the reference material volumes are plotted versus particle number. The total particle concentration of the drug product is determined by extrapolation from this curve and the genome copy (GC) titer is then subtracted to obtain the empty particle titer. The empty to full particle ratio is the ratio of the empty particle titer to the GC titer.

E. Infectious Titer

The infectious unit (IU) assay is used to determine the productive uptake and replication of vector in RC32 cells (rep2 expressing HeLa cells). A 96-well end-point format has been employed similar to that previously published. Briefly, RC32 cells are co-infected by serial dilutions of rAAV9.CB.hIDS and a uniform dilution of Ad5 with 12 replicates at each dilution of rAAV. Seventy-two hours after infection the cells are lysed, and qPCR performed to detect rAAV vector amplification over input. An end-point dilution TCID50 calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways are not usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

The GC/IU ratio is a measure of product consistency. The oqPCR titer (GC/ml) is divided by the infectious unit (IU/ml) to give the calculated GC/IU ratio.

F. Replication-Competent AAV (rcAAV) Assay

A sample is analyzed for the presence of replication competent AAV2/9 (rcAAV) that can potentially arise during the production process. A 3 passage assay has been developed consisting of cell-based amplification and passage followed by detection of rcAAV DNA by real-time qPCR (cap 9 target). The cell-based component consists of inoculating monolayers of HEK293 cells (P1) with dilutions of the test sample and wild-type human adenovirus type 5 (Ad5). $10^{10}$ GC of the vector product is the maximal amount of the product tested. Due to the presence of adenovirus, replication competent AAV amplifies in the cell culture. After 2 days, a cell lysate is generated and Ad5 heat inactivated. The clarified lysate is then passed onto a second round of cells (P2) to enhance sensitivity (again in the presence of Ad5). After 2 days, a cell lysate is generated and Ad5 heat inactivated. The clarified lysate is then passed onto a third round of cells (P3) to maximize sensitivity (again in the presence of Ad5). After 2 days, cells are lysed to release DNA which is then subjected to qPCR to detect AAV9 cap sequences. Amplification of AAV9 cap sequences in an Ad5 dependent manner indicates the presence of rcAAV. The use of a AAV2/9 surrogate positive control containing AAV2 rep and AAV9 cap genes enables the Limit of Detection (LOD) of the assay to be determined (0.1, 1, 10 and 100 IU) and using a serial dilution of rAAV9.CB.hIDS vector ($1\times10^{10}$, $1\times10^{9}$, $1\times10^{8}$, $1\times10^{7}$ GC) the approximate level of rcAAV present in the test sample can be quantitated.

G. In Vitro Potency

To relate the qPCR GC titer to gene expression, an in vitro bioassay is performed by transducing HEK293 (Human Embryonic Kidney) cells with a known multiplicity of GCs per cell and assaying the supernatant for IDS activity 72 hours post-transduction. IDS activity is measured by incubating sample diluted in 0.1 ml water with 0.1 ml of 100 mmol/l 4MU-iduronide-2-sulfate at 37 degrees for 1-3 hours. The reaction is stopped by the addition of 2 ml 290 mmol/l glycine, 180 mmol/l sodium citrate, pH 10.9 and liberated 4MU is quantified by comparing fluorescence to standard dilutions of 4MU. Comparison to highly active pre-clinical and tox vector preparations enables interpretation of product activity.

H. Total Protein, Capsid protein, Protein Purity Determination and Capsid Protein Ratio Vector samples are first quantified for total protein against a Bovine Serum Albumin (BSA) protein standard curve using a bicinchoninic acid (BCA) assay. The determination is made by mixing equal parts of sample with a Micro-BCA reagent provided in the kit. The same procedure is applied to dilutions of a BSA Standard. The mixtures are incubated at 60° C. and absorbance measured at 562 nm. A standard curve is generated from the standard absorbance of the known concentrations using a 4-Parameter fit. Unknown samples are quantified according to the 4-Parameter regression.

To provide a semi-quantitative determination of AAV purity, the samples are then normalized for genome titer and $5 \times 10^9$ GC separated on an SDS-polyacrylamide (SDS-PAGE) gel under reducing conditions. The gel is then stained with SYPRO Ruby dye. Any impurity bands are quantified by densitometry by comparison to co-electrophoresed BSA standards of 25, 50, and 100 ng of protein per lane. These quantities represent 1%, 2% and 4% of the total AAV protein sample. Stained bands that appear in addition to the three AAV specific proteins VP1, VP2 and VP3 are considered protein impurities. All impurity bands are compared to the reference proteins and the impurity mass percent as well as approximate molecular weight are reported. The SDS-PAGE gels are also used to quantify the VP1, VP2 and VP3 proteins and determine their ratio.

Example 6: MPS II Biomarker

In the present study, metabolite profiling of CSF samples from MPS I dogs was performed, which revealed substantial disease related alterations in the CSF metabolome. The most striking difference was an over 30-fold elevation in spermine levels compared to normal controls. This finding was confirmed in MPS I patient samples, as well as in a feline model of MPS I and is expected to be found also in MPS II. Spermine binds to HS, and cellular uptake of spermine is dependent on this interaction [M. Belting, et. al., Proteoglycan involvement in polyamine uptake. Biochemical Journal 338, 317-323 (1999); J. E. Welch, et al., T. H. Van Kuppevelt, M. Belting, Single chain fragment anti-heparan sulfate antibody targets the polyamine transport system and attenuates polyamine-dependent cell proliferation. International journal of oncology 32, 749-756 (2008); published online EpubApr]. Cell surface proteoglycans such as glypican-1 can bind spermine through their HS moieties, and after endocytosis of the glypican protein, intracellular cleavage of the HS chain releases bound spermine into the cell (Belting et al; K. Ding, S et al, The Journal of biological chemistry 276, 46779-46791 (2001); published online Epub December 14). Thus, intact HS recycling is essential for spermine uptake. In MPS I, extracellular spermine accumulation could occur through inhibition of this uptake mechanism due to inefficient HS recycling, or through simple binding of spermine to the extracellular GAGs that accumulate in MPS, shifting the spermine binding equilibrium to favor extracellular distribution. Future studies should address the relative contribution of these mechanisms to spermine accumulation in MPS I CSF.

We found that inhibitors of spermine synthesis blocked excess neurite growth in MPS neurons, and that neurite growth could be induced in WT neurons by spermine concentrations similar to those found in patient CSF. Gene therapy in the dog model of MPS I reversed spermine accumulation and normalized expression of GAP43, suggesting that the same pathway was impacted in vivo. We could not directly evaluate the impact of spermine synthesis inhibition in vivo, as available inhibitors do not cross the blood-brain barrier, and chronic direct CNS administration from birth is not feasible in our animal models. While our in vitro findings support a role for spermine in aberrant neurite growth in MPS I, it is important to note that inhibiting spermine synthesis did not completely reverse the phenotype, and spermine addition to normal neurons did not increase neurite growth to the level of MPS I neurons. The effects of spermine modulation may have been limited by the relatively short period of treatment. It is also possible that spermine accumulation is not the sole mediator contributing to neurite outgrowth in MPS I. Notably many neurotrophic factors bind through HS modified receptors, and interactions with HS in extracellular matrix can influence neurite growth [D. Van Vactor, D. P. Wall, K. G. Johnson, Heparan sulfate proteoglycans and the emergence of neuronal connectivity. Current opinion in neurobiology 16, 40-51 (2006); published online Epub February (10.1016/j.conb.2006.01.011)]. Spermine accumulation may therefore be one of several factors promoting abnormal neurite growth in MPS I.

Of the 15 MPS I dog CSF samples screened, only one fell within the normal range of spermine concentration. At 28 days of age, this was the youngest animal included in the study. This finding indicates that spermine accumulation may be age dependent. Future studies should evaluate CSF spermine levels longitudinally in MPS patients. If spermine increases with age in MPS patients, this could explain the kinetics of cognitive decline, as most patients experience 1-2 years of normal development before the onset of developmental delays.

The potential for impaired HS metabolism to trigger accumulation of a metabolite that alters neuron growth could point to a novel connection between enzyme deficiencies and the abnormal neurite growth phenotype in MPS I, which may explain the cognitive dysfunction associated with these disorders. These findings also indicate that CSF spermine is useful as a noninvasive biomarker for assessing pharmacodynamics of novel CNS-directed therapies for MPSI.

Materials and Methods:

Experimental design: This study was initially designed to detect metabolites that were present at significantly different levels in MPS I patient CSF samples compared to samples from healthy controls. Due to the limited availability of CSF samples from children with MPS IH and healthy controls, the initial screen was performed using CSF samples from MPS I dogs, for which greater numbers were available, with the intention of subsequently evaluating candidate biomarkers in human samples. A total of 15 CSF samples from individual untreated MPS I dogs were available for analysis, and an additional 15 samples were obtained from healthy controls. Following identification of elevated spermine in MPS I dog CSF in the prospective metabolite screen, spermine was retrospectively measured in CSF samples from previous studies of MPS I dogs and cats treated with gene therapy, as well as patient samples. The number of subjects included in each group for these analyses was limited by sample availability and was not based on statistical considerations; therefore in some cases numbers were insufficient for statistical comparisons. For studies of in vitro neurite growth, the number of cells quantified for each condition was based on pilot experiments which indicated that >30 cells per condition was required to detect a 20% difference in arbor length, neurite number or neurite branches per cell. After cells were plated and treated with the designated drug, the wells were coded and the acquisition of cell images and the manual quantification of neurite length and branching were performed by a blinded reviewer. The comparison of wildtype and MPS mouse neurons was repeated using a different substrate [poly-L-lysine (Sigma) coated tissue culture plates rather than chamber slides (Sigma S6815)] with similar results. The comparison of wildtype neurons with and without spermine addition was performed four times using both substrates with similar results.

CSF metabolite profiling: CSF metabolite profiling was performed by Metabolon.

Samples were stored at −80° C. until processing. Samples were prepared using the MicroLab STAR® system (Hamilton Company). A recovery standard was added prior to the first step in the extraction process for QC purposes. Proteins were precipitated with methanol under vigorous shaking for 2 min followed by centrifugation. The resulting extract was divided into five fractions: one for analysis by reverse phase (RP) UPLC-MS/MS with positive ion mode electrospray ionization, one for analysis by RP/UPLC-MS/MS with negative ion mode electrospray ionization, one for analysis by hydrophilic interaction chromatography (HILIC)/UPLC-MS/MS with negative ion mode electrospray ionization, one for analysis by GC-MS, and one sample was reserved for backup. Samples were placed briefly on a TurboVap® (Zymark) to remove the organic solvent. For LC, the samples were stored overnight under nitrogen before preparation for analysis. For GC, each sample was dried under vacuum overnight before preparation for analysis.

The LC/MS portion of the platform was based on a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in solvents compatible to each of the LC/MS methods. Each reconstitution solvent contained a series of standards at fixed concentrations to ensure injection and chromatographic consistency. For RP chromatography, one aliquot was analyzed using acidic positive ion optimized conditions and the other using basic negative ion optimized conditions Each method utilized separate dedicated columns (Waters UPLC BEH C18-2.1× 100 mm, 1.7 μm). The extracts reconstituted in acidic conditions were gradient eluted using water and methanol containing 0.1% formic acid. The basic extracts were similarly eluted using methanol and water, however with 6.5 mM ammonium bicarbonate. The third aliquot was analyzed via negative ionization following elution from a HILIC column (Waters UPLC BEH Amide 2.1×150 mm, 1.7 μm) using a gradient consisting of water and acetonitrile with 10 mM ammonium formate. The MS analysis alternated between MS and data-dependent MSn scans using dynamic exclusion. The scan range varied slightly between methods but covered 80-1000 m/z.

The samples destined for analysis by GC-MS were dried under vacuum for a minimum of 18 h prior to being derivatized under dried nitrogen using bistrimethyl-silyltrifluoroacetamide. Derivatized samples were separated on a 5% diphenyl/95% dimethyl polysiloxane fused silica column (20 m×0.18 mm ID; 0.18 um film thickness) with helium as carrier gas and a temperature ramp from 60° to 340° C. in a 17.5 min period. Samples were analyzed on a Thermo-Finnigan Trace DSQ fast-scanning single-quadrupole mass spectrometer using electron impact ionization (EI) and operated at unit mass resolving power. The scan range was from 50-750 m/z.

Several types of controls were analyzed in concert with the experimental samples: a pooled matrix sample generated by taking a small volume of each experimental sample served as a technical replicate throughout the data set; extracted water samples served as process blanks; and a cocktail of QC standards that were carefully chosen not to interfere with the measurement of endogenous compounds were spiked into every analyzed sample, allowed instrument performance monitoring and aided chromatographic alignment. Instrument variability was determined by calculating the median relative standard deviation (RSD) for the standards that were added to each sample prior to injection into the mass spectrometers. Overall process variability was determined by calculating the median RSD for all endogenous metabolites (i.e., non-instrument standards) present in 100% of the pooled matrix samples. Experimental samples were randomized across the platform run with QC samples spaced evenly among the injections.

Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon. Identification of known chemical entities was based on comparison to metabolomics library entries of purified standards. Peaks were quantified using area-under-the-curve measurements. Raw area counts for each metabolite in each sample were normalized to correct for variation resulting from instrument inter-day tuning differences by the median value for each run-day, therefore, setting the medians to 1.0 for each run. This preserved variation between samples but allowed metabolites of widely different raw peak areas to be compared on a similar graphical scale. Missing values were imputed with the observed minimum after normalization.

Quantitative MS assay: CSF samples (50 μL) were mixed with a spermine-d8 internal standard (IsoSciences). Samples were deproteinized by mixing with a 4-fold excess of methanol and centrifuging at 12,000×g at 4° C. The supernatant was dried under a stream of nitrogen, and then resuspended in 50 μL of water. An aliquot of 5 μL was subjected to LC-MS analysis. The LC separations were carried out using a Waters ACQUITY UPLC system (Waters Corp., Milford, Mass., USA) equipped with an Xbridge® C18 column (3.5 μm, 150×2.1 mm). The flow-rate was 0.15 mL/min, solvent A was 0.1% formic acid and solvent B was 98/2 acetonitrile/$H_2O$ (v/v) with 0.1% formic acid. The elution conditions were as follows: 2% B at 0 min, 2% B at 2 min, 60% B at 5 min, 80% B at 10 min, 98% B at 11 min, 98% B at 16 min, 2% B at 17 min, 2% B at 22 min, with the column temperature being 35° C. A Finnigan TSQ Quantum Ultra spectrometer (Thermo Fisher, San Jose, Calif.) was used to conduct MS/MS analysis in positive ion mode with the following parameters: spray voltage at 4000 V, capillary temperature at 270° C., sheath gas pressure at 35 arbitrary units, ion sweep gas pressure at 2 arbitrary units, auxiliary gas pressure at 10 arbitrary units, vaporizer temperature at 200° C., tube lens offset at 50, capillary offset at 35 and skimmer offset at 0. The following transitions were monitored: 203.1/112.1 (spermine); 211.1/120.1 (spermine-d8) with scan width of 0.002 m/z, and scan time being 0.15 s.

Animal procedures: All animal protocols were approved by the Institutional Animal Care and Use Committee of the University of Pennsylvania. For CSF metabolite screening, samples were collected by suboccipital puncture in normal dogs at 3-26 months of age, and in MPS I dogs at 1-18 months of age. Gene transfer studies in MPS I dogs and cats were performed as previously described (20, 22). CSF samples were collected 6-8 months after vector administration. For mouse cortical neuron experiments, primary cortical neuron cultures were prepared from E18 IDUA−/− or IDUA+/+ embryos.

Patient samples: Informed consent was obtained from each subject's parent or legal guardian. The protocol was approved by the Institutional Review Board of the University of Minnesota. CSF was collected by lumbar puncture. All MPS I patients had a diagnosis of Hurler syndrome and had not received enzyme replacement therapy or hematopoietic stem cell transplantation prior to sample collection. MPS I patients were 6-26 months of age. The healthy controls were 36 and 48 months of age.

Statistical analysis: The random forest analysis and heat map generation were performed using MetaboAnalyst 3.0 R. G. Kalb, Development 120, 3063-3071 (1994); J. Zhong, et al, Journal of neurochemistry 64, 531-539 (1995) D. Van Vactor, D. P. W et al, Current opinion in neurobiology 16, 40-51 (2006); published online Epub February (10.1016/j.conb.2006.01.011). Raw peak data were log transformed and normalized to the mean of normal sample values. All other statistical analyses were performed with GraphPad Prism 6. Cultured neuron arbor length, neurite number, and branching were compared by ANOVA followed by Dunnett's test. CSF spermine and cortical GAP43 were compared by Kruskal-Wallis test followed by Dunn's test.

GAP43 western: Samples of frontal cortex were homogenized in 0.2% triton X-100 using a Qiagen Tissuelyser at 30 Hz for 5 min. Samples were clarified by centrifugation at 4° C. Protein concentration was determined in supernatants by BCA assay. Samples were incubated in NuPAGE LDS buffer with DTT (Thermo Fisher Scientific) at 70° C. for 1 hr and separated on a Bis-Tris 4-12% polyacrylamide gel in MOPS buffer. Protein was transferred to a PVDF membrane, and blocked for 1 hr in 5% nonfat dry milk. The membrane was probed with rabbit polyclonal anti-GAP43 antibody (Abcam) diluted to 1 µg/mL in 5% nonfat dry milk followed by an HRP conjugated polyclonal anti-rabbit antibody (Thermo Fisher Scientific) diluted 1:10,000 in 5% nonfat dry milk. Bands were detected using SuperSignal West Pico substrate (Thermo Fisher Scientific). Densitometry was performed using Image Lab 5.1 (Bio-Rad).

Neurite growth assay: Day 18 embryonic cortical neurons were harvested as described above, and plated at a concentration of 100,000 cells/mL on chamber slides (Sigma 56815) or poly-L-lysine (Sigma) coated tissue culture plates in serum-free Neurobasal medium (Gibco) supplemented by B27 (Gibco). Treatments were applied to duplicate wells 24 hours after plating (day 1). Phase-contrast images for quantification were taken on a Nikon Eclipse Ti at 20× using a 600 ms manual exposure and 1.70× gain on high contrast. An individual blind to treatment conditions captured 10-20 images per well and coded them. Images were converted to 8-bit format in ImageJ (NIH) and traced in NeuronJ [E. Meijering, et al, Design and validation of a tool for neurite tracing and analysis in fluorescence microscopy images. Cytometry. Part A: the journal of the International Society for Analytical Cytology 58, 167-176 (2004); published online Epub April (10.1002/cyto.a.20022)] by a blinded reviewer. Soma diameter, neurite number, branch points, and arbor length were traced manually. Images traced in NeuronJ were converted to micrometers using a conversion factor based on image size; 2560×1920 pixel images were converted to micrometers using a conversion factor of 0.17 micrometers/pixel.

Histology: Brain tissue processing and LIMP2 immunofluorescence were performed as previously described [C. Hinderer, et al, Molecular therapy: the journal of the American Society of Gene Therapy 22, 2018-2027 (2014); published online Epub December (10.1038/mt.2014.135)].

RT-PCR: Samples of frontal cortex from 3 normal dogs and 5 MPS dogs were immediately frozen on dry ice at necropsy. RNA was extracted with TRIzol reagent (Thermo Fisher Scientific), treated with DNAse I (Roche) for 20 min at room temperature, and purified using an RNeasy kit (Qiagen) according to the manufacturer's instructions. Purified RNA (500 ng) was reverse transcribed using the High Capacity cDNA Synthesis Kit (Applied Biosystems) with random hexamer primers. Transcripts for arginase, ornithine decarboxylase, spermine synthase, spermidine synthase, spermine-spermidine acetyltransferase and glyceraldehyde phosphate dehydrogenase were quantified by Sybr green PCR using an Applied Biosystems 7500.

Real-Time PCR System. A standard curve was generated for each target gene using four-fold dilutions of a pooled standard comprised of all individual samples. The highest standard was assigned an arbitrary transcript number, and Ct values for individual samples were converted to transcript numbers based on the standard curve. Values are expressed relative to the GAPDH control.

Statistical analysis: Random forest analysis and heat map generation were performed using MetaboAnalyst 3.0 [J. Xia, et al, MetaboAnalyst 2.0—a comprehensive server for metabolomic data analysis. Nucleic Acids Research, (2012); published online Epub May 2, 2012 (10.1093/nar/gks374); J. Xia, et al., MetaboAnalyst: a web server for metabolomic data analysis and interpretation. Nucleic Acids Research 37, W652-W660 (2009); published online Epub Jul. 1, 2009 (10.1093/nar/gkp356). J. Xia, et al, MetaboAnalyst 3.0—making metabolomics more meaningful. Nucleic Acids Research, (2015); published online Epub Apr. 20, 2015 (10.1093/nar/gkv380)]. Undetectable values in the metabolite screen were imputed with the minimum values observed in the data set. Raw peak data were normalized to the mean of normal sample values and log transformed. All other statistical analyses were performed with GraphPad Prism 6. Cultured neuron arbor length, neurite number, and branching were compared by ANOVA followed by Dunnett's test. CSF spermine and cortical GAP43 were compared by Kruskal-Wallis test followed by Dunn's test.

Results

1. Identification of Elevated CSF Spermine Through Metabolite Profiling

Figure 19A:
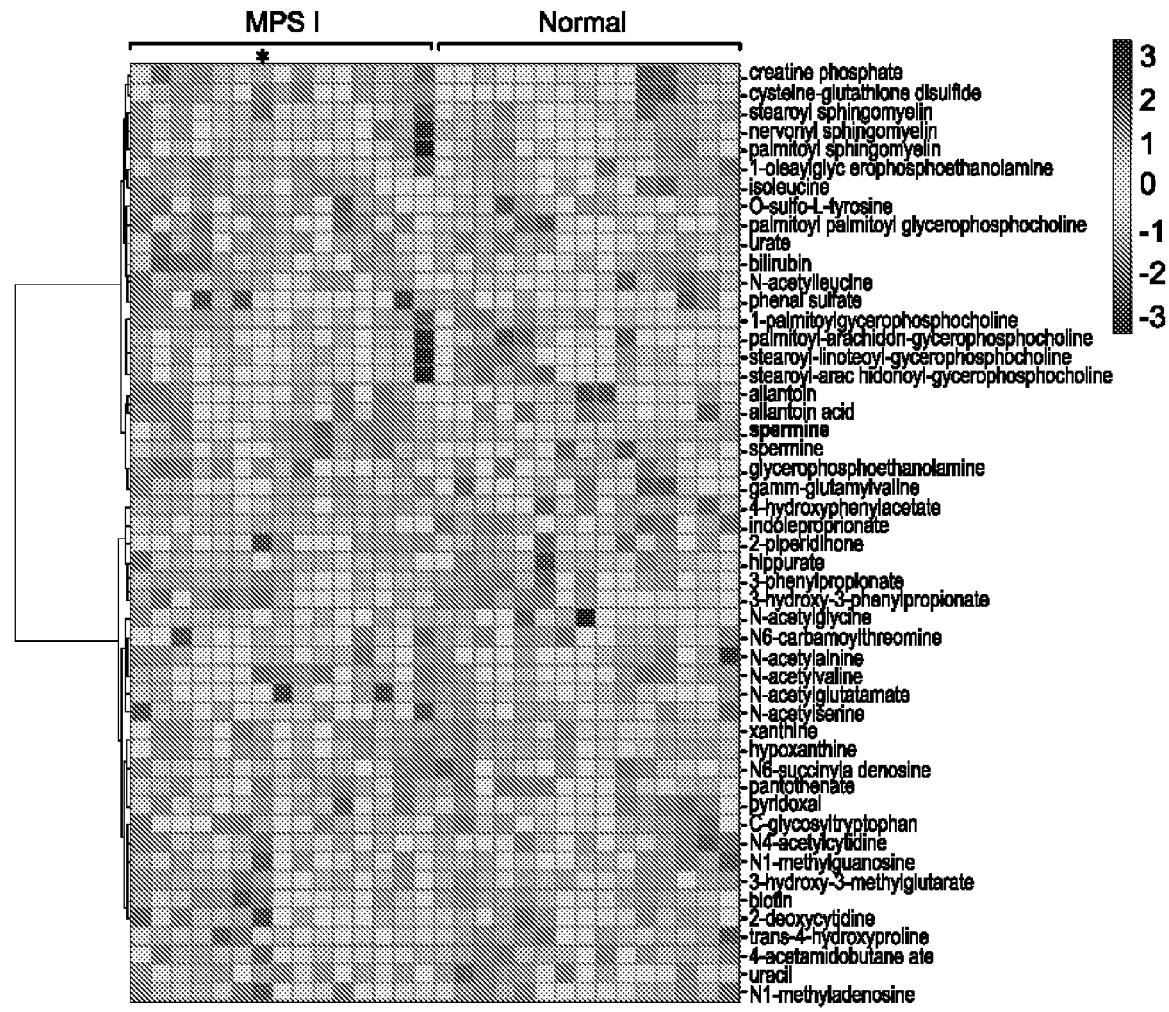
Figure 19B:
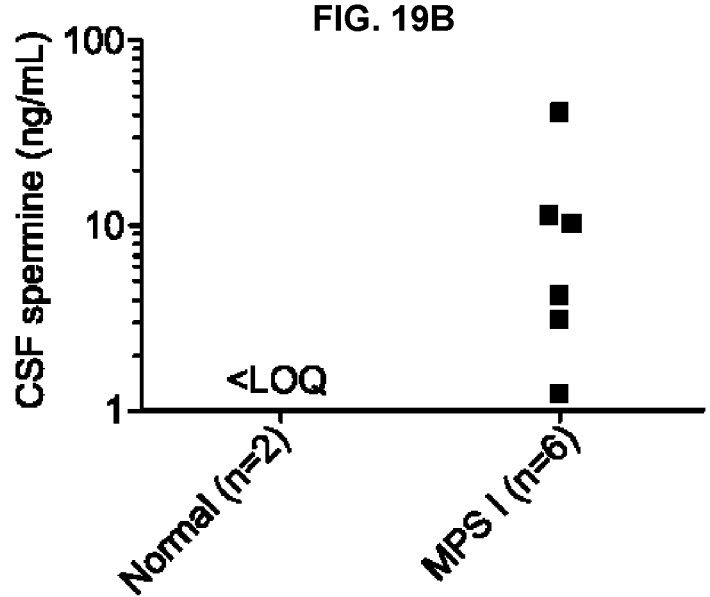
Figure 20F:
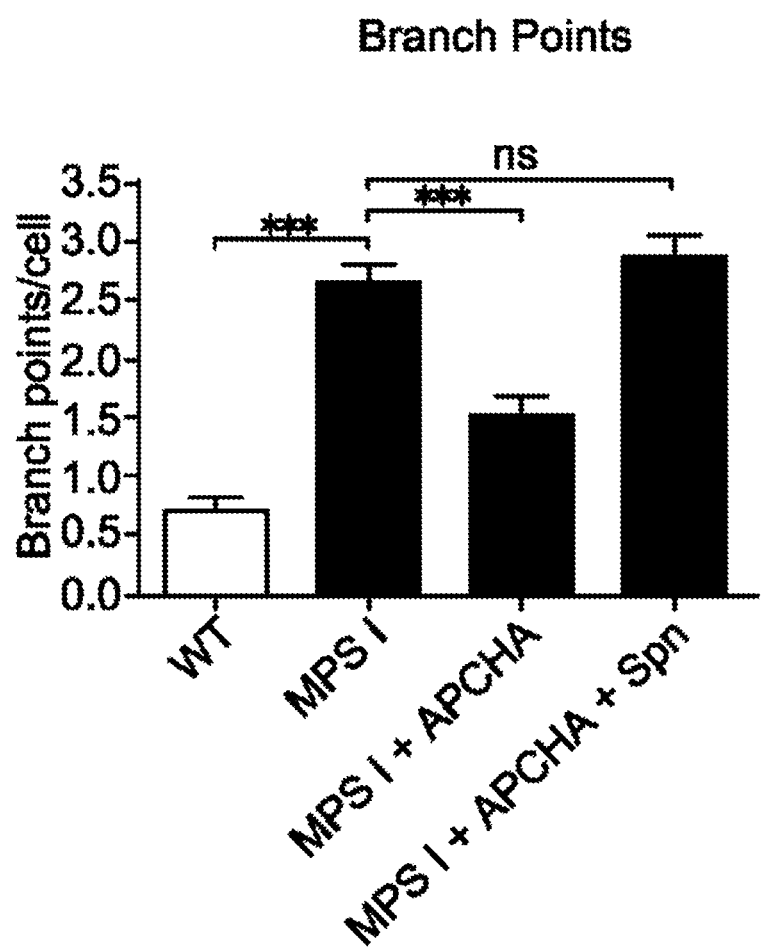
Figure 20G:
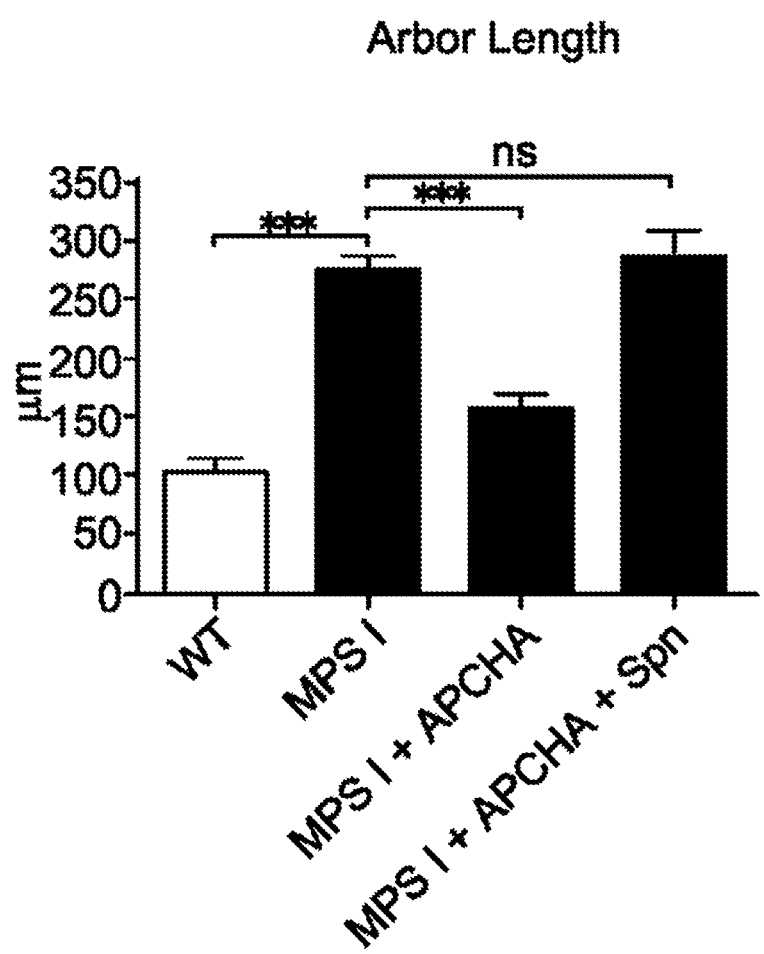
Figures 20H, 20I, 20J:
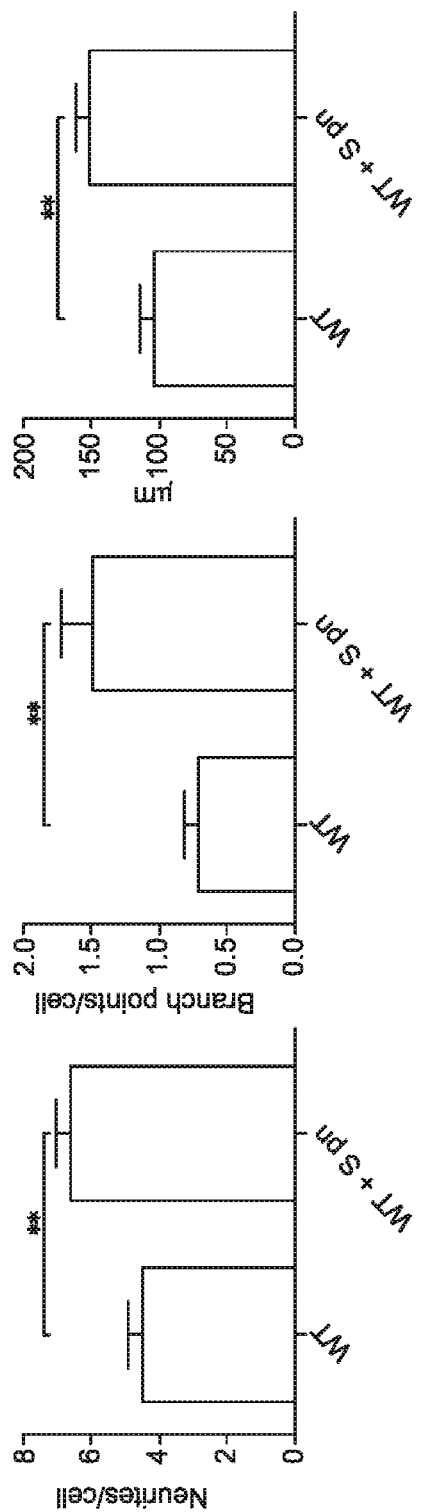
Figure 23:
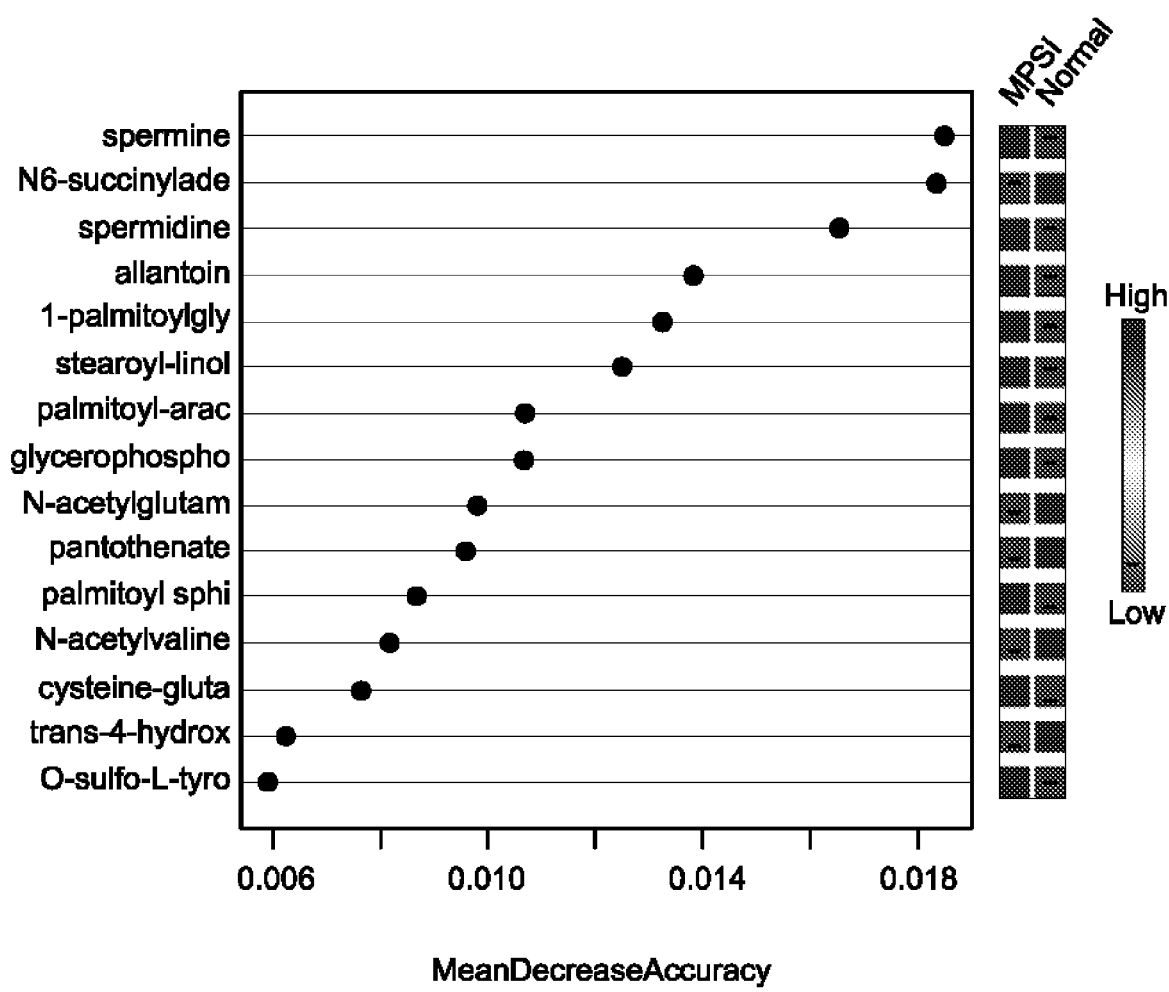
FIG. 23 illustrates the mean decrease accuracy for metabolites identified by random forest analysis.
Figure 24:
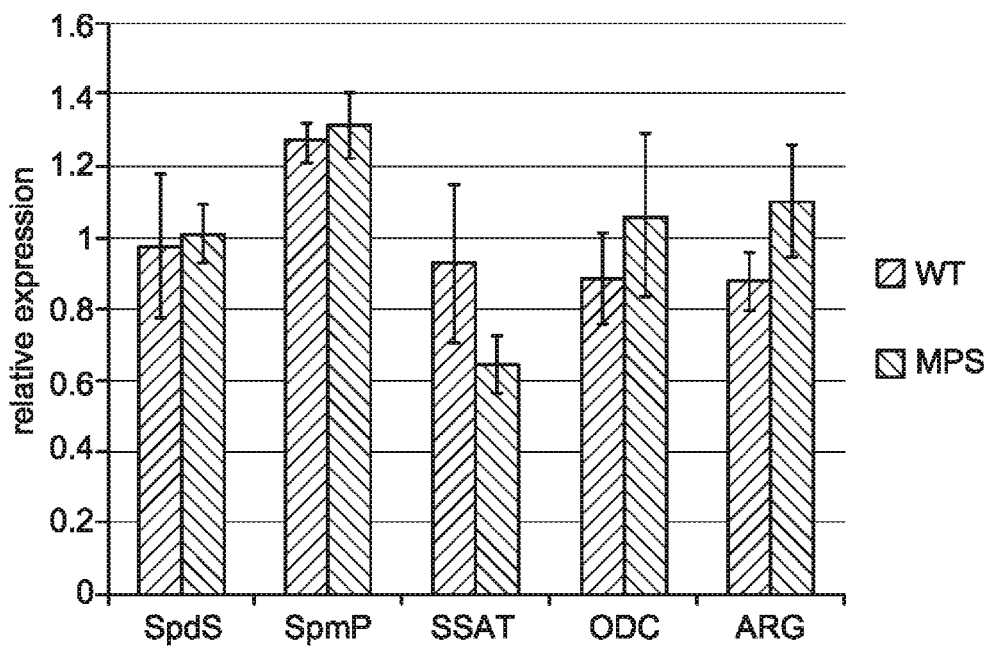
FIG. 24 illustrates the expression of enzymes in the polyamine synthetic pathway in MPS I dog brain samples.
Figure 25:
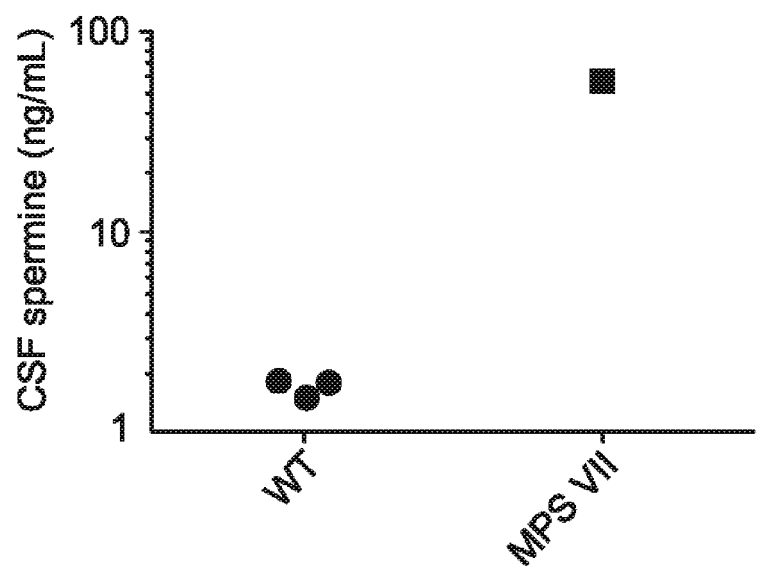
FIG. 25 illustrates spermine concentration in MPS VII dog CSF

An initial screen of CSF metabolites was carried out using a canine model of MPS I. These animals carry a splice site mutation in the IDUA gene, resulting in complete loss of enzyme expression and development of clinical and histological features analogous to those of MPS I patients [K. P. Menon, et al, Genomics 14, 763-768 (1992); R. Shull, et al., The American journal of pathology 114, 487 (1984)]. CSF samples were collected from 15 normal dogs and 15 MPS I dogs. CSF samples were evaluated for relative quantities of metabolites by LC and GC-MS. A total of 281 metabolites could be positively identified in CSF samples by mass spectrometry. Of these, 47 (17%) were significantly elevated in MPS I dogs relative to controls, and 88 (31%) were decreased relative to controls. A heat map of the 50 metabolites most different between groups is shown in FIG. 19A. Metabolite profiling identified marked differences in polyamine, sphingolipid, acetylated amino acid, and nucleotide metabolism between MPS I and normal dogs. Random forest clustering analysis identified the polyamine spermine as the largest contributor to the metabolite differences between MPS I and normal dogs (FIG. 23). On average spermine was more than 30-fold elevated in MPS I dogs, with the exception of one MPS I dog that was under 1 month of age at the time of sample collection. A stable isotope dilution (SID)-LC-MS/MS assay was developed to quantitatively measure spermine in CSF. Samples were screened from 6 children with Hurler syndrome (ages 6-26 months), as well as 2 healthy controls (ages 36 and 48 months). Both healthy controls had CSF spermine levels below the limit of quantification (1 ng/mL) of the assay, whereas CSF samples from MPS I patients were on average 10-fold above the limit of quantification (FIG. 19B). Spermine elevation in MPS IH patients appeared consistent with the known role of HS in spermine binding and uptake [M. Belting, et al, Journal of Biological Chemistry 278, 47181-47189 (2003); M. Belting, et al, Proteoglycan involvement in polyamine uptake. Biochemical Journal 338, 317-323 (1999); J. E. Welch, et al, International journal of oncology 32, 749-756 (2008))]; increased synthesis appeared unlikely as a cause of elevated CSF spermine, as normal and MPS I dog brain samples had similar mRNA expression levels for transcriptionally regulated enzymes in the polyamine synthetic pathway (FIG. 24). To determine whether spermine elevation was a general property of heparan sulfate storage diseases or specific to MPS I, spermine was measured in a CSF sample from a canine model of MPS VII, which exhibited a similar elevation (FIG. 25).

2. Role of Spermine in Abnormal Neurite Growth Associated with MPS

Figure 26C:
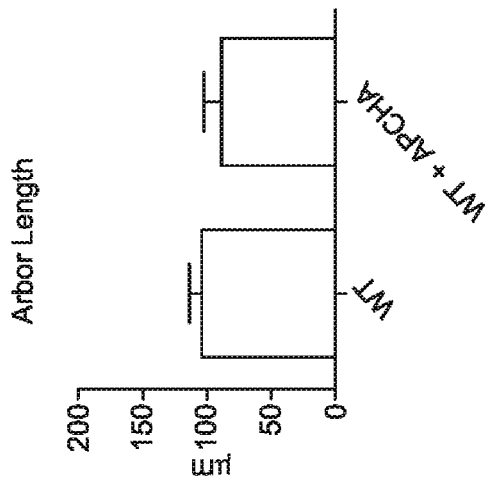
FIGS. 26A to 26C illustrates that there is no impact of APCHA treatment on WT neuron growth.
Figure 26B:
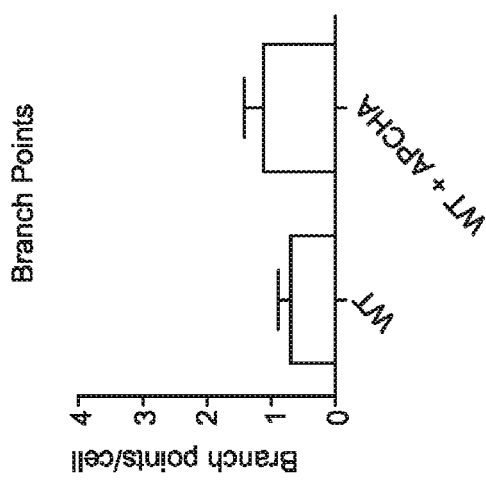
Figure 26A:
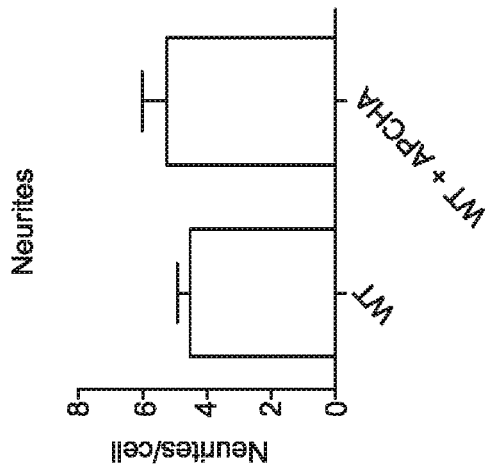

Following axon injury neurons upregulate polyamine synthesis, which promotes neurite outgrowth [D. Cai, et al, Neuron 35, 711-719 (2002); published online Epub August 15; K. Deng, et al, The Journal of neuroscience: the official journal of the Society for Neuroscience 29, 9545-9552 (2009); published online Epub July 29; Y. Gao, et al, Neuron 44, 609-621 (2004); published online Epub November 18; R. C. Schreiber, et al., Neuroscience 128, 741-749 (2004)]. We therefore evaluated the role of spermine in the abnormal neurite overgrowth phenotype that has been described in MPS neurons [Hocquemiller, S., et al, Journal of neuroscience research 88, 202-213 (2010)]. Cultures of E18 cortical neurons from MPS I mice exhibited greater neurite number, branching, and total arbor length after 4 days in culture than neurons derived from wild type mice from the colony (FIGS. 20A-20F). Treatment of MPS neurons with APCHA, an inhibitor of spermine synthesis, significantly reduced neurite growth and branching. The effect was reversible by replacing spermine (FIGS. 20A-20F). The same APCHA concentration did not affect the growth of normal neurons (FIG. 26). Addition of spermine to wild type neuron cultures at concentrations similar to those identified in vivo resulted in significant increases in neurite growth and branching (FIGS. 20A-20F).

3. Impact of Gene Therapy on CSF Spermine and GAP43 Expression

Figure 21A:
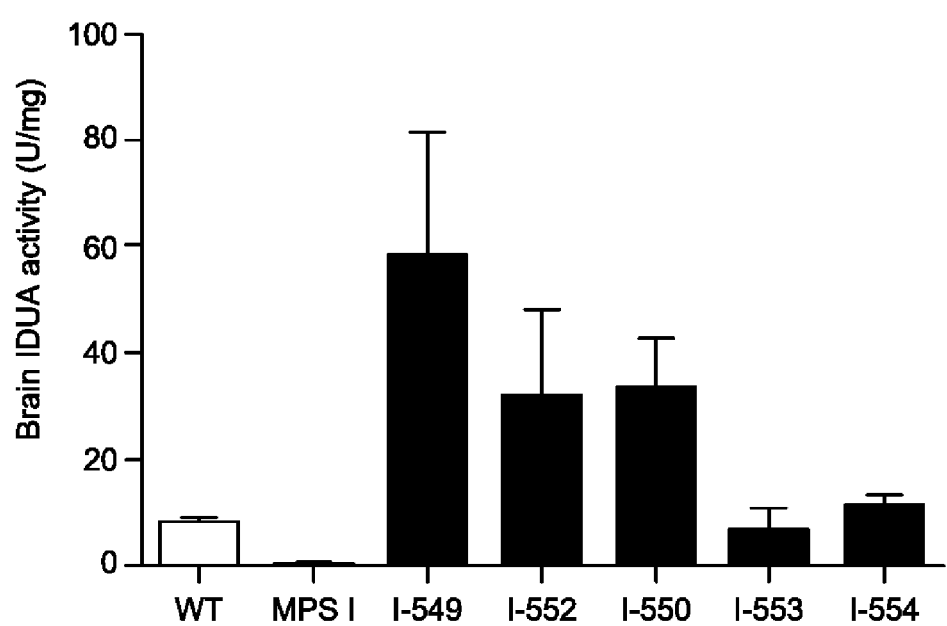
Figure 21J:
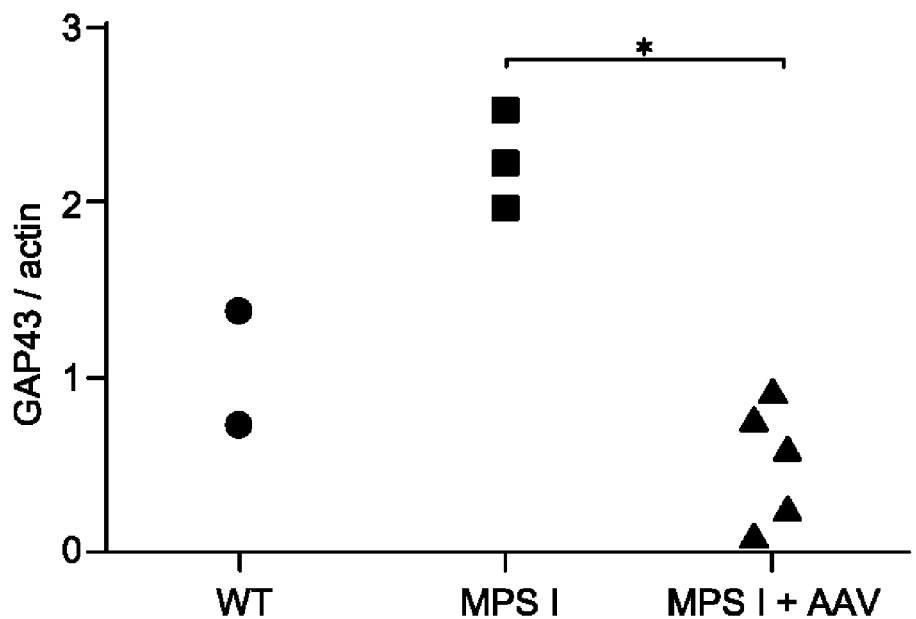
Figure 21K:
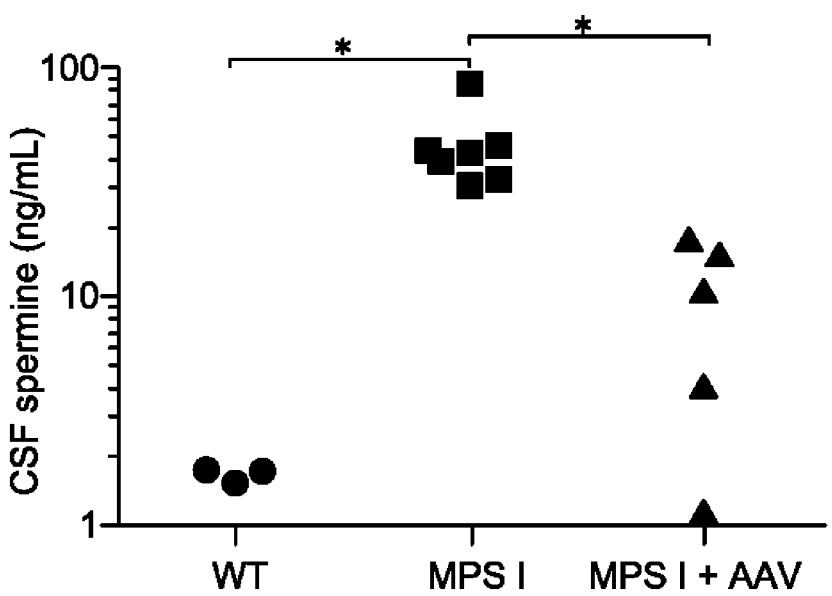

GAP43, a central regulator of neurite growth, is overexpressed by MPS III mouse neurons both in vitro and in vivo, suggesting that the same neurite growth pathway aberrantly activated in neuron cultures is also active in vivo. In order to evaluate the effect of IDUA deficiency on GAP43 expression and spermine accumulation in vivo, we measured CSF spermine and brain GAP43 levels in untreated MPS I dogs as well as those treated with CNS directed gene therapy. We previously described five MPS I dogs that were treated with an intrathecal injection of an adeno-associated virus serotype 9 vector carrying the canine IDUA transgene [C. Hinderer, et al, Molecular therapy: the journal of the American Society of Gene Therapy 23, 1298-1307 (2015); published online Epub August]. MPS I dogs can develop antibodies to the normal IDUA enzyme, so two of the dogs were pre-treated as newborns with hepatic IDUA gene transfer to induce immunological tolerance to the protein. Both tolerized dogs exhibited brain IDUA activity well above normal following AAV9 treatment. The three non-tolerized dogs exhibited varying levels of expression, with one animal reaching levels greater than normal and the other two exhibiting expression near normal (FIG. 21A). CSF spermine reduction was inversely proportional to brain IDUA activity, with a 3-fold reduction relative to untreated animals in the two dogs with the lowest IDUA expression, and more than 20-fold reduction in the animal with the highest expression (FIGS. 21A, 21B to 21H and 21K). GAP43 was upregulated in frontal cortex of MPS I dogs, and expression was normalized in all vector treated animals (FIGS. 21I-21J).

Figure 22A:
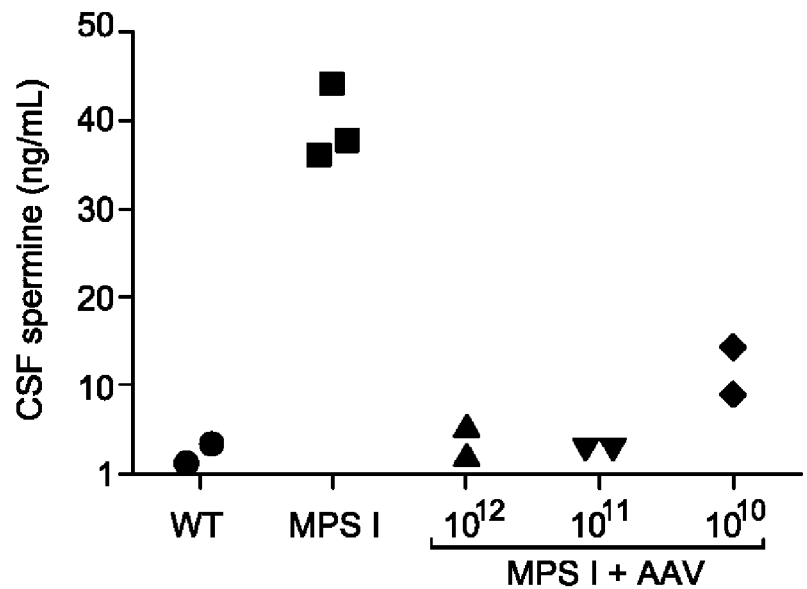
Figure 22B:
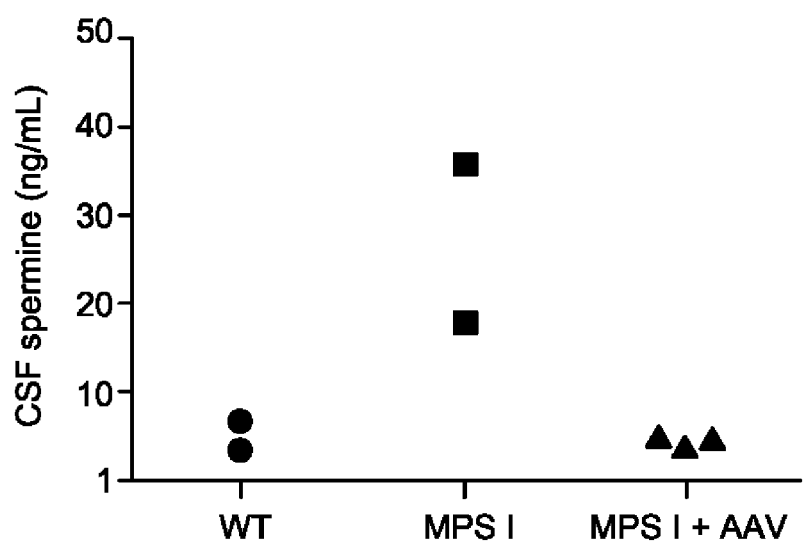

We further evaluated the relationship between CSF spermine levels and IDUA reconstitution in MPS I dogs treated with a range of vector doses. MPS I dogs previously tolerized to human IDUA by neonatal hepatic gene transfer were treated with intrathecal injection of an AAV9 vector expressing human IDUA at one of 3 doses ($10^{10}$, $10^{11}$, $10^{12}$ GC/kg, n=2 per dose) [(C. Hinderer, et al, Neonatal tolerance induction enables accurate evaluation of gene therapy for MPS I in a canine model. Molecular Genetics and Metabolism, dx.doi.org/10.1016/j.ymgme.2016.06.006]. CSF spermine was evaluated 6 months after injection (FIG. 22A). Reduction of CSF spermine was dose dependent, with animals at the mid and high vector doses reaching the normal range, whereas CSF spermine was only partially reduced in the low dose animals. For independent verification of the connection between IDUA deficiency and CSF spermine accumulation, we evaluated CSF spermine levels in a feline model of MPS I. Using CSF samples from our previously reported gene therapy studies, we found that untreated MPS I cats exhibited elevated CSF spermine (FIG. 22B) [C. Hinderer, P. Bell, B. L. Gurda, Q. Wang, J. P. Louboutin, Y. Zhu, J. Bagel, P. O'Donnell, T. Sikora, T. Ruane, P. Wang, M. E. Haskins, J. M. Wilson, Intrathecal gene therapy corrects CNS pathology in a feline model of mucopolysaccharidosis I. Molecular therapy: the journal of the American Society of Gene Therapy 22, 2018-2027 (2014); published online Epub December (10.1038/mt.2014.135)]. Intrathecal administration of a high dose of an AAV9 vector expressing feline IDUA normalized CSF spermine levels (FIG. 22B).

C. Discussion

In the present study we performed metabolite profiling of CSF samples from MPS I dogs, which revealed substantial disease related alterations in the CSF metabolome. The most striking difference was an over 30-fold elevation in spermine levels compared to normal controls. This finding was confirmed in MPS I patient samples, as well as in a feline model of MPS I and a canine model of MPS VII. Spermine binds directly to HS with high affinity, and cellular uptake of spermine is dependent on this interaction [M. Belting, S. PERSSON, L.-A. Fransson, Proteoglycan involvement in polyamine uptake. Biochemical Journal 338, 317-323 (1999); J. E. Welch, et al, International journal of oncology 32, 749-756 (2008)]. Cell surface proteoglycans such as glypican-1 can bind spermine through their HS moieties, and after endocytosis of the glypican protein, intracellular cleavage of the HS chain releases bound spermine into the cell [Belting et al, cited above; K. Ding, et al, The Journal of biological chemistry 276, 46779-46791 (2001); published online Epub December 14]. Thus, intact HS recycling is essential for spermine uptake. Inefficient HS recycling due to IDUA deficiency could inhibit this spermine uptake mechanism, leading to extracellular spermine accumulation. Alternatively, extracellular GAGs may sequester spermine, shifting the equilibrium to favor extracellular distribution. The methanol deproteinization step employed for LC-MS sample preparation in this study also precipitates soluble HS, suggesting that the spermine detected in CSF is unbound, and therefore that uptake inhibition rather than GAG binding is responsible for extracellular spermine accumulation [N. Volpi, Journal of chromatography. B, Biomedical applications 685, 27-34 (1996); published online Epub October 11]. Formation and maintenance of functional neural networks requires precise control of neurite growth and synapse formation. During development, the CNS environment becomes increasingly inhibitory to neurite formation, with myelin associated proteins largely blocking neurite growth in the adult brain. This developmental shift toward decreased neurite growth is paralleled by a decrease in GAP43 expression [S. M. De la Monte, et al, Developmental Brain Research 46, 161-168 (1989); published online Epub4/1/]. The persistent GAP43 expression and exaggerated neurite outgrowth exhibited by MPS neurons may interfere with this normal balance of inhibitory and growth promoting signals, resulting in abnormal connectivity and impaired cognition. How HS storage leads to this increase in neurite growth has not been established. A number of studies have implicated polyamines in neurite outgrowth; following axon injury, the rate-limiting enzymes for the synthesis of spermine and its precursors putrescine and spermidine are elevated, allowing for enhanced neurite outgrowth even in the presence of inhibitory signals from myelin [Cia (2002), Deng (2009), Gao (2004), all cited above. Further, treatment of neurons with putrescine induces neurite growth when injected directly into CSF, an effect that is blocked by inhibitors of spermine synthesis (Deng (2009) cited above). The mechanism by which polyamines exert their effect on neurite growth is not known. One potential target is the NMDA receptor, activation of which is potentiated by spermine binding (J. Lerma, Neuron 8, 343-352 (1992); published online Epub2// (http://dx.doi.org/10.1016/0896-6273(92)90300-3)). NMDA signaling induces neurite outgrowth, and the spermine sensitive subunit of the receptor is highly expressed during development [D. Georgiev, et al, Experimental cell research 314, 2603-2617 (2008); published online Epub August 15 (10.1016/j.yexcr.2008.06.009); R. G. Kalb, Regulation of motor neuron dendrite growth by NMDA receptor activation. Development 120, 3063-3071 (1994); J. Zhong, et al, Journal of neurochemistry 64, 531-539 (1995). Notably many neurotrophic factors bind through HS modified receptors, and interactions with HS in extracellular matrix can influence neurite growth (D. Van Vactor, et al, Current opinion in neurobiology 16, 40-51 (2006); published online Epub February]. Spermine accumulation may therefore be one of several factors promoting abnormal neurite growth in MPS I. Of the 15 MPS I dog CSF samples screened, only one fell within the normal range of spermine concentration. At 28 days of age, this was the youngest animal included in the study. This finding indicates that spermine accumulation may be age dependent, although this study demonstrates that it is already elevated by 6 months of age in infants with Hurler syndrome. Future studies evaluate CSF spermine levels longitudinally in MPS patients. If spermine increases with age in MPS patients, this explains the kinetics of cognitive decline, as most patients experience 1-2 years of normal development before the onset of developmental delays. The potential for impaired HS metabolism to trigger accumulation of a metabolite that alters neuron growth points to a novel connection between enzyme deficiencies and the abnormal neurite growth phenotype in MPS, which may explain the cognitive dysfunction associated with these disorders. Future studies confirm spermine elevation in other MPSs, such as MPS II. These findings also indicate that CSF spermine is useful as a noninvasive biomarker for assessing pharmacodynamics of novel CNS-directed therapies for MPS. Future trials for CNS directed therapies evaluates the correlation between cognitive endpoints and changes in CSF spermine.

Example 7: CT Guided ICV Delivery Device

A. Pre-Procedural Screening Assessments
1. Protocol Visit 1: Screening
The principal investigator describes the screening process that leads up to the intracisternal (IC) procedure, the administration procedure itself, and all potential safety risks in order for the subject (or designated caregiver) to be fully informed upon signing the informed consent.

The following is performed and provided to the neuroradiologist/neurosurgeon/anesthesiologist in their screening assessment of subject eligibility for the IC procedure: Medical history; concomitant medications; physical exam; vital signs; electrocardiogram (ECG); and laboratory testing results.

2. Interval: Screening to Study Visit 2
In order to allow adequate time to review eligibility, the following procedures is performed at any time between the first screening visit and up to one week prior to study Visit 2 (Day 0):
Head/Neck Magnetic Resonance Imaging (MRI) with and without gadolinium [note: Subject must be suitable candidate to receive gadolinium (i.e., eGFR>30 mL/min/1.73 m$^2$)]
In addition to the Head/Neck MRI, the investigator determines the need for any further evaluation of the neck via flexion/extension studies
MRI protocol includes T1, T2, DTI, FLAIR, and CINE protocol images
Head/Neck MRA/MRV as per institutional protocol (note: Subjects with a history of intra/transdural operations may be excluded or may need further testing (e.g., radionucleotide cisternography) that allows for adequate evaluation of CSF flow and identification of possible blockage or lack of communication between CSF spaces.
Neuroradiologist/neurosurgeon subject procedural evaluation meeting: The representatives from the 3 sites have a conference call (or web-meeting) to discuss the eligibility of each subject for the IC procedures based on all available information (scans, medical history, physical exam, labs, etc.). All attempts should be made to achieve consensus on proceeding forward with the IC procedure or screen failing the subject (i.e., each member should be prepared to accept the decision made).
Anesthesia pre-op evaluation Day −28 to Day 1, with detailed assessment of airway, neck (shortened/thickened) and head range-of-motion (degree of neck flexion), keeping in mind the special physiologic needs of the MPS subject.

3. Day 1: Computerized Tomography Suite & Vector Preparation for Administration. Prior to the IC procedure, the CT Suite confirms the following equipment and medications are present:

Adult lumbar puncture (LP) kit (supplied per institution)
BD (Becton Dickinson) 22 or 25 gauge×3-7" spinal needle (Quincke bevel)
Coaxial introducer needle (e.g., 18 G×3.5"), used at the discretion of the interventionalist (for introduction of spinal needle)
4 way small bore stopcock with swivel (Spin) male luer lock
T-connector extension set (tubing) with female luer lock adapter, approximate length 6.7"
Omnipaque 180 (iohexol), for intrathecal administration
Iodinated contrast for intravenous (IV) administration
1% lidocaine solution for injection (if not supplied in adult LP kit)
Prefilled 10 cc normal saline (sterile) flush syringe
Radiopaque marker(s)
Surgical prep equipment/shaving razor
Pillows/supports to allow proper positioning of intubated subject
Endotracheal intubation equipment, general anesthesia machine and mechanical ventilator
Intraoperative neurophysiological monitoring (IONM) equipment (and required personnel)
10 cc syringe containing AAV9.hIDUA vector; prepared and transported to CT/Operating Room (OR) suite in accordance with separate Pharmacy Manual 4. Day 1: Subject Preparation & Dosing Informed Consent for the study and procedure are confirmed and documented within the medical record and/or study file. Separate consent for the procedure from radiology and anesthesiology staff is obtained as per institutional requirements.
Study subject has intravenous access placed within the appropriate hospital care unit according to institutional guidelines (e.g., two IV access sites). Intravenous fluids are administered at the discretion of the anesthesiologist.
At the discretion of the anesthesiologist and per institutional guidelines, study subject is induced and undergo endotracheal intubation with administration of general anesthesia in an appropriate patient care unit, holding area or the surgical/CT procedure suite.
A lumbar puncture is performed, first to remove 5 cc of cerebrospinal fluid (CSF) and subsequently to inject contrast (Omnipaque 180) intrathecally to aid visualization of the cisterna magna. Appropriate subject positioning maneuvers are performed to facilitate diffusion of contrast into the cisterna magna.
If not already done so, intraoperative neurophysiological monitoring (IONM) equipment is attached to subject.
Subject is placed onto the CT scanner table in the prone or lateral decubitus position.
If deemed appropriate, subject is positioned in a manner that provides neck flexion to the degree determined to be safe during pre-operative evaluation and with normal neurophysiologic monitor signals documented after positioning.
The following study staff and investigator(s) is (are) confirmed to be present and identified on-site:
Interventionalist/neurosurgeon performing the procedure
Anesthesiologist and respiratory technician(s)
Nurses and physician assistants
CT (or OR) technicians
Neurophysiology technician
Site Research Coordinator
The subject's skin under the skull base is shaved as appropriate.
CT scout images are performed, followed by a pre-procedure planning CT with IV contrast, if deemed necessary by the interventionalist to localize the target location and to image vasculature.
Once the target site (cisterna magna) is identified and needle trajectory planned, the skin is prepped and draped using sterile technique as per institutional guidelines.
A radiopaque marker is placed on the target skin location as indicated by the interventionalist.
The skin under the marker is anesthetized via infiltration with 1% lidocaine.
A 22 G or 25 G spinal needle is advanced towards the cisterna magna, with the option to use a coaxial introducer needle.
After needle advancement, CT images are obtained using the thinnest CT slice thickness feasible using institutional equipment (ideally ≤2.5 mm). Serial CT images should use the lowest radiation dose possible that allows for adequate visualization of the needle and relevant soft tissues (e.g., paraspinal muscles, bone, brainstem, and spinal cord).
Correct needle placement is confirmed by observation of CSF in the needle hub and visualization of needle tip within the cisterna magna.
The interventionalist confirms the syringe containing vector is positioned close to, but outside of the sterile field. Prior to handling or administering vector, site confirms gloves, mask, and eye protection are donned by staff assisting the procedure within the sterile field (other staff outside of sterile field do not need to take these procedures).
The short (~6") extension tubing is attached to the inserted spinal needle, which is then attached to the 4-way stop cock. Once this apparatus is "self-primed" with the subject's CSF, the 10 cc prefilled normal saline flush syringe will be attached to the 4-way stop cock.
The syringe containing vector is handed to the interventionalist and attached to a port on the 4-way stop cock.
Once the stop cock port to the syringe containing vector is opened, the syringe contents are to be injected slowly (over approximately 1-2 minutes), with care taken not to apply excessive force onto the plunger during the injection.
Once the contents of the syringe containing AAV9.hIDUA are injected, the stop cock is turned so that the stopcock and needle assembly can be flushed with 1-2 cc of normal saline using the attached prefilled syringe.
When ready, the interventionist alerts staff that he/she will remove the apparatus from the subject.
In a single motion, the needle, extension tubing, stopcock, and syringes are slowly removed from the subject and placed onto a surgical tray for discarding into a biohazard waste receptacle or hard container (for the needle).
The needle insertion site is examined for signs of bleeding or CSF leakage and treated as indicated by the investigator. Site is dressed using gauze, surgical tape and/or Tegaderm dressing, as indicated.
Subject is removed from the CT scanner and placed supine onto a stretcher.

Anesthesia is discontinued and subject cared for following institutional guidelines for post-anesthesia care. Neurophysiologic monitors can be removed from study subject.

The head of the stretcher on which the subject lies should be slightly raised (~30 degrees) during recovery.

Subject is transported to a suitable post-anesthesia care unit as per institutional guidelines.

After subject has adequately recovered consciousness and is in stable condition, he/she is admitted to the appropriate floor/unit for protocol mandated assessments. Neurological assessments are followed as per the protocol and the Primary Investigator oversees subject care in collaboration with hospital and research staff.

Example 8: Evaluation of Intrathecal Routes of Administration in Large Animals The purpose of this study was to evaluate more routine methods of administration into the CSF, including intraventricular (ICV) injection, and injection through a lumbar puncture. In brief, in this study ICV and IC AAV administration were compared in dogs. Vector administration was evaluated via lumbar puncture in nonhuman primates with some animals placed in Trendelenburg position after injection, a maneuver which has been suggested to improve cranial distribution of vector. In the dog study, ICV and IC vector administration resulted in similarly efficient transduction throughout brain and spinal cord. However, animals in the ICV cohort developed encephalitis, apparently due to a severe T cell response to the transgene product. The occurrence of this transgene-specific immune response only in the ICV cohort is suspected to be related to the presence of localized inflammation from the injection procedure at the site of transgene expression. In the non-human primate (NHP) study, transduction efficiency following vector administration into the lumbar cistern was improved compared to our previous studies by using an extremely large injection volume (approximately 40% of total CSF volume). However, this approach was still less efficient than IC administration. Positioning animals in Trendelenburg after injection provided no additional benefit. However, it was found that large injection volumes could improve cranial distribution of the vector.

To maximize the effectiveness of intrathecal AAV delivery, it will be critical to determine the optimal route of vector administration into the CSF. We previously reported that vector injection into the cisterna magna (cerebellomedullary cistern) by suboccipital puncture achieved effective vector distribution in nonhuman primates, whereas injection via lumbar puncture resulted in substantially lower transduction of the spinal cord and virtually no distribution to the brain, underscoring the importance of the route of administration [Hinderer, Molecular Therapy—Methods & Clinical Development. 12/10/online 2014; 1]. Others have suggested that vector delivery into the lateral ventricles, a common clinical procedure, results in effective vector distribution [Haurigot et al, J Clin Invest., August 2013; 123(8): 3254-3271]. It has also been reported that delivery via lumbar puncture can be improved by placing animals in the Trendelenburg position after injection to promote cranial vector distribution [Meyer et al, Molecular therapy: the journal of the American Society of Gene Therapy. Oct. 31, 2014]. In this study we compared intraventricular and intracisternal administration of an AAV9 vector expressing a green fluorescent protein (GFP) reporter gene in dogs. We found that both routes achieve effective distribution throughout the CNS, though intraventricular delivery may carry additional risks of a transgene-specific immune response. We also evaluated vector delivery by lumbar puncture in NHPs, and the impact of placing animals in the Trendelenburg position after injection. There was no clear effect of post-injection positioning, although we did find that large injection volumes could improve cranial distribution of the vector.

A. Materials and Methods:

1. Vector production: The GFP vector consisted of an AAV serotype 9 capsid carrying an expression cassette comprising a chicken beta actin promoter with cytomegalovirus immediate early enhancer, an artificial intron, the enhanced green fluorescent protein cDNA, a woodchuck hepatitis virus posttranscriptional regulatory element, and a rabbit beta globin polyadenylation sequence. The GUSB vector consisted of an AAV serotype 9 capsid carrying an expression cassette comprising a chicken beta actin promoter with cytomegalovirus immediate early enhancer, an artificial intron, the canine GUSB cDNA, and a rabbit beta globin polyadenylation sequence. The vectors were produced by triple transfection of HEK 293 cells and purified on an iodixanol gradient as previously described [Lock et al, Human gene therapy. October 2010; 21(10):1259-1271].

2. Animal experiments: All dogs were raised in the National Referral Center for Animal Models of Human Genetic Disease of the School of Veterinary Medicine of the University of Pennsylvania (NIH OD P40-010939) under National Institutes of Health and USDA guidelines for the care and use of animals in research.

3. NHP study: This study included 6 cynomolgus monkeys between 9 and 12 years of age. Animals were between 4 and 8 kg at the time of injection. The vector ($2 \times 10^{13}$ GC) was diluted in 5 mL of Omnipaque (Iohexol) 180 contrast material prior to injection. Injection of the vector via lumbar puncture was performed as previously described [Hinderer, Molecular Therapy—Methods & Clinical Development. 12/10/online 2014; 1]. Correct injection into the intrathecal space was verified by fluoroscopy. For animals in the Trendelenburg group, the head of the bed was lowered 30 degrees for 10 minutes immediately following injection. Euthanasia and tissue collection were performed as previously described [Hinderer, Molecular Therapy—Methods & Clinical Development. 12/10/online 2014; 1].

4. Dog study: This study included 6 one-year-old MPS I dogs, as well as a 2 month old MPS VII dog. Baseline MRIs were performed on all ICV treated dogs to plan the injection coordinates. Intracisternal injection was performed as previously described [Hinderer et al, Molecular therapy: the journal of the American Society of Gene Therapy. August 2015; 23(8):1298-1307]. For ICV injection, dogs were anesthetized with intravenous propofol, endotracheally intubated, maintained under anesthesia with isoflurane and placed in a stereotaxic frame. The skin was sterilely prepped, and an incision was made over the injection site. A single burr hole was drilled at the injection site, through which a 26-gauge needle was advanced to the predetermined depth. Placement was confirmed by CSF return. The vector ($1.8 \times 10^{13}$ GC in 1 mL) was slowly infused over one to two minutes. Euthanasia and tissue collection were performed as previously described [Hinderer et al, Molecular therapy: the journal of the American Society of Gene Therapy. August 2015; 23(8):1298-1307].

5. Histology: Brains were processed as described for evaluation of GFP expression [Hinderer, Molecular Therapy—Methods & Clinical Development. 12/10/online 2014; 1]. GUSB enzyme stains and GM3 stains were performed as previously described [Gurda et al, Molecular therapy: the journal of the American Society of Gene Therapy. Oct. 8, 2015.]

6. ELISPOT: At the time of necropsy blood was collected from vector treated dogs in heparinized tubes. Peripheral blood mononuclear cells were isolated by Ficoll gradient centrifugation. T cell responses to AAV9 capsid peptides and GFP peptides were evaluated by interferon gamma ELISPOT. AAV9 and GFP peptide libraries were synthesized as 15-mers with 10 amino acid overlap (Mimotopes). The AAV9 peptide library was grouped in 3 pools: Pool A from peptide 1 to 50, Pool B from peptide 51 to 100 and Pool C from peptide 101 to 146. The GFP peptide library was also grouped in 3 pools. Phorbol 12-myristate 13-acetate plus Ionomycin salt (PMA+ION) were used as positive control. DMSO was used as negative control. Cells were stimulated with peptide and interferon gamma secretion was detected as described. A response was considered positive if it was both greater than 55 Spots Forming Units (SFU) per million lymphocytes and at least 3 times the DMSO negative control value.

7. Biodistribution: At the time of necropsy tissues for biodistribution were immediately frozen on dry ice. DNA isolation and quantification of vector genomes by TaqMan PCR was performed as described [Wang et al, Human gene therapy. November 2011; 22(11):1389-1401].

8. GUSB enzyme assay: GUSB activity was measured in CSF as described [Gurda et al, Molecular therapy: the journal of the American Society of Gene Therapy. Oct. 8 2015].

B. Results

1. Comparison of Intraventricular and Intracisternal Vector Delivery in Dogs

Our previous studies using a canine model of the lysosomal storage disease mucopolysaccharidosis type I (MPS I) demonstrated that AAV9 injection into the cisterna magna could effectively target the entire brain and spinal cord [Hinderer et al, Molecular therapy: the journal of the American Society of Gene Therapy. August 2015; 23(8):1298-1307]. In this study, we compared distribution of an AAV9 vector expressing a GFP reporter gene administered into the cisterna magna or lateral ventricle of adult MPS I dogs. Three dogs were treated with a single 1 mL injection of the vector ($1.8 \times 10^{13}$ genome copies) into the cisterna magna. Three additional dogs received a single vector injection of the same vector into the lateral ventricle. For dogs treated by ICV injection, a baseline MRI was performed to select the larger lateral ventricle for injection and to define the target coordinates. Injection was performed using a stereotaxic frame to accurately target the designated ventricle.

Figure 13:
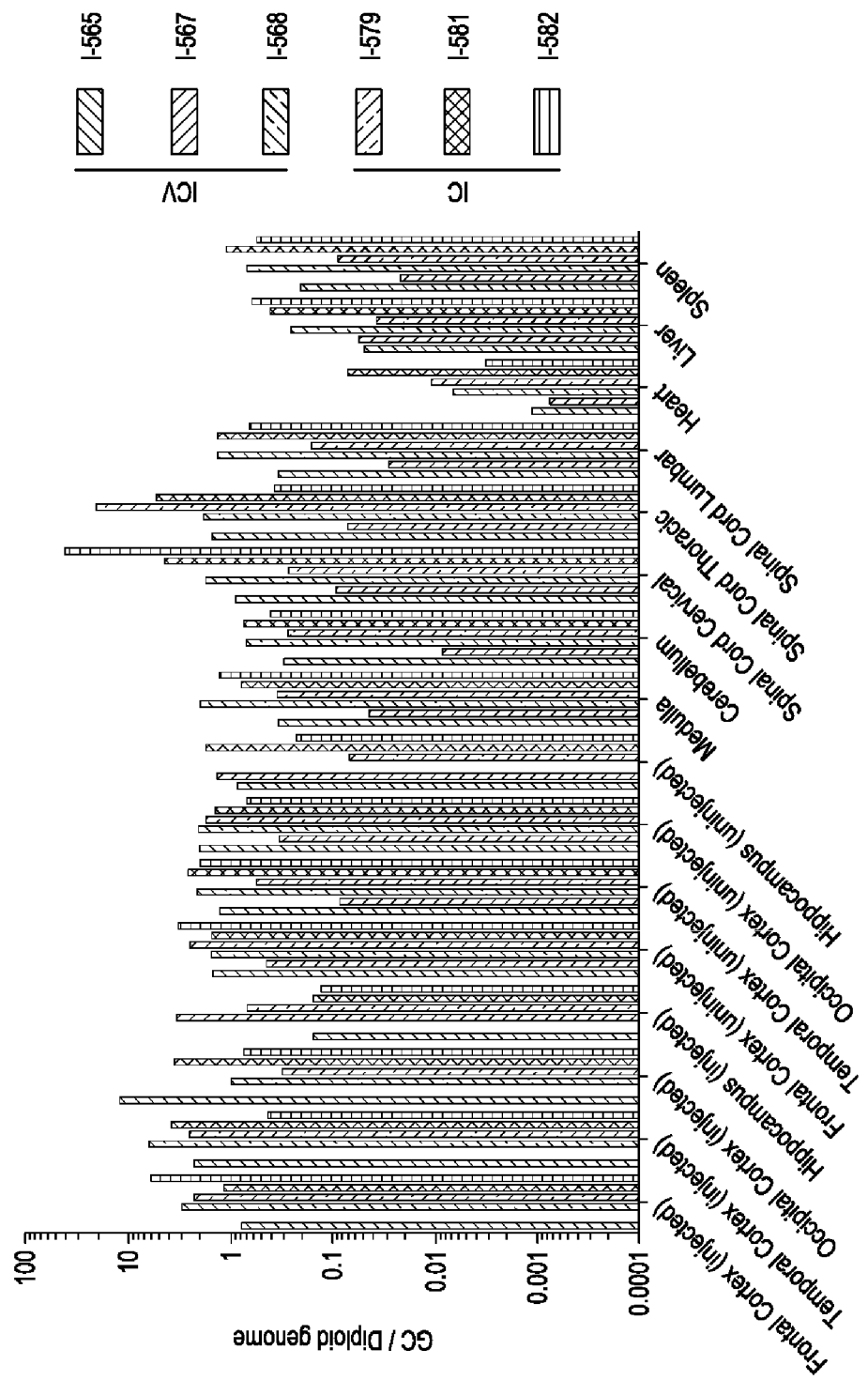

The three dogs treated with IC vector injection appeared healthy throughout the study. They were euthanized two weeks after vector injection for evaluation of vector biodistribution and transgene expression. No gross or microscopic brain lesions were observed in any IC treated dogs (FIGS. 12A-12F). Measurement of vector genomes by quantitative PCR revealed vector deposition throughout all sampled regions of the brain and spinal cord (FIG. 13). Consistent with the distribution of vector genomes, robust transgene expression was detectable in most regions of cerebral cortex, as well as throughout the spinal cord (FIGS. 14A-14H). Spinal cord histology was notable for strong transduction of alpha motor neurons, with a gradient of transduction favoring thoracic and lumbar segments. The three dogs treated with vector injected ICV initially appeared healthy following the procedure. However, one animal (I-567) was found dead 12 days after injection. The other two animals survived to the designated 14 day necropsy time point, although one animal (I-565) became stuporous prior to euthanasia, and the other (I-568) began to exhibit weakness of facial muscles. These clinical findings correlated with significant gross brain lesions (FIGS. 12A-12F). Brains from all three animals exhibited discoloration surrounding the needle track, with associated hemorrhage in the animal that was found dead. Histological evaluation revealed severe lymphocytic inflammation in the region surrounding the injection site. Perivascular lymphocytic infiltration was also observed throughout the brain of each animal (FIGS. 12G and 12H). Given this evidence for immunological toxicity, T cell responses to both the AAV9 capsid protein and the GFP transgene were evaluated in peripheral blood samples collected from one of the ICV-treated dogs (I-565) at the time of necropsy. An interferon gamma ELISPOT showed a strong T cell response directed against GFP, with no evidence of a response to capsid peptides (FIG. 12I). This suggests that the encephalitis observed was caused by a cell-mediated immune response against the transgene product.

Vector distribution in the ICV treated animals was similar to that observed in the IC treated group, although spinal cord transduction was somewhat greater in the IC cohort (FIG. 13). GFP expression was observed throughout the CNS regions examined in the ICV treated animals (FIGS. 14A to 14H).

Figure 17:
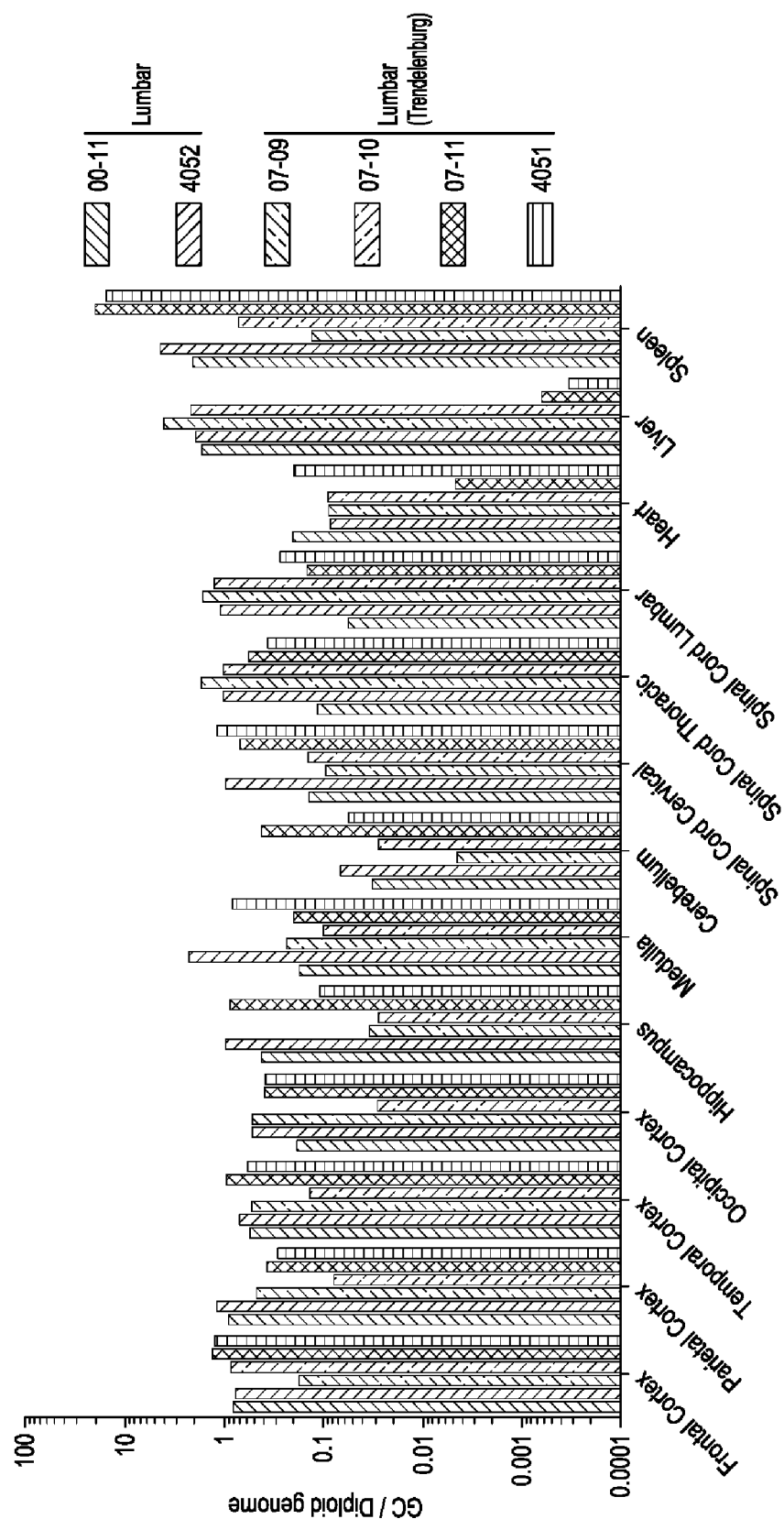

2. Impact of the Trendelenburg Position on CNS Transduction after AAV9 Administration by Lumbar Puncture in NHP We previously compared AAV9 injection into the cisterna magna or lumbar cistern of NHPs and found that the lumbar route was 10-fold less efficient for targeting the spinal cord and 100-fold less efficient for targeting the brain [C. Hinderer, et al, Molecular Therapy—Methods & Clinical Development. 12/10/online 2014; 1]. Other investigators have since demonstrated better transduction using AAV9 administration by lumbar puncture, with improvements in cranial distribution of the vector achieved by placing animals in the Trendelenburg position after injection [Myer et al, Molecular therapy: the journal of the American Society of Gene Therapy. Oct. 31, 2014]. In this approach the vector was diluted into an excess volume of contrast material to increase the density of the solution and promote gravity driven distribution while in Trendelenburg. Six adult cynomolgus monkeys were treated with a single injection of AAV9 expressing GFP ($2 \times 10^{13}$ genome copies) in the L3-4 interspace. The vector was diluted to a final volume of 5 mL in Iohexol 180 contrast material. Four of the animals were positioned with the head of the procedure table at a −30° angle for 10 minutes immediately after injection. After 10 minutes fluoroscopic images were captured to verify contrast distribution in the CSF. Notably with this large injection volume (approximately 40% of the total CSF volume of the animal)[Reiselbach et al, New England Journal of Medicine. 1962; 267(25):1273-1278] contrast material was rapidly distributed along the entire spinal subarachnoid space and into the basal cisterns even in animals that were not placed in Trendelenburg position (FIGS. 16A and 16B). Analysis of vector genome distribution by PCR (FIG. 17) and GFP expression (FIGS. 18A to 18H) demonstrated transduction throughout the brain and spinal cord. There was no apparent impact of post-injection positioning on the number or distribution of transduced cells. As previously reported, there was vector escape to the periphery and hepatic transduction after intrathecal AAV administration [Hinderer et al, Molecular Therapy—Methods & Clinical Development.

12/10/online 2014; 1; Haurigot et al, Journal of Clinical Investigation. August 2013; 123(8):3254-3271]. The extent of liver transduction was dependent on the presence of pre-existing neutralizing antibodies (nAb) against AAV9. Four out of six animals had no detectable baseline AAV9 nAbs (titer <1:5) and two animals (4051 and 07-11) had detectable pre-existing antibodies to AAV9 with a titer of 1:40. Consistent with previous results, pre-existing antibodies blocked liver transduction, and resulted in increased vector distribution to the spleen [Wang et al, Human gene therapy. November 2011; 22(11):1389-1401, but had no impact on CNS transduction; Haurigot et al, Journal of Clinical Investigation. August 2013; 123(8):3254-3271].

C. Discussion

Because suboccipital puncture is not a common procedure in clinical practice, we evaluated more routine sites of CSF access, including the lateral ventricle and the lumbar cistern. Here we evaluated a method employing vector solutions with higher density and post-injection Trendelenburg positioning to improve vector distribution cranially from the lumbar region.

In the dog study, both IC and ICV vector injection yielded similarly effective vector distribution, but encephalitis occurred only in the ICV group. A T cell response against the GFP transgene was detectable in one of the ICV treated dogs, suggesting that the lymphocytic encephalitis observed in these animals was due to a transgene-specific immune response. Induction of a T cell response to a new antigen requires two elements—recognition of an epitope from the protein by a naïve T cell, and an inflammatory "danger signal" that promotes activation of the T cell. AAV is believed to be capable of expressing foreign transgenes without eliciting immunity against the transgene product because it does not activate the innate immune system, thereby avoiding inflammatory signals and promoting tolerance rather than immunity when naïve lymphocytes encounter the newly expressed antigen. Local inflammation caused by the trauma of penetrating the brain parenchyma, occurring at the same location that the foreign transgene product is expressed, may provide the danger signal needed to induce an immune response to the transgene product. This is supported by previous studies in MPS I dogs, which develop cell-mediated immune responses to an enzyme expressed from an AAV vector delivered by direct brain injection but not by IC injection [Ciron et al, Annals of Neurology. August 2006; 60(2):204-213; Hinderer, et al, Molecular therapy: the journal of the American Society of Gene Therapy. August 2015; 23(8):1298-1307]. The potential for such an immune response depends on whether the transgene product is recognized as foreign—for delivery of vectors expressing a protein that is also produced endogenously, even an inflammatory response caused by injection may not break tolerance to the self-protein. The results in the study of ICV vector delivery in the MPS VII dog support this concept, as the similarity of the transgene product to an endogenous protein was likely responsible for the absence of the type of T cell response that was observed to GFP. The same may be true for patients with recessive diseases who carry missense mutations that allow for production of a protein similar to the transgene product. Risk of immunity could, therefore, vary depending on patient population and transgene product, and in some cases immunosuppression may be necessary to prevent destructive T cell responses to a transgene. The present findings suggest that the risk of deleterious immune responses can likely be mitigated by using an IC rather than ICV route of administration.

The study of AAV9 administration via lumbar puncture in NHPs showed greater transduction throughout the CNS than we have previously observed with this route of administration. This difference appears to be due to the large injection volume in the present study, which was necessary in order to dilute the vector into an excess volume of contrast material. Previous studies have shown that such large volume injections (approximately 40% of CSF volume) can drive injected material directly into the basal cisterns and even the ventricular CSF of macaques [Reiselbach, cited above]. The potential to translate this approach to humans is unclear, given that replicating this approach would require extremely large injection volumes (>60 mL) that are not routinely administered to patients. Moreover, even with this high volume approach, injection via lumbar puncture was less efficient than previous results with IC delivery. In this previous study, animals were dosed by weight, so only one animal received an IC vector dose equivalent to that used here [Hinderer, et al, Molecular Therapy—Methods & Clinical Development. 12/10/online 2014; 1]. That animal had on average 3-fold higher vector distribution in the brain and spinal cord, indicating that even very large volume vector delivery to the lumbar cistern is less efficient than IC delivery. In contrast to reports in the literature, we found no additional benefit to placing animals in the Trendelenburg position after lumbar vector injection [Meyer et al, Molecular therapy: the journal of the American Society of Gene Therapy. Oct. 31, 2014].

Together these findings support vector administration at the level of the cisterna magna, as this approach achieves more efficient vector distribution than administration via lumbar puncture, and appears to carry less risk of immunity to the transgene product than ICV administration. Vector delivery to the cisterna magna could be carried out clinically using the suboccipital puncture approach that was used in preclinical studies. Additionally, injection into the subarachnoid space between the first and second cervical vertebra using a lateral approach (C1-2 puncture) is likely to produce similar vector distribution given the proximity of the injection site to the cisterna magna. The C1-2 approach has the additional advantage that, unlike suboccipital puncture, it is widely used clinically for CSF access, particularly for intrathecal contrast administration.

Example 9: Non-clinical Pharmacology/Toxicology Study of AAV2/9.CB7.CI.serhIDS.RBG Injected Intrathecally in Rhesus Macaques A study designed to evaluate the safety of intrathecal administration of two doses of AAV2/9.CB7.CI.hIDS.RBG, a vector encoding human IDS, in rhesus macaques is performed, to obtain an adequate safety margin above the Minimum Efficacious Dose (MED) for human dosing.

Control article is administered via suboccipital puncture to a single macaque randomized to Group 1. Test Article is administered via suboccipital puncture to 6 rhesus macaques randomized to Groups 2-3. Macaques in Group 2 receive test article at a high dose of $5 \times 10^{13}$ Genome Copy (GC) (N=3); macaques in Group 3 receive test article administered at a low dose of $1.7 \times 10^{13}$ GC (N=3). Blood and cerebrospinal fluid are collected as part of a general safety panel.

Following completion of the in-life phase of these studies at 90±3 days post-vector administration, macaques are necropsied with tissues harvested for a comprehensive histopathological examination. Lymphocytes are harvested from the liver, spleen, and bone marrow to examine the presence of cytotoxic T lymphocytes (CTLs) in these organs at the time of necropsy.

I. Experimental Design

A. Materials

Test article—AAV9.CB7.hIDS is also known as AAV2/9.CB7.CI.hIDS.RBG, also known as AAV2/9.CB7.CI.hIDS.RBG.KanR. These designations are synonymous and may be used interchangeably.

The test article was produced as a single lot with a concentration of $5.72 \times 10^{13}$ GC/ml measured by Droplet digital (dd) PCR is used. Vectors are stored at ≤−60° C. after production until the day of injection. On the day of injection, vector is diluted with the control article. Once diluted, vector is stored at 2-4° C. in a refrigerator or on wet ice until the time of injection. Vector preparations are performed on the day of injection.

Control group animals are administered with the control article Elliot's Formulation Buffer (EFB) and no test article (EFB+0.001% Pluronic F68). Control article is stored at room temperature after production and until the day of injection.

B. Test System

Justification for Test System Selection: This study involves intrathecal (IT) delivery of a gene therapy vector for CNS diseases. The dimensions of the CNS in the non-human primate (NHP) acts as the best representative model of our clinical target population. This study provides data about dose-related toxicity of the vector after IT injection.

Seven (7) 3-7 year old male *Macaca mulatta* (Rhesus macaques) with a weight between 3 to 10 kg supplied by Covance Research Products, Inc. (Alice, Tex.) are used.

II. General Design Procedures 7 rhesus macaques (males) are used in the study Animals are divided into three study groups as listed in Table 1. All 7 animals receive an IT injection via suboccipital puncture.

TABLE 1

Group Designations

| | Group designation | | |
|---|---|---|---|
| | 1 | 2 | 3 |
| Number of animals per group | 1 | 3 | 3 |
| Gender | M | M | M |
| Treatment | control article 1 mL | AAV9.CB7.HIDS high dose $5 \times 10^{13}$ GC in 1 mL | AAV9.CB7.HIDS low dose $1.7 \times 10^{13}$ GC in 1 mL |
| Necropsy day | 90 | 90 | 90 |

Animals are anesthetized and dosed with test article via sub-occipital puncture into the cisterna magna.

Anesthetized macaques are prepped in a procedure room and transferred to the Fluoroscopy Suite and placed on an imaging table in the lateral decubitus position with the head flexed forward for CSF collection and dosing into the cisterna magna. The site of injection is aseptically prepared. Using aseptic technique, a 21-27 gauge, 1-1.5 inch Quincke spinal needle (Becton Dickinson) is advanced into the sub occipital space until the flow of CSF is observed. Up to 1.0 mL of CSF is collected for baseline analysis and prior to dosing. The anatomical structures that are traversed include the skin, subcutaneous fat, epidural space, dura and atlanto-occipital fascia. The needle is directed at the wider superior gap of the cisterna magna to avoid blood contamination and potential brainstem injury. Correct placement of needle puncture is verified via myelography, using a fluoroscope (OEC9800 C-Arm, GE). The fluoroscope is operated in accordance with manufacturer recommendations. After CSF collection, a leur access extension catheter is connected to the spinal needle to facilitate dosing of Iohexal (Trade Name. Omnipaque 180 mg/mL, General Electric Healthcare) contrast media and test or control article. One (1) mL of Iohexol is administered via the catheter and spinal needle. After verifying needle placement, a syringe containing the test article (volume equivalent to 1 mL plus the volume of syringe and linker dead space) is connected to the flexible linker and slowly injected over 20-60 seconds. The needle is removed and direct pressure applied to the puncture site. Residual test article remaining in the injection apparatus is collected and stored at ≤−60° C.

In the event that an animal cannot be dosed successfully to the cisterna magna, dosing into the C1-C2 intrathecal space (atlanto-axial joint) may be used as an alternate site of dosing. Dosing procedure is as follows. The animal is placed in the lateral decubitus position with the head flexed forward for CSF collection and dosing into the C1-C2 intrathecal space. The site of injection is aseptically prepared. Using aseptic techniques, a 21-27 gauge, 1-1.5 inch Quincke spinal needle (Becton Dickinson) is advanced into the intrathecal space until the flow of CSF is observed. Up to 1.0 mL of CSF is collected for baseline analysis and prior to dosing. The anatomical structures that is traversed include the skin, subcutaneous fat, epidural space, dura and fascia. The needle is inserted superior to C2 vertebra and into the vertebral space as to avoid blood contamination and potential injury to the cervical spinal cord. The rest of the procedure is similar to that previously described for cisterna magna administration.

The animals receive an intrathecal injection of either AAV9.CB7.hIDS or control article. The frequency of dosing is outlined in Table 3. The high dose of AAV9.CB7.hIDS is $5 \times 10^{13}$ GC and the low dose $1.7 \times 10^{13}$ GC. The total volume of diluted AAV9.CB7.hIDS or control article to be injected per macaque is 1 mL.

III. Results

CSF pleocytosis was observed in 2 out of 3 animals in the high-dose treated group (Group 2) and 1 out of 3 animals in the low-dose treated group (Group 3) shown as white blood cell count in CSF (FIG. 28). Such pleocytosis was resolved on Day 90 in all animals but one high-dose treated animal (RA 2203).

In addition, dorsal columns axonopathy is present (data not shown).

In certain embodiments, the low dose corresponds to $1.9 \times 10^{11}$ GC/g brain weight and the high dose is $9.4 \times 10^{10}$ GC/g brain weight. In certain embodiments, the high dose corresponds to $5.6 \times 10^{11}$ GC/g brain weight. In other embodiments, the low and high doses correspond to $1.3 \times 10^{10}$ GC/g brain mass and $6.5 \times 10^{10}$ GC/g brain mass, respectively. In certain embodiments, total volume of product administered does not exceed 5 mL.

ELISA assay of anti-hIDS antibody was performed on the serum samples collected from the animals described above. Results obtained on Day 60 were plotted in FIG. 29 and shown in Table 2 below. CSF samples were diluted 20 times for evaluation via ELISA assay of anti-hIDS antibody. The result is shown in Table 3. Decreased immunogenicity was observed in the low-dose treated group (Group 2) compared to the high-dose one (Group 3) in both serum and CSF. No immunogenicity against hIDS was observed in the non-treated control.

TABLE 2 anti hIDS antibody ELISA (Serum)

|  | Titer |
|---|---|
| RA2198 vehicle | <50 |
| RA2197 low dose | 400 |
| RA 2203 high dose | 1600 |
| RS 2231 high dose | 6400 |

TABLE 3 anti hIDS antibody ELISA (CSF)

|  | CSF 1:20 |
|---|---|
| RA2198 vehicle | 0.050066667 |
| RA2197 low dose | 0.052133333 |
| RA 2203 high dose | 0.058833333 |
| RS 2231 high dose | 0.141566667 |

Example 10: Non-Clinical Pharmacology/Toxicology Study of AAV9.CB7.hIDS Injected Intrathecally in Immunosuppressed Rhesus Macaques A study designed to evaluate the impact of chemically induced immunosuppression (IS) on the safety of intrathecal administration of two doses of AAV9.CB7.hIDS, a vector encoding human IDS, in rhesus macaques, is performed. The study is as described in Example 9 with modifications noted below.

Control article dosed animal are repeated as in Example 9. Test Article is administered via suboccipital puncture to 6 rhesus macaques randomized to Groups 1-2. Macaques in Group 1 receive test article at a high dose of $5 \times 10^{13}$ Genome Copy (GC) (N=3); macaques in Group 2 receive test article administered at a low dose of $1.7 \times 10^{13}$ GC (N=3). Blood and cerebrospinal fluid are collected as part of a general safety panel. Monkeys from group 1 and 2 receive mycofenolate mofetil (MMF) at least 2 weeks prior to AAV9.CB7.hIDS dosing and up to and including day 60 after dosing, and rapamycin at least 2 weeks prior to dosing and up to and including day 90 (+/−3 days) after dosing. Plasma trough levels for both immunosuppressive drugs are monitored and doses adjusted to maintain a range of 2-3.5 mg/L for mycofenolate acid (MPA, active metabolite of MMF) and 10-15 μg/L for rapamycin.

Following completion of the in-life phase of these studies at 90±3 days post-vector administration, macaques are necropsied with tissues harvested for a comprehensive histopathological examination. Lymphocytes are harvested from the blood, spleen, and bone marrow to examine the presence of cytotoxic T lymphocytes (CTLs) in these tissues at the time of necropsy.

A. Materials

The test article, control article, preparation thereof is described in Example 9.

B. Test System

*Macaca mulatta* (Rhesus macaques) is utilized and kept as described in Example 9. A cohort of 6 animals (6 males) is used for the study. Animals are assigned a number from 1-6 from the lowest ID to the highest. A random list of numbers 1-6 is generated by random.org and once randomized the animals are assigned in order as follows: Group 1 is assigned three animals; and Group 2 is assigned three animals.

C. General Design Procedures

Sample Size and Group Designations:

6 rhesus macaques are used in the study. Animals are divided into 2 study groups as listed in Table 4. All 6 animals receive an IT injection via suboccipital puncture

TABLE 4

Group Designations

|  | Group designation | |
|---|---|---|
|  | 1 | 2 |
| Number of animals per group | 3 | 3 |
| Gender | M | M |
| Treatment | AAV9.CB7.hIDS high dose $5 \times 10^{13}$ GC in 1 mL | AAV9.CB7.hIDS low dose $1.7 \times 10^{13}$ GC in 1 mL |
| Immunosuppression | Yes | Yes |
| Necropsy day | 90 | 90 |

An immunosuppression regimen is administered to all animals in Groups 1 and 2. Drug combinations, dose, and administration schedule for each group of animals is summarized in Table 5. Animals may be treated with systemic antibiotics and/or antifungals to treat opportunistic infections associated with immunosuppression if they occur.

Animals are dosed with a combination therapy of Mycophenolate mofetil (MMF) and Rapamycin. Both immunosuppression drugs are administered through an orogastric feeding tube or nasogastric feeding tube to anesthetized or conscious chair restrained macaques. Anesthesized animals are not be fasted to allow aspiration of gastric content from the tube (correct placement verification). The immunosuppression regimen start at least two weeks prior to intrathecal dosing of the test article. Starting doses of IS drugs are based upon efficacy previously described in rhesus macaques, upon doses previously used at GTP for other studies, and are adjusted upon plasma trough level monitoring.

The weight of animals on the first day of immune suppression is used to calculate the initial dose. Animals are then weighed every morning and the dose recalculated if the weight change exceeds +/−10%.

Trough levels are monitored 2 times per week initially, and once a week after Day 60 (when rapamycin only will be administered).

TABLE 5

Immunosuppression Regimen

| Group | MMF, oral administration | | Rapamycin, oral administration | |
|---|---|---|---|---|
| | Dose/schedule | Duration | Dose/schedule | Duration |
| 2 | 20-100 mg/kg BID | d-14 to d 60 | 0.5-4 mg/kg SID | d-14 to d 90 |
| 3 | 20-100 mg/kg BID | d-14 to d 60 | 0.5-4 mg/kg SID | d-14 to d 90 | c. IS Drugs

Rapamycin is administered at a dose of 0.5-4 mg/kg PO, SID a minimum of 14 days prior to intrathecal dosing and up to and including Day 90 (+/−3 days) of the study. Starting dose is 1 mg/kg. Rapamycin doses are calculated to maintain target trough levels as close to 10-15 µg/L as possible for the duration of the study. If the target trough drug levels are not achieved within one week, the doses are titrated in 0.25-2 mg/kg dose intervals. After the stabilization period, if the trough levels are too low for 2 consecutive bleedings, an adjustment is made. If they are too high, immediate adjustment is made.

MMF is administered for a minimum of 14 days prior to intrathecal dosing and up to and including Day 60 of the study at a starting dose of 50 mg/kg PO, BID. Trough levels results are then used to adjust the doses that are titrated in 5-25 mg/kg dose intervals. Trough levels for MPA are maintained as close to 2-3.5 mg/L as possible. After stabilization period, if the trough levels are too low for 2 consecutive bleedings, an adjustment is made. If they are too high, immediate adjustment is made.

d. Formulation of IS Drugs

MMF is administered orally to the test system using a commercially available oral solution at a concentration of 200 mg/mL.

Rapamycin is administered orally to the test system using one or more of the following commercially available formulations: 0.5 mg coated tablets; 1 mg coated tablet; 2 mg coated tablet.

When administering pill formulations, tablets are prepared as follows:

Each rapamycin pill is placed in a diluent of either room temperature or warm water (warm water is used to accelerate the dissolution if needed) to dissolve the outer coating of the tablet. Approximately 10 ml of water is used. The pill is white under the yellow coating.

Once the outer coating is dissolved, each pill is crushed using a mortar and pestle until it is a fine powder, creating a uniform solution. The total volume of the diluent used to dissolve the tablet(s) is recorded in the study record.

The total mixture is drawn into a dose syringe and administered through a OG or NG tube as previously described in this Example Following dosing of MMF and/or Rapamycin the orogastric or nasogastric feeding tube is flushed with drinking water. The volume of flush is recorded in the study record.

The following studies were performed to evaluate the efficacy of intracerebroventricular (ICV) delivery of AAV9.CB7.CI.hIDS in MPS II mice and to determine the minimum effective dose. Efficacy was based on evidence of a pharmacodynamic response to the vector (generation of enzymatically active hIDS protein) and an effect on behavioral and histological manifestations of MPS II disease (IDS deficiency).

This study evaluated the safety, biodistribution, and pharmacology of 2 dose levels of AAV9.CB.hIDS, a vector encoding human iduronate-2-sulfatase (hIDS), for up to 90 days after administration by image-guided suboccipital puncture in chemically immunosuppressed rhesus macaques. Control article was administered via suboccipital puncture to a single non-immunosuppressed macaque. AAV9.CB.hIDS was administered via suboccipital puncture to 5 rhesus macaques randomized to Groups 1-2. Macaques in Group 1 received test article at a high dose (HD) of $5 \times 10^{13}$ GC (n=3); macaques in Group 2 received test article administered at a low dose (LD) of $1.7 \times 10^{13}$ GC (n=3). Blood and cerebrospinal fluid (CSF) were collected as part of a general safety panel at baseline, Day 7, 14, 21, 30, 45, 60, and 90. Humoral response to the transgene product hIDS and to the AAV9 capsid, and hI2S enzymatic activity were analysed in serum and CSF at the same timepoints. T-cell responses to the transgene product hI2S and to the AAV9 capsid were evaluated at baseline, Day 30, 60, and 90 in the blood, and at Day 90 in spleen and bone marrow. Vector genomes were quantified in the total blood and CSF at baseline, Day 7, 14, 21, 30, 45, 60, and 90, and in urine and feces (shedding) at baseline, Day 5, 30, and 90. Following completion of the in-life phase of the study at 90±3 days post-vector administration, macaques were necropsied and tissues harvested for further evaluation. Histopathologic evaluation and biodistribution of the vector genome were done in a comprehensive list of tissues from the central nervous system (CNS), peripheral nervous system (PNS) and peripheral organs.

There were no AEs associated with the administration procedure, and no AAV9.CB.HIDS-related abnormalities on clinical general observations, body weight change, organ weights, CBC, serum chemistry, or coagulation parameters. IS procedure caused intestinal signs with increase of some inflammation parameters and anemia that were not related to AAV9.CB.HIDS administration. Only one animal from the LD group (RA2233) had a lymphocytic CSF pleocytosis (23 cells per µL) on the necropsy day.

Humoral immune response to hI2S was efficiently prevented by IS and was absent or reduced to a minimal response in other animals. There was no T cell response to hI2S in IS animals and minimal to moderate response to AAV9 in the LD group only. No rebound immune response was seen following the withdrawal of MMF on Day 60.

There was a mild AAV9 Nab response following vector administration that was more obvious in the LD animals than in the HD animals. IS had no clear effect on AAV9 Nab response of the LD animals (low in both IS and non IS animals) but seemed efficient in modulating the AAV9 Nab response of the HD animals.

IS completely prevented CSF AAV9 Nab response in both HD and LD animals treated with AAV9.CB.HIDS.

Treatment related findings were observed similarly in both high and low dose groups and consisted of minimal to mild axonopathy of the spinal cord dorsal white matter tracts and sciatic nerve. Minimal to mild neuronal cell body degeneration with mononuclear cell infiltration in the dorsal root ganglia, that project in the dorsal white matter tracts, and trigeminal ganglia, were generally similar to Study #2, therefore chemically induced immunosuppression did not affect these findings.

No inflammation was seen within the brain or spinal cord, despite the presence of high vector copy number, likely reflecting the anatomic specificity of dorsal root ganglia that are highly vascularized and lack a protective blood-brain-barrier unlike central nervous system [Sapunar D, et al., Dorsal root ganglion—a potential new therapeutic target for neuropathic pain. Journal of Pain Research. 2012; 5:31-38. doi:10.2147/JPR.S26603.]

High levels of AAV vector genomes were detected throughout the brain, spinal cord, and dorsal root ganglia of all AAV9.CB.HIDS-treated animals yielding an average across all CNS and dorsal root ganglia samples of $2\times10^5$ GC/μg DNA in the low dose group, and $3.4\times10^5$ GC/μg DNA in the high dose group. Significant vector biodistribution was also found in the periphery, especially in the liver that had levels about 10 times higher than in the CNS for the HD animals and equivalent to the CNS for the LD animals. The least transduced organs were eye, kidney, testicle, and thyroid gland with average levels between 54 GC/μg DNA in the thyroid and 8,540 GC/μg DNA in the kidney.

One animal (RA2233) had pre-existing AAV9 NAb (baseline titer 1:40) that completely inhibited the transduction of liver, eye, heart, lung, testicles, and thyroid (undetected genome copies), whereas the CNS and PNS vector biodistribution was not affected. Corresponding to the presence of vector genome copies in the CNS, PNS, and peripheral organs, I2S activity rapidly increased over the baseline in all but one animal in the serum and in all animals in the CSF, showing that AAV9.CB.hIDS expresses functional I2S enzyme that is present both in the CSF and in the serum of intrathecally treated animals. Vector DNA was present in all blood samples collected from AAV9.CB.HIDS administered animals with a peak at Day 7. Levels of vector DNA declined overtime but were not completely negative by day 90, the last time point post-test article administration of the study.

Vector DNA was more abundant in the blood than in the CSF, including in the earliest time point, showing the rapid transfer from the CSF to the blood compartment.

Vector DNA shedding occurred through biliary clearance mostly, with higher genome copy values detected in the feces than in the urine. Shedding was also more durable in the feces (up to Day 30-90) than in the urine (up to Day 5).

Example 11: Efficacy of Intracerebroventricular AAV9.CB7.CI.hIDS.rBG in a Mouse Model of MPS II I. Summary Hunter syndrome, mucopolysaccharidosis type II (MPS II), is a X-linked inherited disorder caused by the deficiency of the enzyme iduronate-2-sulfatase (I2S), involved in the lysosomal catabolism of the glycosaminoglycans (GAG) dermatan and heparan sulfate. This deficiency leads to the intracellular accumulation of undegraded GAG and eventually to a progressive severe clinical phenotype. Many attempts have been made in the last two to three decades to identify possible therapeutic strategies for the disorder, including gene therapy and somatic cell therapy. Study was performed to evaluate the short-term (21 days) biodistribution, expression, and activity of a single intracerebroventricular (ICV) administration of AAV9.CB7.CI.hIDS.rBG, an AAV9 vector expressing human I2S, in a murine model of MPS II. A further study was designed and performed to determine the minimum effective dose (MED) of AAV9.CB7.CI.hIDS.rBG administered through the ICV route as a single dose with a 3 months post-injection (pi) observation period, in a murine model of MPS II. The study also included some safety endpoints (evaluation of the humoral immune response to the transgene and brain histopathology).

AAV9.CB7.CI.hIDS.rBG was administered intracerebroventricularly to 2-3 month old C57BL/6 I2S γ/− (MPS II) mice (16 males/group) at doses of $3\times10^8$ GC or $3\times10^9$ GC or $3\times10^{10}$ GC (determined by qPCR tittering of the vector) on Day 0. At Day 21, mice from groups 3-5 (Table 6) were euthanized and necropsied for evaluation of CNS I2S activity, biodistribution and anti-hI2S immunogenicity. Between Days 60 and 89, wildtype mice and untreated MPS II mice were evaluated in a series of neurobehavioral assays (open field, Y-maze, contextual fear conditioning and novel object recognition) to characterize effect of the disease state on these endpoints. Based on the results of these initial assays, remaining treated mice were evaluated in the two assays that evaluated long term memory (contextual fear conditioning and novel object recognition). Approximately 3 months after ICV dosing of AAV9.CB7.CI.hIDS.rBG, all the remaining mice were euthanized and necropsied. Serum and CSF were evaluated for I2S activity as well as serum for anti-I2S antibodies. Liver and heart were evaluated for GAG tissue content. Brain overall lysosomal storage (both primary GAG storage and secondary ganglioside storage) was assessed by immunohistochemical staining of LIMP2 and GM3. Tissue hexosaminidase levels have been shown to be higher in MPS II mice and MPS II patients, and to be a biomarker of lysosomal homeostasis disruption. Tissue hexosaminidase enzymatic activity was thus measured as a biomarker of lysosomal function secondary to AAV9.CB7.CI.hIDS.rBG administration. Histopathology of the brain was evaluated to investigate both efficacy and safety.

TABLE 6

Combined Study Design for Studies W2301 and W2356

| | | | | | N per Endpoint (Animal IDs) | |
| --- | --- | --- | --- | --- | --- | --- |
| Group # | Genotype | Dose (GC qPCR) | Dose (GC ddPCR) | Dose Volume (μL) | Study W2356 Necropsy Day 21 | Study W2301 Neurobehavioral Testing Days 60-89 Necropsy 3 months pi |
| t | C57BL/6J I2S$^{γ/+}$ (Wildtype) | 0 (untreated) | 0 (untreated) | 0 | 3* (351, 353, 365) | 8 (33, 36, 43, 44, 45, 64, 78, 79) |
| 2 | C57BL/6J I2S$^{γ/−}$ (MPS II) | 0 (untreated) | 0 (untreated) | 0 | 5* (157, 194, 201, 258, 276) | 8 (27, 34, 35, 42, 46, 57, 71, 72) |

TABLE 6-continued

Combined Study Design for Studies W2301 and W2356

| | | | | | N per Endpoint (Animal IDs) | |
|---|---|---|---|---|---|---|
| Group # | Genotype | Dose (GC qPCR) | Dose (GC ddPCR) | Dose Volume (µL) | Study W2356 Necropsy Day 21 | Study W2301 Neurobehavioral Testing Days 60-89 Necropsy 3 months pi |
| 3 | C57BL/6J I2S$^{\gamma/-}$ (MPS II) | 3e8 | 5.2e8 | 5 | 8 (158, 166, 232, 233, 234, 263, 265, 270) | 8 (84‡, 89, 100, 101, 117, 140, 141, 142) |
| 4 | C57BL/6J I2S$^{\gamma/-}$ (MPS II) | 3e9 | 5.2e9 | 5 | 8 (148, 149, 187, 219, 220, 244, 245, 247) | 8 (107, 108, 120, 121, 122, 123, 136, 139) |
| 5 | C57BL/6J I2S$^{\gamma/-}$ (MPS II) | 3e10 | 5.2e10 | 5 | 8 (208, 211, 212, 251, 253, 267, 268, 269) | 8 (91, 93, 94, 95, 128, 129, 130, 132) |

*Control values for brain and CSF I2S activity were based on tissue samples collected from untreated wildtype and MPS II animals that were taken from the breeding colony.
‡Animal 84 was incorrectly genotyped as MPS II (I2Sγ/−) but proved on regenotyping to be wildtype (I2Sγ/+). Data from this animal was excluded from all analyses.

ICV administration of AAV9.CB7.CI.hIDS.rBG to C57BL/6 I2S γ/− (MPS II) mice at up to 3×10$^{10}$ GC (5.2×10$^{10}$ GC by ddPCR method) was well tolerated, with no clinical signs or mortality, and resulted in distribution to the CNS as well as to peripheral tissues, particularly liver, thus demonstrating partial redistribution of injected viral particles from the CSF to the peripheral blood.

There was evidence of I2S gene expression in the brain as evidenced by detection of the vector and dose dependent increases in I2S activity in the brain at Day 21 and in the CSF 3 months pi, with enzymatic activity close to wildtype level at the highest dose (brain tissue) and comparable to higher than wildtype at the mid and high doses (CSF). There was dose dependent normalization of the lysosomal compartment, as shown by reductions in LIMP2 and GM3 staining in the CNS at all doses 3 months pi. In H&E stained brain sections, dose dependent reductions in the amount and frequency of glial vacuolation and neuronal accumulation of amphophilic material, indicators of MPS II CNS phenotype, were also observed. Corresponding to the changes in CNS lysosomal content and improvements in disease-related morphology in the H&E stained sections, there were improvements in one measure of long term memory (novel object recognition, NOR) but not in the other, contextual fear conditioning (CFC). No clear dose response was apparent in the improvement in NOR.

Dose dependent increases in serum I2S activity were also observed 3 months pi, with enzymatic activity comparable to or higher than wild type at the mid and high doses. Reflecting the normalization of I2S activity in serum, the treated MPS II mice had dose dependent decreases in hexosaminidase activity and GAG content in the liver and heart. Hepatic Hexosaminidase and GAG levels were normalized at all dose levels in lever and at the mid and high doses in the heart. The highly transduced liver (1 to 10 GC per diploid genome) probably acted as a depot organ for the secretion of I2S in the serum and cross-correction of the heart at the higher doses.

There was no evidence of test-article related toxicity in the brain, although changes related to the ICV administration procedure itself were observed in some mice. Humoral immune response to the transgene was minor, observed only in some mid- and high-dose animals without impact on the health or brain histopathology of those animals.

In conclusion, AAV9.CB7.CI.IDS.rBG was well tolerated in MPS II mice at all dose levels and resulted in dose-dependent increases in I2S levels (expression and enzymatic activity) that were associated with improvements in both CNS and peripheral parameters of MPS II. The lowest dose administered, 3×108 GC (5.2×10$^8$ GC ddPCR method), was the minimum effective dose in this study.

II. Materials and Methods

A. Test article identified as AAV9.CB7.CI.hIDS.rBG is clear, colorless liquid with a titer at 1.18×10$^{13}$ GC/mL measured by qPCR and 2.057×10$^{13}$ GV/mL measured by ddPCR. Endotoxin is <1.0 EU/mL. Purity is 100%. The test article was stored at ≤−60° C.

B. Dose Formulation and Analysis

1. Preparation of Test Article:

The test article was diluted with sterile phosphate buffered saline (PBS) to the appropriate concentration for each dose group. Diluted vector was kept on wet ice and injected to the animals within 4 hours after dilution.

C. Test System

*Mus musculus* C57BL/6J I2Sγ/− (MPS II phenotype, N=56 males) and C57BL/6J I2Sγ/+(Wild type phenotype, N=8 males) were bred at the Translational Research Laboratories (TRL) Vivarium from stock originally obtained from Jackson Laboratories (Stock No. 024744). Animals were 2-3 months of age at Day 0 (day of dosing).

D. Experimental Design

1. Study W2356

On day 0, all animals from groups 3-5 (16 males/group, W2356 and W2301 studies combined) were dosed ICV with AAV9.CB7.CI.hIDS.rBG. On day 21, mice/group from groups 3-5 (8 males/group, W2356 study) were euthanized and necropsied and brain, heart, lung, liver, and spleen were collected and snap frozen on dry ice for an evaluation of brain I2S activity and tissue vector biodistribution.

TABLE 7

W2356 Study Design

| Group # | Genotype | Dose (GC qPCR) | Dose (GC ddPCR) | Dose Volume (μL) | N per Endpoint (Animal IDs) NecropsyDay 21 |
|---|---|---|---|---|---|
| 1 | C57BL/6J I2S$^{γ/+}$ (Wildtype) | 0 (untreated) | 0 (untreated) | 0 | 3* (351, 353, 365) |
| 2 | C57BL/6J I2S$^{γ/-}$ (MPS II) | 0 (untreated) | 0 (untreated) | 0 | 5* (157, 194, 201, 258, 276) |
| 3 | C57BL/6J I2S$^{γ/-}$ (MPS II) | $3 \times 10^8$ | $5.2 \times 10^8$ | 5 | 8 (158, 166, 232, 233, 234, 263, 265, 270) |
| 4 | C57BL/6J I2S$^{γ/-}$ (MPS II) | $3 \times 10^9$ | $5.2 \times 10^9$ | 5 | 8 (148, 149, 187, 219, 220, 244, 245, 247) |
| 5 | C57BL/6J I2S$^{γ/-}$ (MPS II) | $3 \times 10^{10}$ | $5.2 \times 10^{10}$ | 5 | 8 (208, 211, 212, 251, 253, 267, 268, 269) |

*Control values for brain and CSF I2S activity were based on tissue samples collected from untreated wildtype and MPS II animals that were taken from the breeding colony.

2. Study W2301

On Day 0, all animals from groups 3-5 (16 males/group) were dosed ICV with AAV9.CB7.CI.hIDS.rBG. From 2 to 3 months pi: Animals from groups 1 and 2 (8 mice/group) were evaluated in a series of neurobehavioral assays including open field activity, Y-maze activity, contextual fear conditioning, and novel object recognition to determine if there were effects of the disease state (MPS II genotype) on these endpoints. If an apparent effect of disease was observed, 8 mice/group from Groups 3-5 were also evaluated in that assay to determine if treatment with the vector had an effect on response.

Animals from groups 1-5 (same animals evaluated in neurobehavioral assays, 8 mice/group) were deeply anesthetized (ketamine-xylazine) to collect CSF (cisterna magna puncture) and blood (cardiac puncture) for evaluation of serum and CSF I2S activity and serum anti-hI2S antibodies. The mice were then euthanized and necropsied and samples were collected for brain histopathology; brain lysosomal storage (assessed by immunohistochemistry and image analysis); liver and heart hexosaminidase activity; and liver and heart GAG content (assessed by tissue content).

TABLE 8

W2301 Study Design

| Group # | Genotype | Dose (GC qPCR) | Dose (GC ddPCR) | Dose Volume (μL) | N per Endpoint (Animal IDs) Neurobehavioral Testing Days 60-89 Necropsy 3 months pi |
|---|---|---|---|---|---|
| 1 | C57BL/6J I2S$^{γ/+}$ (Wildtype) | 0 (untreated) | 0 (untreated) | 0 | 8 (33, 36, 43, 44, 45, 64, 78, 79) |
| 2 | C57BL/6J I2S$^{γ/-}$ (MPS II) | 0 (untreated) | 0 (untreated) | 0 | 8 (27, 34, 35, 42, 46, 57, 71, 72) |
| 3 | C57BL/6J I2S$^{γ/-}$ (MPS II) | $3 \times 10^8$ | $5.2 \times 10^8$ | 5 | 8 (84‡, 89, 100, 101, 117, 140, 141, 142) |
| 4 | C57BL/6J I2S$^{γ/-}$ (MPS II) | $3 \times 10^9$ | $5.2 \times 10^9$ | 5 | 8 (107, 108, 120, 121, 122, 123, 136, 139) |
| 5 | C57BL/6J I2S$^{γ/-}$ (MPS II) | $3 \times 10^{10}$ | $5.2 \times 10^{10}$ | 5 | 8 (91, 93, 94, 95, 128, 129, 130, 132) |

‡Animal 84 was incorrectly genotyped as MPS II (I2Sγ/−) but proved on regenotyping to be wildtype (I2Sγ/+). Data from this animal was excluded from all analyses.

3. Administration of Test Article

The ICV route was chosen because it is minimally invasive and requires no surgical procedure in the mouse (compared to the cisterna magna route that necessitates neck skin and muscle incision). As this study included some neurobehavioral endpoints involving mice activity recording, a non-invasive injection that did not involve survival surgery was preferred. It was demonstrated previously by us and others that in both mice and large animals, a single injection of AAV9 into the cerebrospinal fluid (ICV or cisterna magna) targets neurons within the whole CNS (Dirren at al., Hum. Gene. Therapy 25, 109-120 (2014); Snyder et al. Hum. Gene Ther 22, 1129-1135 (2011), Federici et al. Gene Therapy 19, 852-859 (2012), Haurigot et al. J Clin Invest 123, 3254-3271 (2013), Bucher et al. Gene Therapy 21, 522-528 (2014), Hinderer et al. Mol Ther: 22, 2018-2027 (2014) and Mol Ther—Methods & Clin Dev 1, 14051 (2014)]. The data published by Haurigot et al. (2013) specifically addresses the comparison between ICV and cisterna magna injection in the context of another lysosomal storage disease, demonstrating that the two routes of administration are equivalent in terms of transgene expression and biodistribution.

The maximum feasible dose due to volume constraint (5 µL for ICV injections in adult mice) was approximately $6\times10^{10}$ GC per mouse (qPCR tittering method). Due to previous results obtained at GTP for the treatment of other MPSs and due to the concerns regarding scalability to larger animals, the vector was diluted in order to inject $3\times10^{10}$, $3\times10^9$, or $3\times10^8$ GC per mouse (qPCR tittering method). Based on the ddPCR method, the actual doses were $5.2\times10^{10}$, $5.2\times10^9$, and $5.2\times10^8$ GC per mouse. Considering an average brain mass of 0.4 g in young adults C57B16 mice (Biology of the laboratory mouse by the staff of the Jackson laboratory, second revised edition, Earl L. Green Editor), this is equivalent to $1.31\times10^{11}$ GC per gram of brain mass at the highest dose and $1.31\times10^9$ GC per gram of brain mass at the lowest dose.

Vector was administered ICV into the right lateral ventricle. Mice were anesthetized with Isoflurane. Each anesthetized mouse was grasped firmly by the loose skin behind the head and injected free hand anterior and lateral to the bregma with a Hamilton syringe fitted with a 26-gauge needle, which was adjusted to be inserted 3 mm deep. The injection method was previously validated in mice by injection of dye or substance P into the right lateral ventricle. Success was defined as visualization of blue dye or by itching behavior (after substance P administration) of the mice following injection into the cerebrospinal fluid.

F. Procedures, Observations and Measurements

Animals were monitored daily for morbidity/mortality. The animals were monitored by daily cage-side visual observations for general appearance, signs of toxicity, distress and changes in behavior. These data were not recorded in this non-GLP study.

Between Days 60 and 90 (2-3 months after vector administration), 8 animals from Groups 1 and 2 of Study W2356 were subjected to behavioral and neurocognitive tests to determine effect of genotype on these endpoints. If an effect of genotype was identified, additional testing was done using 8 animals from Study W2356 Groups 3-5 to determine if there was an effect of treatment. All behavior procedures were performed by operators blinded to genotype and group.

General Locomotion (Open Field Activity):

Spontaneous activity in an open field was measured with a Photobeam Activity System (PAS)—Open Field (San Diego Instruments). In this assessment, mice were individually placed in the arena for a single 10-minute trial. Horizontal and vertical beam breaks were collected to assess general locomotion and rearing activity.

b) Short Term Memory (Y Maze Activity):

Y Maze Spontaneous Alternation is a behavioral test for measuring the willingness of rodents to explore new environments. Testing occurs in a Y-shaped maze with three white, opaque plastic arms at a 120° angle from each other. After introduction to the center of the maze, the animal is allowed to freely explore the three arms. Rodents typically prefer to investigate a new arm of the maze rather than returning to one that was previously visited. Over the course of multiple arm entries, the subject should show a tendency to enter a less recently visited arm. The number of arm entries and the number of triads are recorded in order to calculate the percentage of alternation. An entry is defined as all four limbs present within the arm. This test is used to quantify cognitive deficits in transgenic strains of mice and evaluate novel chemical entities for their effects on cognition. Many parts of the brain—including the hippocampus, septum, basal forebrain, and prefrontal cortex—are involved in this task. In this study, a standard Y-shaped maze (San Diego Instruments) was used, and the sequence and number of arm entries was recorded during an 8-minute trial. A spontaneous alternation (SA) was defined as sequential entry into all 3 arms of the maze without immediately returning to a previously entered arm. Total arm entries (AE) as collected as a measure of motor activity. The percent spontaneous alternation was calculated as % $SA=(SA/(AE-2)*100)$.

c) Long Term Memory (Contextual Fear Conditioning):

In these tasks, animals learn to fear a new environment or an emotionally neutral conditioned stimulus (CS), such as a tone, because of its temporal association with an aversive unconditioned stimulus (US), usually foot shock. When exposed to the same context or the same CS, conditioned animals show freezing behavior (Abel et al, Cell 88: 615-626. 1997). On the training day, mice were allowed to explore the unique conditioning chamber (Med Associates Inc) for 300 seconds. Between 248-250 seconds of the 300 second period, a non-signaled, 1.5 mA continuous foot shock was delivered. After an additional 30 seconds in the chamber, the mice were returned to their home cage. Twenty four hours later, recall of spatial context was assessed for 5 consecutive minutes in the same chamber where training occurred. Memory was assessed with software used to score freezing behavior (Freezescan, CleverSys Inc). The percent freezing in the 2.5 minute prestimulus epoch of the training session (prior to the administration of the foot shock) is compared to the percent freezing upon reexposure to the chamber. An increase in freezing indicates recall of the foot shock (i.e. that learning has occurred, and the animals associate the chamber with the foot shock).

d) Long Term Memory (Novel Object Recognition):

The Novel Object Recognition (NOR) task is used to evaluate cognition, particularly recognition memory, in rodent models of CNS disorders. This test is based on the spontaneous tendency of rodents to spend more time exploring a novel object than a familiar one. The choice to explore the novel object reflects the use of learning and recognition memory. The Novel Object Recognition task is conducted in an open field arena with two different kinds of objects that are generally consistent in height and volume, but are different in shape and appearance. During habituation, the animals are allowed to explore an empty arena. Twenty-four hours after habituation, the animals are exposed to the familiar arena with two identical objects placed at an equal distance. The next day, the mice are allowed to explore the open field in the presence of the familiar object and a novel object to test long-term recognition memory. The time spent exploring each object and the discrimination index percentage are recorded. In this study, the experimental apparatus consisted of a gray rectangular arena (60 cm×50 cm×26 cm) on a white floor and the two unique objects were metal bars 3.8×3.8×15 cm and PVC pipes 3.2 cm diameter×15 cm in length. During a 5-day habituation phase, mice were handled 1-2 minutes/day and permitted to explore the empty arena for 5 minutes/day. During the training phase, two identical objects were placed in the arena and the mice were permitted to explore the objects for 15 minutes. In the recall phase, mice were returned to the arena with one familiar object and one novel object. Normal mice preferentially explore the novel object. All sessions were recorded, and time spent exploring the objects was scored with an open source image analysis program [Patel et al Front Behav Neurosci 8:349 (2014)].

I. Laboratory Evaluations

1. I2S Activity in Serum and CSF

Blood for serum and CSF I2S activity was collected at necropsy approximately 3 months post injection. Serum was separated from blood and serum and CSF frozen on dry ice and stored at −80° C. until analyzed. I2S activity was measured by incubating 10 µL sample with 20 µL of 1.25 mM 4-methylumbelliferyl (MU) α-L-idopyranosiduronic acid 2-sulfate (Santa Cruz Biotechnology) dissolved in 0.1M sodium acetate with 0.01M lead acetate, pH 5.0. After incubating 2 h at 37° C., 45 µL of McIlvain's buffer (0.4M sodium phosphate, 0.2M sodium citrate, pH 4.5) and 5 µL recombinant human iduronidase (Aldurazyme, 0.58 mg/mL, Genzyme) were added to the reaction mixture and incubated overnight at 37° C. The mixture was diluted in glycine buffer, pH 10.9, and released 4-MU was quantified by fluorescence (excitation 365 nm, emission 450 nm) compared with standard dilutions of free 4-MU.

2. Serum Anti-I2S Antibodies

Blood for measurement of serum anti-hI2S antibodies was collected at terminal necropsy endpoints of study W2356 (Day 21) and study W2301 (approximately 3 month) by cardiac puncture. Serum was separated and frozen on dry ice and stored at −80° C. until analyzed. Polystyrene plates were coated overnight with recombinant human I2S (R&D Systems), 5 µg/mL in PBS, titrated to pH 5.8. Plates were washed and blocked 1 hour in 2% bovine serum albumin (BSA) in neutral PBS. Plates were then incubated with serum samples diluted 1:1000 in PBS. Bound antibody was detected with horseradish peroxidase (HRP)-conjugated goat anti-mouse antibody (Abcam) diluted 1:10,000 in PBS with 2% BSA. The assay was developed using tetramethylbenzidine substrate and stopped with 2N sulfuric acid before measuring absorbance at 450 nm. Titers were determined from a standard curve generated by serial dilution of a positive serum sample arbitrarily assigned a titer of 1:10,000.

DNA was isolated from tissues of the high dose group using the QIAmp DNA Mini Kit and vector genomes quantified by TaqMan PCR as previously described (Bell et al, 2006). Total cellular DNA was extracted from tissues using a QIAamp DNA Mini Kit (Qiagen, Valencia, Calif., USA). Detection and quantification of vector genomes in extracted DNA were performed by real-time PCR (TaqMan Universal Master Mix, Applied Biosystems, Foster City, Calif., USA) using primer and probe sets targeted to the rBG polyA sequence.

```
Forward primer:
                                  SEQ ID NO: 16
  5V-TTCCCTCTGCCAAAAATTATGG-3V;

Reverse primer:
                                  SEQ ID NO: 17
  5V-CCTTTATTAGCCAGAAGTCAGATGCT-3V;

Probe:
                                  SEQ ID NO: 18
  6FAM-ACATCATGAAGCCCC-MGBNFQ.
```

The PCR conditions were set at 100 ng total cellular DNA as template, 300 nM primers, and 200 nM probes each. Cycles were for 10 min at 95 C, 40 cycles of 15 s at 95° C., and 1 min at 60° C. A value of $1 \times 10^4$ genome copies per 100 ng DNA was calculated to represent one genome copy per cell.

H&E staining was performed on formalin-fixed paraffin-embedded rostral brain sections from the 3 months pi necropsy, according to standard protocols. H&E sections of the brain were evaluated for evidence of toxicity by a board certified veterinary pathologist and the range of findings related to the MPS II phenotype were characterized. Subsequently, the pathologist re-examined the slides without knowledge of treatment and scored the histologic manifestations of MPS II phenotype including glial cytoplasmic vacuolation, neuronal cytoplasmic swelling and accumulation of amphophilic material. The number of cells staining positive for LIMP2 and GM3 was quantified in 2-4 brain sections from each animal of W2356 study by trained GTP Morphology core personnel.

GM3 (Frozen Sections): GM3 immunostaining was performed on 30 µm thick floating cryosections as described using monoclonal antibody DH2 (Glycotech, Gaithersburg, Md.) as primary antibody followed by a biotinylated secondary anti-mouse antibody (Jackson Immunoresearch, West Grove, Pa.) and detection with a Vectastain Elite ABC kit (Vector Labs, Burlingame, Calif.). Stained sections were transferred onto glass slides and mounted with Fluoromount G (Electron Microscopy Sciences, Hatfield, Pa.).

LIMP2 (Formalin-fixed Sections): LIMP2 immunostaining was performed on 6 µm sections from formalin-fixed paraffin-embedded brain tissue. Sections were deparaffinized through an ethanol and xylene series, boiled in a microwave for 6 minutes in 10 mmol/L citrate buffer (pH 6.0) for antigen retrieval, and blocked with 1% donkey serum in PBS+0.2% Triton for 15 minutes followed by sequential incubation with primary (1 hour) and labeled secondary (45 minutes) antibodies diluted in blocking buffer. The primary antibody was rabbit anti-LIMP2 (Novus Biologicals, Littleton, Colo., 1:200) and the secondary antibody was FITC- or TRITC-labeled donkey anti-rabbit (Jackson Immunoresearch).

Tissue samples obtained as described above (section b) were homogenized in lysis buffer (0.2% Triton-X100, 0.9% NaCl, pH 4.0) using a TissueLyser (Qiagen). Samples were freeze-thawed and clarified by centrifugation. Protein was quantified by BCA assay. I2S activity was measured using the fluorogenic substrate 4-methylumbelliferyl α-L-idopyranosiduronic acid 2-sulfate (Santa Cruz Biotechnology). Hexosaminidase activity and GAG concentration were measured using standard procedures as described (Hinderer et al. 2015).

IV. Computerized Systems

For Open Field, data were entered into Excel and analyzed using Graphpad Prism. For Y-maze, data were entered into Excel and analyzed using Graphpad Prism. For CFC, Freezescan, CleverSys Inc was used. For NOR, MATLAB Implementation and User Guide: www.seas.upenn.edu/~molneuro/autotyping.html was utilized.

V. Statistical Analysis

Tissue GAG content, Hex activity and brain storage lesions in treated and untreated mice were compared using a one-way ANOVA followed by Dunnett's multiple comparisons test. Open field and Y-maze data were analyzed with Student's t-test. A two-way ANOVA and Dunnett's post-hoc analysis was applied to the fear conditioning data to assess trial and genotype effects. For the novel object recognition test, time exploring the novel object vs familiar object was compared using a t-test for each group, followed by a Bonferroni correction for multiple comparisons.

VI. RESULTS

No mortality was observed. There were no clinical observations that were considered related to the treatment with the vector.

To evaluate general locomotor activity, open field test was performed. I2Sγ/− mice showed normal exploratory activity in an open field arena compared to wildtype littermates (FIGS. 9A-9C).

Comparison of wildtype and I2S γ/− (MPS II) mouse performance in Open Field Arena (Horizontal Movement) was performed (FIG. 9A). Spontaneous activity during a 10 minutes trial was automatically recorded based on XY-axis beam breaks that capture horizontal movement. No difference was seen between WT and MPS II mice.

Comparison of wildtype and I2S γ/− (MPS II) mouse performance in Open Field Arenas (Vertical Movement or Rearing) was performed (FIG. 9B). Spontaneous activity during a 10 minutes trial was automatically recorded based on Z-axis beam breaks that capture rearing of the mice on their hind legs. No difference was seen between WT and MPS II mice.

Comparison of wildtype and I2S γ/− (MPS II) mouse performance in Open Field Arena (Center Activity) was performed (FIG. 9C). Spontaneous activity during a 10 minutes trial was automatically recorded based on center beam breaks that capture time spent in open areas, as a marker of anxiety. No significant difference was seen between WT and MPS II mice.

Figure 9D:
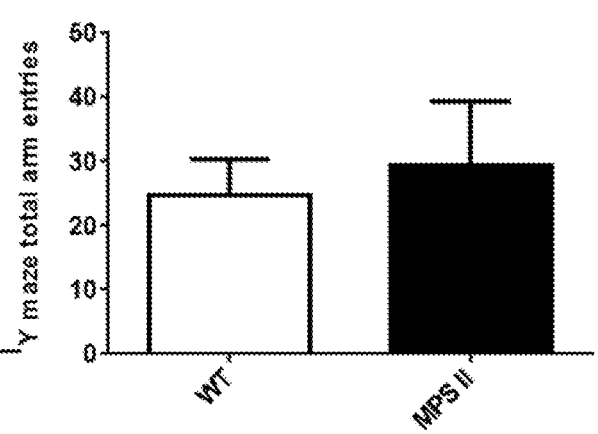

To evaluate short term memory, Y-Maze activity was analyzed. Comparison of wildtype and I2S γ/− (MPS II) mouse during an 8-Minute Y-Maze Testing Session. No difference was seen in the total number of arm entries between WT and MPS II mice. The I2Sγ/− mice also had similar numbers of arm entries and equivalent spontaneous alternations in the Y-maze compared to wildtype littermates, indicating that the disease process does not affect short term memory (FIG. 9D).

To evaluate long term memory, contextual fear conditioning (FC) was performed. Evaluation of treatment effect on cognition using the contextual fear conditioning was tested in wildtype, untreated, and treated MPS II mice. Percent Freezing was plotted on y axis (FIG. 6B). Freezing behavior prior to learning (Pre) is compared to freezing behavior after conditioning (Probe) for each group (FIG. 6B). In the FC assay, all mice (I2Sγ/− and wildtype) showed an increase in the percent time freezing during the recall phase of the test, demonstrating that learning had occurred, but I2Sγ/− mice showed reduced freezing relative to wild type littermates (data not shown). In mice treated with AAV9.CB7.CI.hIDS.rBG, there was no clear improvement in response to contextual fear conditioning, although treatment-related effects were difficult to evaluate due to the small difference between normal and untreated I2Sγ/− mice (FIG. 6B).

To further evaluate long term memory, Novel Object Recognition was performed. Evaluation of treatment effect on cognition using the Novel Object Recognition was tested in wildtype, untreated and treated MPS II Mice. Comparison of time spent exploring the novel object versus the familiar object for wildtype, untreated and treated I2S γ/− (MPS II) Mice was performed. Increased time spent exploring the novel object (showing memorization of the familiar object) was seen in all group of treated mice but was statistically significant in the mid-dose group only (FIG. 6C). Wild type mice demonstrated a preference for a novel object, as expected, but I2Sγ/− did not show a preference showing a lack of memorization of the familiar object (long term memory impairment). Intrathecal AAV9 gene therapy produced improvements in the NOR deficits observed in the I2Sγ/− (MPS II) mice but with no clear dose response. The preference for the novel object was statistically significant only in the mid-dose cohort, although the study was not sufficiently powered to compare the relative degree of rescue of behavioral deficits among dosing groups (FIG. 6C).

Dose-dependent increase in Brain I2S Activity (Day 21) in wildtype, untreated and treated MPS II mice was observed (FIG. 2B). Only the high dose group had levels similar to the wild-type at this early time point, which was expected as the expression had not reached its maximum yet.

Dose-dependent increase in I2S Activity (Day 90) in wildtype, untreated and treated MPS II Mice was observed in CSF collected at necropsy 3 months pi (FIG. 2A). Essentially no I2S activity was detected in untreated I2S γ/− (MPS II) mice.

Furthermore, dose-dependent increase in serum I2S Activity (Day 90) in wildtype, untreated and treated MPS II Mice was detected at necropsy 3 months pi (FIG. 2C). Essentially no activity was detected in serum of untreated I2S γ/− (MPS II) mice.

Three months pi, hexosaminidase activity (Day 90) was normalized in a dose-dependent fashion in both liver (FIG. 4C) and heart (FIG. 4D) of wildtype, untreated and treated MPS II Mice. This normalization of a secondary increased enzymatic activity showed restoration of lysosomal homeostasis.

Hepatic and Cardiac GAG Storage in wildtype, untreated and treated MPS II mice was investigated. Three months pi, tissue content of GAG was dose dependently reduced in both heart (FIG. 4B) and liver (FIG. 4A) and was comparable to the wildtype tissue content at the mid and high dose levels. Liver was corrected at all doses and heart showed partial improvement mostly at mid and high doses.

Furthermore, humoral immunogenicity represented by antibody response against human I2S was evaluated in MPS II mice treated with ICV AAV9.CB7.CI.hIDS.rBG. Antibodies to human I2S were detected in serum of several animals in the mid- and high-dose cohorts only at both Days 21 and 90 (FIG. 8). At both timepoints, most animals had no detectable humoral immune response (similar to control). About one third of the animals in mid-dose and about 20% of the animals groups had antibodies levels above the background. The response was less pronounced in the high dose group. FIG. 8 shows both necropsy endpoints data in aggregate.

There were no treatment-related histopathology findings in the brain. All microscopic findings present in this study were considered to be either normal background for animals of this species, age, and sex, related to the disease model, or related to the vector administration procedure.

A scoring system based on cytoplasmic vacuolation was established and used for subsequent re-evaluation of all test animals without knowledge of treatment or phenotype. Cytoplasmic vacuolation in glia, characterized by large clear vacuoles with eccentric or peripheral displacement of nuclei, was a distinctive feature of the I2Sγ/– genotype. There was regional variability in the amount of vacuolation in the brain regions that were evaluated. Neuronal accumulation of amphophilic material was less prominent and only observed in untreated I2Sγ/– mice. Treatment with AAV9.CB7.CI.hIDS.RBG decreased the amount and frequency of glial vacuolation and neuronal accumulation of amphophilic material in all brain regions examined Cumulative pathology scores demonstrate a treatment-related improvement in glial and neuronal lesions (FIG. 27).

Immunohistochemical staining of GM3 and LIMP2 in wildtype, untreated and treated MPS II Mice was performed. The brains of untreated I2S γ/– mice showed clear histological evidence of lysosomal storage in neurons, including accumulation of the lysosomal membrane protein LIMP2, as well as secondary storage of gangliosides including GM3 (FIGS. 5A to 5J). Images demonstrated that there was reduction of lysosomal storage at all doses, with the high dose group animals being essentially similar to the WT controls (FIGS. 5A to 5J). Quantitation of dose-dependent reduction in GM3- and LIMP2-Positive Cells was performed in wildtype, untreated and treated MPS II Mice. There was significant reduction of lysosomal storage at all doses, with the high dose group animals being essentially similar to the WT controls. Treated mice demonstrated dose-dependent decreases in neuronal storage lesions, evidenced by reduced LIMP2 and GM3 staining (FIGS. 5K and 5L).

Biodistribution of AAV9.CB7.CI.hIDS.rBG in MPS II Mice from the high dose group (Day 21) was analyzed. Biodistribution data demonstrated that the brain tissue was transduced (1 to 10 GC per diploid genome), as were all the peripheral tissues that were evaluated, especially the liver (FIG. 3). Concentrations in the liver and CNS were between 1 and 10 GC/diploid genome; concentrations in lung between 0.1 and 1 GC/diploid genome, and concentrations in heart and spleen less than 0.1 GC/diploid genome.

VIII. Conclusion

ICV administration of AAV9.CB7.CI.hIDS.rBG to C57BL/6 I2S γ/– (MPS II) mice at up to $3 \times 10^{10}$ GC ($5.2 \times 10^{10}$ GC ddPCR) was well tolerated, with no clinical signs or mortality, and resulted in distribution to the CNS as well as to peripheral tissues, particularly liver, showing partial redistribution of injected viral particles from the CSF to the peripheral blood.

There was evidence of I2S gene expression in the brain as evidenced by detection of the vector and dose dependent increases in I2S activity in the brain at Day 21 and in the CSF 3 months pi, with enzymatic activity close to wildtype level at the high dose (brain tissue) and comparable to higher than wildtype at the mid and high doses (CSF). There was dose dependent normalization of the lysosomal compartment, as shown by reductions in LIMP2 and GM3 staining in the CNS at all doses 3 months pi. In H&E stained brain sections, dose dependent reductions in the amount and frequency of glial vacuolation and neuronal accumulation of amphophilic material, indicators of MPS II CNS phenotype, were also observed. Corresponding to the changes in CNS lysosomal content and improvements in disease-related morphology in the H&E stained sections, there were improvements in one measure of long term memory (novel object recognition) but not in the other measure of long term memory, contextual fear conditioning. No clear dose response was apparent in the improvement in NOR. Performance of MPS II mice in other tests of CNS function, the open field test and the Y-maze, was comparable to that of wild type mice and therefore mice treated with vector were not evaluated in these assays.

Dose dependent increases in serum I2S activity were also observed 3 months pi with levels comparable to (low dose) or higher than the wild type (mid/high doses). Reflecting the normalization of I2S activity in serum, the MPS II mice had dose dependent decreases in hexosaminidase activity and GAG content in the liver and heart; hepatic hexosaminidase and GAG levels were normalized at all dose levels and cardiac hexosaminidase and GAG activity was normalized at the mid and high doses, respectively. The highly transduced liver (1 to 10 GC per diploid genome) probably acted as a depot organ for the secretion of I2S in the serum and cross-correction of the heart at the higher doses.

There was no evidence of test-article related toxicity in the brain, although changes related to the ICV administration procedure itself were observed in some mice. Humoral immune response to the transgene was minor, observed only in some mid- and high-dose animals without impact on the health or brain histopathology of those animals.

In conclusion, AAV9.CB7.CI.IDS.rBG was well tolerated in MPS II mice at all dose levels and resulted in dose-dependent increases in I2S levels that were associated with improvements in both CNS and peripheral parameters of MPS II.

The lowest dose administered, $3 \times 10^8$ GC ($5.2 \times 10^8$ GC ddPCR), was the minimum effective dose in this study.

Example 12—Delivery of Gene Therapy Vector to Humans

AAV9.CB7.hIDS (recombinant adeno-associated virus serotype 9 capsid containing human iduronate-2-sulfatase expression cassette). Product is delivered as a single-dose intracisternal (IC) administration. Two dose levels will be evaluated, $1.3 \times 10^{10}$ genome copies (GC)/g brain mass (dose 1) and $6.5 \times 10^{10}$ GC/g brain mass (dose 2). Total dose administered will account for estimated brain size of study subjects based on their age. Total volume of product administered will be less than 5 mL.

Primary objective:
    To evaluate the safety and tolerability of AAV9.hIDS test product through 24 weeks following a single intracisternal (IC) dose administered to pediatric subjects who have or are expected to have severe MPS II.

Secondary Objectives:
    To evaluate the long-term safety and tolerability of AAV9.hIDS test product
    To evaluate the effect of AAV9.hIDS test product on biomarkers in cerebrospinal fluid (CSF), plasma, and urine
    To evaluate the effect of AAV9.hIDS test product on neurodevelopmental parameters of cognitive, behavioral and adaptive function
    To evaluate vector shedding in CSF, plasma, and urine Exploratory Objectives:

To evaluate immunogenicity of AAV9.hIDS test product

To explore the effect of AAV9.hIDS test product on physical changes to the CNS

To explore the effect of AAV9.hIDS test product on systemic manifestations of disease To explore the effect of AAV9.hIDS test product on auditory capacity To explore the effect of AAV9.hIDS test product on biomarkers in plasma and urine in subjects who temporarily discontinue IV ERT (ELAPRASE®));

To explore the effect of AAV9.hIDS test product on quality of life and sleep measures This is a Phase I/II, first-in-human, multicenter, open-label, single arm dose escalation study of AAV9.hIDS test product. No control group is included. Approximately 6 pediatric subjects who have or are expected to have severe MPS II could be enrolled into 2 dose cohorts, $1.3 \times 10^{10}$ GC/g brain mass (dose 1) or $6.5 \times 10^{10}$ GC/g brain mass (dose 2), and will receive a single dose of AAV9.hIDS test product administered by IC injection. Safety will be the primary focus for the initial 24 weeks after treatment (primary study period). Following completion of the primary study period, subjects will continue to be assessed (safety and efficacy) for up to a total of 104 weeks following treatment with AAV9.hIDS test product. At the end of the study, subjects will be invited to participate in a long-term follow-up study.

The first 3 eligible subjects will be enrolled into the Dose 1 cohort ($1.3 \times 10^{10}$ GC/g brain mass). After AAV9.hIDS test product administration to the first subject, there will be an 8-week observation period for safety.

Potential subjects will be screened up to 35 days prior to dosing to determine eligibility for the study. Those subjects who meet the eligibility criteria will be admitted to the hospital between Day −2 and the morning of Day 1 (according to institutional practice), and baseline assessments will be performed pre-dose. Subjects will receive a single IC dose of AAV9.hIDS on Day 1 and will remain in the hospital for approximately 30-36 hours after dosing for observation. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 64, 78, and 104. The Week 12, 40, and 64 visits may be performed by a home health nurse. The Week 20 and 28 assessments will be limited to evaluation of AEs and concomitant therapies by telephone contact.

All subjects will initially receive immune suppression (IS) in the study based on findings of potential immunogenicity in the preclinical safety/toxicology study conducted in animals and will include corticosteroids (methylprednisolone 10 mg/kg intravenously [IV] once on Day 1 predose and oral prednisone starting at 0.5 mg/kg/day on Day 2 with gradual tapering and discontinuation by Week 12), tacrolimus (1 mg twice daily [BID] by mouth [PO] Day 2 to Week 24 with target blood level of 4-8 ng/mL and tapering over 8 weeks between Week 24 and 32) and sirolimus (a loading dose of 1 mg/m$^2$ every 4 hours×3 doses on Day −2 and then from Day −1: sirolimus 0.5 mg/m$^2$/day divided in BID dosing with target blood level of 4-8 ng/ml until Week 48). Neurologic assessments and tacrolimus/sirolimus blood level monitoring will be conducted.

Because of the relatively rapid brain growth that occurs early in a developing child, the total dose of RGX-121 administered IC depends on the assumed brain mass across different age strata. The assumed brain mass by age for the study subjects will be based on published data (Dekaban Ann Neurol. 1978 October; 4(4):345-56 (1978).

Endpoints:
Primary Endpoints:
 Safety through Week 24: AEs and serious adverse events (SAEs)
Secondary Endpoints:
 Safety through Week 104: AE reporting, laboratory evaluations, vital signs, ECGs, physical examinations, and neurologic assessments
 Biomarkers in CSF (GAGs, I2S activity), plasma (GAS, I2S activity), and urine (GAGs)
 Neurodevelopmental parameters of cognitive, behavioral, and adaptive function:
  Bayley Scales of Infant and Toddler Development, 3$^{rd}$ Edition (BSID-III) (Bayley 2005) or Kaufman Assessment Battery for Children, 2nd Edition (KABC-II) (Kaufman 2004)
  Vineland Adaptive Behavior Scales, 2d Edition, Comprehensive Interview Form (VABS-II) (Sparrow et al 2005
 Vector concentration in CSF, plasma, and urine by quantitative polymerase chain reaction (PCR) to AAV9.hIDS deoxyribonucleic acid (DNA)
Exploratory Endpoints:
 Immunogenicity measurements
  Neutralizing antibody titers to AAV9 and binding antibody titers to I2S in CSF and serum
  Enzyme-linked immunospot (ELISPOT) assay: T-cell response to AAV9 and I2S
  Flow cytometry: AAV- and I2S-specific regulatory T cells
 CNS structural abnormalities assessed by magnetic resonance imaging (MRI) of the brain
 Liver and spleen size assessed by MRI and ultrasound of the abdomen
 Auditory capacity changes measured by auditory brainstem response (ABR) testing
 Plasma and urine total GAG, heparan sulfate and dermatan sulfate in subjects who temporarily discontinue IV ERT (ELAPRASE®)
 PedsQL (Version 4)
 Global impression of sleep scale
Approximately 6 subjects will be enrolled.
 3 subjects in dose 1 cohort
 3 subjects in dose 2 cohort
 The IDMC may recommend to add additional subjects.
The total duration of the study will be 104 weeks post-dose with a primary safety evaluation time point of 24 weeks. Screening may take up to 35 days.

In certain embodiments, key inclusion criteria include:
Has a documented diagnosis of MPS II confirmed by enzyme activity as measured in plasma, fibroblasts, or leukocytes.
Is a male ≥18 months of age and meets one of the following criteria:
 Is <6 years of age AND a neurocognitive score testing ≤77 but above lower limit of scoring (BSID-III or KABC-II) at screening, OR
 Is <6 years of age and has a decline of >1 standard deviation on sequential
 neurocognitive testing (BSID-III or KABC-II), OR
 Is <4 years of age at screening and meets both of the following criteria:
  a complete deletion of IDS or large (i.e., spanning ≥1 exon) deletion/rearrangement of the IDS gene AND
  a sibling diagnosed with severe MPS II carrying the same IDS mutation.

In certain embodiments, key exclusion criteria include:
Has a contraindication for an IC injection
Has a contraindication to IS
Has a ventriculoperitoneal (VP) shunt
Has undergone hematopoietic stem cell transplantation (HSCT)
Has received idursulfase [Elaprase®] via intrathecal (IT) administration
within 3 months prior to screening
Has received IT idursulfase [Elaprase®] at any time and experienced a significant AE considered related to IT administration that in opinion of the PI would put the subject at undue risk.
Has received IV idursulfase [ELAPRASE®] and experienced a serious hypersensitivity reaction, including anaphylaxis, deemed related to IV
idursulfase [ELAPRASE®] administration. (If currently receiving IV idursulfase and required dose interruptions or a dose regimen different than weekly, then discussion with Medical Monitor needed)

In certain embodiments, to be eligible to participate in this study, a subject must meet all the following inclusion criteria:

1. The subject's legal guardian(s) is(are) willing and able to provide written, signed informed consent after the nature of the study has been explained, and prior to any research-related procedures.
2. Is a male ≥18 months of age
3. Meets one of the following criteria:
   a. Has a documented diagnosis of MPS II AND is ≥4 months to <5 years of age AND a has a neurocognitive testing score >55 and ≤77 (BSID-III or KABC-II), OR
   b. Has a documented diagnosis of MPS II AND is ≥4 months and <5 years of age AND has a decline of ≥1 standard deviation on sequential neurocognitive testing (BSID-III or KABC-II) and a testing score >55, OR
   c. Has a relative diagnosed with severe MPS II who has the same IDS mutation as the subject AND in the opinion of a geneticist has inherited a severe form of MPS II
4. Has sufficient auditory and visual capacity, with or without aids, to complete the required protocol testing, and be compliant with wearing the aid, if applicable, on testing days Subjects who meet any of the following exclusion criteria will not be eligible to participate in the study:

5. Has a contraindication for an IC injection, including any of the following:
   a. Review of baseline MRI testing by the team of neuroradiologists/neurosurgeons participating in study (1 per site) shows a contraindication for an IC injection
   b. History of prior head/neck surgery, which resulted in a contraindication to IC injection, based on review of available information by the team of neuroradiologists/neurosurgeons participating in study
   c. Has any contraindication to computed tomography (CT), contrast agent, or to general anesthesia
   d. Has any contraindication to MRI or gadolinium
6. e. Has estimated glomerular filtration rate (eGFR)<30 mL/min/1.73 m$^2$Has any condition that would contraindicate treatment with prednisone, tacrolimus or sirolimus
7. Has any neurocognitive deficit not attributable to MPS II or diagnosis of a neuropsychiatric condition that may in the opinion of the PI confound interpretation of study results
8. Has any contraindication to lumbar puncture
9. Has a ventricular shunt
10. Has undergone hematopoietic stem cell transplantation (HSCT)
11. Has had prior treatment with an AAV-based gene therapy product
12. Has received idursulfase [ELAPRASE®] via intrathecal (IT) administration
13. Has received idursulfase[ELAPRASE®] IV and experienced a serious hypersensitivity reaction, including anaphylaxis, deemed related to IV idursulfase] administration. If currently receiving IV idursulfase and required dose interruptions or a dose regimen different than weekly, then discussion with REGENXBIO Medical Monitor is needed.
14. Has received any investigational product within 30 days of Day 1 or 5 half-lives before signing of the Informed Consent Form (ICF), whichever is longer
15. Has any history of lymphoma or history of another cancer, other than squamous cell or basal cell carcinoma of the skin, that has not been in full remission for at least 3 months before screening
16. Has a platelet count <100,000 per microliter (μL)
17. Has aminotransferase (ALT) or aspartate aminotransferase (AST)>3×ULN or total bilirubin >1.5×ULN at screening unless the subject has a previously known history of Gilbert's syndrome and a fractionated bilirubin that shows conjugated bilirubin <35% of total bilirubin
18. Uncontrolled hypertension (systolic blood pressure [BP]>180 mmHg, diastolic BP>100 mmHg) despite maximal medical treatment
19. Has a history of human immunodeficiency virus (HIV) or hepatitis B or hepatitis C virus infection, or positive screening tests for hepatitis B surface antigen or hepatitis B core antibody, or hepatitis C or HIV antibodies
20. Is a first-degree family member of a clinical site employee or any other individual involved with the conduct of the study or is a clinical site employee or other individual involved with the conduct of the study
21. Has a clinically significant ECG abnormality that, in the opinion of the PI, would compromise the subject's safety
22. Has a serious or unstable medical or psychological condition that, in the opinion of the PI, would compromise the subject's safety or successful participation in the study or interpretation of study results
23. Has uncontrolled seizures that in opinion of the PI would put the subject at undue risk Exclusion criteria related to immunosuppressive therapy:
24. Has a history of a hypersensitivity reaction to tacrolimus, sirolimus, or prednisone
25. Has a history of a primary immunodeficiency (e.g., common variable immunodeficiency syndrome), splenectomy, or any underlying condition that predisposes the subject to infection
26. Has herpes zoster (VZV), cytomegalovirus (CMV), or Epstein-Barr virus (EBV) infection that has not completely resolved at least 12 weeks prior to screening
27. Has any infection requiring hospitalization or treatment with parenteral anti-infectives not resolved at least 8 weeks prior to Visit 2

28. Has any active infection requiring oral anti-infectives (including antivirals) within 10 days prior to Visit 2
29. Has a history of active tuberculosis (TB) or a positive Quantiferon-TB Gold test during screening
30. Has any live vaccine within 8 weeks prior to signing the ICF
31. Had major surgery within 8 weeks before signing the ICF or major surgery planned during the study period
32. Anticipate the need for adenoidectomy or tonsillectomy within 6 months of enrollment
33. Has an absolute neutrophil count <1.3×10³/μL
34. Has any condition or laboratory abnormality that the PI believes would not be appropriate for immunosuppressive therapy

SEQUENCE LISTING FREE TEXT

The following information is provided for sequences containing free text under numeric identifier <223>.

| SEQ ID NO: (containing free text) | Free text under <223> |
|---|---|
| 1 | <223> human IDS enzyme |
| 3 | <223> CB7.CI.hIDS.RBG |
|  | <220> |
|  | <221> misc_feature |
|  | <222> (2) . . . (131) |
|  | <223> 5' ITR |
|  | <220> |
|  | <221> promoter |
|  | <222> (199) . . . (580) |
|  | <223> CMV IE promoter |
|  | <220> |
|  | <221> promoter |
|  | <222> (583) . . . (864) |
|  | <223> CB promoter |
|  | <220> |
|  | <221> TATA_signal |
|  | <222> (837) . . . (840) |
|  | <220> |
|  | <221> Intron |
|  | <222> (959) . . . (1930) |
|  | <223> chicken beta-actin intron |
|  | <220> |
|  | <221> CDS |
|  | <222> (1937) . . . (3589) |
|  | <223> hIDS |
|  | <220> |
|  | <221> polyA_signal |
|  | <222> (3623) . . . (3749) |
|  | <223> rabbit globin polyA |
|  | <220> |
|  | <221> misc_feature |
|  | <222> (3838) . . . (3967) |
|  | <223> 3' ITR |
| 4 | <223> Synthetic Construct |
| 5 | <223> CB6.hIDS.IRES.SUMF1 |
|  | <220> |
|  | <221> misc_feature |
|  | <222> (11) . . . (140) |
|  | <223> 5'ITR |
|  | <220> |
|  | <221> enhancer |
|  | <222> (208) . . . (589) |
|  | <223> CMV IE enhancer |
|  | <220> |
|  | <221> promoter |
|  | <222> (600) . . . (859) |
|  | <223> CB promoter |
|  | <220> |
|  | <221> TATA_signal |
|  | <222> (835) . . . (842) |
|  | <220> |
|  | <221> Intron |

-continued

| SEQ ID NO: (containing free text) | Free text under <223> |
|---|---|
|  | <222> (976) . . . (1108) |
|  | <220> |
|  | <221> CDS |
|  | <222> (1177) . . . (2829) |
|  | <223> hIDS |
|  | <220> |
|  | <221> misc_feature |
|  | <222> (2830) . . . (3422) |
|  | <223> IRES |
|  | <220> |
|  | <221> CDS |
|  | <222> (3423) . . . (4547) |
|  | <223> hSUMF |
|  | <220> |
|  | <221> polyA_signal |
|  | <222> (4620) . . . (4746) |
|  | <223> rabbit globin polyA |
|  | <220> |
|  | <221> misc_feature |
|  | <222> (4835) . . . (4964) |
|  | <223> 3'ITR |
| 6 | <223> Synthetic Construct |
| 7 | <223> Synthetic Construct |
| 8 | <223> CB6.hIDSco.IRES.hSUMF1co |
|  | <220> |
|  | <221> misc_feature |
|  | <222> (11) . . . (140) |
|  | <223> 5'ITR |
|  | <220> |
|  | <221> enhancer |
|  | <222> (208) . . . (589) |
|  | <223> CMV IE enhancer |
|  | <220> |
|  | <221> promoter |
|  | <222> (600) . . . (859) |
|  | <223> CB promoter |
|  | <220> |
|  | <221> TATA_signal |
|  | <222> (835) . . . (842) |
|  | <220> |
|  | <221> Intron |
|  | <222> (976) . . . (1108) |
|  | <220> |
|  | <221> CDS |
|  | <222> (1177) . . . (2829) |
|  | <223> hIDSco |
|  | <220> |
|  | <221> misc_feature |
|  | <222> (2830) . . . (3422) |
|  | <223> IRES |
|  | <220> |
|  | <221> CDS |
|  | <222> (3423) . . . (4553) |
|  | <223> hSUMF1co |
|  | <220> |
|  | <221> polyA_signal |
|  | <222> (4620) . . . (4746) |
|  | <223> rabbit globin polyA |
|  | <220> |
|  | <221> misc_feature |
|  | <222> (4835) . . . (4964) |
|  | <223> 3'ITR |
| 9 | <223> Synthetic Construct |
| 10 | <223> Synthetic Construct |
| 11 | <223> CB7.hIDSco.RBG |
|  | <220> |
|  | <221> misc_feature |
|  | <222> (2) . . . (131) |
|  | <223> 5'ITR |
|  | <220> |
|  | <221> promoter |
|  | <222> (199) . . . (580) |
|  | <223> CMV IE promoter |
|  | <220> |
|  | <221> promoter |

| SEQ ID NO: (containing free text) | Free text under <223> |
|---|---|
| | <222> (583) ... (864) |
| | <223> CB promoter |
| | <220> |
| | <221> TATA_signal |
| | <222> (837) ... (840) |
| | <220> |
| | <221> Intron |
| | <222> (959) ... (1930) |
| | <223> chicken beta-actin intron |
| | <220> |
| | <221> CDS |
| | <222> (1937) ... (3589) |
| | <223> hIDSco |
| | <220> |
| | <221> polyA_signal |
| | <222> (3623) ... (3749) |
| | <223> rabbit globin polyA |
| | <220> |
| | <221> misc_feature |
| | <222> (3838) ... (3967) |
| | <223> 3' ITR |
| 12 | <223> Synthetic Construct |
| 13 | <223> AAV9 capsid amino acid sequence |
| 14 | <223> CB7.CI.hIDS.RBG |
| | <220> |
| | <221> misc_feature |
| | <222> (2) ... (131) |
| | <223> 5'ITR |
| | <220> |
| | <221> promoter |
| | <222> (199) ... (580) |
| | <223> CMV IE promoter |
| | <220> |
| | <221> promoter |
| | <222> (583) ... (864) |
| | <223> CB promoter |
| | <220> |
| | <221> TATA_signal |
| | <222> (837) ... (840) |
| | <220> |

| SEQ ID NO: (containing free text) | Free text under <223> |
|---|---|
| | <221> Intron |
| | <222> (957) ... (1928) |
| | <223> chicken beta-actin intron |
| | <220> |
| | <221> CDS |
| | <222> (1935) ... (3587) |
| | <223> hIDS |
| | <220> |
| | <221> polyA_signal |
| | <222> (3621) ... (3747) |
| | <223> rabbit globin polyA |
| | <220> |
| | <221> misc_feature |
| | <222> (3836) ... (3965) |
| | <223> 3'ITR |
| 15 | <223> Synthetic Construct |
| 16 | <223> synthesized sequence |
| 17 | <223> synthesized sequence |
| 18 | <223> Synthesized sequence |

All publications, patents, and patent applications cited in this application, as well as U.S. Provisional Patent Application No. 62/573,841, filed Oct. 18, 2017, U.S. Provisional Patent Application No. 62/562,179, filed Sep. 22, 2017, and U.S. Provisional Patent Application No. 62/561,769, filed Sep. 22, 2017, as well as the Sequence Listing filed herewith, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A therapeutic regimen for treating human iduronate-2-sulfatase (hIDS) deficiency which comprises administering a co-therapy comprising:
   (a) a suspension of replication deficient recombinant adeno-associated virus (rAAV), wherein:
      (i) the rAAV comprises an AAV9 capsid and a vector genome, wherein the vector genome comprises an AAV 5' inverted terminal repeat (ITR), an expression cassette, and an AAV 3' ITR,
      wherein the expression cassette comprises a nucleic acid sequence having the sequence of SEQ ID NO: 1 or s sequence of at least 80% identical to SEQ ID NO: 1 encoding human iduronate-2-sulfatase (hIDS) under the control of regulatory sequences which direct expression of the hIDS, wherein the regulatory sequences comprise a cytomegalovirus immediate early (CMV IE) enhancer, a chicken beta actin promoter, a chicken beta actin intron, and a rabbit beta-globin polyadenylation (polyA) signal sequence; and
      (ii) a formulation buffer suitable for intrathecal delivery comprising a physiologically compatible aqueous buffer, and optional surfactants and excipients;
   (b) at least a first immunosuppressive agent which is an intravenous corticosteroid; and
   (c) at least a second immunosuppressive agent which is an oral corticosteroid,
   wherein administration of at least one immunosuppressive agent begins prior to or on the same day as delivery of the rAAV, and
   wherein administration of at least one of the immunosuppressive agents continues for at least 8 weeks post-rAAV administration.

2. The therapeutic regimen according to claim 1, wherein the rAAV has a vector genome selected from:
   (a) SEQ ID NO: 3;
   (b) SEQ ID NO: 11; or
   (c) SEQ ID NO: 14.

3. The therapeutic regimen according to claim 1, wherein the patient is predosed initially with the intravenous corticosteroid prior to rAAV delivery.

4. The therapeutic regimen according to claim 1, wherein the patient is dosed with the oral corticosteroid following rAAV delivery.

5. The therapeutic regimen according to claim 1, wherein the regimen further comprises dosing a patient with tacrolimus.

6. The therapeutic regimen according to claim 1, wherein the regimen further comprises dosing a patient with one or more macrolides, wherein a first dose of a macrolide is delivered pre-dosing with rAAV.

7. The therapeutic regimen according to claim 1, wherein the immune suppressive regimen is discontinued at week 48 post-dosing with the rAAV.

8. The therapeutic regimen according to claim 1, wherein the suspension has a pH of 6 to 9.

9. The therapeutic regimen according to claim 8, wherein the suspension has a pH of 6.8 to 7.8.

10. The therapeutic regimen according to claim 1, wherein the rAAV is administrable by intrathecal injection at a dose of about $1.3 \times 10^{10}$ genome copies (GC)/g brain mass.

11. The therapeutic regimen according to claim 1, wherein the rAAV is administrable by intrathecal injection at a dose of about $1.9 \times 10^{10}$ GC/g brain mass.

12. The therapeutic regimen according to claim 1, wherein the rAAV is administrable by intrathecal injection at a dose of about $6.5 \times 10^{10}$ GC/g brain mass.

13. The therapeutic regimen according to claim 1, wherein the rAAV comprises vector genome comprising nucleotide (nt) 2 to nt 3967 of SEQ ID NO: 3.

14. The therapeutic regimen according to claim 1, wherein the rAAV comprises vector genome comprising nucleotide (nt) 2 to nt 3965 of SEQ ID NO: 14.

15. The therapeutic regimen according to claim 1, wherein the expression cassette comprises a nucleic acid sequence having the sequence of SEQ ID NO: 1.

16. The therapeutic regimen according to claim 5, wherein the regimen further comprises dosing a patient with tacrolimus to a blood trough level of about 4 ng/mL to about 8 ng/ml.

17. The therapeutic regimen according to claim 1, wherein the rAAV is administrable by intracerebroventricular or intracisternal delivery.

18. The therapeutic regimen according to claim 1, wherein the rAAV is administrable by intrathecal injection at a dose of about $10^9$ to $10^{11}$ GC/g brain mass.

19. The therapeutic regimen according to claim 18, wherein the rAAV comprises vector genome comprising SEQ ID NO: 14.

20. The therapeutic regimen according to claim 19, wherein the rAAV is administrable by intracerebroventricular or intracisternal delivery.

21. The therapeutic regimen according to claim 20, wherein the regimen further comprises dosing a patient with tacrolimus to a blood trough level of about 4 ng/mL to about 8 ng/ml.

22. The therapeutic regimen according to claim 20, wherein the patient is predosed initially with the intravenous corticosteroid prior to rAAV delivery.

23. The therapeutic regimen according to claim 22, wherein the intravenous corticosteroid is methylprednisolone given at 10 mg/kg on Day 1 prior to rAAV delivery.

24. The therapeutic regimen according to claim 23, wherein the patient is dosed with the oral corticosteroid following rAAV delivery.

25. The therapeutic regimen according to claim 24, wherein the oral corticosteroid is prednisone given starting at 0.5 mg/kg/day on Day 2 after rAAV delivery.

26. The therapeutic regimen according to claim 25, wherein the regimen further comprises dosing a patient with tacrolimus to a blood trough level of about 4 ng/mL to about 8 ng/ml.

27. The therapeutic regimen according to claim 3, wherein the intravenous corticosteroid is methylprednisolone given at 10 mg/kg once on Day 1 prior to rAAV delivery.

28. The therapeutic regimen according to claim 4, wherein the oral corticosteroid is prednisone given starting at 0.5 mg/kg/day on Day 2 after rAAV delivery.

29. The therapeutic regimen according to claim 1, wherein the regimen further comprises dosing a patient with sirolimus.

30. The therapeutic regimen according to claim 1, wherein the regimen further comprises dosing a patient with combination of tacrolimus and sirolimus.

* * * * *

SEQUENCE LISTING

```
<160> NUMBER OF SEQ ID NOS: 18

<210> SEQ ID NO 1
<211> LENGTH: 1653
<212> TYPE: DNA
<213> ORGANISM: Homo sapiens
<220> FEATURE:
<221> NAME/KEY: CDS
<222> LOCATION: (1)..(1653)
<223> OTHER INFORMATION: human IDS enzyme

<400> SEQUENCE: 1 atg ccg cca ccc cgg acc ggc cga ggc ctt ctc tgg ctg ggt ctg gtt      48
Met Pro Pro Pro Arg Thr Gly Arg Gly Leu Leu Trp Leu Gly Leu Val
1               5                   10                  15 ctg agc tcc gtc tgc gtc gcc ctc gga tcc gaa acg cag gcc aac tcg      96
Leu Ser Ser Val Cys Val Ala Leu Gly Ser Glu Thr Gln Ala Asn Ser
            20                  25                  30 acc aca gat gct ctg aac gtt ctt ctc atc atc gtg gat gac ctg cgc     144
Thr Thr Asp Ala Leu Asn Val Leu Leu Ile Ile Val Asp Asp Leu Arg
        35                  40                  45 ccc tcc ctg ggc tgt tat ggg gat aag ctg gtg agg tcc cca aat att     192
Pro Ser Leu Gly Cys Tyr Gly Asp Lys Leu Val Arg Ser Pro Asn Ile
    50                  55                  60
```

```
                                        -continued gac caa ctg gca tcc cac agc ctc ctc ttc cag aat gcc ttt gcg cag      240
Asp Gln Leu Ala Ser His Ser Leu Leu Phe Gln Asn Ala Phe Ala Gln
 65                  70                  75                  80 caa gca gtg tgc gcc ccg agc cgc gtt tct ttc ctc act ggc agg aga      288
Gln Ala Val Cys Ala Pro Ser Arg Val Ser Phe Leu Thr Gly Arg Arg
                 85                  90                  95 cct gac acc acc cgc ctg tac gac ttc aac tcc tac tgg agg gtg cac      336
Pro Asp Thr Thr Arg Leu Tyr Asp Phe Asn Ser Tyr Trp Arg Val His
            100                 105                 110 gct gga aac ttc tcc acc atc ccc cag tac ttc aag gag aat ggc tat      384
Ala Gly Asn Phe Ser Thr Ile Pro Gln Tyr Phe Lys Glu Asn Gly Tyr
        115                 120                 125 gtg acc atg tcg gtg gga aaa gtc ttt cac cct ggg ata tct tct aac      432
Val Thr Met Ser Val Gly Lys Val Phe His Pro Gly Ile Ser Ser Asn
    130                 135                 140 cat acc gat gat tct ccg tat agc tgg tct ttt cca cct tat cat cct      480
His Thr Asp Asp Ser Pro Tyr Ser Trp Ser Phe Pro Pro Tyr His Pro
145                 150                 155                 160 tcc tct gag aag tat gaa aac act aag aca tgt cga ggg cca gat gga      528
Ser Ser Glu Lys Tyr Glu Asn Thr Lys Thr Cys Arg Gly Pro Asp Gly
                165                 170                 175 gaa ctc cat gcc aac ctg ctt tgc cct gtg gat gtg ctg gat gtt ccc      576
Glu Leu His Ala Asn Leu Leu Cys Pro Val Asp Val Leu Asp Val Pro
            180                 185                 190 gag ggc acc ttg cct gac aaa cag agc act gag caa gcc ata cag ttg      624
Glu Gly Thr Leu Pro Asp Lys Gln Ser Thr Glu Gln Ala Ile Gln Leu
        195                 200                 205 ttg gaa aag atg aaa acg tca gcc agt cct ttc ttc ctg gcc gtt ggg      672
Leu Glu Lys Met Lys Thr Ser Ala Ser Pro Phe Phe Leu Ala Val Gly
    210                 215                 220 tat cat aag cca cac atc ccc ttc aga tac ccc aag gaa ttt cag aag      720
Tyr His Lys Pro His Ile Pro Phe Arg Tyr Pro Lys Glu Phe Gln Lys
225                 230                 235                 240 ttg tat ccc ttg gag aac atc acc ctg gcc ccc gat ccc gag gtc cct      768
Leu Tyr Pro Leu Glu Asn Ile Thr Leu Ala Pro Asp Pro Glu Val Pro
                245                 250                 255 gat ggc cta ccc cct gtg gcc tac aac ccc tgg atg gac atc agg caa      816
Asp Gly Leu Pro Pro Val Ala Tyr Asn Pro Trp Met Asp Ile Arg Gln
            260                 265                 270 cgg gaa gac gtc caa gcc tta aac atc agt gtg ccg tat ggt cca att      864
Arg Glu Asp Val Gln Ala Leu Asn Ile Ser Val Pro Tyr Gly Pro Ile
        275                 280                 285 cct gtg gac ttt cag cgg aaa atc cgc cag agc tac ttt gcc tct gtg      912
Pro Val Asp Phe Gln Arg Lys Ile Arg Gln Ser Tyr Phe Ala Ser Val
    290                 295                 300 tca tat ttg gat aca cag gtc ggc cgc ctc ttg agt gct ttg gac gat      960
Ser Tyr Leu Asp Thr Gln Val Gly Arg Leu Leu Ser Ala Leu Asp Asp
305                 310                 315                 320 ctt cag ctg gcc aac agc acc atc att gca ttt acc tcg gat cat ggg     1008
Leu Gln Leu Ala Asn Ser Thr Ile Ile Ala Phe Thr Ser Asp His Gly
                325                 330                 335 tgg gct cta ggt gaa cat gga gaa tgg gcc aaa tac agc aat ttt gat     1056
Trp Ala Leu Gly Glu His Gly Glu Trp Ala Lys Tyr Ser Asn Phe Asp
            340                 345                 350 gtt gct acc cat gtt ccc ctg ata ttc tat gtt cct gga agg acg gct     1104
Val Ala Thr His Val Pro Leu Ile Phe Tyr Val Pro Gly Arg Thr Ala
        355                 360                 365 tca ctt ccg gag gca ggc gag aag ctt ttc cct tac ctc gac cct ttt     1152
Ser Leu Pro Glu Ala Gly Glu Lys Leu Phe Pro Tyr Leu Asp Pro Phe
    370                 375                 380
```

```
gat tcc gcc tca cag ttg atg gag cca ggc agg caa tcc atg gac ctt   1200
Asp Ser Ala Ser Gln Leu Met Glu Pro Gly Arg Gln Ser Met Asp Leu
385                 390                 395                 400 gtg gaa ctt gtg tct ctt ttt ccc acg ctg gct gga ctt gca gga ctg   1248
Val Glu Leu Val Ser Leu Phe Pro Thr Leu Ala Gly Leu Ala Gly Leu
                405                 410                 415 cag gtt cca cct cgc tgc ccc gtt cct tca ttt cac gtt gag ctg tgc   1296
Gln Val Pro Pro Arg Cys Pro Val Pro Ser Phe His Val Glu Leu Cys
            420                 425                 430 aga gaa ggc aag aac ctt ctg aag cat ttt cga ttc cgt gac ttg gaa   1344
Arg Glu Gly Lys Asn Leu Leu Lys His Phe Arg Phe Arg Asp Leu Glu
        435                 440                 445 gag gat ccg tac ctc cct ggt aat ccc cgt gaa ctg att gcc tat agc   1392
Glu Asp Pro Tyr Leu Pro Gly Asn Pro Arg Glu Leu Ile Ala Tyr Ser
    450                 455                 460 cag tat ccc cgg cct tca gac atc cct cag tgg aat tct gac aag ccg   1440
Gln Tyr Pro Arg Pro Ser Asp Ile Pro Gln Trp Asn Ser Asp Lys Pro
465                 470                 475                 480 agt tta aaa gat ata aag atc atg ggc tat tcc ata cgc acc ata gac   1488
Ser Leu Lys Asp Ile Lys Ile Met Gly Tyr Ser Ile Arg Thr Ile Asp
                485                 490                 495 tat agg tat act gtg tgg gtt ggc ttc aat cct gat gaa ttt cta gct   1536
Tyr Arg Tyr Thr Val Trp Val Gly Phe Asn Pro Asp Glu Phe Leu Ala
            500                 505                 510 aac ttt tct gac atc cat gca ggg gaa ctg tat ttt gtg gat tct gac   1584
Asn Phe Ser Asp Ile His Ala Gly Glu Leu Tyr Phe Val Asp Ser Asp
        515                 520                 525 cca ttg cag gat cac aat atg tat aat gat tcc caa ggt gga gat ctt   1632
Pro Leu Gln Asp His Asn Met Tyr Asn Asp Ser Gln Gly Gly Asp Leu
    530                 535                 540 ttc cag ttg ttg atg cct tga                                       1653
Phe Gln Leu Leu Met Pro
545                 550

<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140
```

```
His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550
```

```
<210> SEQ ID NO 3
<211> LENGTH: 3967
<212> TYPE: DNA
<213> ORGANISM: Artificial Sequence
<220> FEATURE:
<223> OTHER INFORMATION: CB7.CI.hIDS.RBG
<220> FEATURE:
<221> NAME/KEY: misc_feature
<222> LOCATION: (2)..(131)
<223> OTHER INFORMATION: 5' ITR
<220> FEATURE:
<221> NAME/KEY: promoter
<222> LOCATION: (199)..(580)
<223> OTHER INFORMATION: CMV IE promoter
<220> FEATURE:
<221> NAME/KEY: promoter
<222> LOCATION: (583)..(864)
<223> OTHER INFORMATION: CB promoter
<220> FEATURE:
<221> NAME/KEY: TATA_signal
<222> LOCATION: (837)..(840)
<220> FEATURE:
<221> NAME/KEY: Intron
<222> LOCATION: (959)..(1930)
<223> OTHER INFORMATION: chicken beta-actin intron
<220> FEATURE:
<221> NAME/KEY: CDS
<222> LOCATION: (1937)..(3589)
<223> OTHER INFORMATION: hIDS
<220> FEATURE:
<221> NAME/KEY: polyA_signal
<222> LOCATION: (3623)..(3749)
<223> OTHER INFORMATION: rabbit globin polyA
<220> FEATURE:
<221> NAME/KEY: misc_feature
<222> LOCATION: (3838)..(3967)
<223> OTHER INFORMATION: 3' ITR

<400> SEQUENCE: 3
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120 tagggggttcc ttgtagttaa tgattaaccc gccatgctac ttatctacca gggtaatggg    180
gatcctctag aactatagct agtcgacatt gattattgac tagttattaa tagtaatcaa    240
ttacggggtc attagttcat agcccatata tggagttccg cgttacataa cttacggtaa    300
atggcccgcc tggctgaccg cccaacgacc cccgcccatt gacgtcaata atgacgtatg    360
ttcccatagt aacgccaata gggactttcc attgacgtca atgggtggac tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctcccccc cctccccacc cccaattttg tatttattta    660
ttttttaatt attttgtgca gcgatggggg cggggggggg ggggggcgc gcgccaggcg     720 gggcggggcg gggcgagggg cgggcgggg cgaggcggag aggtgcggcg gcagccaatc     780
agagcggcgc gctccgaaag tttcctttta tggcgaggcg gcggcggcgg cggccctata    840
aaaagcgaag cgcgcggcgg gcggggagtc gctgcgacgc tgccttcgcc ccgtgccccg    900
ctccgccgcc gcctcgcgcc gcccgccccg gctctgactg accgcgttac tcccacaggt    960
gagcgggcgg gacggcccct tctcctccggg ctgtaattag cgcttggttt aatgacggct   1020
tgtttctttt ctgtggctgc gtgaaagcct tgaggggctc cggagggcc ctttgtgcgg    1080 ggggagcggc tcggggggtg cgtgcgtgtg tgtgtgcgtg gggagcgccg cgtgcggctc   1140
```

-continued

| | |
|---|---|
| cgcgctgccc ggcggctgtg agcgctgcgg gcgcggcgcg gggctttgtg cgctccgcag | 1200 |
| tgtgcgcgag gggagcgcgg ccggggggcgg tgccccgcgg tgcggggggg gctgcgaggg | 1260 |
| gaacaaaggc tgcgtgcggg gtgtgtgcgt ggggggggtga gcaggggggtg tgggcgcgtc | 1320 |
| ggtcgggctg caaccccccc tgcaccccccc tccccgagtt gctgagcacg gcccggcttc | 1380 |
| gggtgcgggg ctccgtacgg ggcgtggcgc ggggctcgcc gtgccgggcg gggggtggcg | 1440 |
| gcaggtgggg gtgccgggcg gggcggggcc gcctcgggcc ggggagggct cggggggaggg | 1500 |
| gcgcggcggc ccccggagcg ccggcggctg tcgaggcgcg gcgagccgca gccattgcct | 1560 |
| tttatggtaa tcgtgcgaga gggcgcaggg acttcctttg tcccaaatct gtgcggagcc | 1620 |
| gaaatctggg aggcgccgcc gcaccccctc tagcgggcgc ggggcgaagc ggtgcggcgc | 1680 |
| cggcaggaag gaaatgggcg gggagggcct tcgtgcgtcg ccgcgccgcc gtccccttct | 1740 |
| ccctctccag cctcggggct gtccgcgggg ggacggctgc cttcgggggg gacggggcag | 1800 |
| ggcggggttc ggcttctggc gtgtgaccgg cggctctaga gcctctgcta accatgttca | 1860 |
| tgccttcttc ttttttcctac agctcctggg caacgtgctg gttattgtgc tgtctcatca | 1920 |
| ttttggcaaa gaattc atg ccg cca ccc cgg acc ggc cga ggc ctt ctc tgg | 1972 |
|                                                     Met Pro Pro Pro Arg Thr Gly Arg Gly Leu Leu Trp<br>                                                     1                    5                        10 | |
| ctg ggt ctg gtt ctg agc tcc gtc tgc gtc gcc ctc gga tcc gaa acg<br>Leu Gly Leu Val Leu Ser Ser Val Cys Val Ala Leu Gly Ser Glu Thr<br>            15                        20                          25 | 2020 |
| cag gcc aac tcg acc aca gat gct ctg aac gtt ctt ctc atc atc gtg<br>Gln Ala Asn Ser Thr Thr Asp Ala Leu Asn Val Leu Leu Ile Ile Val<br>     30                        35                          40 | 2068 |
| gat gac ctg cgc ccc tcc ctg ggc tgt tat ggg gat aag ctg gtg agg<br>Asp Asp Leu Arg Pro Ser Leu Gly Cys Tyr Gly Asp Lys Leu Val Arg<br>45                        50                        55                          60 | 2116 |
| tcc cca aat att gac caa ctg gca tcc cac agc ctc ctc ttc cag aat<br>Ser Pro Asn Ile Asp Gln Leu Ala Ser His Ser Leu Leu Phe Gln Asn<br>                    65                        70                        75 | 2164 |
| gcc ttt gcg cag caa gca gtg tgc gcc ccg agc cgc gtt tct ttc ctc<br>Ala Phe Ala Gln Gln Ala Val Cys Ala Pro Ser Arg Val Ser Phe Leu<br>     80                        85                          90 | 2212 |
| act ggc agg aga cct gac acc acc cgc ctg tac gac ttc aac tcc tac<br>Thr Gly Arg Arg Pro Asp Thr Thr Arg Leu Tyr Asp Phe Asn Ser Tyr<br>              95                        100                      105 | 2260 |
| tgg agg gtg cac gct gga aac ttc tcc acc atc ccc cag tac ttc aag<br>Trp Arg Val His Ala Gly Asn Phe Ser Thr Ile Pro Gln Tyr Phe Lys<br>     110                        115                        120 | 2308 |
| gag aat ggc tat gtg acc atg tcg gtg gga aaa gtc ttt cac cct ggg<br>Glu Asn Gly Tyr Val Thr Met Ser Val Gly Lys Val Phe His Pro Gly<br>125                        130                        135                        140 | 2356 |
| ata tct tct aac cat acc gat gat tct ccg tat agc tgg tct ttt cca<br>Ile Ser Ser Asn His Thr Asp Asp Ser Pro Tyr Ser Trp Ser Phe Pro<br>                    145                        150                        155 | 2404 |
| cct tat cat cct tcc tct gag aag tat gaa aac act aag aca tgt cga<br>Pro Tyr His Pro Ser Ser Glu Lys Tyr Glu Asn Thr Lys Thr Cys Arg<br>               160                        165                        170 | 2452 |
| ggg cca gat gga gaa ctc cat gcc aac ctg ctt tgc cct gtg gat gtg<br>Gly Pro Asp Gly Glu Leu His Ala Asn Leu Leu Cys Pro Val Asp Val<br>175                        180                        185 | 2500 |
| ctg gat gtt ccc gag ggc acc ttg cct gac aaa cag agc act gag caa<br>Leu Asp Val Pro Glu Gly Thr Leu Pro Asp Lys Gln Ser Thr Glu Gln<br>     190                        195                        200 | 2548 |
| gcc ata cag ttg ttg gaa aag atg aaa acg tca gcc agt cct ttc ttc | 2596 |

```
                Ala Ile Gln Leu Leu Glu Lys Met Lys Thr Ser Ala Ser Pro Phe Phe
                205                 210                 215                 220 ctg gcc gtt ggg tat cat aag cca cac atc ccc ttc aga tac ccc aag           2644
Leu Ala Val Gly Tyr His Lys Pro His Ile Pro Phe Arg Tyr Pro Lys
                    225                 230                 235 gaa ttt cag aag ttg tat ccc ttg gag aac atc acc ctg gcc ccc gat           2692
Glu Phe Gln Lys Leu Tyr Pro Leu Glu Asn Ile Thr Leu Ala Pro Asp
                240                 245                 250 ccc gag gtc cct gat ggc cta ccc cct gtg gcc tac aac ccc tgg atg           2740
Pro Glu Val Pro Asp Gly Leu Pro Pro Val Ala Tyr Asn Pro Trp Met
            255                 260                 265 gac atc agg caa cgg gaa gac gtc caa gcc tta aac atc agt gtg ccg           2788
Asp Ile Arg Gln Arg Glu Asp Val Gln Ala Leu Asn Ile Ser Val Pro
        270                 275                 280 tat ggt cca att cct gtg gac ttt cag cgg aaa atc cgc cag agc tac           2836
Tyr Gly Pro Ile Pro Val Asp Phe Gln Arg Lys Ile Arg Gln Ser Tyr
285                 290                 295                 300 ttt gcc tct gtg tca tat ttg gat aca cag gtc ggc cgc ctc ttg agt           2884
Phe Ala Ser Val Ser Tyr Leu Asp Thr Gln Val Gly Arg Leu Leu Ser
                    305                 310                 315 gct ttg gac gat ctt cag ctg gcc aac agc acc atc att gca ttt acc           2932
Ala Leu Asp Asp Leu Gln Leu Ala Asn Ser Thr Ile Ile Ala Phe Thr
                320                 325                 330 tcg gat cat ggg tgg gct cta ggt gaa cat gga gaa tgg gcc aaa tac           2980
Ser Asp His Gly Trp Ala Leu Gly Glu His Gly Glu Trp Ala Lys Tyr
            335                 340                 345 agc aat ttt gat gtt gct acc cat gtt ccc ctg ata ttc tat gtt cct           3028
Ser Asn Phe Asp Val Ala Thr His Val Pro Leu Ile Phe Tyr Val Pro
        350                 355                 360 gga agg acg gct tca ctt ccg gag gca ggc gag aag ctt ttc cct tac           3076
Gly Arg Thr Ala Ser Leu Pro Glu Ala Gly Glu Lys Leu Phe Pro Tyr
365                 370                 375                 380 ctc gac cct ttt gat tcc gcc tca cag ttg atg gag cca ggc agg caa           3124
Leu Asp Pro Phe Asp Ser Ala Ser Gln Leu Met Glu Pro Gly Arg Gln
                    385                 390                 395 tcc atg gac ctt gtg gaa ctt gtg tct ctt ttt ccc acg ctg gct gga           3172
Ser Met Asp Leu Val Glu Leu Val Ser Leu Phe Pro Thr Leu Ala Gly
                400                 405                 410 ctt gca gga ctg cag gtt cca cct cgc tgc ccc gtt cct tca ttt cac           3220
Leu Ala Gly Leu Gln Val Pro Pro Arg Cys Pro Val Pro Ser Phe His
            415                 420                 425 gtt gag ctg tgc aga gaa ggc aag aac ctt ctg aag cat ttt cga ttc           3268
Val Glu Leu Cys Arg Glu Gly Lys Asn Leu Leu Lys His Phe Arg Phe
        430                 435                 440 cgt gac ttg gaa gag gat ccg tac ctc cct ggt aat ccc cgt gaa ctg           3316
Arg Asp Leu Glu Glu Asp Pro Tyr Leu Pro Gly Asn Pro Arg Glu Leu
445                 450                 455                 460 att gcc tat agc cag tat ccc cgg cct tca gac atc cct cag tgg aat           3364
Ile Ala Tyr Ser Gln Tyr Pro Arg Pro Ser Asp Ile Pro Gln Trp Asn
                    465                 470                 475 tct gac aag ccg agt tta aaa gat ata aag atc atg ggc tat tcc ata           3412
Ser Asp Lys Pro Ser Leu Lys Asp Ile Lys Ile Met Gly Tyr Ser Ile
                480                 485                 490 cgc acc ata gac tat agg tat act gtg tgg gtt ggc ttc aat cct gat           3460
Arg Thr Ile Asp Tyr Arg Tyr Thr Val Trp Val Gly Phe Asn Pro Asp
            495                 500                 505 gaa ttt cta gct aac ttt tct gac atc cat gca ggg gaa ctg tat ttt           3508
Glu Phe Leu Ala Asn Phe Ser Asp Ile His Ala Gly Glu Leu Tyr Phe
        510                 515                 520
```

-continued

```
gtg gat tct gac cca ttg cag gat cac aat atg tat aat gat tcc caa    3556
Val Asp Ser Asp Pro Leu Gln Asp His Asn Met Tyr Asn Asp Ser Gln
525                 530                 535                 540 ggt gga gat ctt ttc cag ttg ttg atg cct tga ctcgaggacg gggtgaacta   3609
Gly Gly Asp Leu Phe Gln Leu Leu Met Pro
                545                 550 cgcctgagga tccgatcttt ttccctctgc caaaaattat ggggacatca tgaagcccct   3669
tgagcatctg acttctggct aataaaggaa atttattttc attgcaatag tgtgttggaa   3729
ttttttgtgt ctctcactcg gaagcaattc gttgatctga atttcgacca cccataatac   3789
ccattaccct ggtagataag tagcatggcg ggttaatcat taactacaag gaacccctag   3849
tgatggagtt ggccactccc tctctgcgcg ctcgctcgct cactgaggcc gggcgaccaa   3909
aggtcgcccg acgcccgggc tttgcccggg cggcctcagt gagcgagcga gcgcgcag    3967
```

<210> SEQ ID NO 4
<211> LENGTH: 550
<212> TYPE: PRT
<213> ORGANISM: Artificial Sequence
<220> FEATURE:
<223> OTHER INFORMATION: Synthetic Construct

<400> SEQUENCE: 4

```
Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
```

```
                260                 265                 270
Arg Glu Asp Val Gln Ala Leu Asn Ile Ser Val Pro Tyr Gly Pro Ile
            275                 280                 285

Pro Val Asp Phe Gln Arg Lys Ile Arg Gln Ser Tyr Phe Ala Ser Val
        290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 5
<211> LENGTH: 4964
<212> TYPE: DNA
<213> ORGANISM: Artificial Sequence
<220> FEATURE:
<223> OTHER INFORMATION: CB6.hIDS.IRES.SUMF1
<220> FEATURE:
<221> NAME/KEY: misc_feature
<222> LOCATION: (11)..(140)
<223> OTHER INFORMATION: 5'ITR
<220> FEATURE:
<221> NAME/KEY: enhancer
<222> LOCATION: (208)..(589)
<223> OTHER INFORMATION: CMV IE enhancer
<220> FEATURE:
<221> NAME/KEY: promoter
<222> LOCATION: (600)..(859)
<223> OTHER INFORMATION: CB promoter
<220> FEATURE:
<221> NAME/KEY: TATA_signal
<222> LOCATION: (835)..(842)
<220> FEATURE:
```

```
<221> NAME/KEY: Intron
<222> LOCATION: (976)..(1108)
<220> FEATURE:
<221> NAME/KEY: CDS
<222> LOCATION: (1177)..(2829)
<223> OTHER INFORMATION: hIDS
<220> FEATURE:
<221> NAME/KEY: misc_feature
<222> LOCATION: (2830)..(3422)
<223> OTHER INFORMATION: IRES
<220> FEATURE:
<221> NAME/KEY: CDS
<222> LOCATION: (3423)..(4547)
<223> OTHER INFORMATION: hSUMF
<220> FEATURE:
<221> NAME/KEY: polyA_signal
<222> LOCATION: (4620)..(4746)
<223> OTHER INFORMATION: rabbit globin polyA
<220> FEATURE:
<221> NAME/KEY: misc_feature
<222> LOCATION: (4835)..(4964)
<223> OTHER INFORMATION: 3'ITR

<400> SEQUENCE: 5
cttaattagg ctgcgcgctc gctcgctcac tgaggccgcc cgggcaaagc ccgggcgtcg      60
ggcgaccttt ggtcgcccgg cctcagtgag cgagcgagcg cgcagagagg gagtggccaa     120
ctccatcact aggggttcct tgtagttaat gattaacccg ccatgctact tatctaccag     180
ggtaatgggg atcctctaga actatagcta gtcgacattg attattgact agttattaat     240
agtaatcaat tacggggtca ttagttcata gcccatatat ggagttccgc gttacataac     300
ttacggtaaa tggcccgcct ggctgaccgc ccaacgaccc ccgcccattg acgtcaataa     360
tgacgtatgt tcccatagta acgccaatag ggactttcca ttgacgtcaa tgggtggact     420
atttacggta aactgcccac ttggcagtac atcaagtgta tcatatgcca agtacgcccc     480
ctattgacgt caatgacggt aaatggcccg cctggcatta tgcccagtac atgaccttat     540
gggactttcc tacttggcag tacatctacg tattagtcat cgctattacc atgtcgaggc     600
cacgttctgc ttcactctcc ccatctcccc ccctcccca ccccaatttt tgtatttatt     660
tattttttaa ttattttgtg cagcgatggg ggcgggggggg ggggcgcgc gccaggcggg     720 gcggggcggg gcgaggggcg gggcggggcg aggcggagag gtgcggcggc agccaatcag     780
agcggcgcgc tccgaaagtt tccttttatg gcgaggcggc ggcggcggcg ccctataaa     840 aagcgaagcg cgcggcgggc gggagcaagc tttattgcgg tagtttatca cagttaaatt     900
gctaacgcag tcagtgcttc tgacacaaca gtctcgaact taagctgcag aagttggtcg     960
tgaggcactg ggcaggtaag tatcaaggtt acaagacagg tttaaggaga ccaatagaaa    1020
ctgggcttgt cgagacagag aagactcttg cgtttctgat aggcacctat tggtcttact    1080
gacatccact ttgcctttct ctccacaggt gtccactccc agttcaatta cagctcttaa    1140
ggctagagta cttaatacga ctcactatag gctagc atg ccg cca ccc cgg acc      1194
                                        Met Pro Pro Pro Arg Thr
                                        1               5 ggc cga ggc ctt ctc tgg ctg ggt ctg gtt ctg agc tcc gtc tgc gtc      1242
Gly Arg Gly Leu Leu Trp Leu Gly Leu Val Leu Ser Ser Val Cys Val
            10                  15                  20 gcc ctc gga tcc gaa acg cag gcc aac tcg acc aca gat gct ctg aac      1290
Ala Leu Gly Ser Glu Thr Gln Ala Asn Ser Thr Thr Asp Ala Leu Asn
        25                  30                  35 gtt ctt ctc atc atc gtg gat gac ctg cgc ccc tcc ctg ggc tgt tat      1338
Val Leu Leu Ile Ile Val Asp Asp Leu Arg Pro Ser Leu Gly Cys Tyr
    40                  45                  50
```

```
ggg gat aag ctg gtg agg tcc cca aat att gac caa ctg gca tcc cac    1386
Gly Asp Lys Leu Val Arg Ser Pro Asn Ile Asp Gln Leu Ala Ser His
 55              60                  65                  70 agc ctc ctc ttc cag aat gcc ttt gcg cag caa gca gtg tgc gcc ccg    1434
Ser Leu Leu Phe Gln Asn Ala Phe Ala Gln Gln Ala Val Cys Ala Pro
         75                  80                  85 agc cgc gtt tct ttc ctc act ggc agg aga cct gac acc acc cgc ctg    1482
Ser Arg Val Ser Phe Leu Thr Gly Arg Arg Pro Asp Thr Thr Arg Leu
         90                  95                 100 tac gac ttc aac tcc tac tgg agg gtg cac gct gga aac ttc tcc acc    1530
Tyr Asp Phe Asn Ser Tyr Trp Arg Val His Ala Gly Asn Phe Ser Thr
            105                 110                 115 atc ccc cag tac ttc aag gag aat ggc tat gtg acc atg tcg gtg gga    1578
Ile Pro Gln Tyr Phe Lys Glu Asn Gly Tyr Val Thr Met Ser Val Gly
    120                 125                 130 aaa gtc ttt cac cct ggg ata tct tct aac cat acc gat gat tct ccg    1626
Lys Val Phe His Pro Gly Ile Ser Ser Asn His Thr Asp Asp Ser Pro
135                 140                 145                 150 tat agc tgg tct ttt cca cct tat cat cct tcc tct gag aag tat gaa    1674
Tyr Ser Trp Ser Phe Pro Pro Tyr His Pro Ser Ser Glu Lys Tyr Glu
                155                 160                 165 aac act aag aca tgt cga ggg cca gat gga gaa ctc cat gcc aac ctg    1722
Asn Thr Lys Thr Cys Arg Gly Pro Asp Gly Glu Leu His Ala Asn Leu
            170                 175                 180 ctt tgc cct gtg gat gtg ctg gat gtt ccc gag ggc acc ttg cct gac    1770
Leu Cys Pro Val Asp Val Leu Asp Val Pro Glu Gly Thr Leu Pro Asp
        185                 190                 195 aaa cag agc act gag caa gcc ata cag ttg ttg gaa aag atg aaa acg    1818
Lys Gln Ser Thr Glu Gln Ala Ile Gln Leu Leu Glu Lys Met Lys Thr
200                 205                 210 tca gcc agt cct ttc ttc ctg gcc gtt ggg tat cat aag cca cac atc    1866
Ser Ala Ser Pro Phe Phe Leu Ala Val Gly Tyr His Lys Pro His Ile
215                 220                 225                 230 ccc ttc aga tac ccc aag gaa ttt cag aag ttg tat ccc ttg gag aac    1914
Pro Phe Arg Tyr Pro Lys Glu Phe Gln Lys Leu Tyr Pro Leu Glu Asn
            235                 240                 245 atc acc ctg gcc ccc gat ccc gag gtc cct gat ggc cta ccc cct gtg    1962
Ile Thr Leu Ala Pro Asp Pro Glu Val Pro Asp Gly Leu Pro Pro Val
        250                 255                 260 gcc tac aac ccc tgg atg gac atc agg caa cgg gaa gac gtc caa gcc    2010
Ala Tyr Asn Pro Trp Met Asp Ile Arg Gln Arg Glu Asp Val Gln Ala
    265                 270                 275 tta aac atc agt gtg ccg tat ggt cca att cct gtg gac ttt cag cgg    2058
Leu Asn Ile Ser Val Pro Tyr Gly Pro Ile Pro Val Asp Phe Gln Arg
280                 285                 290 aaa atc cgc cag agc tac ttt gcc tct gtg tca tat ttg gat aca cag    2106
Lys Ile Arg Gln Ser Tyr Phe Ala Ser Val Ser Tyr Leu Asp Thr Gln
295                 300                 305                 310 gtc ggc cgc ctc ttg agt gct ttg gac gat ctt cag ctg gcc aac agc    2154
Val Gly Arg Leu Leu Ser Ala Leu Asp Asp Leu Gln Leu Ala Asn Ser
            315                 320                 325 acc atc att gca ttt acc tcg gat cat ggg tgg gct cta ggt gaa cat    2202
Thr Ile Ile Ala Phe Thr Ser Asp His Gly Trp Ala Leu Gly Glu His
        330                 335                 340 gga gaa tgg gcc aaa tac agc aat ttt gat gtt gct acc cat gtt ccc    2250
Gly Glu Trp Ala Lys Tyr Ser Asn Phe Asp Val Ala Thr His Val Pro
    345                 350                 355 ctg ata ttc tat gtt cct gga agg acg gct tca ctt ccg gag gca ggc    2298
Leu Ile Phe Tyr Val Pro Gly Arg Thr Ala Ser Leu Pro Glu Ala Gly
360                 365                 370
```

| | |
|---|---|
| gag aag ctt ttc cct tac ctc gac cct ttt gat tcc gcc tca cag ttg<br>Glu Lys Leu Phe Pro Tyr Leu Asp Pro Phe Asp Ser Ala Ser Gln Leu<br>375                    380                   385                   390 | 2346 |
| atg gag cca ggc agg caa tcc atg gac ctt gtg gaa ctt gtg tct ctt<br>Met Glu Pro Gly Arg Gln Ser Met Asp Leu Val Glu Leu Val Ser Leu<br>                   395                   400                   405 | 2394 |
| ttt ccc acg ctg gct gga ctt gca gga ctg cag gtt cca cct cgc tgc<br>Phe Pro Thr Leu Ala Gly Leu Ala Gly Leu Gln Val Pro Pro Arg Cys<br>           410                         415                   420 | 2442 |
| ccc gtt cct tca ttt cac gtt gag ctg tgc aga gaa ggc aag aac ctt<br>Pro Val Pro Ser Phe His Val Glu Leu Cys Arg Glu Gly Lys Asn Leu<br>         425                       430                   435 | 2490 |
| ctg aag cat ttt cga ttc cgt gac ttg gaa gag gat ccg tac ctc cct<br>Leu Lys His Phe Arg Phe Arg Asp Leu Glu Glu Asp Pro Tyr Leu Pro<br>440                    445                   450 | 2538 |
| ggt aat ccc cgt gaa ctg att gcc tat agc cag tat ccc cgg cct tca<br>Gly Asn Pro Arg Glu Leu Ile Ala Tyr Ser Gln Tyr Pro Arg Pro Ser<br>455                    460                   465                   470 | 2586 |
| gac atc cct cag tgg aat tct gac aag ccg agt tta aaa gat ata aag<br>Asp Ile Pro Gln Trp Asn Ser Asp Lys Pro Ser Leu Lys Asp Ile Lys<br>                   475                   480                   485 | 2634 |
| atc atg ggc tat tcc ata cgc acc ata gac tat agg tat act gtg tgg<br>Ile Met Gly Tyr Ser Ile Arg Thr Ile Asp Tyr Arg Tyr Thr Val Trp<br>           490                         495                   500 | 2682 |
| gtt ggc ttc aat cct gat gaa ttt cta gct aac ttt tct gac atc cat<br>Val Gly Phe Asn Pro Asp Glu Phe Leu Ala Asn Phe Ser Asp Ile His<br>         505                       510                   515 | 2730 |
| gca ggg gaa ctg tat ttt gtg gat tct gac cca ttg cag gat cac aat<br>Ala Gly Glu Leu Tyr Phe Val Asp Ser Asp Pro Leu Gln Asp His Asn<br>520                    525                   530 | 2778 |
| atg tat aat gat tcc caa ggt gga gat ctt ttc cag ttg ttg atg cct<br>Met Tyr Asn Asp Ser Gln Gly Gly Asp Leu Phe Gln Leu Leu Met Pro<br>535                    540                   545                   550 | 2826 |
| tga gcccctctcc ctccccccc cctaacgtta ctggccgaag ccgcttggaa | 2879 |
| taaggccggt gtgcgtttgt ctatatgtta ttttccacca tattgccgtc ttttggcaat | 2939 |
| gtgagggccc ggaaacctgg ccctgtcttc ttgacgagca ttcctagggg tctttcccct | 2999 |
| ctcgccaaag gaatgcaagg tctgttgaat gtcgtgaagg aagcagttcc tctggaagct | 3059 |
| tcttgaagac aaacaacgtc tgtagcgacc ctttgcaggc agcggaaccc cccacctggc | 3119 |
| gacaggtgcc tctgcggcca aaagccacgt gtataagata cacctgcaaa ggcggcacaa | 3179 |
| ccccagtgcc acgttgtgag ttggatagtt gtggaaagag tcaaatggct ctcctcaagc | 3239 |
| gtattcaaca aggggctgaa ggatgcccag aaggtacccc attgtatggg atctgatctg | 3299 |
| gggcctcggt acacatgctt tacatgtgtt tagtcgaggt taaaaaaacg tctaggcccc | 3359 |
| ccgaaccacg gggacgtggc tttcctttga aaaacacgat gataatatgg ccacaaccat | 3419 |
| ggt atg gct gcg ccc gca cta ggg ctg gtg tgt gga cgt tgc cct gag<br>    Met Ala Ala Pro Ala Leu Gly Leu Val Cys Gly Arg Cys Pro Glu<br>                          555                           560                   565 | 3467 |
| ctg ggt ctc gtc ctc ttg ctg ctg ctc tcg ctg ctg tgt gga gcg<br>Leu Gly Leu Val Leu Leu Leu Leu Leu Ser Leu Leu Cys Gly Ala<br>                 570                       575                   580 | 3515 |
| gca ggg agc cag gag gcc ggg acc ggt gcg ggc gcg ggg tcc ctt gcg<br>Ala Gly Ser Gln Glu Ala Gly Thr Gly Ala Gly Ala Gly Ser Leu Ala<br>                   585                     590                   595 | 3563 |
| ggt tct tgc ggc tgc ggc acg ccc cag cgg cct ggc gcc cat ggc agt<br>Gly Ser Cys Gly Cys Gly Thr Pro Gln Arg Pro Gly Ala His Gly Ser | 3611 |

```
                   600                 605                 610
tcg gca gcc gct cac cga tac tcg cgg gag gct aac gct ccg ggc ccc    3659
Ser Ala Ala Ala His Arg Tyr Ser Arg Glu Ala Asn Ala Pro Gly Pro
    615                 620                 625 gta ccc gga gag cgg caa ctc gcg cac tca aag atg gtc ccc atc cct    3707
Val Pro Gly Glu Arg Gln Leu Ala His Ser Lys Met Val Pro Ile Pro
630                 635                 640                 645 gct gga gta ttt aca atg ggc aca gat gat cct cag ata aag cag gat    3755
Ala Gly Val Phe Thr Met Gly Thr Asp Asp Pro Gln Ile Lys Gln Asp
                650                 655                 660 ggg gaa gca cct gcg agg aga gtt act att gat gcc ttt tac atg gat    3803
Gly Glu Ala Pro Ala Arg Arg Val Thr Ile Asp Ala Phe Tyr Met Asp
            665                 670                 675 gcc tat gaa gtc agt aat act gaa ttt gag aag ttt gtg aac tca act    3851
Ala Tyr Glu Val Ser Asn Thr Glu Phe Glu Lys Phe Val Asn Ser Thr
        680                 685                 690 ggc tat ttg aca gag gct gag aag ttt ggc gac tcc ttt gtc ttt gaa    3899
Gly Tyr Leu Thr Glu Ala Glu Lys Phe Gly Asp Ser Phe Val Phe Glu
    695                 700                 705 ggc atg ttg agt gag caa gtg aag acc aat att caa cag gca gtt gca    3947
Gly Met Leu Ser Glu Gln Val Lys Thr Asn Ile Gln Gln Ala Val Ala
710                 715                 720                 725 gct gct ccc tgg tgg tta cct gtg aaa ggc gct aac tgg aga cac cca    3995
Ala Ala Pro Trp Trp Leu Pro Val Lys Gly Ala Asn Trp Arg His Pro
                730                 735                 740 gaa ggg cct gac tct act att ctg cac agg ccg gat cat cca gtt ctc    4043
Glu Gly Pro Asp Ser Thr Ile Leu His Arg Pro Asp His Pro Val Leu
            745                 750                 755 cat gtg tcc tgg aat gat gcg gtt gcc tac tgc act tgg gca ggg aag    4091
His Val Ser Trp Asn Asp Ala Val Ala Tyr Cys Thr Trp Ala Gly Lys
        760                 765                 770 cgg ctg ccc acg gaa gct gag tgg gaa tac agc tgt cga gga ggc ctg    4139
Arg Leu Pro Thr Glu Ala Glu Trp Glu Tyr Ser Cys Arg Gly Gly Leu
    775                 780                 785 cat aat aga ctt ttc ccc tgg ggc aac aaa ctg cag ccc aaa ggc cag    4187
His Asn Arg Leu Phe Pro Trp Gly Asn Lys Leu Gln Pro Lys Gly Gln
790                 795                 800                 805 cat tat gcc aac att tgg cag ggc gag ttt ccg gtg acc aac act ggt    4235
His Tyr Ala Asn Ile Trp Gln Gly Glu Phe Pro Val Thr Asn Thr Gly
                810                 815                 820 gag gat ggc ttc caa gga act gcg cct gtt gat gcc ttc cct ccc aat    4283
Glu Asp Gly Phe Gln Gly Thr Ala Pro Val Asp Ala Phe Pro Pro Asn
            825                 830                 835 ggt tat ggc tta tac aac ata gtg ggg aac gca tgg gaa tgg act tca    4331
Gly Tyr Gly Leu Tyr Asn Ile Val Gly Asn Ala Trp Glu Trp Thr Ser
        840                 845                 850 gac tgg tgg act gtt cat cat tct gtt gaa gaa acg ctt aac cca aaa    4379
Asp Trp Trp Thr Val His His Ser Val Glu Glu Thr Leu Asn Pro Lys
    855                 860                 865 ggt ccc cct tct ggg aaa gac cga gtg aag aaa ggt gga tcc tac atg    4427
Gly Pro Pro Ser Gly Lys Asp Arg Val Lys Lys Gly Gly Ser Tyr Met
870                 875                 880                 885 tgc cat agg tct tat tgt tac agg tat cgc tgt gct gct cgg agc cag    4475
Cys His Arg Ser Tyr Cys Tyr Arg Tyr Arg Cys Ala Ala Arg Ser Gln
                890                 895                 900 aac aca cct gat agc tct gct tcg aat ctg gga ttc cgc tgt gca gcc    4523
Asn Thr Pro Asp Ser Ser Ala Ser Asn Leu Gly Phe Arg Cys Ala Ala
            905                 910                 915 gac cgc ctg ccc acc atg gac tga gaattcacgc gtggtacctc tagagtcgac    4577
Asp Arg Leu Pro Thr Met Asp
```

Asp Arg Leu Pro Thr Met Asp
        920 ccgggcggcc tcgaggacgg ggtgaactac gcctgaggat ccgatctttt tccctctgcc      4637 aaaaattatg gggacatcat gaagccccct gagcatctga cttctggcta ataaaggaaa      4697 tttattttca ttgcaatagt gtgttggaat tttttgtgtc tctcactcgg aagcaattcg      4757 ttgatctgaa tttcgaccac ccataatacc cattaccctg gtagataagt agcatggcgg      4817 gttaatcatt aactacaagg aacccctagt gatggagttg gccactccct ctctgcgcgc      4877 tcgctcgctc actgaggccg ggcgaccaaa ggtcgcccga cgcccgggct tgccccgggc      4937 ggcctcagtg agcgagcgag cgcgcag                                          4964

<210> SEQ ID NO 6
<211> LENGTH: 550
<212> TYPE: PRT
<213> ORGANISM: Artificial Sequence
<220> FEATURE:
<223> OTHER INFORMATION: Synthetic Construct

<400> SEQUENCE: 6

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile

```
                275                 280                 285
Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
                340                 345                 350

Val Ala Thr His Val Pro Leu Ile Phe Tyr Val Pro Gly Arg Thr Ala
                355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
                435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 7
<211> LENGTH: 374
<212> TYPE: PRT
<213> ORGANISM: Artificial Sequence
<220> FEATURE:
<223> OTHER INFORMATION: Synthetic Construct

<400> SEQUENCE: 7

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
                20                  25                  30

Gly Ser Gln Glu Ala Gly Thr Gly Ala Gly Ala Gly Ser Leu Ala Gly
                35                  40                  45

Ser Cys Gly Cys Gly Thr Pro Gln Arg Pro Gly Ala His Gly Ser Ser
                50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
```

|        |     |     |     |     | 85  |     |     |     |     | 90  |     |     |     |     | 95  |     |     |
|--------|-----|-----|-----|-----|-----|-----|-----|-----|-----|-----|-----|-----|-----|-----|-----|-----|-----|

Gly Val Phe Thr Met Gly Thr Asp Asp Pro Gln Ile Lys Gln Asp Gly
                    100                 105                 110

Glu Ala Pro Ala Arg Arg Val Thr Ile Asp Ala Phe Tyr Met Asp Ala
                115                 120                 125

Tyr Glu Val Ser Asn Thr Glu Phe Glu Lys Phe Val Asn Ser Thr Gly
            130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
                180                 185                 190

Gly Pro Asp Ser Thr Ile Leu His Arg Pro Asp His Pro Val Leu His
            195                 200                 205

Val Ser Trp Asn Asp Ala Val Ala Tyr Cys Thr Trp Ala Gly Lys Arg
210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
            275                 280                 285

Tyr Gly Leu Tyr Asn Ile Val Gly Asn Ala Trp Glu Trp Thr Ser Asp
        290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

```
<210> SEQ ID NO 8
<211> LENGTH: 4964
<212> TYPE: DNA
<213> ORGANISM: Artificial Sequence
<220> FEATURE:
<223> OTHER INFORMATION: CB6.hIDSco.IRES.hSUMF1co
<220> FEATURE:
<221> NAME/KEY: misc_feature
<222> LOCATION: (11)..(140)
<223> OTHER INFORMATION: 5'ITR
<220> FEATURE:
<221> NAME/KEY: enhancer
<222> LOCATION: (208)..(589)
<223> OTHER INFORMATION: CMV IE enhancer
<220> FEATURE:
<221> NAME/KEY: promoter
<222> LOCATION: (600)..(859)
<223> OTHER INFORMATION: CB promoter
<220> FEATURE:
<221> NAME/KEY: TATA_signal
<222> LOCATION: (835)..(842)
<220> FEATURE:
```

```
<221> NAME/KEY: Intron
<222> LOCATION: (976)..(1108)
<220> FEATURE:
<221> NAME/KEY: CDS
<222> LOCATION: (1177)..(2829)
<223> OTHER INFORMATION: hIDSco
<220> FEATURE:
<221> NAME/KEY: misc_feature
<222> LOCATION: (2830)..(3422)
<223> OTHER INFORMATION: IRES
<220> FEATURE:
<221> NAME/KEY: CDS
<222> LOCATION: (3423)..(4553)
<223> OTHER INFORMATION: hSUMF1co
<220> FEATURE:
<221> NAME/KEY: polyA_signal
<222> LOCATION: (4620)..(4746)
<223> OTHER INFORMATION: rabbit globin polyA
<220> FEATURE:
<221> NAME/KEY: misc_feature
<222> LOCATION: (4835)..(4964)
<223> OTHER INFORMATION: 3'ITR

<400> SEQUENCE: 8
cttaattagg ctgcgcgctc gctcgctcac tgaggccgcc cgggcaaagc ccgggcgtcg      60
ggcgaccttt ggtcgcccgg cctcagtgag cgagcgagcg cgcagagagg gagtggccaa     120
ctccatcact aggggttcct tgtagttaat gattaacccg ccatgctact tatctaccag     180
ggtaatgggg atcctctaga actatagcta gtcgacattg attattgact agttattaat     240
agtaatcaat tacggggtca ttagttcata gcccatatat ggagttccgc gttacataac     300
ttacggtaaa tggcccgcct ggctgaccgc ccaacgaccc ccgcccattg acgtcaataa     360
tgacgtatgt tcccatagta acgccaatag ggactttcca ttgacgtcaa tgggtggact     420
atttacggta aactgcccac ttggcagtac atcaagtgta tcatatgcca agtacgcccc     480
ctattgacgt caatgacggt aaatggcccg cctggcatta tgcccagtac atgaccttat     540
gggactttcc tacttggcag tacatctacg tattagtcat cgctattacc atgtcgaggc     600
cacgttctgc ttcactctcc ccatctcccc ccccctcccca ccccaatttt gtatttatt     660 tatttttaa ttattttgtg cagcgatggg ggcgggggg ggggcgcgc gccaggcggg     720 gcggggcggg gcgaggggcg gggcggggcg aggcggagag gtgcggcggc agccaatcag     780
agcggcgcgc tccgaaagtt tccttttatg gcgaggcggc ggcggcggcg ccctataaa     840 aagcgaagcg cgcggcgggc gggagcaagc tttattgcgg tagtttatca cagttaaatt     900
gctaacgcag tcagtgcttc tgacacaaca gtctcgaact taagctgcag aagttggtcg     960
tgaggcactg ggcaggtaag tatcaaggtt acaagacagg tttaaggaga ccaatagaaa    1020
ctgggcttgt cgagacagag aagactcttg cgtttctgat aggcacctat tggtcttact    1080
gacatccact tgcctttct ctccacaggt gtccactccc agttcaatta cagctcttaa    1140
ggctagagta cttaatacga ctcactatag gctagc atg ccc ccc ccc agg aca    1194
                                         Met Pro Pro Pro Arg Thr
                                          1               5 gga aga gga ctg ctg tgg ctc gga ctc gtc ctc tcc agc gtg tgc gtg            1242
Gly Arg Gly Leu Leu Trp Leu Gly Leu Val Leu Ser Ser Val Cys Val
            10                  15                  20 gct ctc gga tcc gaa acc cag gct aat tcc aca acc gat gcc ctg aac            1290
Ala Leu Gly Ser Glu Thr Gln Ala Asn Ser Thr Thr Asp Ala Leu Asn
        25                  30                  35 gtc ctg ctc atc atc gtg gat gac ctg agg ccc tcc ctg ggc tgt tac            1338
Val Leu Leu Ile Ile Val Asp Asp Leu Arg Pro Ser Leu Gly Cys Tyr
    40                  45                  50
```

-continued

| | | |
|---|---|---|
| ggc gac aag ctc gtc agg tcc ccc aac att gat cag ctc gcc tcc cat<br>Gly Asp Lys Leu Val Arg Ser Pro Asn Ile Asp Gln Leu Ala Ser His<br>55                        60                    65                  70 | 1386 |
| tcc ctg ctg ttt caa aac gcc ttc gct cag caa gcc gtg tgc gct cct<br>Ser Leu Leu Phe Gln Asn Ala Phe Ala Gln Gln Ala Val Cys Ala Pro<br>               75                    80                    85 | 1434 |
| agc aga gtc agc ttc ctc acc gga agg aga cct gac acc acc agg ctg<br>Ser Arg Val Ser Phe Leu Thr Gly Arg Arg Pro Asp Thr Thr Arg Leu<br>          90                    95                   100 | 1482 |
| tac gac ttc aac tcc tat tgg agg gtc cac gct ggc aac ttc agc acc<br>Tyr Asp Phe Asn Ser Tyr Trp Arg Val His Ala Gly Asn Phe Ser Thr<br>         105                  110               115 | 1530 |
| att ccc cag tac ttc aag gag aac ggc tac gtc acc atg tcc gtc ggc<br>Ile Pro Gln Tyr Phe Lys Glu Asn Gly Tyr Val Thr Met Ser Val Gly<br>120                     125               130 | 1578 |
| aag gtg ttc cac cct ggc att tcc tcc aac cac acc gat gac agc ccc<br>Lys Val Phe His Pro Gly Ile Ser Ser Asn His Thr Asp Asp Ser Pro<br>135                140              145             150 | 1626 |
| tac tcc tgg tcc ttc cct ccc tac cac ccc agc agc gaa aag tac gag<br>Tyr Ser Trp Ser Phe Pro Pro Tyr His Pro Ser Ser Glu Lys Tyr Glu<br>               155                    160               165 | 1674 |
| aat acc aag acc tgt aga ggc ccc gac ggc gaa ctc cac gct aac ctc<br>Asn Thr Lys Thr Cys Arg Gly Pro Asp Gly Glu Leu His Ala Asn Leu<br>         170                  175               180 | 1722 |
| ctg tgt cct gtc gat gtc ctc gac gtg ccc gaa ggc aca ctc ccc gac<br>Leu Cys Pro Val Asp Val Leu Asp Val Pro Glu Gly Thr Leu Pro Asp<br>185                     190               195 | 1770 |
| aag cag tcc aca gaa caa gcc atc cag ctc ctg gag aag atg aag acc<br>Lys Gln Ser Thr Glu Gln Ala Ile Gln Leu Leu Glu Lys Met Lys Thr<br>200                     205               210 | 1818 |
| tcc gct tcc ccc ttt ttc ctg gcc gtg ggc tac cac aaa ccc cac att<br>Ser Ala Ser Pro Phe Phe Leu Ala Val Gly Tyr His Lys Pro His Ile<br>215                220              225             230 | 1866 |
| ccc ttc agg tac ccc aag gag ttc cag aag ctg tat ccc ctg gag aac<br>Pro Phe Arg Tyr Pro Lys Glu Phe Gln Lys Leu Tyr Pro Leu Glu Asn<br>               235                    240               245 | 1914 |
| att acc ctc gcc cct gat ccc gaa gtg cct gac ggc ctg cct cct gtc<br>Ile Thr Leu Ala Pro Asp Pro Glu Val Pro Asp Gly Leu Pro Pro Val<br>         250                  255               260 | 1962 |
| gct tac aac ccc tgg atg gac atc agg cag aga gaa gac gtg caa gcc<br>Ala Tyr Asn Pro Trp Met Asp Ile Arg Gln Arg Glu Asp Val Gln Ala<br>265                     270               275 | 2010 |
| ctc aac atc agc gtg ccc tac ggc cct atc ccc gtg gac ttc cag aga<br>Leu Asn Ile Ser Val Pro Tyr Gly Pro Ile Pro Val Asp Phe Gln Arg<br>280                     285               290 | 2058 |
| aag atc agg cag agc tac ttc gcc tcc gtc agc tac ctg gac acc cag<br>Lys Ile Arg Gln Ser Tyr Phe Ala Ser Val Ser Tyr Leu Asp Thr Gln<br>295                     300               305             310 | 2106 |
| gtg gga aga ctc ctg tcc gcc ctc gac gat ctc cag ctg gcc aac agc<br>Val Gly Arg Leu Leu Ser Ala Leu Asp Asp Leu Gln Leu Ala Asn Ser<br>               315                    320               325 | 2154 |
| acc atc att gcc ttc acc agc gac cat ggc tgg gct ctc gga gag cat<br>Thr Ile Ile Ala Phe Thr Ser Asp His Gly Trp Ala Leu Gly Glu His<br>         330                  335               340 | 2202 |
| ggc gaa tgg gcc aag tac tcc aac ttc gat gtg gcc acc cac gtc ccc<br>Gly Glu Trp Ala Lys Tyr Ser Asn Phe Asp Val Ala Thr His Val Pro<br>345                     350               355 | 2250 |
| ctc atc ttc tac gtc ccc gga agg acc gcc agc ctg cct gaa gct gga<br>Leu Ile Phe Tyr Val Pro Gly Arg Thr Ala Ser Leu Pro Glu Ala Gly<br>360                     365               370 | 2298 |

| | | |
|---|---|---|
| gag aag ctc ttc ccc tac ctg gac cct ttt gat tcc gcc agc caa ctc<br>Glu Lys Leu Phe Pro Tyr Leu Asp Pro Phe Asp Ser Ala Ser Gln Leu<br>375                      380                      385                      390 | | 2346 |
| atg gaa ccc ggc agg caa agc atg gac ctc gtg gag ctg gtc tcc ctg<br>Met Glu Pro Gly Arg Gln Ser Met Asp Leu Val Glu Leu Val Ser Leu<br>                      395                      400                      405 | | 2394 |
| ttc cct acc ctg gct gga ctc gcc gga ctc caa gtc cct ccc aga tgc<br>Phe Pro Thr Leu Ala Gly Leu Ala Gly Leu Gln Val Pro Pro Arg Cys<br>            410                      415                      420 | | 2442 |
| cct gtg cct agc ttc cat gtg gag ctc tgc aga gag ggc aag aac ctg<br>Pro Val Pro Ser Phe His Val Glu Leu Cys Arg Glu Gly Lys Asn Leu<br>        425                      430                      435 | | 2490 |
| ctg aag cac ttc agg ttt agg gac ctg gag gag gat cct tac ctc ccc<br>Leu Lys His Phe Arg Phe Arg Asp Leu Glu Glu Asp Pro Tyr Leu Pro<br>440                      445                      450 | | 2538 |
| gga aac cct aga gag ctc atc gct tac tcc cag tat cct agg ccc tcc<br>Gly Asn Pro Arg Glu Leu Ile Ala Tyr Ser Gln Tyr Pro Arg Pro Ser<br>455                      460                      465                      470 | | 2586 |
| gac atc ccc cag tgg aac agc gat aag ccc agc ctg aag gat atc aaa<br>Asp Ile Pro Gln Trp Asn Ser Asp Lys Pro Ser Leu Lys Asp Ile Lys<br>                475                      480                      485 | | 2634 |
| atc atg gga tac tcc att agg aca atc gac tac agg tac acc gtc tgg<br>Ile Met Gly Tyr Ser Ile Arg Thr Ile Asp Tyr Arg Tyr Thr Val Trp<br>            490                      495                      500 | | 2682 |
| gtc gga ttc aac ccc gat gag ttc ctg gcc aac ttc tcc gac atc cac<br>Val Gly Phe Asn Pro Asp Glu Phe Leu Ala Asn Phe Ser Asp Ile His<br>        505                      510                      515 | | 2730 |
| gct ggc gag ctg tat ttc gtg gac agc gac cct ctg cag gac cac aac<br>Ala Gly Glu Leu Tyr Phe Val Asp Ser Asp Pro Leu Gln Asp His Asn<br>520                      525                      530 | | 2778 |
| atg tac aac gac tcc cag gga ggc gat ctg ttt caa ctc ctg atg ccc<br>Met Tyr Asn Asp Ser Gln Gly Gly Asp Leu Phe Gln Leu Leu Met Pro<br>535                      540                      545                      550 | | 2826 |
| tga gcccctctcc ctccccccccc cctaacgtta ctggccgaag ccgcttggaa | | 2879 |
| taaggccggt gtgcgtttgt ctatatgtta ttttccacca tattgccgtc ttttggcaat | | 2939 |
| gtgagggccc ggaaacctgg ccctgtcttc ttgacgagca ttcctagggg tctttcccct | | 2999 |
| ctcgccaaag gaatgcaagg tctgttgaat gtcgtgaagg aagcagttcc tctggaagct | | 3059 |
| tcttgaagac aaacaacgtc tgtagcgacc ctttgcaggc agcggaaccc cccacctggc | | 3119 |
| gacaggtgcc tctgcggcca aaagccacgt gtataagata cacctgcaaa ggcggcacaa | | 3179 |
| ccccagtgcc acgttgtgag ttggatagtt gtggaaagag tcaaatggct ctcctcaagc | | 3239 |
| gtattcaaca aggggctgaa ggatgcccag aaggtacccc attgtatggg atctgatctg | | 3299 |
| gggcctcggt acacatgctt tacatgtgtt tagtcgaggt taaaaaaacg tctaggcccc | | 3359 |
| ccgaaccacg gggacgtggt tttcctttga aaaacacgat gataatatgg ccacaaccat | | 3419 |
| ggt atg gcc gcc cct gcc ctc gga ctg gtg tgt ggc agg tgc cct gag<br>    Met Ala Ala Pro Ala Leu Gly Leu Val Cys Gly Arg Cys Pro Glu<br>                      555                      560                      565 | | 3467 |
| ctg gga ctg gtg ctg ctg ctg ctc ctg ctg agc ctc ctg tgt ggc gct<br>Leu Gly Leu Val Leu Leu Leu Leu Leu Leu Ser Leu Leu Cys Gly Ala<br>              570                      575                      580 | | 3515 |
| gcc gga agc caa gag gct gga aca gga gct ggc gcc gga agc ctg gct<br>Ala Gly Ser Gln Glu Ala Gly Thr Gly Ala Gly Ala Gly Ser Leu Ala<br>                      585                      590                      595 | | 3563 |
| ggc agc tgc gga tgt ggc aca ccc cag agg cct gga gct cat gga agc<br>Gly Ser Cys Gly Cys Gly Thr Pro Gln Arg Pro Gly Ala His Gly Ser | | 3611 |

-continued

```
                600                 605                 610
agc gcc gct gcc cac agg tac tcc aga gaa gcc aat gcc cct gga cct      3659
Ser Ala Ala Ala His Arg Tyr Ser Arg Glu Ala Asn Ala Pro Gly Pro
615                 620                 625 gtg ccc ggc gaa aga cag ctg gcc cac tcc aag atg gtg ccc atc cct      3707
Val Pro Gly Glu Arg Gln Leu Ala His Ser Lys Met Val Pro Ile Pro
630                 635                 640                 645 gcc gga gtg ttt aca atg ggc acc gat gac cct cag atc aag cag gat      3755
Ala Gly Val Phe Thr Met Gly Thr Asp Asp Pro Gln Ile Lys Gln Asp
                650                 655                 660 gga gag gct ccc gcc agg agg gtg aca atc gac gcc ttc tac atg gac      3803
Gly Glu Ala Pro Ala Arg Arg Val Thr Ile Asp Ala Phe Tyr Met Asp
            665                 670                 675 gcc tac gag gtg agc aac acc gag ttc gaa aaa ttc gtg aac agc acc      3851
Ala Tyr Glu Val Ser Asn Thr Glu Phe Glu Lys Phe Val Asn Ser Thr
        680                 685                 690 ggc tac ctg acc gag gcc gaa aag ttc ggc gat agc ttc gtc ttc gag      3899
Gly Tyr Leu Thr Glu Ala Glu Lys Phe Gly Asp Ser Phe Val Phe Glu
695                 700                 705 ggc atg ctg agc gag cag gtg aag acc aac atc cag cag gcc gtg gcc      3947
Gly Met Leu Ser Glu Gln Val Lys Thr Asn Ile Gln Gln Ala Val Ala
710                 715                 720                 725 gct gct cct tgg tgg ctg ccc gtg aag ggc gcc aat tgg agg cat ccc      3995
Ala Ala Pro Trp Trp Leu Pro Val Lys Gly Ala Asn Trp Arg His Pro
                730                 735                 740 gag ggc ccc gat agc acc atc ctg cac agg ccc gac cat cct gtg ctg      4043
Glu Gly Pro Asp Ser Thr Ile Leu His Arg Pro Asp His Pro Val Leu
            745                 750                 755 cac gtc agc tgg aac gac gct gtg gcc tac tgc aca tgg gcc ggc aaa      4091
His Val Ser Trp Asn Asp Ala Val Ala Tyr Cys Thr Trp Ala Gly Lys
        760                 765                 770 agg ctg cct acc gaa gcc gag tgg gag tac agc tgc agg ggc ggc ctg      4139
Arg Leu Pro Thr Glu Ala Glu Trp Glu Tyr Ser Cys Arg Gly Gly Leu
775                 780                 785 cac aat agg ctc ttc ccc tgg ggc aac aaa ctc cag ccc aag ggc cag      4187
His Asn Arg Leu Phe Pro Trp Gly Asn Lys Leu Gln Pro Lys Gly Gln
790                 795                 800                 805 cat tat gcc aat atc tgg cag ggc gag ttc cct gtg aca aac acc ggc      4235
His Tyr Ala Asn Ile Trp Gln Gly Glu Phe Pro Val Thr Asn Thr Gly
                810                 815                 820 gag gat ggc ttt caa ggc acc gct ccc gtg gac gcc ttt ccc ccc aat      4283
Glu Asp Gly Phe Gln Gly Thr Ala Pro Val Asp Ala Phe Pro Pro Asn
            825                 830                 835 ggc tac ggc ctg tac aat atc gtg ggc aac gcc tgg gag tgg aca tcc      4331
Gly Tyr Gly Leu Tyr Asn Ile Val Gly Asn Ala Trp Glu Trp Thr Ser
        840                 845                 850 gac tgg tgg acc gtg cat cac agc gtg gag gaa aca ctc aac ccc aag      4379
Asp Trp Trp Thr Val His His Ser Val Glu Glu Thr Leu Asn Pro Lys
855                 860                 865 ggc cct ccc agc gga aag gat agg gtc aag aag ggc ggc agc tac atg      4427
Gly Pro Pro Ser Gly Lys Asp Arg Val Lys Lys Gly Gly Ser Tyr Met
870                 875                 880                 885 tgc cac aga tcc tac tgc tac aga tac agg tgc gcc gcc agg agc cag      4475
Cys His Arg Ser Tyr Cys Tyr Arg Tyr Arg Cys Ala Ala Arg Ser Gln
                890                 895                 900 aac acc ccc gat agc agc gcc tcc aat ctg ggc ttt agg tgt gcc gcc      4523
Asn Thr Pro Asp Ser Ser Ala Ser Asn Leu Gly Phe Arg Cys Ala Ala
            905                 910                 915 gat agg ctg ccc acc atg gac tga gaa ttc acgcgtggta cctctagagt        4573
Asp Arg Leu Pro Thr Met Asp
```

```
Asp Arg Leu Pro Thr Met Asp     Glu Phe
        920                 925 cgacccgggc ggcctcgagg acggggtgaa ctacgcctga ggatccgatc ttttcccctc      4633
tgccaaaaat tatggggaca tcatgaagcc ccttgagcat ctgacttctg gctaataaag      4693
gaaatttatt ttcattgcaa tagtgtgttg aatttttttg tgtctctcac tcggaagcaa      4753
ttcgttgatc tgaatttcga ccacccataa tacccattac cctggtagat aagtagcatg      4813
gcgggttaat cattaactac aaggaacccc tagtgatgga gttggccact ccctctctgc      4873
gcgctcgctc gctcactgag gccgggcgac caaaggtcgc ccgacgcccg ggctttgccc      4933
gggcggcctc agtgagcgag cgagcgcgca g                                     4964
```

<210> SEQ ID NO 9
<211> LENGTH: 550
<212> TYPE: PRT
<213> ORGANISM: Artificial Sequence
<220> FEATURE:
<223> OTHER INFORMATION: Synthetic Construct

<400> SEQUENCE: 9

```
Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
```

```
                    275                 280                 285
Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 10
<211> LENGTH: 374
<212> TYPE: PRT
<213> ORGANISM: Artificial Sequence
<220> FEATURE:
<223> OTHER INFORMATION: Synthetic Construct

<400> SEQUENCE: 10

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
```

-continued

```
                    85                  90                  95
Gly Val Phe Thr Met Gly Thr Asp Asp Pro Gln Ile Lys Gln Asp Gly
                100                 105                 110

Glu Ala Pro Ala Arg Arg Val Thr Ile Asp Ala Phe Tyr Met Asp Ala
            115                 120                 125

Tyr Glu Val Ser Asn Thr Glu Phe Glu Lys Phe Val Asn Ser Thr Gly
        130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

<210> SEQ ID NO 11
<211> LENGTH: 3967
<212> TYPE: DNA
<213> ORGANISM: Artificial Sequence
<220> FEATURE:
<223> OTHER INFORMATION: CB7.hIDSco.RBG
<220> FEATURE:
<221> NAME/KEY: misc_feature
<222> LOCATION: (2)..(131)
<223> OTHER INFORMATION: 5'ITR
<220> FEATURE:
<221> NAME/KEY: promoter
<222> LOCATION: (199)..(580)
<223> OTHER INFORMATION: CMV IE promoter
<220> FEATURE:
<221> NAME/KEY: promoter
<222> LOCATION: (583)..(864)
<223> OTHER INFORMATION: CB promoter
<220> FEATURE:
<221> NAME/KEY: TATA_signal
<222> LOCATION: (837)..(840)
<220> FEATURE:
```

```
<221> NAME/KEY: Intron
<222> LOCATION: (959)..(1930)
<223> OTHER INFORMATION: chicken beta-actin intron
<220> FEATURE:
<221> NAME/KEY: CDS
<222> LOCATION: (1937)..(3589)
<223> OTHER INFORMATION: hIDSco
<220> FEATURE:
<221> NAME/KEY: polyA_signal
<222> LOCATION: (3623)..(3749)
<223> OTHER INFORMATION: rabbit globin polyA
<220> FEATURE:
<221> NAME/KEY: misc_feature
<222> LOCATION: (3838)..(3967)
<223> OTHER INFORMATION: 3' ITR

<400> SEQUENCE: 11
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120 tagggggttcc ttgtagttaa tgattaaccc gccatgctac ttatctacca gggtaatggg    180
gatcctctag aactatagct agtcgacatt gattattgac tagttattaa tagtaatcaa    240
ttacggggtc attagttcat agcccatata tggagttccg cgttacataa cttacggtaa    300
atggcccgcc tggctgaccg cccaacgacc cccgcccatt gacgtcaata atgacgtatg    360
ttcccatagt aacgccaata gggactttcc attgacgtca atgggtggac tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctcccccc cctccccacc cccaattttg tatttattta    660 tttttttaatt attttgtgca gcgatggggg cggggggggg ggggggcgc gcgccaggcg    720 ggcggggcg gggcgagggg cggggcgggg cgaggcggag aggtgcggcg gcagccaatc    780
agagcggcgc gctccgaaag tttccttta tggcgaggcg gcggcggcgg cggccctata    840
aaaagcgaag cgcgcggcgg gcggggagtc gctgcgacgc tgccttcgcc ccgtgccccg    900
ctccgccgcc gcctcgcgcc gcccgccccg gctctgactg accgcgttac tcccacaggt    960
gagcgggcgg gacggcccctt ctcctccggg ctgtaattag cgcttggttt aatgacggct   1020 tgttctttttt ctgtggctgc gtgaaagcct tgagggctc cggagggcc ctttgtgcgg    1080 ggggagcggc tcgggggggtg cgtgcgtgtg tgtgtgcgtg gggagcgccg cgtgcggctc   1140
cgcgctgccc ggcggctgtg agcgctgcgg gcgcggcgcg gggctttgtg cgctccgcag   1200
tgtgcgcgag gggagcgcgg ccgggggcgg tgccccgcgg tgcgggggg gctgcgaggg    1260 gaacaaaggc tgcgtgcggg gtgtgtgcgt gggggggtga gcaggggtg tgggcgcgtc    1320 ggtcgggctg caaccccccc tgcaccccc tccccgagtt gctgagcacg gcccggcttc    1380
gggtgcgggg ctccgtacgg ggcgtggcgc gggctcgcc gtgccgggcg ggggtggcg    1440 gcaggtgggg gtgccgggcg gggcggggcc gcctcgggcc ggggagggct cggggagggg    1500
gcgcggcggc ccccggagcg ccggcggctg tcgaggcgcg gcgagccgca gccattgcct    1560
tttatggtaa tcgtgcgaga gggcgcaggg acttcctttg tcccaaatct gtgcggagcc    1620
gaaatctggg aggcgccgcc gcacccctc tagcgggcgc gggggcgaagc ggtgcggcgc    1680 cggcaggaag gaaatgggcg gggagggcct tcgtgcgtcg ccgcgccgcc gtccccttct    1740
ccctctccag cctcgggct gtccgcgggg gacggctgc cttcgggggg gacggggcag    1800
ggcggggttc ggcttctggc gtgtgaccgg cggctctaga gcctctgcta accatgttca    1860
```

-continued

```
tgccttcttc tttttcctac agctcctggg caacgtgctg gttattgtgc tgtctcatca         1920
ttttggcaaa gaattc atg ccc ccc ccc agg aca gga aga gga ctg ctg tgg         1972
               Met Pro Pro Pro Arg Thr Gly Arg Gly Leu Leu Trp
                 1               5                  10 ctc gga ctc gtc ctc tcc agc gtg tgc gtg gct ctc gga tcc gaa acc         2020
Leu Gly Leu Val Leu Ser Ser Val Cys Val Ala Leu Gly Ser Glu Thr
         15                  20                  25 cag gct aat tcc aca acc gat gcc ctg aac gtc ctg ctc atc atc gtg         2068
Gln Ala Asn Ser Thr Thr Asp Ala Leu Asn Val Leu Leu Ile Ile Val
     30                  35                  40 gat gac ctg agg ccc tcc ctg ggc tgt tac ggc gac aag ctc gtc agg         2116
Asp Asp Leu Arg Pro Ser Leu Gly Cys Tyr Gly Asp Lys Leu Val Arg
 45                  50                  55                  60 tcc ccc aac att gat cag ctc gcc tcc cat tcc ctg ctg ttt caa aac         2164
Ser Pro Asn Ile Asp Gln Leu Ala Ser His Ser Leu Leu Phe Gln Asn
                 65                  70                  75 gcc ttc gct cag caa gcc gtg tgc gct cct agc aga gtc agc ttc ctc         2212
Ala Phe Ala Gln Gln Ala Val Cys Ala Pro Ser Arg Val Ser Phe Leu
             80                  85                  90 acc gga agg aga cct gac acc acc agg ctg tac gac ttc aac tcc tat         2260
Thr Gly Arg Arg Pro Asp Thr Thr Arg Leu Tyr Asp Phe Asn Ser Tyr
         95                 100                 105 tgg agg gtc cac gct ggc aac ttc agc acc att ccc cag tac ttc aag         2308
Trp Arg Val His Ala Gly Asn Phe Ser Thr Ile Pro Gln Tyr Phe Lys
110                 115                 120 gag aac ggc tac gtc acc atg tcc gtc ggc aag gtg ttc cac cct ggc         2356
Glu Asn Gly Tyr Val Thr Met Ser Val Gly Lys Val Phe His Pro Gly
125                 130                 135                 140 att tcc tcc aac cac acc gat gac agc ccc tac tcc tgg tcc ttc cct         2404
Ile Ser Ser Asn His Thr Asp Asp Ser Pro Tyr Ser Trp Ser Phe Pro
                145                 150                 155 ccc tac cac ccc agc agc gaa aag tac gag aat acc aag acc tgt aga         2452
Pro Tyr His Pro Ser Ser Glu Lys Tyr Glu Asn Thr Lys Thr Cys Arg
            160                 165                 170 ggc ccc gac ggc gaa ctc cac gct aac ctc ctg tgt cct gtc gat gtc         2500
Gly Pro Asp Gly Glu Leu His Ala Asn Leu Leu Cys Pro Val Asp Val
        175                 180                 185 ctc gac gtg ccc gaa ggc aca ctc ccc gac aag cag tcc aca gaa caa         2548
Leu Asp Val Pro Glu Gly Thr Leu Pro Asp Lys Gln Ser Thr Glu Gln
    190                 195                 200 gcc atc cag ctc ctg gag aag atg aag acc tcc gct tcc ccc ttt ttc         2596
Ala Ile Gln Leu Leu Glu Lys Met Lys Thr Ser Ala Ser Pro Phe Phe
205                 210                 215                 220 ctg gcc gtg ggc tac cac aaa ccc cac att ccc ttc agg tac ccc aag         2644
Leu Ala Val Gly Tyr His Lys Pro His Ile Pro Phe Arg Tyr Pro Lys
                225                 230                 235 gag ttc cag aag ctg tat ccc ctg gag aac att acc ctc gcc cct gat         2692
Glu Phe Gln Lys Leu Tyr Pro Leu Glu Asn Ile Thr Leu Ala Pro Asp
            240                 245                 250 ccc gaa gtg cct gac ggc ctg cct cct gtc gct tac aac ccc tgg atg         2740
Pro Glu Val Pro Asp Gly Leu Pro Pro Val Ala Tyr Asn Pro Trp Met
        255                 260                 265 gac atc agg cag aga gaa gac gtg caa gcc ctc aac atc agc gtg ccc         2788
Asp Ile Arg Gln Arg Glu Asp Val Gln Ala Leu Asn Ile Ser Val Pro
    270                 275                 280 tac ggc cct atc ccc gtg gac ttc cag aga aag atc agg cag agc tac         2836
Tyr Gly Pro Ile Pro Val Asp Phe Gln Arg Lys Ile Arg Gln Ser Tyr
285                 290                 295                 300
```

| | | |
|---|---|---|
| ttc gcc tcc gtc agc tac ctg gac acc cag gtg gga aga ctc ctg tcc<br>Phe Ala Ser Val Ser Tyr Leu Asp Thr Gln Val Gly Arg Leu Leu Ser<br>305 310 315 | | 2884 |
| gcc ctc gac gat ctc cag ctg gcc aac agc acc atc att gcc ttc acc<br>Ala Leu Asp Asp Leu Gln Leu Ala Asn Ser Thr Ile Ile Ala Phe Thr<br>320 325 330 | | 2932 |
| agc gac cat ggc tgg gct ctc gga gag cat ggc gaa tgg gcc aag tac<br>Ser Asp His Gly Trp Ala Leu Gly Glu His Gly Glu Trp Ala Lys Tyr<br>335 340 345 | | 2980 |
| tcc aac ttc gat gtg gcc acc cac gtc ccc ctc atc ttc tac gtc ccc<br>Ser Asn Phe Asp Val Ala Thr His Val Pro Leu Ile Phe Tyr Val Pro<br>350 355 360 | | 3028 |
| gga agg acc gcc agc ctg cct gaa gct gga gag aag ctc ttc ccc tac<br>Gly Arg Thr Ala Ser Leu Pro Glu Ala Gly Glu Lys Leu Phe Pro Tyr<br>365 370 375 380 | | 3076 |
| ctg gac cct ttt gat tcc gcc agc caa ctc atg gaa ccc ggc agg caa<br>Leu Asp Pro Phe Asp Ser Ala Ser Gln Leu Met Glu Pro Gly Arg Gln<br>385 390 395 | | 3124 |
| agc atg gac ctc gtg gag ctg gtc tcc ctg ttc cct acc ctg gct gga<br>Ser Met Asp Leu Val Glu Leu Val Ser Leu Phe Pro Thr Leu Ala Gly<br>400 405 410 | | 3172 |
| ctc gcc gga ctc caa gtc cct ccc aga tgc cct gtg cct agc ttc cat<br>Leu Ala Gly Leu Gln Val Pro Pro Arg Cys Pro Val Pro Ser Phe His<br>415 420 425 | | 3220 |
| gtg gag ctc tgc aga gag ggc aag aac ctg ctg aag cac ttc agg ttt<br>Val Glu Leu Cys Arg Glu Gly Lys Asn Leu Leu Lys His Phe Arg Phe<br>430 435 440 | | 3268 |
| agg gac ctg gag gag gat cct tac ctc ccc gga aac cct aga gag ctc<br>Arg Asp Leu Glu Glu Asp Pro Tyr Leu Pro Gly Asn Pro Arg Glu Leu<br>445 450 455 460 | | 3316 |
| atc gct tac tcc cag tat cct agg ccc tcc gac atc ccc cag tgg aac<br>Ile Ala Tyr Ser Gln Tyr Pro Arg Pro Ser Asp Ile Pro Gln Trp Asn<br>465 470 475 | | 3364 |
| agc gat aag ccc agc ctg aag gat atc aaa atc atg gga tac tcc att<br>Ser Asp Lys Pro Ser Leu Lys Asp Ile Lys Ile Met Gly Tyr Ser Ile<br>480 485 490 | | 3412 |
| agg aca atc gac tac agg tac acc gtc tgg gtc gga ttc aac ccc gat<br>Arg Thr Ile Asp Tyr Arg Tyr Thr Val Trp Val Gly Phe Asn Pro Asp<br>495 500 505 | | 3460 |
| gag ttc ctg gcc aac ttc tcc gac atc cac gct ggc gag ctg tat ttc<br>Glu Phe Leu Ala Asn Phe Ser Asp Ile His Ala Gly Glu Leu Tyr Phe<br>510 515 520 | | 3508 |
| gtg gac agc gac cct ctg cag gac cac aac atg tac aac gac tcc cag<br>Val Asp Ser Asp Pro Leu Gln Asp His Asn Met Tyr Asn Asp Ser Gln<br>525 530 535 540 | | 3556 |
| gga ggc gat ctg ttt caa ctc ctg atg ccc tga ctcgaggacg gggtgaacta<br>Gly Gly Asp Leu Phe Gln Leu Leu Met Pro<br>545 550 | | 3609 |
| cgcctgagga tccgatcttt ttccctctgc caaaaattat ggggacatca tgaagcccct | | 3669 |
| tgagcatctg acttctggct aataaaggaa atttattttc attgcaatag tgtgttggaa | | 3729 |
| tttttttgtgt ctctcactcg gaagcaattc gttgatctga atttcgacca cccataatac | | 3789 |
| ccattaccct ggtagataag tagcatggcg ggttaatcat taactacaag gaaccccctag | | 3849 |
| tgatggagtt ggccactccc tctctgcgcg ctcgctcgct cactgaggcc gggcgaccaa | | 3909 |
| aggtcgcccg acgcccgggc tttgcccggg cggcctcagt gagcgagcga gcgcgcag | | 3967 |

<210> SEQ ID NO 12
<211> LENGTH: 550

```
<212> TYPE: PRT
<213> ORGANISM: Artificial Sequence
<220> FEATURE:
<223> OTHER INFORMATION: Synthetic Construct

<400> SEQUENCE: 12

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380
```

-continued

```
Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
            405                 410                 415

Gln Val Pro Pro Arg Cys Pro Val Pro Ser Phe His Val Glu Leu Cys
        420                 425                 430

Arg Glu Gly Lys Asn Leu Leu Lys His Phe Arg Phe Arg Asp Leu Glu
    435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
            485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 13
<211> LENGTH: 736
<212> TYPE: PRT
<213> ORGANISM: Unknown
<220> FEATURE:
<223> OTHER INFORMATION: AAV9 capsid amino acid sequence

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190
```

-continued

```
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
```

```
                  610              615              620
Thr Asp Gly Asn Phe His Pro Ser Pro Leu Met Gly Gly Phe Gly Met
625                  630              635              640

Lys His Pro Pro Pro Gln Ile Leu Ile Lys Asn Thr Pro Val Pro Ala
                 645              650              655

Asp Pro Pro Thr Ala Phe Asn Lys Asp Lys Leu Asn Ser Phe Ile Thr
                 660              665              670

Gln Tyr Ser Thr Gly Gln Val Ser Val Glu Ile Glu Trp Glu Leu Gln
                 675              680              685

Lys Glu Asn Ser Lys Arg Trp Asn Pro Glu Ile Gln Tyr Thr Ser Asn
                 690              695              700

Tyr Tyr Lys Ser Asn Asn Val Glu Phe Ala Val Asn Thr Glu Gly Val
705              710              715              720

Tyr Ser Glu Pro Arg Pro Ile Gly Thr Arg Tyr Leu Thr Arg Asn Leu
                 725              730              735

<210> SEQ ID NO 14
<211> LENGTH: 3965
<212> TYPE: DNA
<213> ORGANISM: Artificial Sequence
<220> FEATURE:
<223> OTHER INFORMATION: CB7.CI.hIDS.RBG
<220> FEATURE:
<221> NAME/KEY: misc_feature
<222> LOCATION: (2)..(131)
<223> OTHER INFORMATION: 5'ITR
<220> FEATURE:
<221> NAME/KEY: promoter
<222> LOCATION: (199)..(580)
<223> OTHER INFORMATION: CMV IE promoter
<220> FEATURE:
<221> NAME/KEY: promoter
<222> LOCATION: (583)..(864)
<223> OTHER INFORMATION: CB promoter
<220> FEATURE:
<221> NAME/KEY: TATA_signal
<222> LOCATION: (837)..(840)
<220> FEATURE:
<221> NAME/KEY: Intron
<222> LOCATION: (957)..(1928)
<223> OTHER INFORMATION: chicken beta-actin intron
<220> FEATURE:
<221> NAME/KEY: CDS
<222> LOCATION: (1935)..(3587)
<223> OTHER INFORMATION: hIDS
<220> FEATURE:
<221> NAME/KEY: polyA_signal
<222> LOCATION: (3621)..(3747)
<223> OTHER INFORMATION: rabbit globin polyA
<220> FEATURE:
<221> NAME/KEY: misc_feature
<222> LOCATION: (3836)..(3965)
<223> OTHER INFORMATION: 3'ITR

<400> SEQUENCE: 14
gctgcgcgct cgctcgctca ctgaggccgc ccgggcaaag cccgggcgtc gggcgacctt    60
tggtcgcccg gcctcagtga gcgagcgagc gcgcagagag gagtggccaa actccatcac   120 tagggggttcc ttgtagttaa tgattaaccc gccatgctac ttatctacca gggtaatggg   180
gatcctctag aactatagct agtcgacatt gattattgac tagttattaa tagtaatcaa   240
ttacggggtc attagttcat agcccatata tggagttccg cgttacataa cttacggtaa   300
atggcccgcc tggctgaccg cccaacgacc cccgcccatt gacgtcaata atgacgtatg   360
ttcccatagt aacgccaata gggactttcc attgacgtca atgggtggag tatttacggt   420
aaactgccca cttggcagta catcaagtgt atcatatgcc aagtacgccc cctattgacg   480
```

```
tcaatgacgg taaatggccc gcctggcatt atgcccagta catgacctta tgggactttc      540
ctacttggca gtacatctac gtattagtca tcgctattac catggtcgag gtgagcccca      600
cgttctgctt cactctcccc atctccccc cctccccacc cccaattttg tatttattta       660 tttttttaatt attttgtgca gcgatggggg cgggggggg gggggggcgc gcgccaggcg      720
gggcggggcg gggcgagggg cggggcgggg cgaggcggag aggtgcggcg gcagccaatc      780
agagcggcgc gctccgaaag tttccttta ggcgaggcg gcggcggcgg cggccctata       840
aaaagcgaag cgcgcggcgg gcgggagtcg ctgcgcgctg ccttcgcccc gtgccccgct      900
ccgccgccgc ctcgcgccgc ccgccccggc tctgactgac cgcgttactc ccacaggtga      960
gcgggcggga cggcccttct cctccgggct gtaattagcg cttggtttaa tgacggcttg     1020
tttcttttct gtggctgcgt gaaagccttg aggggctccg ggaggccct ttgtgcgggg      1080 ggagcggctc gggggtgcg tgcgtgtgtg tgtgcgtggg gagcgccgcg tgcggctccg      1140
cgctgcccgg cggctgtgag cgctgcgggc gcggcgcggg gctttgtgcg ctccgcagtg     1200
tgcgcgaggg gagcgcggcc ggggcggtg ccccgcggtg cgggggggc tgcgagggga      1260 acaaaggctg cgtgcggggt gtgtgcgtgg ggggtgagc aggggtgtg ggcgcgtcgg       1320 tcgggctgca acccccctg caccccctc cccgagttgc tgagcacggc ccggcttcgg       1380
gtgcggggct ccgtacgggg cgtggcgcgg ggctcgccgt gccgggcggg gggtggcggc     1440
aggtgggggt gccgggcggg gcggggccgc ctcgggccgg ggagggctcg ggggagggc      1500 gcggcggccc ccggagcgcc ggcggctgtc gaggcgcggc gagccgcagc cattgccttt     1560
tatggtaatc gtgcgagagg gcgcagggac ttcctttgtc ccaaatctgt gcggagccga    1620
aatctgggag gcgccgccgc accccctcta gcgggcgcgg ggcgaagcgg tgcggcgccg    1680
gcaggaagga aatgggcggg gagggccttc gtgcgtcgcc gcgccgccgt cccctcctcc    1740
ctctccagcc tcggggctgt ccgcggggg acggctgcct tcggggggga cggggcaggg     1800
cggggttcgg cttctggcgt gtgaccggcg gctctagagc ctctgctaac catgttcatg    1860
ccttcttctt tttcctacag ctcctgggca acgtgctggt tatttgtgctg tctcatcatt    1920 ttggcaaaga attc atg ccg cca ccc cgg acc ggc cga ggc ctt ctc tgg       1970
              Met Pro Pro Pro Arg Thr Gly Arg Gly Leu Leu Trp
                1               5                   10 ctg ggt ctg gtt ctg agc tcc gtc tgc gtc gcc ctc gga tcc gaa acg       2018
Leu Gly Leu Val Leu Ser Ser Val Cys Val Ala Leu Gly Ser Glu Thr
        15                  20                  25 cag gcc aac tcg acc aca gat gct ctg aac gtt ctt ctc atc atc gtg       2066
Gln Ala Asn Ser Thr Thr Asp Ala Leu Asn Val Leu Leu Ile Ile Val
        30                  35                  40 gat gac ctg cgc ccc tcc ctg ggc tgt tat ggg gat aag ctg gtg agg       2114
Asp Asp Leu Arg Pro Ser Leu Gly Cys Tyr Gly Asp Lys Leu Val Arg
45                  50                  55                  60 tcc cca aat att gac caa ctg gca tcc cac agc ctc ctc ttc cag aat       2162
Ser Pro Asn Ile Asp Gln Leu Ala Ser His Ser Leu Leu Phe Gln Asn
                65                  70                  75 gcc ttt gcg cag caa gca gtg tgc gcc ccg agc cgc gtt tct ttc ctc       2210
Ala Phe Ala Gln Gln Ala Val Cys Ala Pro Ser Arg Val Ser Phe Leu
            80                  85                  90 act ggc agg aga cct gac acc acc cgc ctg tac gac ttc aac tcc tac       2258
Thr Gly Arg Arg Pro Asp Thr Thr Arg Leu Tyr Asp Phe Asn Ser Tyr
        95                  100                 105 tgg agg gtg cac gct gga aac ttc tcc acc atc ccc cag tac ttc aag       2306
Trp Arg Val His Ala Gly Asn Phe Ser Thr Ile Pro Gln Tyr Phe Lys
```

-continued

```
            110                 115                 120
gag aat ggc tat gtg acc atg tcg gtg gga aaa gtc ttt cac cct ggg    2354
Glu Asn Gly Tyr Val Thr Met Ser Val Gly Lys Val Phe His Pro Gly
125                 130                 135                 140 ata tct tct aac cat acc gat gat tct ccg tat agc tgg tct ttt cca    2402
Ile Ser Ser Asn His Thr Asp Asp Ser Pro Tyr Ser Trp Ser Phe Pro
                145                 150                 155 cct tat cat cct tcc tct gag aag tat gaa aac act aag aca tgt cga    2450
Pro Tyr His Pro Ser Ser Glu Lys Tyr Glu Asn Thr Lys Thr Cys Arg
            160                 165                 170 ggg cca gat gga gaa ctc cat gcc aac ctg ctt tgc cct gtg gat gtg    2498
Gly Pro Asp Gly Glu Leu His Ala Asn Leu Leu Cys Pro Val Asp Val
        175                 180                 185 ctg gat gtt ccc gag ggc acc ttg cct gac aaa cag agc act gag caa    2546
Leu Asp Val Pro Glu Gly Thr Leu Pro Asp Lys Gln Ser Thr Glu Gln
190                 195                 200 gcc ata cag ttg ttg gaa aag atg aaa acg tca gcc agt cct ttc ttc    2594
Ala Ile Gln Leu Leu Glu Lys Met Lys Thr Ser Ala Ser Pro Phe Phe
205                 210                 215                 220 ctg gcc gtt ggg tat cat aag cca cac atc ccc ttc aga tac ccc aag    2642
Leu Ala Val Gly Tyr His Lys Pro His Ile Pro Phe Arg Tyr Pro Lys
                225                 230                 235 gaa ttt cag aag ttg tat ccc ttg gag aac atc acc ctg gcc ccc gat    2690
Glu Phe Gln Lys Leu Tyr Pro Leu Glu Asn Ile Thr Leu Ala Pro Asp
            240                 245                 250 ccc gag gtc cct gat ggc cta ccc cct gtg gcc tac aac ccc tgg atg    2738
Pro Glu Val Pro Asp Gly Leu Pro Pro Val Ala Tyr Asn Pro Trp Met
        255                 260                 265 gac atc agg caa cgg gaa gac gtc caa gcc tta aac atc agt gtg ccg    2786
Asp Ile Arg Gln Arg Glu Asp Val Gln Ala Leu Asn Ile Ser Val Pro
270                 275                 280 tat ggt cca att cct gtg gac ttt cag cgg aaa atc cgc cag agc tac    2834
Tyr Gly Pro Ile Pro Val Asp Phe Gln Arg Lys Ile Arg Gln Ser Tyr
285                 290                 295                 300 ttt gcc tct gtg tca tat ttg gat aca cag gtc ggc cgc ctc ttg agt    2882
Phe Ala Ser Val Ser Tyr Leu Asp Thr Gln Val Gly Arg Leu Leu Ser
                305                 310                 315 gct ttg gac gat ctt cag ctg gcc aac agc acc atc att gca ttt acc    2930
Ala Leu Asp Asp Leu Gln Leu Ala Asn Ser Thr Ile Ile Ala Phe Thr
            320                 325                 330 tcg gat cat ggg tgg gct cta ggt gaa cat gga gaa tgg gcc aaa tac    2978
Ser Asp His Gly Trp Ala Leu Gly Glu His Gly Glu Trp Ala Lys Tyr
        335                 340                 345 agc aat ttt gat gtt gct acc cat gtt ccc ctg ata ttc tat gtt cct    3026
Ser Asn Phe Asp Val Ala Thr His Val Pro Leu Ile Phe Tyr Val Pro
350                 355                 360 gga agg acg gct tca ctt ccg gag gca ggc gag aag ctt ttc cct tac    3074
Gly Arg Thr Ala Ser Leu Pro Glu Ala Gly Glu Lys Leu Phe Pro Tyr
365                 370                 375                 380 ctc gac cct ttt gat tcc gcc tca cag ttg atg gag cca ggc agg caa    3122
Leu Asp Pro Phe Asp Ser Ala Ser Gln Leu Met Glu Pro Gly Arg Gln
                385                 390                 395 tcc atg gac ctt gtg gaa ctt gtg tct ctt ttt ccc acg ctg gct gga    3170
Ser Met Asp Leu Val Glu Leu Val Ser Leu Phe Pro Thr Leu Ala Gly
            400                 405                 410 ctt gca gga ctg cag gtt cca cct cgc tgc ccc gtt cct tca ttt cac    3218
Leu Ala Gly Leu Gln Val Pro Pro Arg Cys Pro Val Pro Ser Phe His
        415                 420                 425 gtt gag ctg tgc aga gaa ggc aag aac ctt ctg aag cat ttt cga ttc    3266
```

```
Val Glu Leu Cys Arg Glu Gly Lys Asn Leu Leu Lys His Phe Arg Phe
            430                 435                 440 cgt gac ttg gaa gag gat ccg tac ctc cct ggt aat ccc cgt gaa ctg      3314
Arg Asp Leu Glu Glu Asp Pro Tyr Leu Pro Gly Asn Pro Arg Glu Leu
445                 450                 455                 460 att gcc tat agc cag tat ccc cgg cct tca gac atc cct cag tgg aat      3362
Ile Ala Tyr Ser Gln Tyr Pro Arg Pro Ser Asp Ile Pro Gln Trp Asn
                465                 470                 475 tct gac aag ccg agt tta aaa gat ata aag atc atg ggc tat tcc ata      3410
Ser Asp Lys Pro Ser Leu Lys Asp Ile Lys Ile Met Gly Tyr Ser Ile
            480                 485                 490 cgc acc ata gac tat agg tat act gtg tgg gtt ggc ttc aat cct gat      3458
Arg Thr Ile Asp Tyr Arg Tyr Thr Val Trp Val Gly Phe Asn Pro Asp
        495                 500                 505 gaa ttt cta gct aac ttt tct gac atc cat gca ggg gaa ctg tat ttt      3506
Glu Phe Leu Ala Asn Phe Ser Asp Ile His Ala Gly Glu Leu Tyr Phe
    510                 515                 520 gtg gat tct gac cca ttg cag gat cac aat atg tat aat gat tcc caa      3554
Val Asp Ser Asp Pro Leu Gln Asp His Asn Met Tyr Asn Asp Ser Gln
525                 530                 535                 540 ggt gga gat ctt ttc cag ttg ttg atg cct tga ctcgaggacg gggtgaacta    3607
Gly Gly Asp Leu Phe Gln Leu Leu Met Pro
                545                 550 cgcctgagga tccgatcttt ttccctctgc caaaaattat ggggacatca tgaagcccct    3667
tgagcatctg acttctggct aataaaggaa atttattttc attgcaatag tgtgttggaa    3727
ttttttgtgt ctctcactcg gaagcaattc gttgatctga atttcgacca cccataatac    3787
ccattaccct ggtagataag tagcatggcg ggttaatcat taactacaag gaacccctag    3847
tgatggagtt ggccactccc tctctgcgcg ctcgctcgct cactgaggcc gggcgaccaa    3907
aggtcgcccg acgcccgggc tttgcccggg cggcctcagt gagcgagcga gcgcgcag     3965

<210> SEQ ID NO 15
<211> LENGTH: 550
<212> TYPE: PRT
<213> ORGANISM: Artificial Sequence
<220> FEATURE:
<223> OTHER INFORMATION: Synthetic Construct

<400> SEQUENCE: 15

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140
```

```
His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550
```

```
<210> SEQ ID NO 16
<211> LENGTH: 22
<212> TYPE: DNA
<213> ORGANISM: Artificial Sequence
<220> FEATURE:
<223> OTHER INFORMATION: synthesized sequence

<400> SEQUENCE: 16
ttccctctgc caaaaattat gg                                              22

<210> SEQ ID NO 17
<211> LENGTH: 26
<212> TYPE: DNA
<213> ORGANISM: Artificial Sequence
<220> FEATURE:
<223> OTHER INFORMATION: synthesized sequence

<400> SEQUENCE: 17
cctttattag ccagaagtca gatgct                                          26

<210> SEQ ID NO 18
<211> LENGTH: 15
<212> TYPE: DNA
<213> ORGANISM: Artificial Sequence
<220> FEATURE:
<223> OTHER INFORMATION: Synthesized sequence

<400> SEQUENCE: 18
acatcatgaa gcccc                                                      15
```